US012496348B2

(12) United States Patent
Qi et al.

(10) Patent No.: US 12,496,348 B2
(45) Date of Patent: Dec. 16, 2025

(54) SMALL MOLECULE TARGET BROMO/ACETYL PROTEINS AND USES THEREOF

(71) Applicant: DANA-FARBER CANCER INSTITUTE, INC., Boston, MA (US)

(72) Inventors: Jun Qi, Sharon, MA (US); Deyao Li, Quincy, MA (US); Virangika K. Wimalasena, Brookline, MA (US); Paul Park, Winthrop, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1044 days.

(21) Appl. No.: 17/617,226

(22) PCT Filed: Jun. 17, 2020

(86) PCT No.: PCT/US2020/038130
§ 371 (c)(1),
(2) Date: Dec. 7, 2021

(87) PCT Pub. No.: WO2020/257278
PCT Pub. Date: Dec. 24, 2020

(65) Prior Publication Data

US 2022/0241425 A1 Aug. 4, 2022

Related U.S. Application Data

(60) Provisional application No. 62/862,879, filed on Jun. 18, 2019.

(51) Int. Cl.

| | |
|---|---|
| ***A61K 31/42*** | (2006.01) |
| ***A61K 47/54*** | (2017.01) |
| ***C07D 401/14*** | (2006.01) |
| ***C07D 413/14*** | (2006.01) |
| ***C07D 417/14*** | (2006.01) |
| ***C07D 471/04*** | (2006.01) |

(52) U.S. Cl.
CPC .......... *A61K 47/555* (2017.08); *A61K 47/545* (2017.08); *C07D 401/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | | | |
|---|---|---|---|---|
| 2016/0176916 | A1 | 6/2016 | Bradner et al. | |
| 2016/0317632 | A1 | 11/2016 | Albrecht et al. | |
| 2017/0312292 | A1 | 11/2017 | Romero et al. | |
| 2019/0076542 | A1* | 3/2019 | Phillips ................ | C07D 471/08 |
| 2019/0151457 | A1 | 5/2019 | Bradner et al. | |

FOREIGN PATENT DOCUMENTS

| | | | |
|---|---|---|---|
| JP | 2016534044 | A | 11/2016 |
| JP | 2017530176 | A | 10/2017 |
| JP | 2018502097 | A | 1/2018 |
| JP | 2018519249 | A | 7/2018 |
| NO | 2018237026 | A1 | 12/2018 |
| WO | 2015054642 | A2 | 4/2015 |
| WO | 2016055028 | A1 | 4/2016 |
| WO | 2016105518 | A1 | 6/2016 |
| WO | 2016170324 | A1 | 10/2016 |
| WO | 2019060742 | A1 | 3/2019 |
| WO | 2020092907 | A1 | 5/2020 |

OTHER PUBLICATIONS

Conery et al., eLife 2016;5:e10483, 17 pages (Year: 2016).*
Attar et al., "Exploitation of EP300 and CREBBP Lysine Acetyltransferases by Cancer", Cold Spring Harbor Perspectives in Medicine, 2017, vol. 7, No. 3, pp. 1-15.
Conery, et al., "Bromodomain inhibition of the transcriptional coactivators CBP/EP300 as a therapeutic strategy to target the IRF4 network in multiple myeloma," eLIFE, 2016, 5:1-17.

* cited by examiner

*Primary Examiner* — Michael G. Hartley
*Assistant Examiner* — Samantha L Mejias
(74) *Attorney, Agent, or Firm* — ArentFox Schiff LLP; Daniel W. Clarke; Shawn P. Foley

(57) ABSTRACT

Disclosed are bispecific compounds (degraders) that target EP300/CBP for degradation. Also disclosed are pharmaceutical compositions containing the degraders and methods of using the compounds to treat disease.

25 Claims, 11 Drawing Sheets

SMALL MOLECULE TARGET BROMO/ACETYL PROTEINS AND USES THEREOF

RELATED APPLICATIONS

The present application is a national stage application, filed under 35 U.S.C. § 371, of International Application No. PCT/US2020/038130, filed Jun. 17, 2020, which claims the benefit of priority under 35 U.S.C. § 119(e) to U.S. Provisional Application No. 62/862,879, filed on Jun. 18, 2019, each of which is incorporated herein by reference in its entirety.

BACKGROUND OF THE INVENTION

High-risk neuroblastoma (NB) is a pediatric tumor of the peripheral sympathetic nervous system derived from primitive neural crest cells. It has a poor survival rate. These neuroendocrine tumors are characterized by high expression of oncogenic MYC family members. (Matthay et al., Nat. Rev. Dis. Primers 2:16078 (2016); Zimmerman et al., Cancer Discov. 8(3):320-35 (2018)). MYCN is an integral member of a positive, feed-forward autoregulatory loop of transcription factors (TFs) that establish cell fate in MYCN-amplified NB. This group of TFs is termed the core-regulatory circuitry (CRC). Each member is regulated by a super-enhancer (SE) gene which is critically required for NB viability. One mechanism by which the MYC family oncogenes drive tumor growth is by invading gene enhancers and recruiting transcriptional and epigenetic machinery (Zeid et al., Nat. Genet. 50(4):515-23 (2018)). Combination pharmacologic inhibition of SE-mediated transcriptional initiation and elongation has been shown to rapidly disrupt the NB CRC in vitro and in vivo, resulting in transcriptional collapse and apoptosis (Durbin et al., Nat. Genet. 50(9):1240-60 (2018)). Since transcriptional inhibition has been insufficient to drive tumor regression in vivo (Morton et al., Mol. Oncol. 7(2):248-58 (2013)), an alternative approach is needed.

EP300, or histone acetyltransferase (HAT) p300, was recently identified as a necessary component in the survival of NB cells (Durbin et al., Nat. Genet. 50(9):1240-60 (2018)). Like its paralog cAMP-response element (CREB)-binding protein (CBP, CREBBP), EP300 catalyzes the H3K27ac mark typical of SE elements (Dancy et al., Chem. Rev. 115(6):2419-52 (2015)). Numerous tumor types display dependency on EP300 and not CBP, suggesting that this finding may be a generalizable property of distinct human cancer subsets. Other EP300-dependent and MYC-family dependent cancers include acute myeloid leukemia (AML), multiple myeloma (MM), melanoma, rhabdomyosarcoma, and diffuse large B cell lymphoma.

SUMMARY OF THE INVENTION

A first aspect of the present invention is directed to a bispecific compound comprising a moiety (targeting ligand) that binds histone acetyltransferase p300 (also referred to herein as EP300) and cAMP-responsive element-binding protein-binding protein (CBP), a degron that binds an E3 ubiquitin ligase, and a linker (L) that covalently attaches the targeting ligand and the degron, wherein the compound has a structure represented by formula (I):

(I)

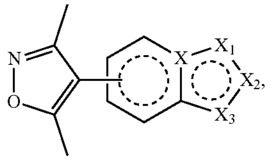

wherein X represents C or N, $X_1$ is $CR_1$ or $NR_3$, $X_2$ is $CR_2$ or $CR_4$, $X_3$ is N, provided that when X is N, $X_1$ is $CR_1$, $X_2$ is $CR_2$ and $X_3$ is N, and when X is C, $X_1$ is $NR_3$, $X_2$ is $CR_4$, and $X_3$ is N;

$R_1$ represents $NHR^1$, wherein $R^1$ is an optionally substituted C1-C3 alkyl or an optionally substituted C5-C6 carbocyclic;

$R_2$ represents

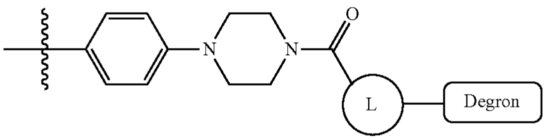

or

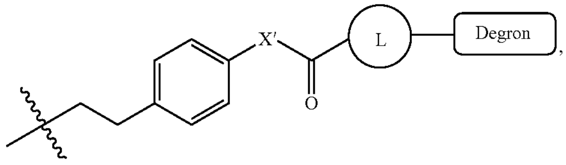

wherein X' is O, $HNC_2H_4NH$, or NH;

$R_3$ represents an optionally substituted C1-C3 alkyl,

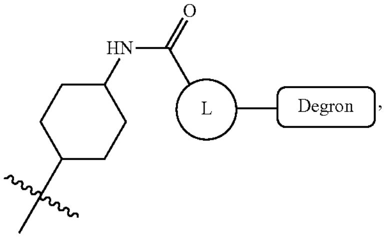

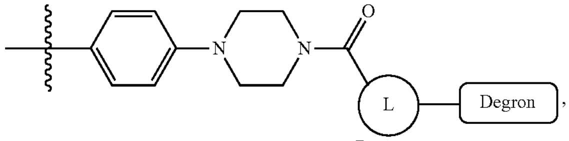

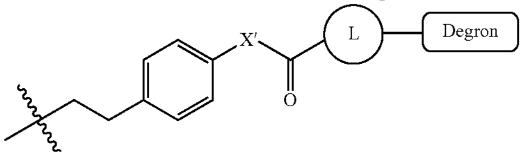

or

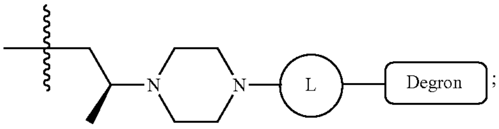

and $R_4$ represents an optionally substituted C5-C6 carbocyclic group or an optionally substituted C5-C6 heterocyclic group,

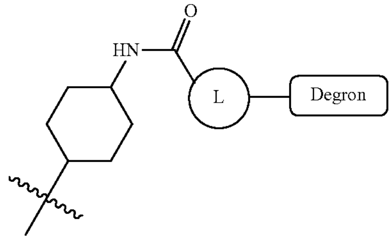
,

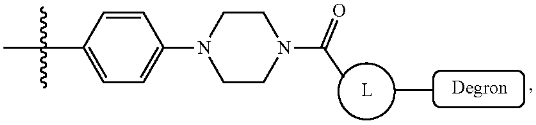
,

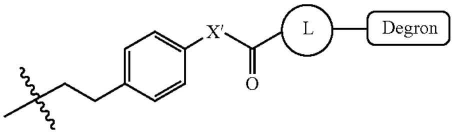
or

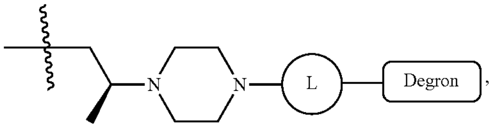
, provided that one of $R_3$ and $R_4$ is

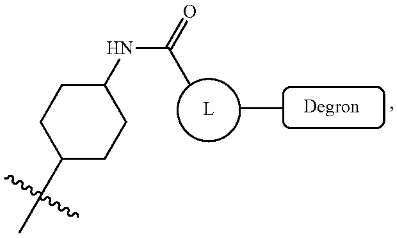
,

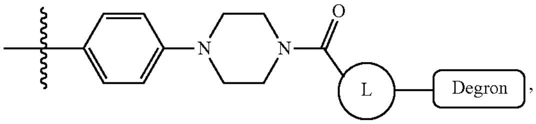
,

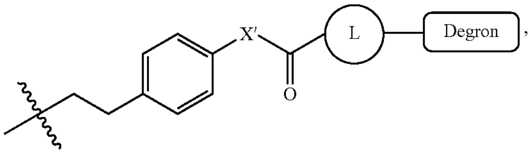
, or

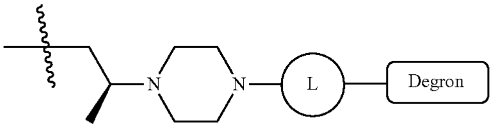
, or a pharmaceutically acceptable salt or stereoisomer thereof.

In some embodiments, X represents N, $X_1$ is $CR_1$, $X_2$ is $CR_2$, $X_3$ is N, $R_1$ represents $NHR^1$, $R^1$ is an optionally substituted C1-C3 alkyl or an optionally substituted C5-C6 carbocyclic, and $R_2$ represents

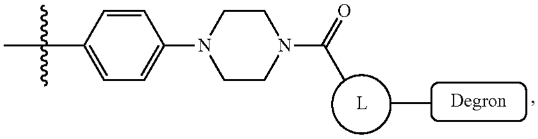
, or

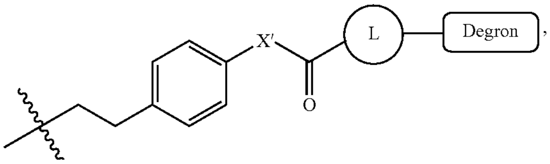
, and X' is O or NH.

In some embodiments, X represents C, $X_1$ is $NR_3$, $X_2$ is $CR_4$, $X_3$ is N, $R_3$ represents optionally an substituted C1-C3 alkyl,

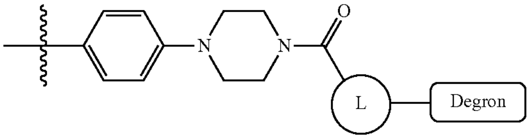
,

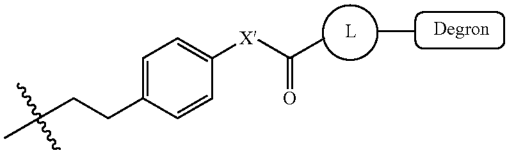
or

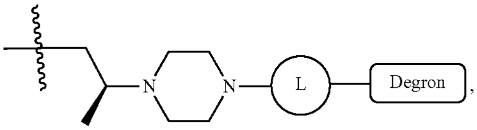
, and $R_4$ represents an optionally substituted C5-C6 carbocyclic group,

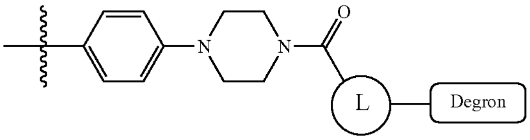
,

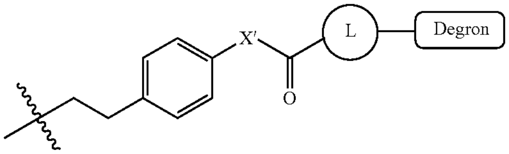
or

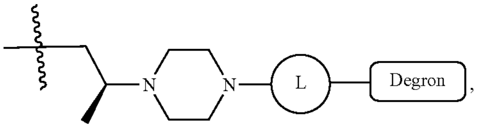
, provided that one of $R_3$ and $R_4$ is

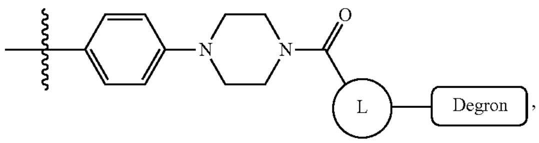

,

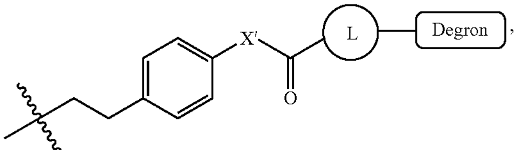

, or

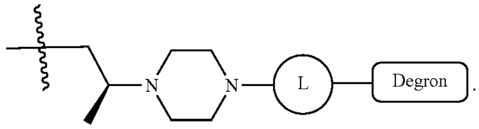

.

In some embodiments, X represents N, $X_1$ is $CR_1$, $R_1$ represents $NHR^1$, $R^1$ is an optionally substituted C1-C3 alkyl or an optionally substituted C5-C6 carbocyclic, $X_2$ is $CR_2$, and $X_3$ is N, and when X is C, $X_1$ is $NR_3$, $X_2$ is $CR_4$, and $X_3$ is N, $R_2$ represents

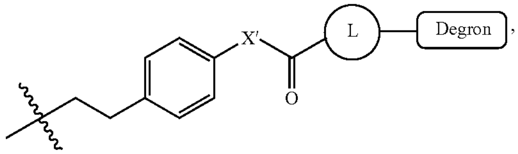

, wherein X' represents $NHC_2H_4NH$.

In some embodiments, when X is C, $X_1$ is $NR_3$, $X_2$ is $CR_4$, and $X_3$ is N, $R_3$ represents an optionally substituted C1-C3 alkyl or,

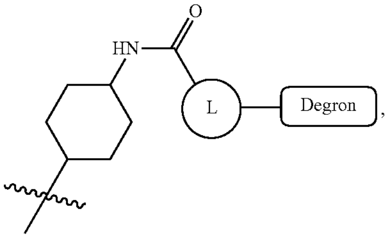

, and $R_4$ represents an optionally substituted C5-C6 carbocyclic or an optionally substituted C5-C6 heterocyclic,

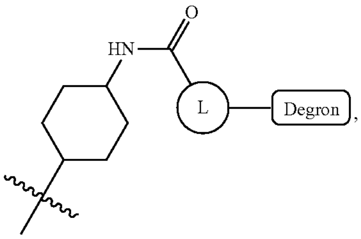

, provided that one of $R_3$ and $R_4$ is

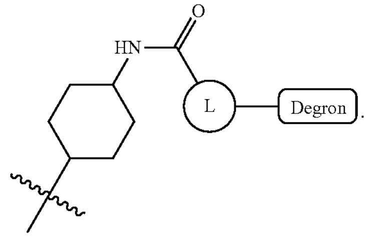

.

In some embodiments, $R^1$ is an optionally substituted C1-C3 alkyl.

In some embodiments, $R^1$ is an optionally substituted C5-C6 carbocyclic. In some embodiments, the optionally substituted C5-C6 carbocyclic is optionally substituted aralkyl.

In some embodiments, $R_2$ is

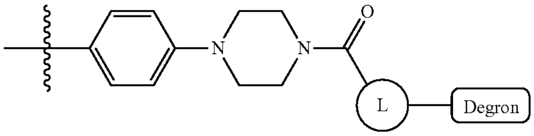

, or

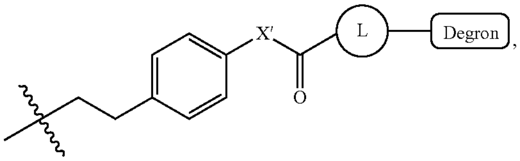

, wherein X' is O, $HNC_2H_4NH$, or NH.

In some embodiments, $R_3$ is an optionally substituted C1-C3 alkyl and $R_4$ is

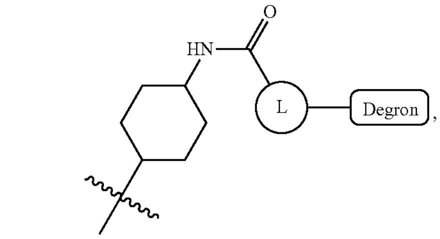

,

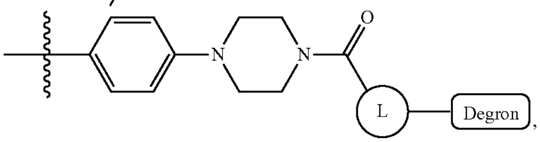

,

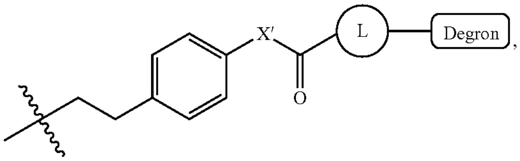

, or

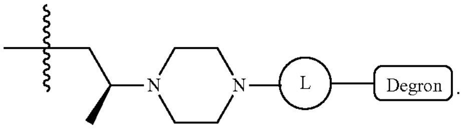

.

In some embodiments, $R_4$ is an optionally substituted C5-C6 carbocyclic or an optionally substituted C5-C6 heterocyclic and $R_3$ is

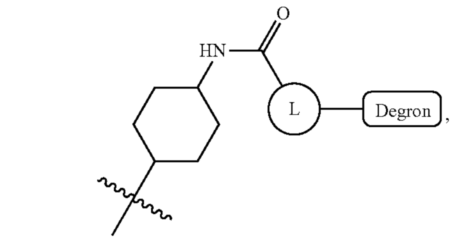

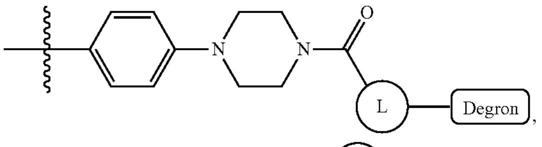

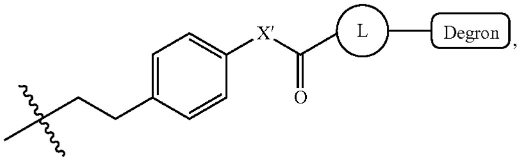

or

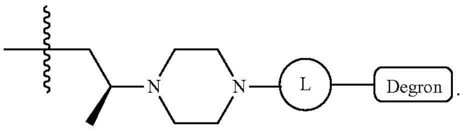

In some embodiments, the optionally substituted C5-C6 carbocyclic is an optionally substituted aralkyl. In some embodiments the optionally substituted C5-C6 heterocyclic is

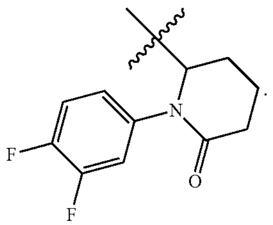 [SMILES: *C1CCCC(=O)N1c1ccc(F)c(F)c1]

In some embodiments, the bispecific compounds of the present invention have a structure represented by formula (II):

(II)

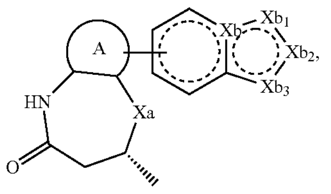

wherein

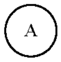

represents an optionally substituted phenyl or an optionally C6 heteroaryl;

Xa represents NH, O, S, or $C(Ra)_2$, wherein each Ra independently represents H, C1-C6 alkyl, C2-C6 alkenyl, C2-C6 alkynyl, or C3-C6 carbocyclyl;

Xb represents C or N, $Xb_1$ represents $CRb_1$ or $CRb_3$, $Xb_2$ represents $CRb_2$, $CR_4$, or N, $Xb_3$ represents N or NMe, provided that when Xb is N, $Xb_1$ is $CRb_1$, $Xb_2$ is $CRb_2$ and $Xb_3$ is N, and when Xb is C, $Xb_1$ is $CRb_3$, $Xb_2$ is $CR_4$ or N, and $Xb_3$ is N or NMe; wherein $Rb_1$ represents $NHR^{b1}$, wherein $R^{b1}$ is an optionally substituted C1-C3 alkyl or an optionally substituted C5-C6 carbocyclic;

$Rb_2$ represents

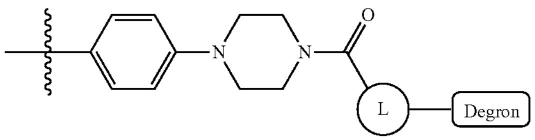

or

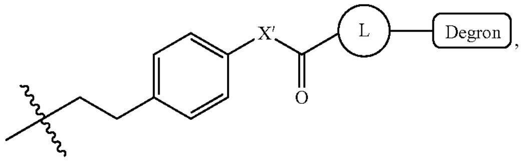

wherein X' is O, $HNC_2H_4NH$, or NH;

$Rb_3$ represents an optionally substituted C1-C3 alkyl,

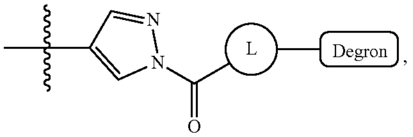

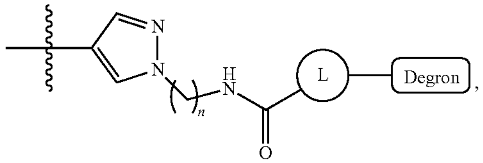

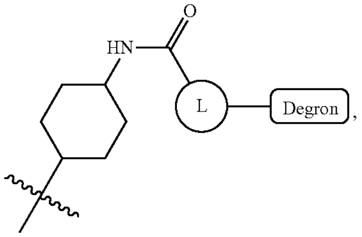

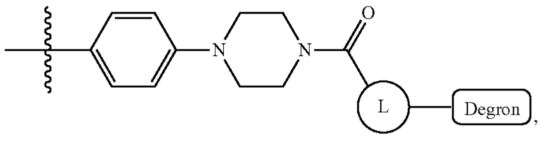

-continued

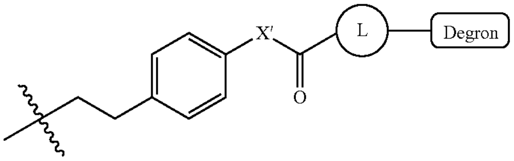
or

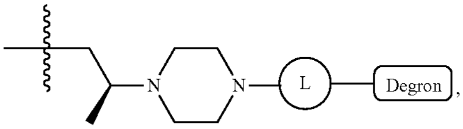
, wherein n is 1, 2, 3, or 4; and $Rb_4$ represents an optionally substituted C5-C6 carbocyclic or an optionally substituted C5-C6 heterocyclic,

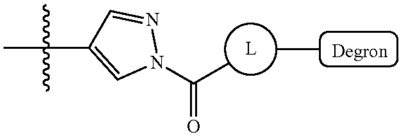
,

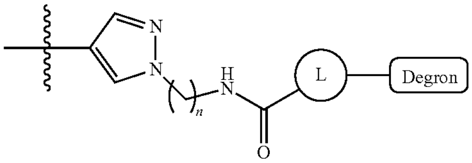
,

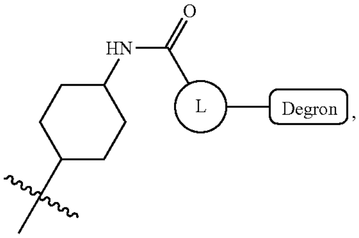
,

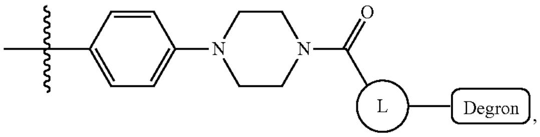
,

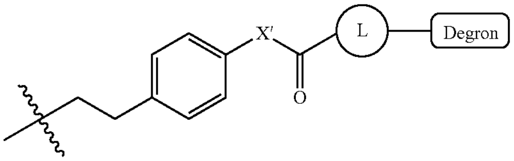
or

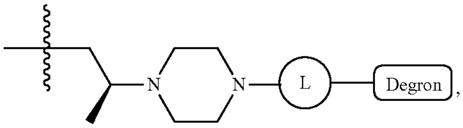
, provided that one of $Rb_3$ and $Rb_4$ is

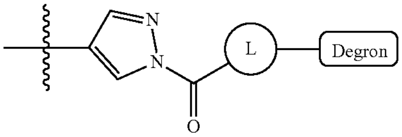
,

-continued

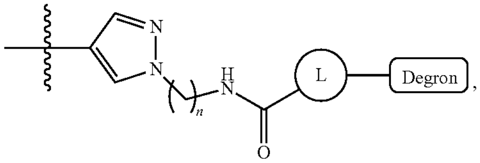
,

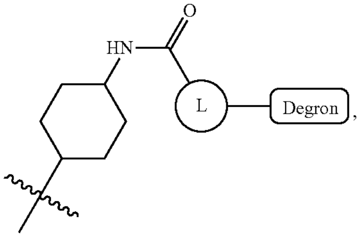
,

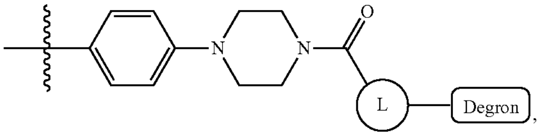
,

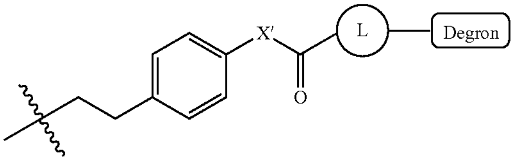
, or

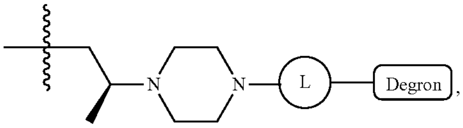
, or a pharmaceutically acceptable salt or stereoisomer thereof.

Another aspect of the present invention is directed to a pharmaceutical composition that includes a therapeutically effective amount of the bispecific compound of formula (I) or (II), or a pharmaceutically acceptable salt or stereoisomer thereof, and a pharmaceutically acceptable carrier.

A further aspect of the present invention is directed to methods for making bispecific compounds of formula (I) or (II) or pharmaceutically acceptable salts or stereoisomers thereof.

Further aspects of the present invention are directed to methods of treating diseases or disorders involving aberrant (e.g., dysfunctional or dysregulated) EP300 and CBP (hereinafter "EP300/CBP") activity, that entail administration of a therapeutically effective amount of a bispecific compound of formula (I) or a pharmaceutically acceptable salt or stereoisomer thereof, to a subject in need thereof.

In some embodiments, the disease or disorder is high-risk neuroblastoma (NB).

In some embodiments, the disease or disorder is a hematological cancer such as acute myeloid leukemia (AML), multiple myeloma (MM), or diffuse large B cell lymphoma.

In other embodiments, the disease or disorder is a solid tumor. In some embodiments, the disease or disorder is melanoma, rhabdomyosarcoma, colon cancer, rectum cancer, stomach cancer, breast cancer or pancreatic cancer.

Without intending to be bound by any particular theory of operation, bispecific compounds of the present invention are believed to inhibit EP300/CBP activity, at least in some instances, by recruitment of cells' Ubiquitin/Proteasome System, whose function is to routinely identify and remove damaged proteins, into close proximity with EP300/CBP as a result of binding between the bromodomains of EP300/CPB, and the targeting ligand. After degradation of an EP300 or CBP molecule, the degrader is released and continues to be active. Thus, by engaging and exploiting the body's own natural protein disposal system, the bispecific compounds of the present invention may represent a potential improvement over current small molecule inhibitors of EP300/CBP. Thus, effective intracellular concentrations of the degraders may be significantly lower than for small molecule EP300 and CBP inhibitors. Collectively, the present bispecific compounds may represent an advancement over known EP300/CBP inhibitors and may overcome one or more limitations regarding their use, and at least in the case of compound 31, may also be selective in targeting EP300 and CBP.

The present bispecific compounds may be useful in the treatment of MYC-driven cancers (e.g., neuroblastoma) by transcriptional silencing of MYC expression.

DETAILED DESCRIPTION OF THE INVENTION

Figure 1A:
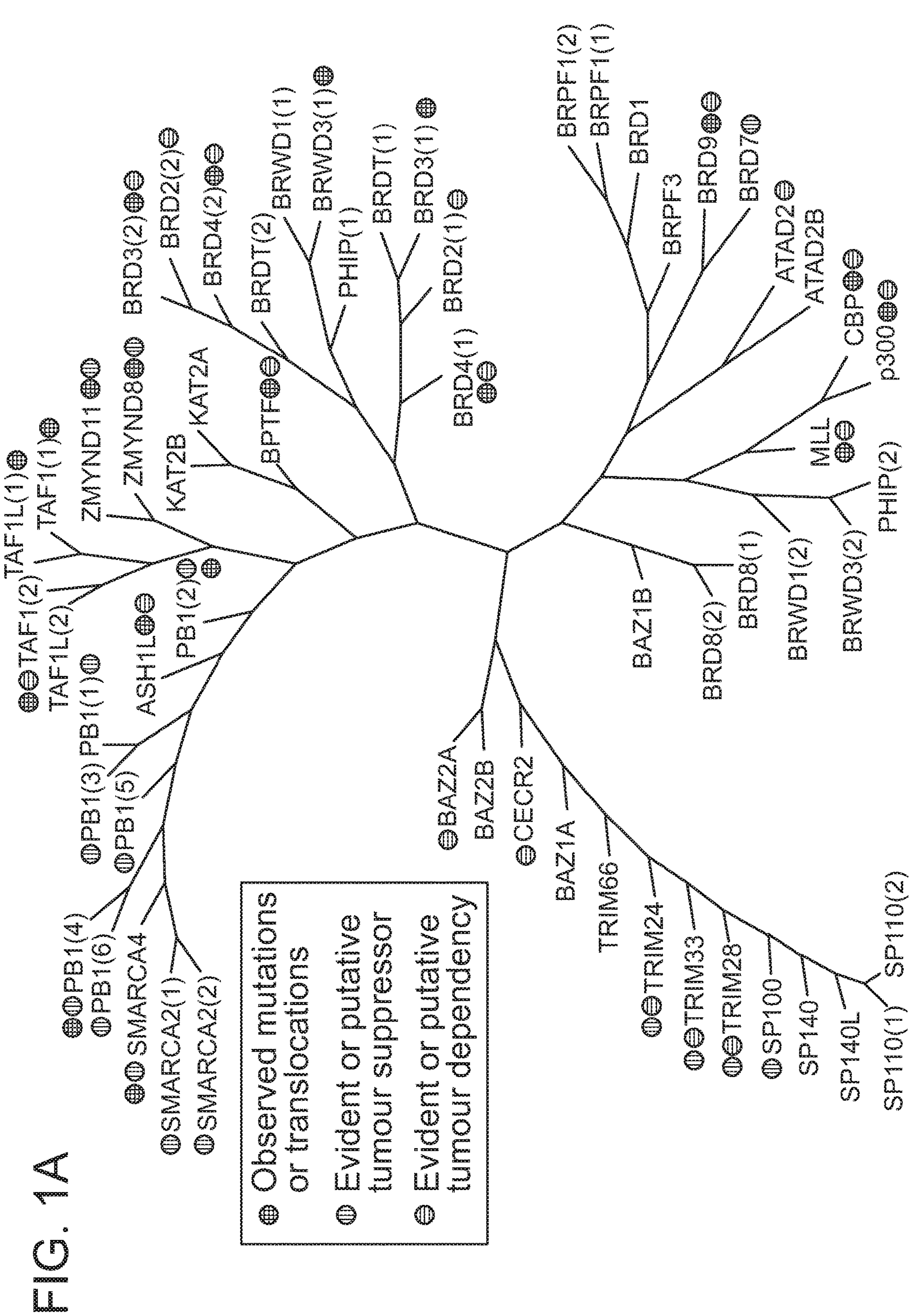
FIG. 1A is a tree diagram of the human bromodomain family (Shortt et al., Nat. Rev. Cancer 17:160-183 (2017)).

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a C1-C18 group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2, or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3, or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may include alkyl, substituted alkyl (e.g., $C_1$-$C_6$, $C_1$-$C_5$, $C_1$-$C_4$, $C_1$-$C_3$, $C_1$-$C_2$, alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

Figure 1B:
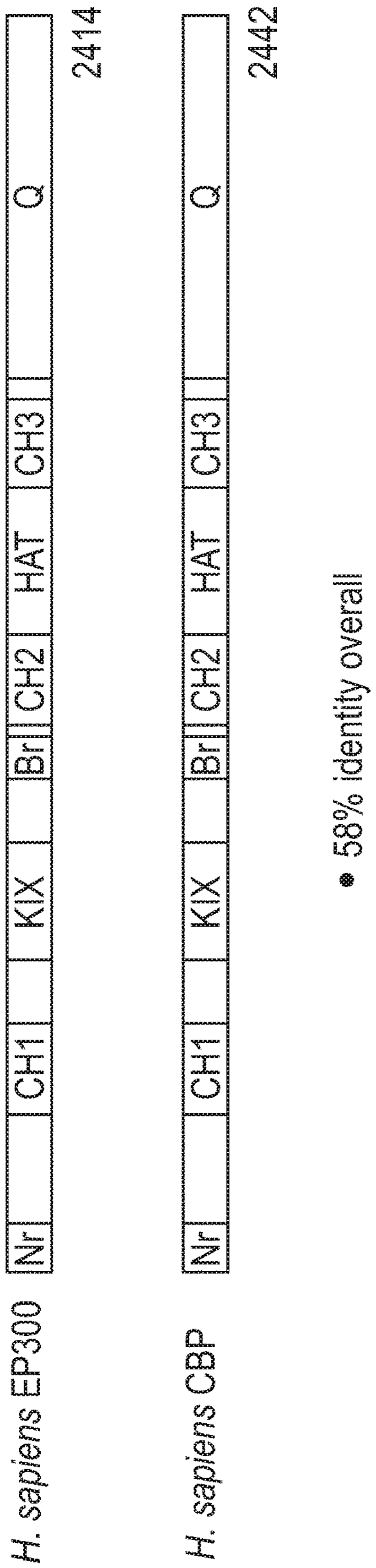
FIG. 1B is an image that shows histone acetyltransferase p300 (EP300) and cAMP-response element binding protein (CREB)-binding protein (CBP) as multidomain proteins.
Figure 1C:
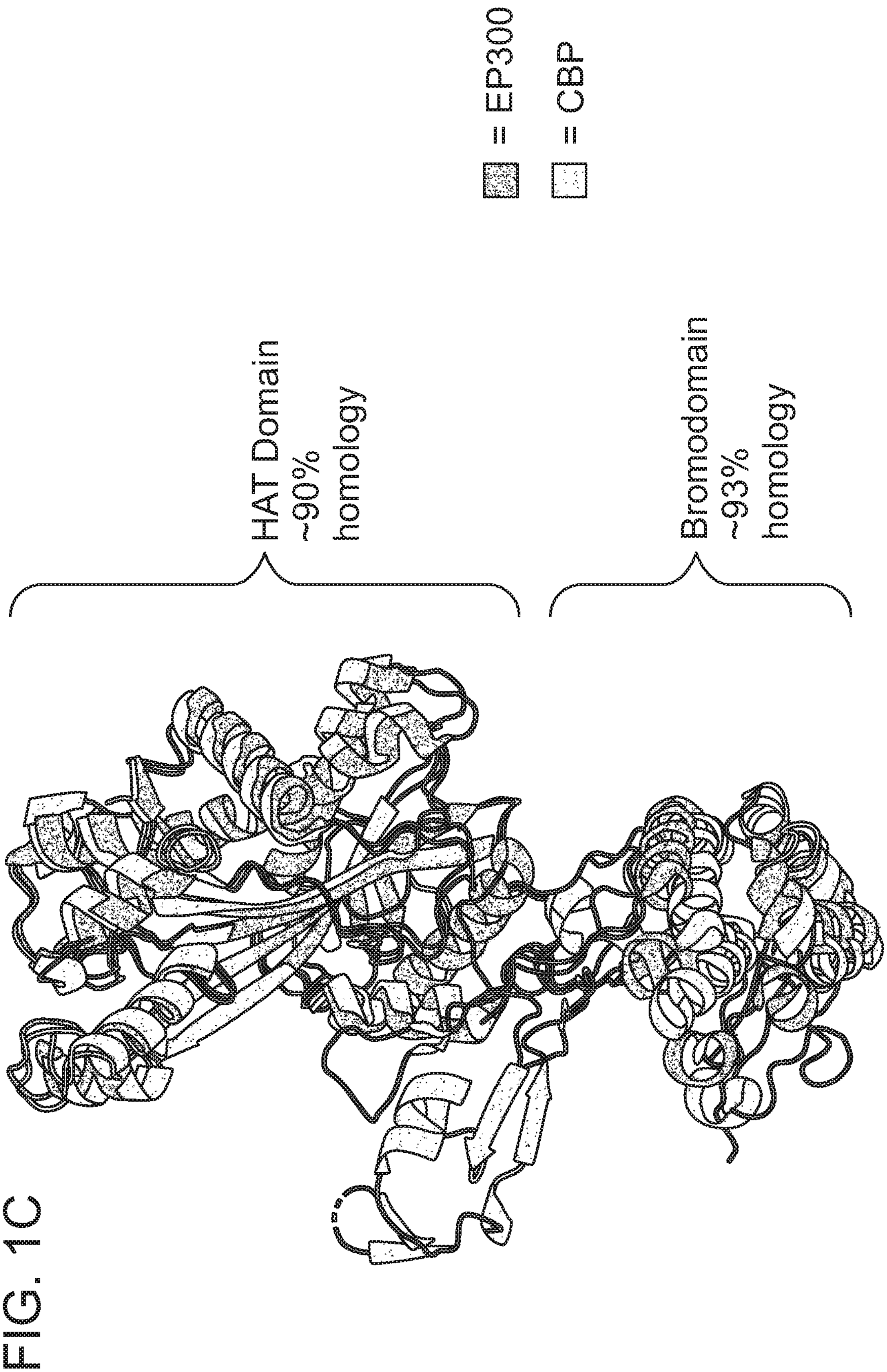
FIG. 1C is an image that shows the EP300/CBP catalytic core structural homology (Henry et al., Biochemistry 52:5746-5759 (2013).
Figure 2:
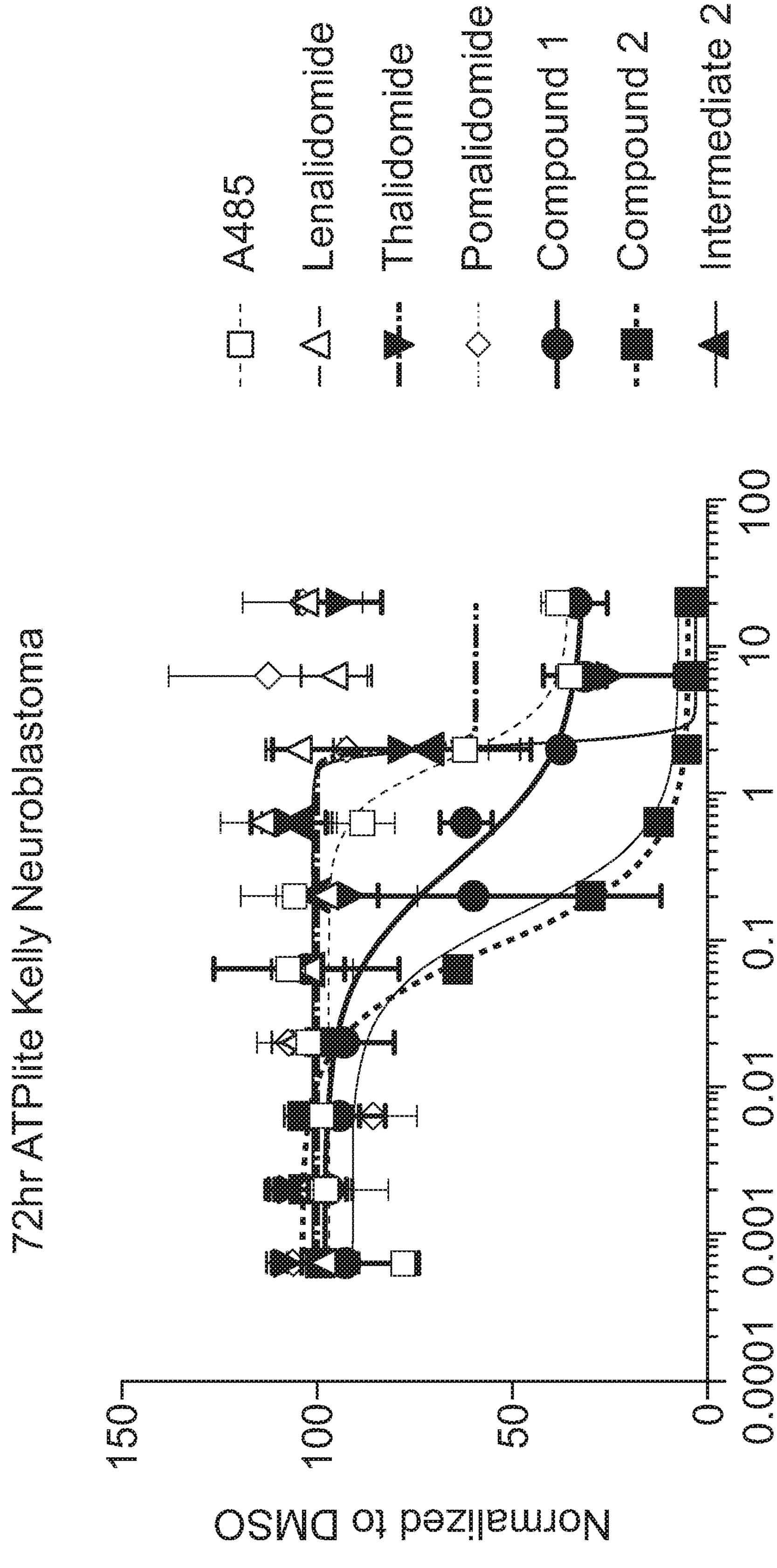
FIG. 2 is a graph that shows relative cell growth after a 72-hour treatment of Kelly neuroblastoma cell lines with A485, lenalidomide, thalidomide, pomalidomide and inventive bispecific compounds 1, 2, and intermediate 2 (int-2) by ATPlite™ Luminescence Assay.

The term "binding" as it relates to interaction between the targeting ligand and the targeted proteins, which for purposes of this invention is EP300, CPB and mutant forms thereof (collectively "EP300/CPB"), typically refers to an inter-molecular interaction that may, at least in one embodiment, be preferential or substantially specific (also referred to herein as "selective") in that binding of the targeting ligand with other proteinaceous entities present in the cell is functionally insignificant (FIG. 1A, FIG. 1B, and FIG. 2). The present bispecific compounds may preferentially bind and recruit EP300 and CBP, and mutant forms thereof, for inhibition, e.g., by targeted degradation.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bispecific compounds include a moiety (targeting ligand) that binds EP300/CBP, a degron (D) that binds an E3 ubiquitin ligase, and a linker (L) that covalently attaches the targeting ligand and the degron. The inventive bispecific compounds have a structure represented by formula (I):

(I)

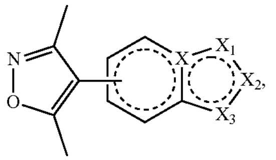

wherein X represents C or N, $X_1$ is $CR_1$ or $NR_3$, $X_2$ is $CR_2$ or $CR_4$, $X_3$ is N, provided that when X is N, $X_1$ is $CR_1$, $X_2$ is $CR_2$, and $X_3$ is N,

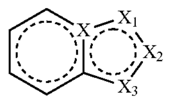

represents

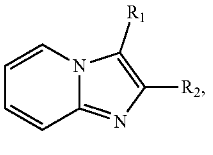

and when X is C, $X_1$ is $NR_3$, $X_2$ is $CR_4$, and $X_3$ is N,

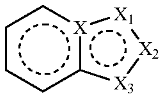

represents

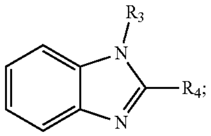

$R_1$ represents $NHR^1$, wherein $R^1$ is an optionally substituted C1-C3 alkyl or an optionally substituted C5-C6 carbocyclic; $R_2$ represents

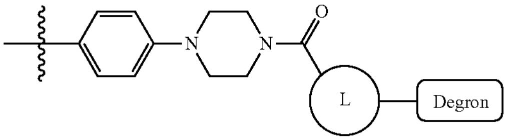

, or

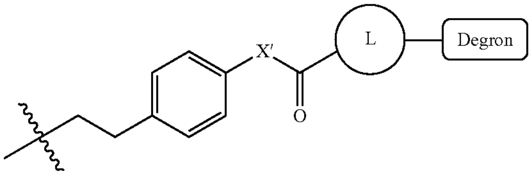

, wherein X' is O, $HNC_2H_4NH$, or NH;
$R_3$ represents an optionally substituted $C_1$-$C_3$ alkyl,

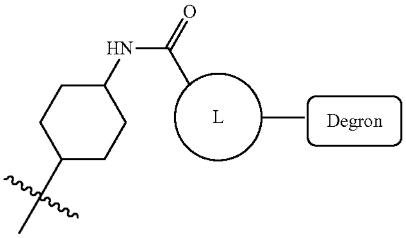

,

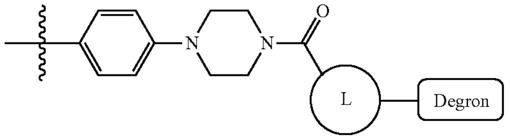

,

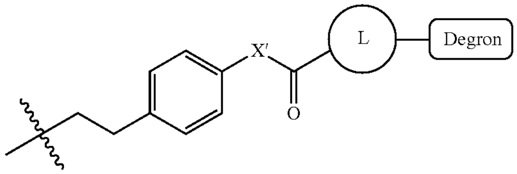

or

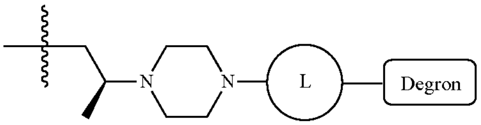

;

$R_4$ represents an optionally substituted $C_5$-$C_6$ carbocyclic,

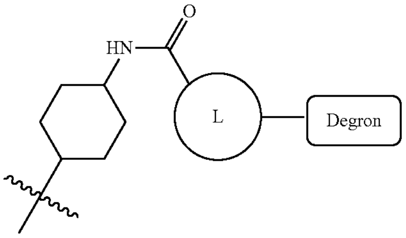

,

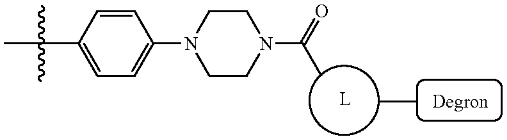

,

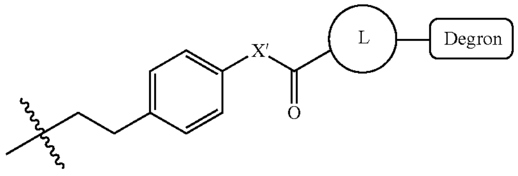

or

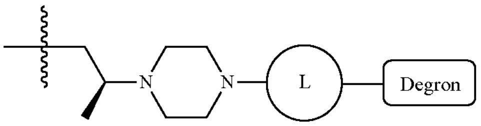

, provided that one of $R_3$ and $R_4$ is

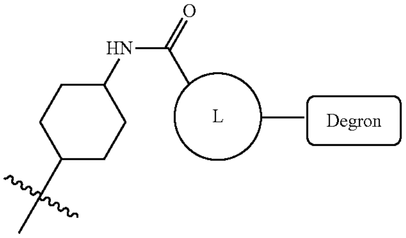

,

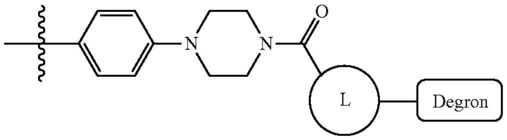

,

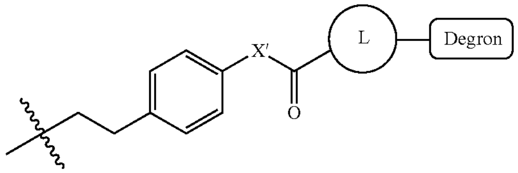

, or

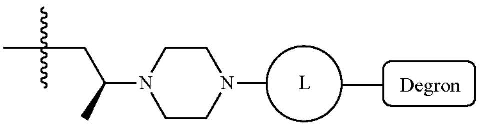

, or a pharmaceutically acceptable salt or stereoisomer thereof.

In some embodiments, when X is N, $X_1$ is $CR_1$, $X_2$ is $CR_2$, and $X_3$ is N,

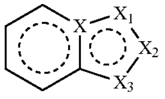

represents

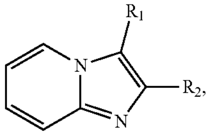

$R_1$ represents $NHR_1$, $R^1$ is an optionally substituted C1-C3 alkyl or an optionally substituted C5-C6 carbocyclic, $R_2$ represents

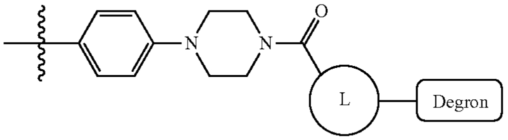

, or

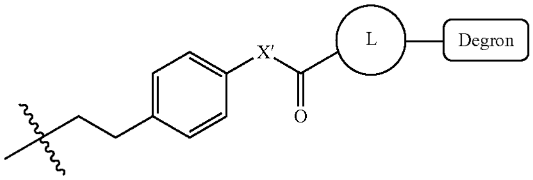

, wherein X' is O or NH, or a pharmaceutically acceptable salt or stereoisomer thereof.

In some embodiments, when X is C, $X_1$ is $NR_3$, $X_2$ is $CR_4$, and $X_3$ is N,

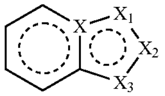

represents

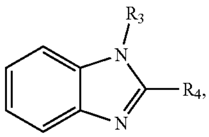

$R_3$ represents an optionally substituted C1-C3 alkyl,

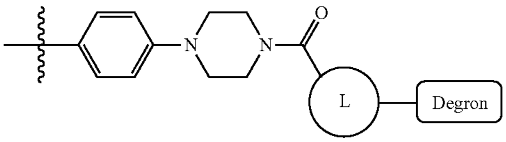

,

-continued

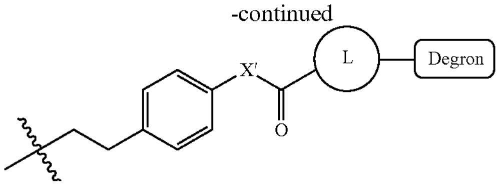

or

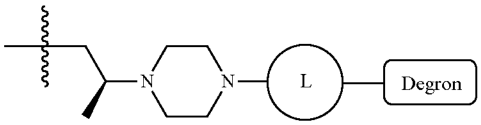

, and $R_4$ represents an optionally substituted C5-C6 carbocyclic,

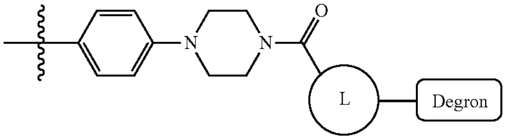

,

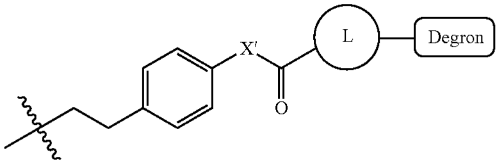

or

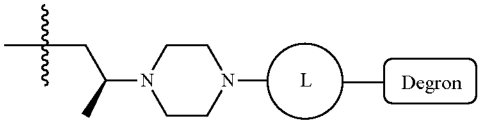

, provided that one of $R_3$ and $R_4$ is

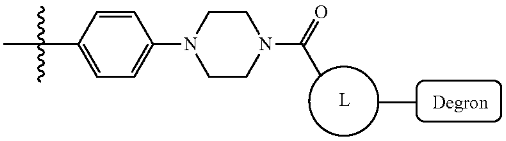

, or

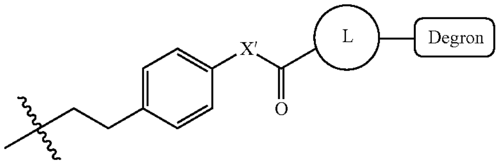

, or

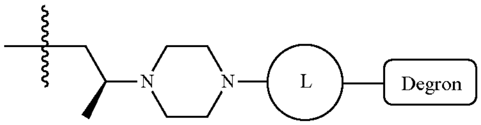

, or a pharmaceutically acceptable salt or stereoisomer thereof.

In some embodiments, when X is N, $X_1$ is $CR_1$, $X_2$ is $CR_2$, and $X_3$ is N,

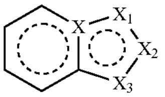

represents

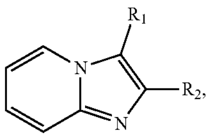

$R_1$ represents $NHR^1$, $R^1$ is an optionally substituted C1-C3 alkyl or an optionally substituted C5-C6 carbocyclic, $R_2$ represents

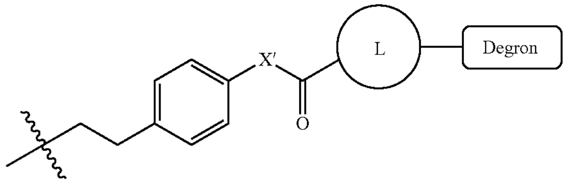

and X' is $HNC_2H_4NH$, or a pharmaceutically acceptable salt or stereoisomer thereof.

In some embodiments, when X is C, $X_1$ is $NR_3$, $X_2$ is $CR_4$ is and $X_3$ is N,

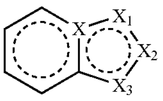

represents

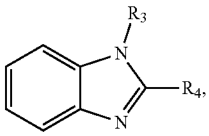

$R_3$ represents an optionally substituted C1-C3 alkyl or

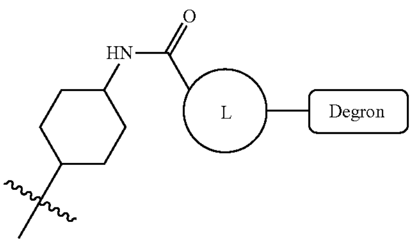

, and $R_4$ represents an optionally substituted C5-C6 carbocyclic or an optionally substituted C5-C6 heterocyclic, or

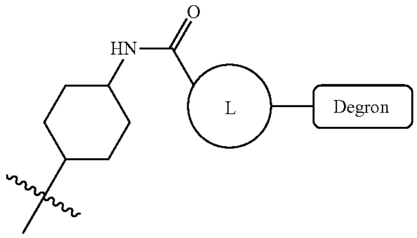

, provided that one of $R_3$ and $R_4$ is

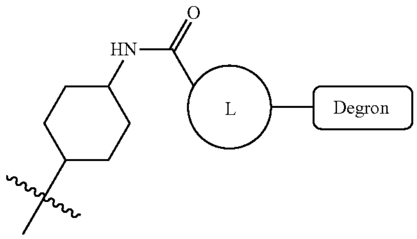

, or a pharmaceutically acceptable salt or stereoisomer thereof.

In some embodiments, $R^1$ is an optionally substituted C1-C3 alkyl.

In some embodiments, $R^1$ is an optionally substituted C5-C6 carbocyclic. In some embodiments, the optionally substituted C5-C6 carbocyclic is an optionally substituted aralkyl.

In some embodiments, $R^1$ is substituted with methyl or methoxy.

In some embodiments, $R_2$ is

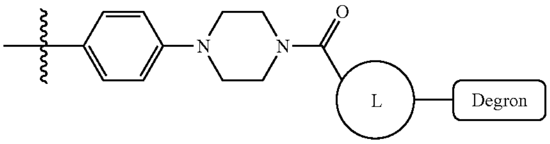

or

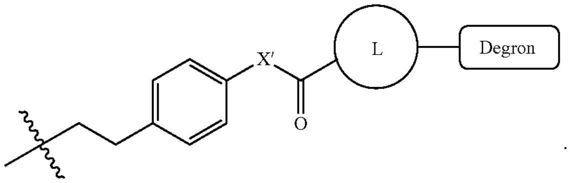

.

In some embodiments, $R_3$ is an optionally substituted C1-C3 alkyl and $R_4$ is

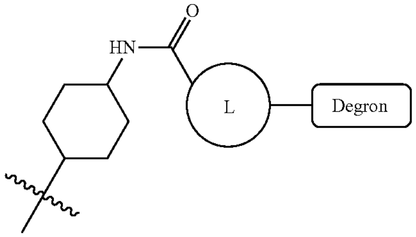
,

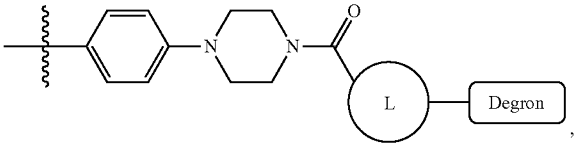
,

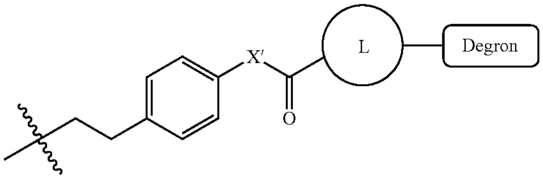
, or

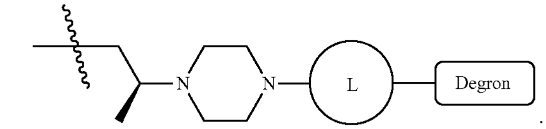
.

In some embodiments, $R_3$ is substituted with dimethylaminyl, morpholinyl, or piperazinyl.

In some embodiments, $R_4$ is an optionally substituted C5-C6 carbocyclic and $R_3$ is

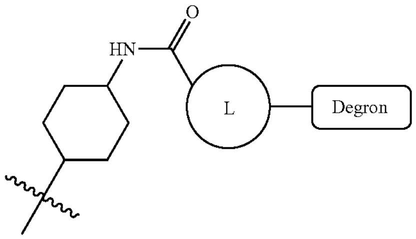
,

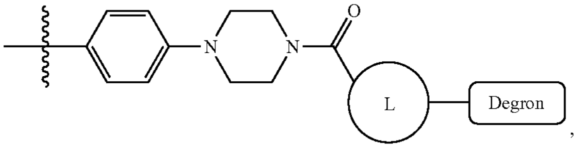
,

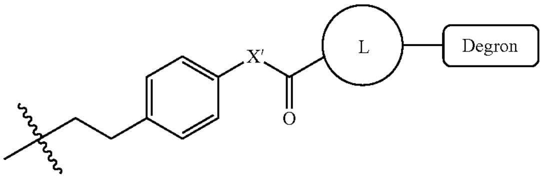
, or

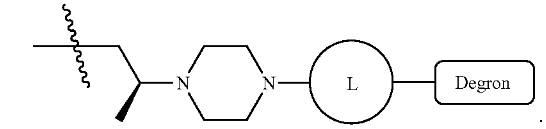
.

In some embodiments, the optionally substituted C5-C6 carbocyclic is an optionally substituted aralkyl. In some embodiments the optionally substituted C5-C6 heterocyclic is

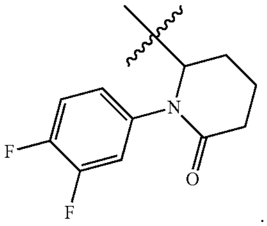 [SMILES: *C1CCCC(=O)N1c1ccc(F)c(F)c1]
.

In some embodiments, $R_4$ is substituted with halogen, $NH_2$, OH, or methoxy.

In some embodiments, wherein X is N, $X_1$ is $CR_1$, $X_2$ is $CR_2$, and $X_3$ is N, the bispecific compounds of present invention have a structure represented by formula (I-1):

(I-1)

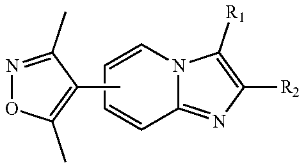

or a pharmaceutically acceptable salt or stereoisomer thereof.

In some embodiments, wherein X is N, $X_1$ is $CR_1$, $X_2$ is $CR_2$, $X_3$ is N, $R^1$ is an optionally an optionally substituted C1-C3 alkyl, and $R_2$ is

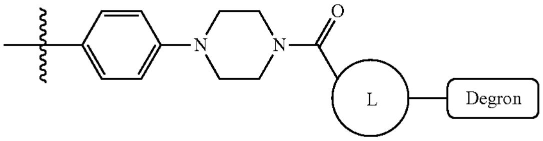
or

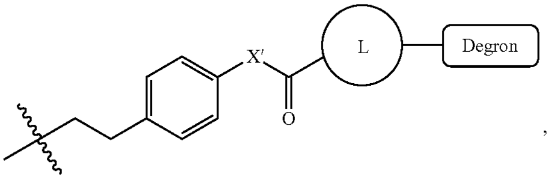
, the bispecific compounds of the present invention have a structure represented by any one of formulas (I-1a) to (I-1d):

(I-1a)
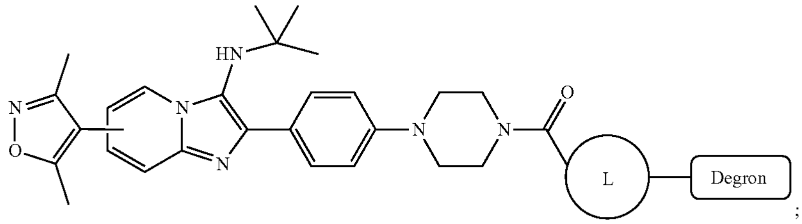
;
(I-1b)
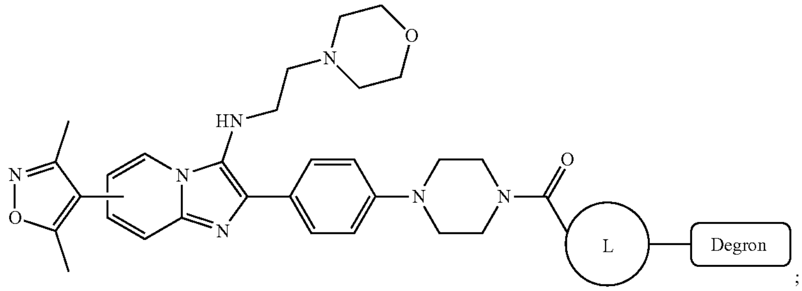
;
(I-1c)
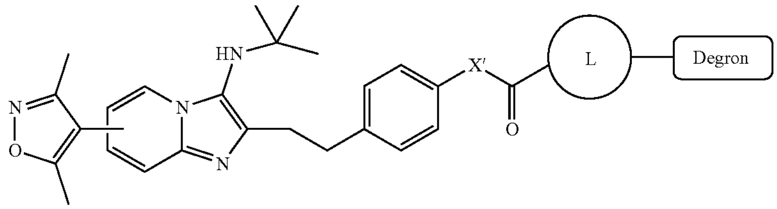
; and
(I-1d)
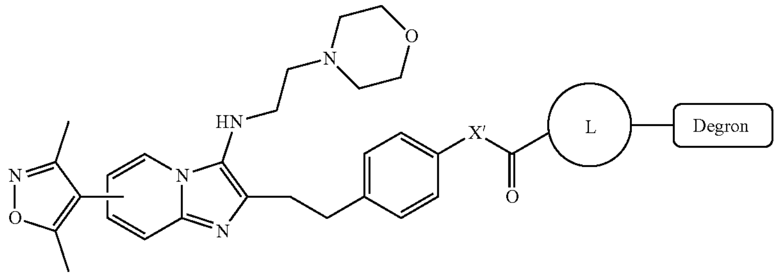
,
or a pharmaceutically acceptable salt or stereoisomer thereof.
In some embodiments, wherein X is N, $X_1$ is $CR_1$, $X_2$ is $CR_2$, $X_3$ is N, $R^1$ is an optionally substituted C5-C6 carbocyclic, and $R_2$ is
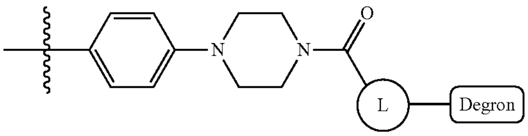
or
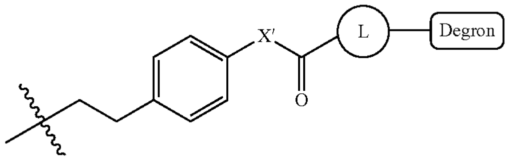
,
the bispecific compounds of the present invention have a structure as represented by formula (I-1e) or (I-1f):

(I-1e)
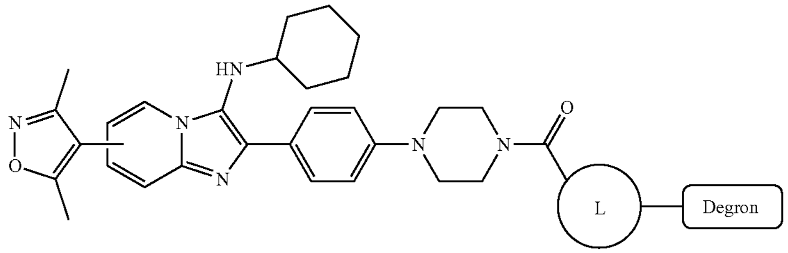
or
(I-1f)
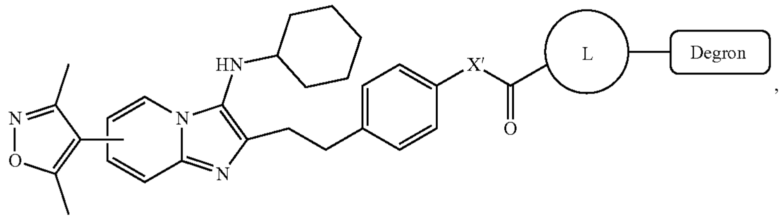
or a pharmaceutically acceptable salt or stereoisomer thereof.
In some embodiments, wherein X is N, $X_1$ is $CR_1$, $X_2$ is $CR_2$, $X_3$ is N, $R^1$ is an optionally substituted C5-C6 aralkyl, and $R_2$ is
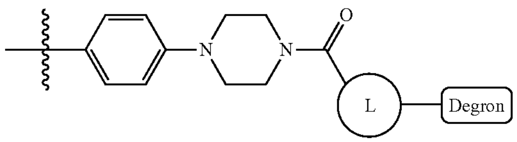
or
-continued
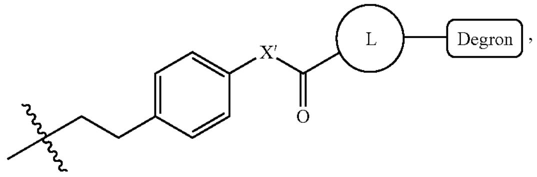
the bispecific compounds of the present invention have a structure represented by any one of formulas (I-1g) to (I-1j):
(I-1g)
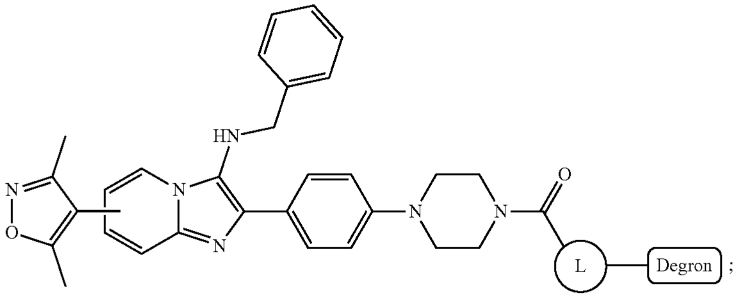
(I-1h)
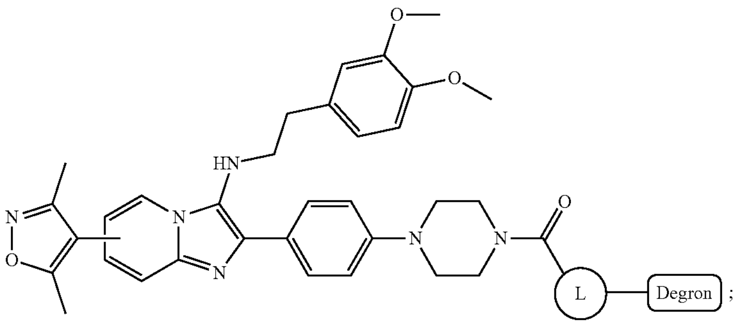

-continued (I-1i)

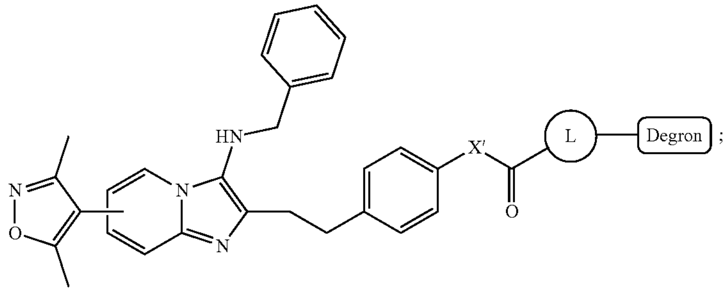

; and (I-1j)

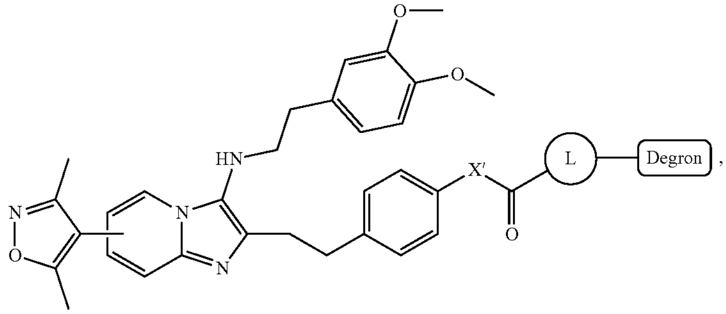

, or a pharmaceutically acceptable salt or stereoisomer thereof.

In some embodiments, wherein when X is C, $X_1$ is $NR_3$, $X_2$ is $CR_4$, and $X_3$ is N, the compounds of present invention have a structure represented by formula (I-2):

(I-2)

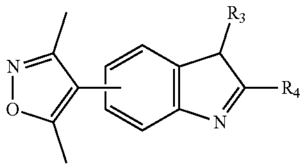

or a pharmaceutically acceptable salt or stereoisomer thereof.

In some embodiments, wherein X is C, $X_1$ is $NR_3$, $X_2$ is $CR_4$, $X_3$ is N, $R_3$ is an optionally substituted C1-C3 alkyl, and $R_4$ is

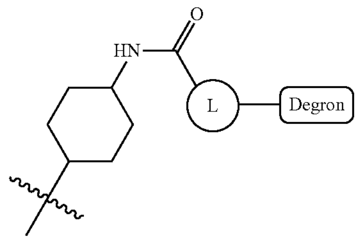

,

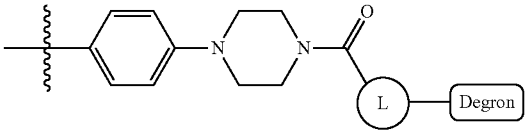

,

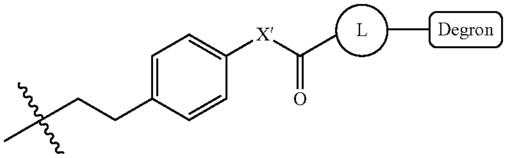

, or

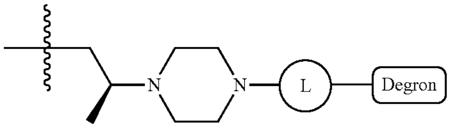

, the bispecific compounds of the present invention have a structure represented by any one of formulas (I-2a) to (I-2p):

(I-2a)
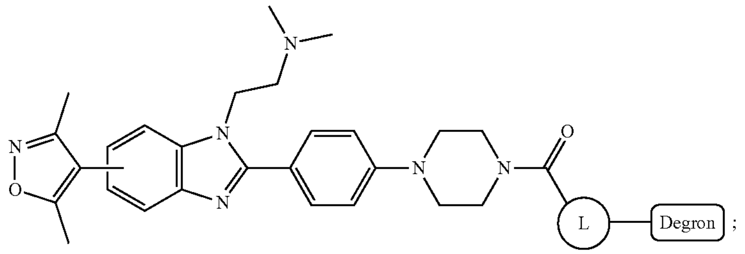
(I-2b)
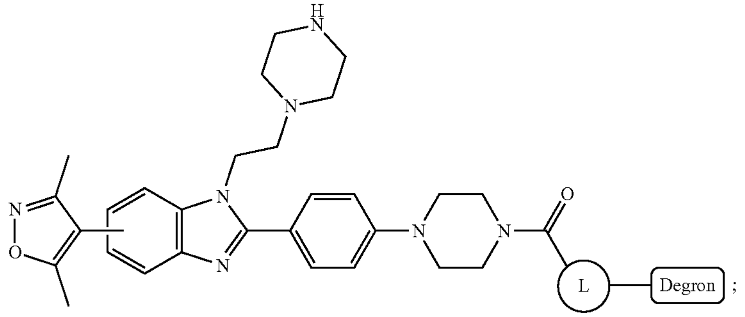
(I-2c)
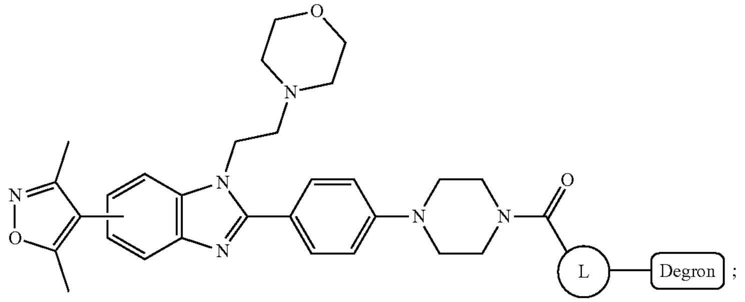
(I-2d)
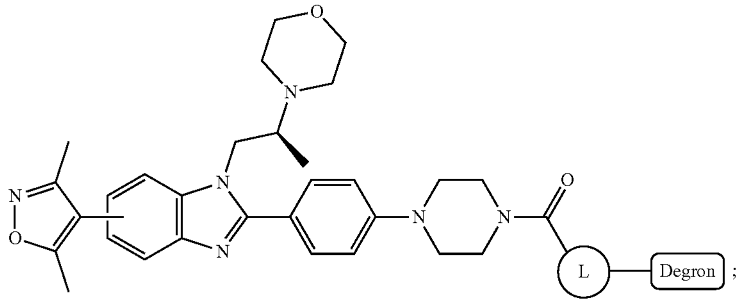
(I-2e)
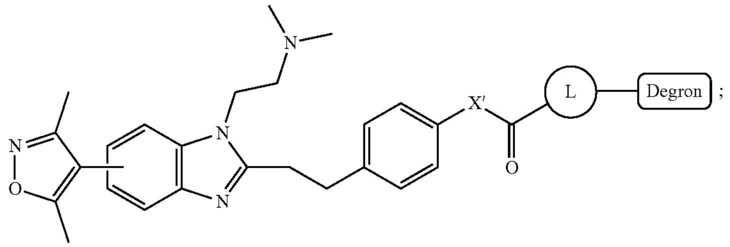

-continued
(I-2f)
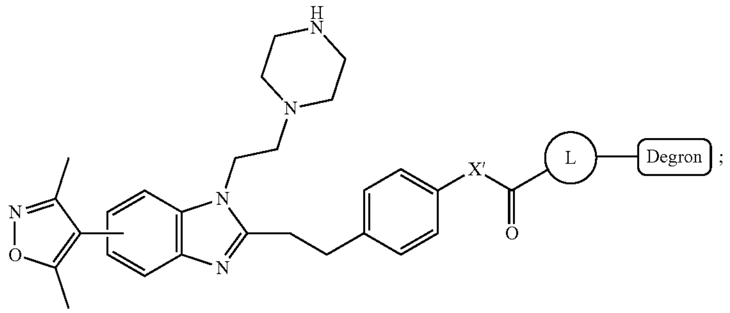
(I-2g)
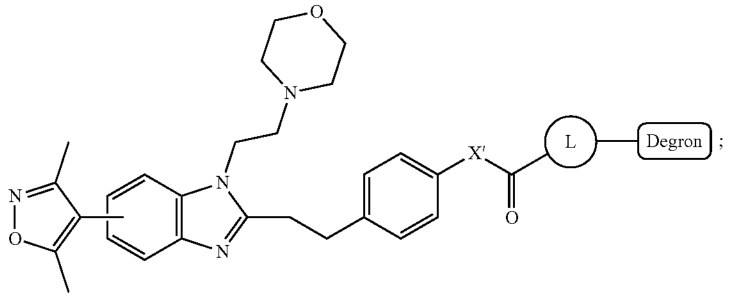
(I-2h)
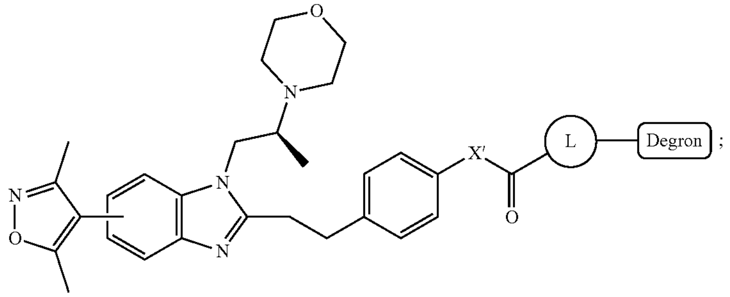
(I-2i)
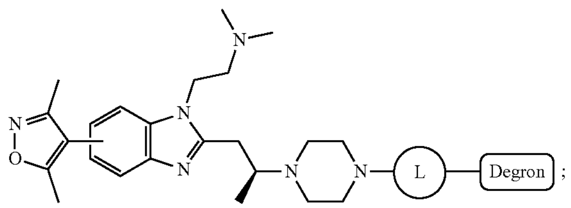
(I-2j)
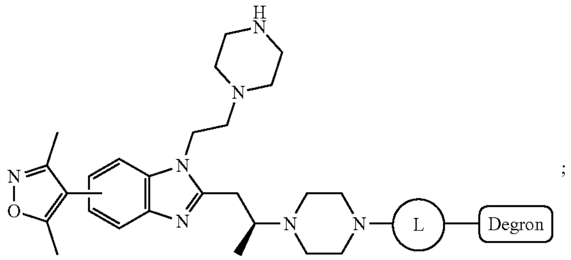
(I-2k)
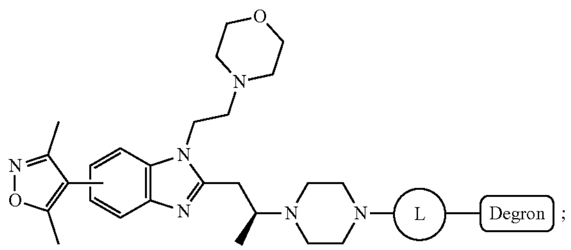
(I-2l)
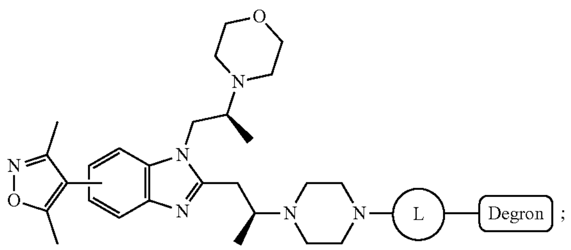

-continued
(I-2m)
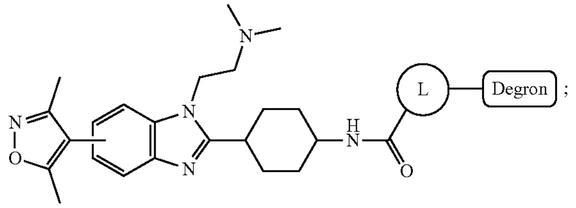
(I-2n)
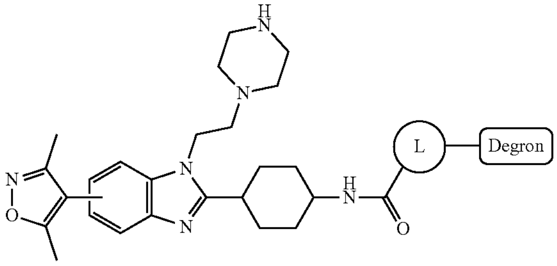
(I-2o)
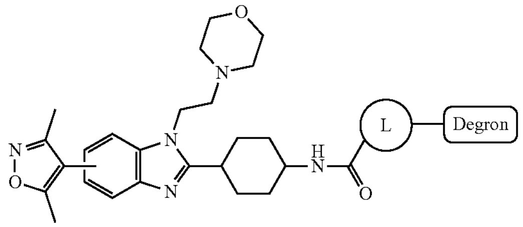
and
(I-2p)
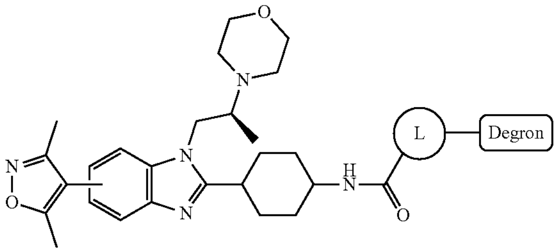
or a pharmaceutically acceptable salt or stereoisomer thereof.
In some embodiments, wherein X is C, $X_1$ is $NR_3$, $X_2$ is $CR_4$, $X_3$ is N, $R_3$ is an optionally substituted C5-C6 aralkyl or
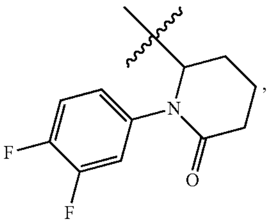
and $R_4$ is
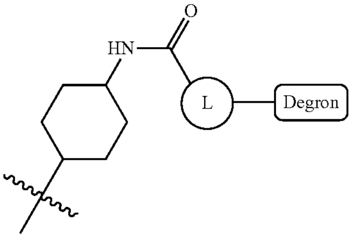
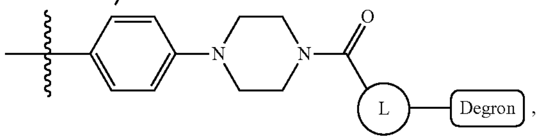
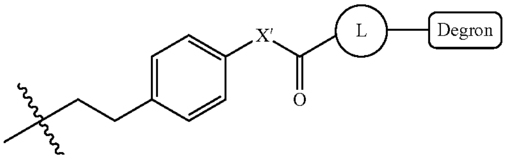
or
-continued
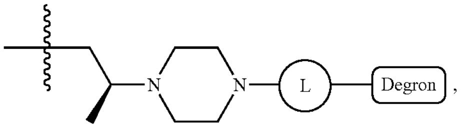
the compounds of the present invention have a structure represented by any one of formulas (I-2q) to (I-2z) and from (I-2a') to (I-2k'):
(I-2q)
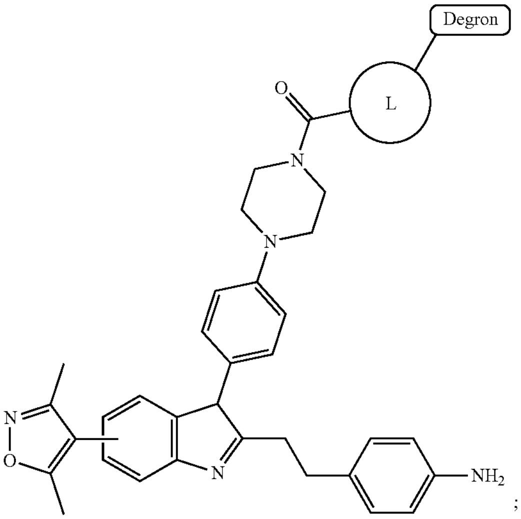
;

-continued
(I-2r)
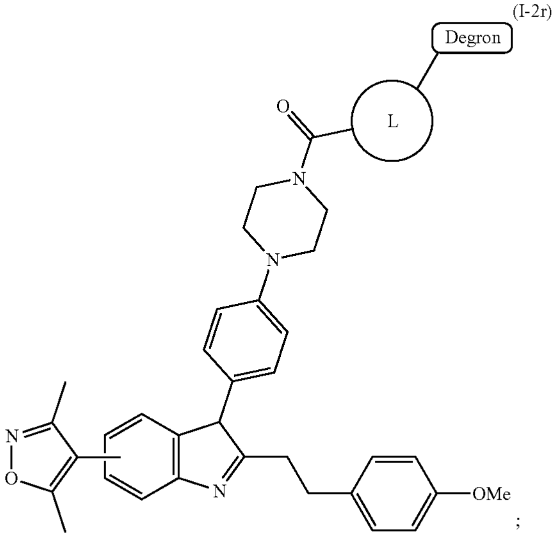
;
(I-s)
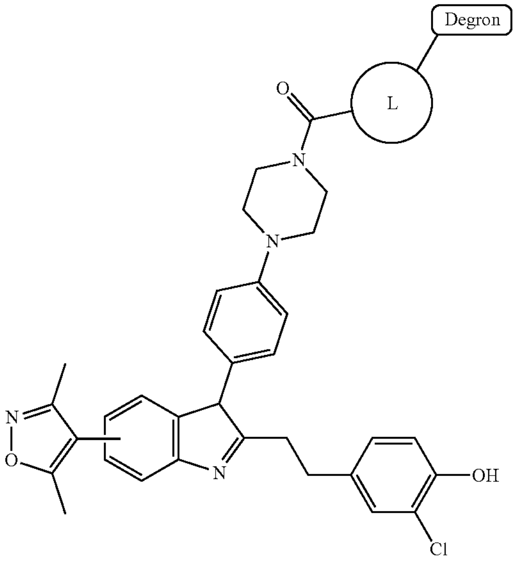
;
(I-2t)
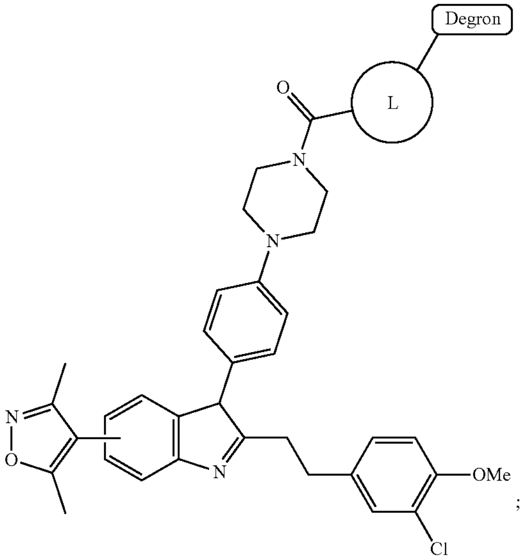
;
-continued
(I-2u)
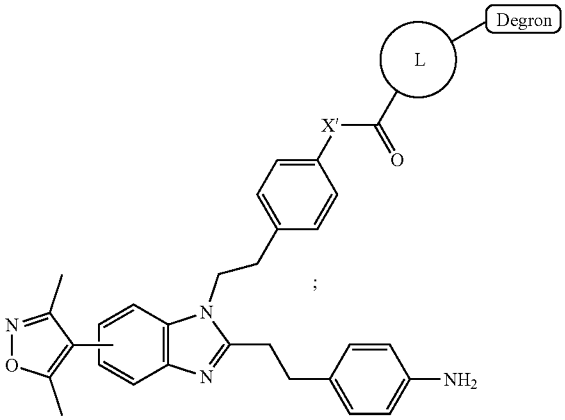
;
(I-2v)
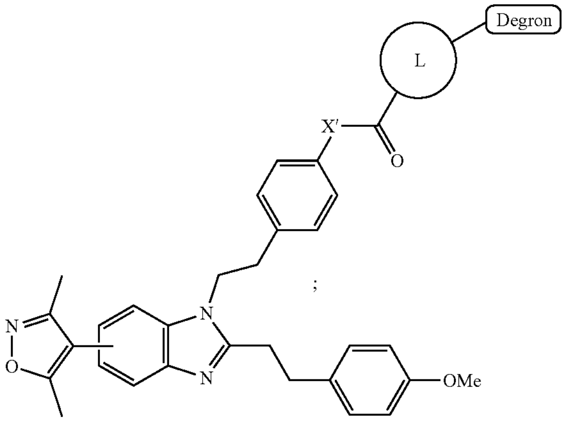
;
(I-2w)
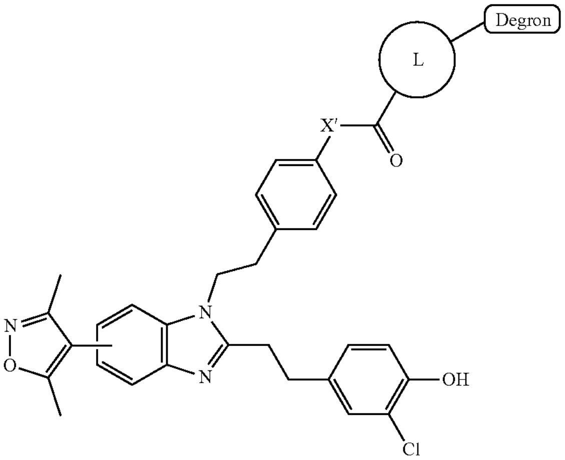
;

-continued
(I-2x)
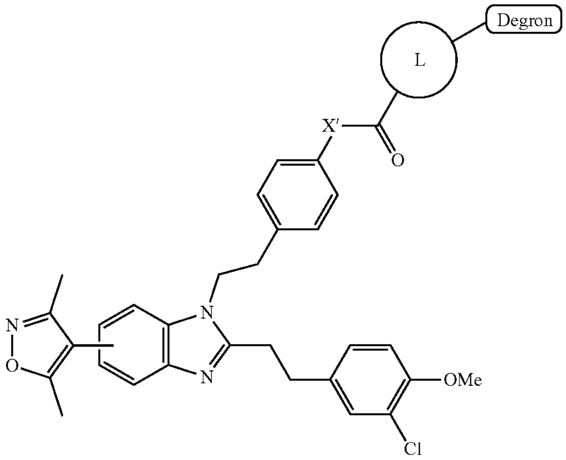
;
(I-2y)
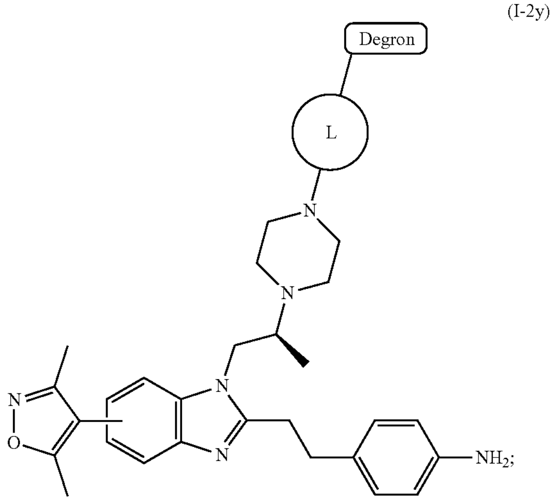
(I-2z)
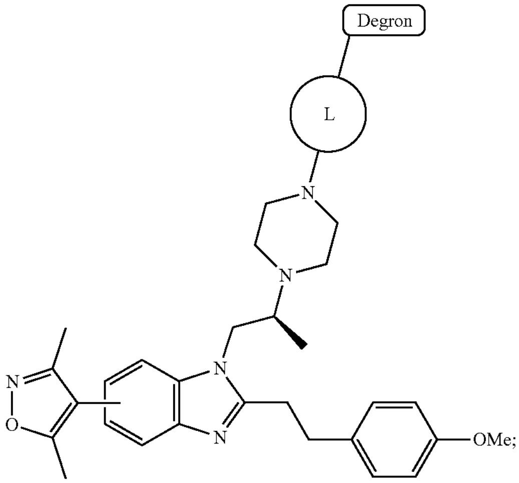
-continued
(I-2a′)
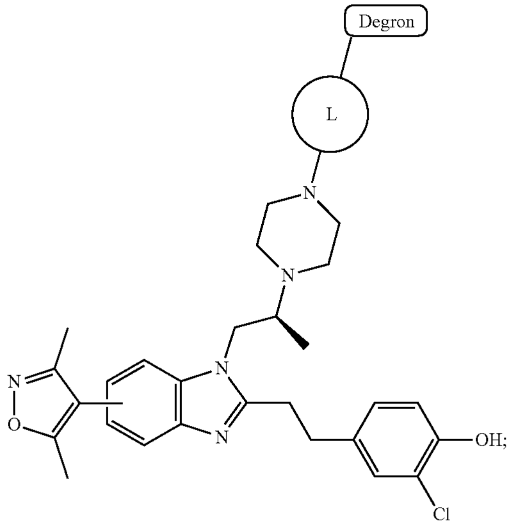
(I-2b′)
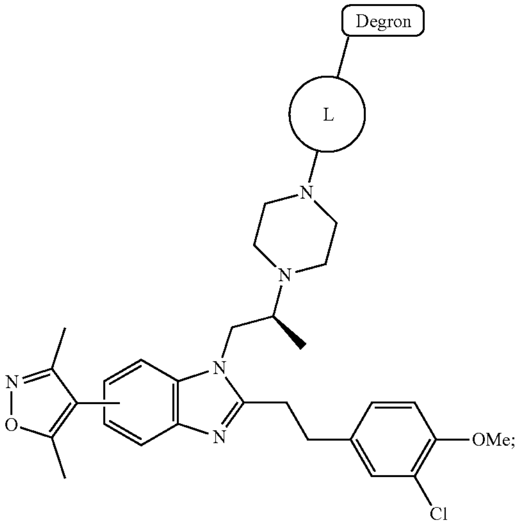
(I-2c′)
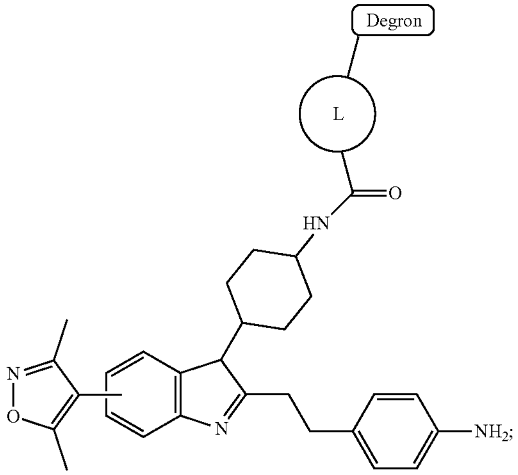

-continued
(I-2d')
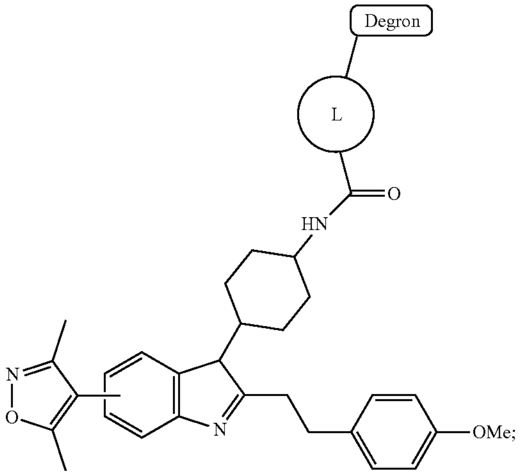
(I-e')
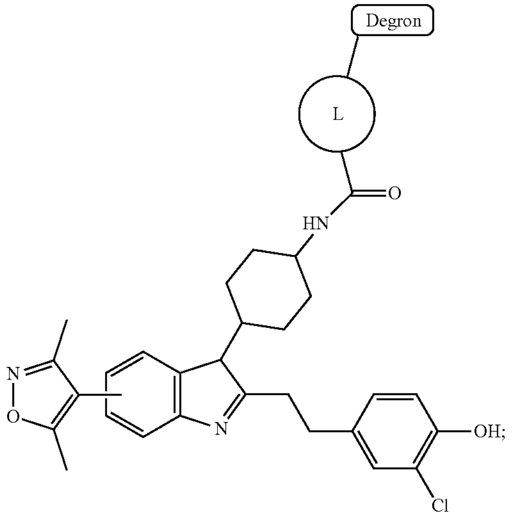
(I-2f')
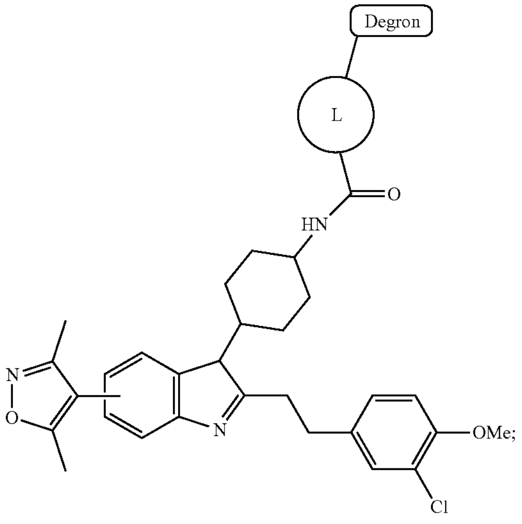
-continued
(I-2g')
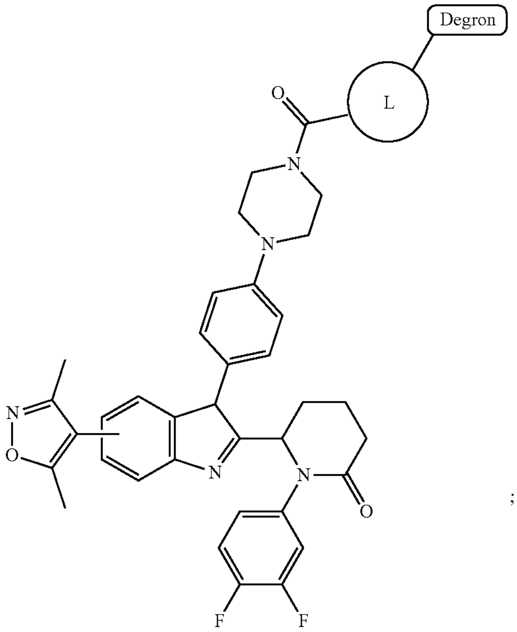
;
(I-2i')
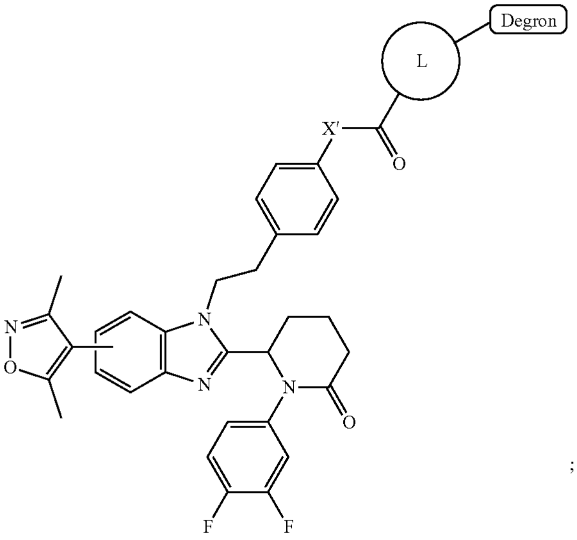
;

-continued (I-2j')

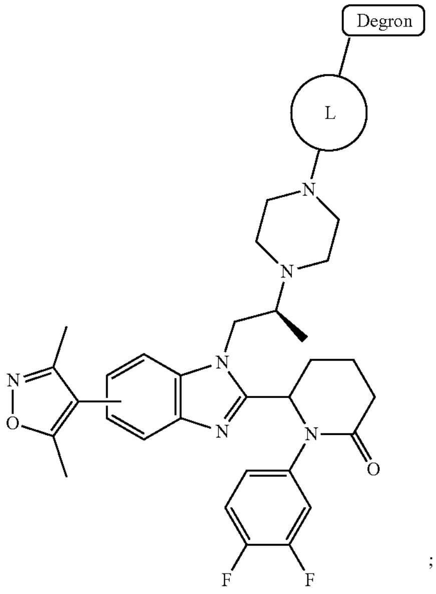

; and (I-2k')

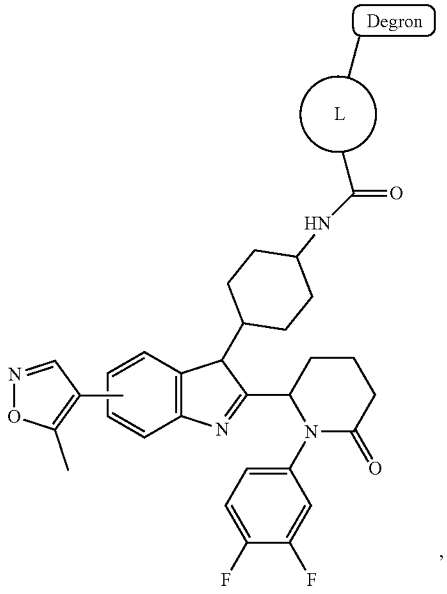

, or a pharmaceutically acceptable salt or stereoisomer thereof.

In some embodiments, the bispecific compounds of the present invention have a structure represented by formula (II):

(II)

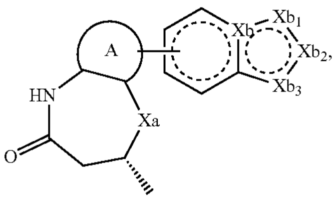

wherein

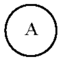

represents an optionally substituted phenyl or a C6 heteroaryl;

Xa represents NH, O, S, or $C(Ra)_2$, wherein each Ra independently represents H, C1-C6 alkyl, C2-C6 alkenyl, C2-C6 alkynyl, or C3-C6 carbocyclyl;

Xb represents C or N, $Xb_1$ represents $CRb_1$ or $CRb_3$, $Xb_2$ represents $CRb_2$, $CR_4$, or N, $Xb_3$ represents N or NMe, provided that when Xb is N, $Xb_1$ is $CRb_1$, $Xb_2$ is $CRb_2$ and $Xb_3$ is N, and when Xb is C, $Xb_1$ is $CRb_3$, $Xb_2$ is $CR_4$ or N, and $Xb_3$ is N or NMe;

wherein $Rb_1$ represents $NHR^{b1}$, wherein $R^{b1}$ is an optionally substituted C1-C3 alkyl or an optionally substituted C5-C6 carbocyclic;

$Rb_2$ represents

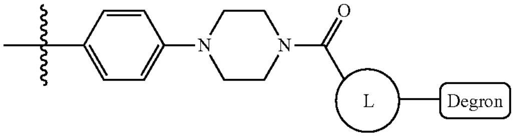

or

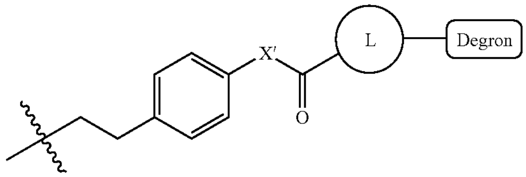

, wherein X' is O, $HNC_2H_4NH$, or NH;

$Rb_3$ represents an optionally substituted C1-C3 alkyl,

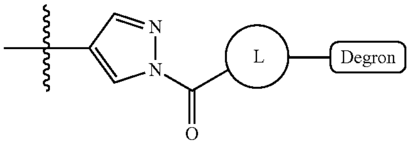

,

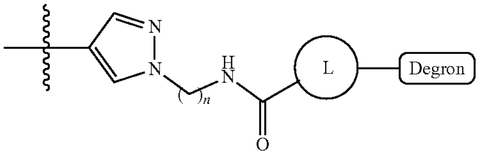

,

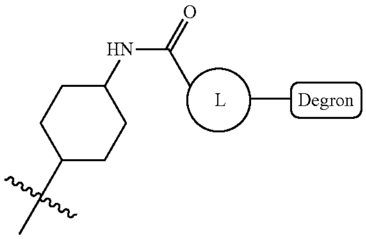

,

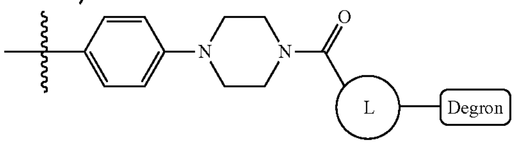

,

-continued

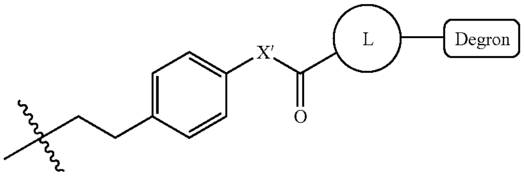
or
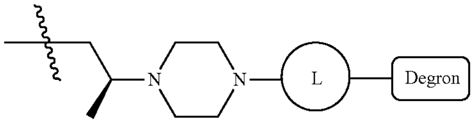
, wherein n is 1, 2, 3, or 4; and $Rb_4$ represents an optionally substituted C5-C6 carbocyclic or an optionally substituted C5-C6 heterocyclic,

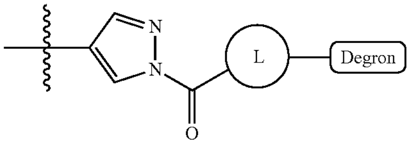
,
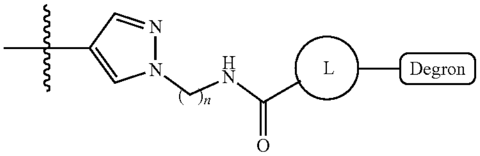
,
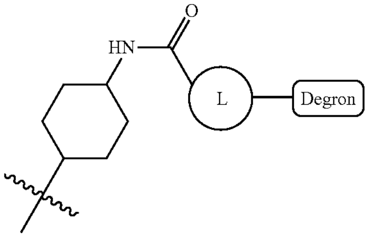
,
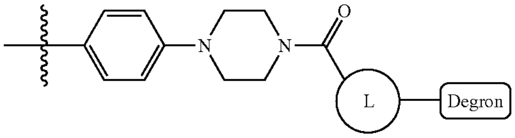
,
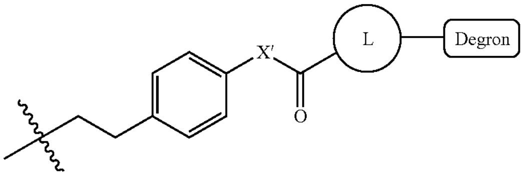
or
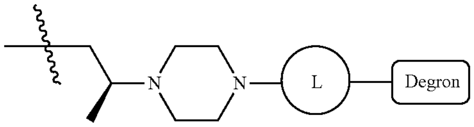
, provided that one of $Rb_3$ and $Rb_4$ is

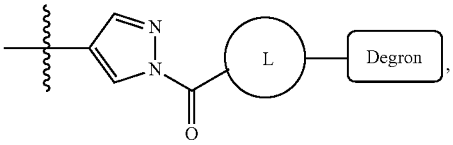
,

-continued

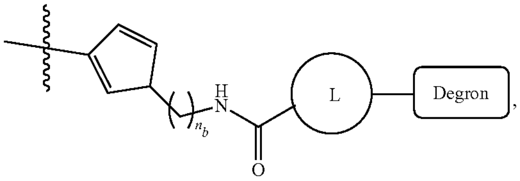
,
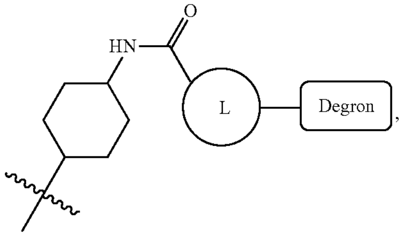
,
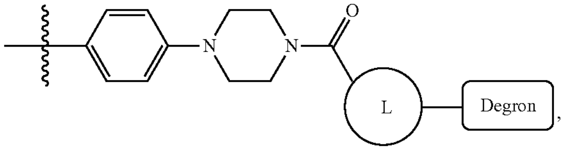
,
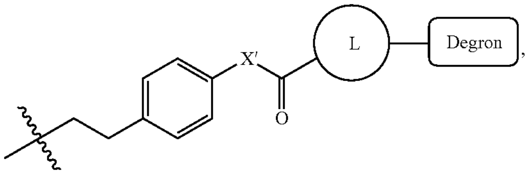
, or
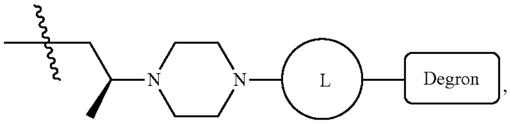
, or a pharmaceutically acceptable salt or stereoisomer thereof.

In some embodiments, wherein

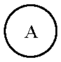

is phenyl, Xa is NH, Xb is C, $X_1$ is $CRb_3$, $Rb_3$ is

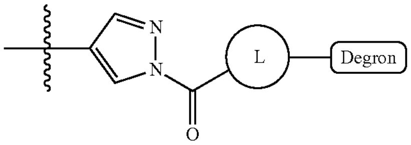
or
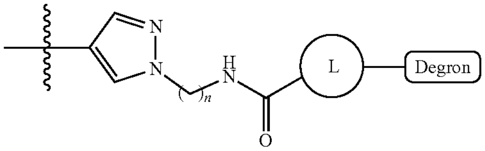
, $Xb_2$ is N, $Xb_3$ is NMe, and n is 1, 2, 3, or 4, the bispecific compounds of the present invention have a structure represented by formula (II-1) or (II-2):

(II-1)

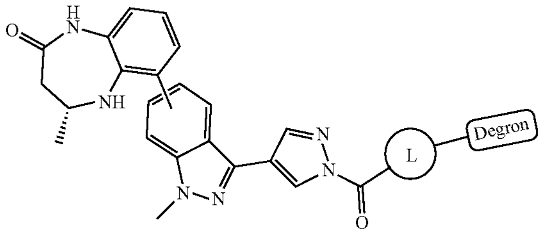

or (II-2)

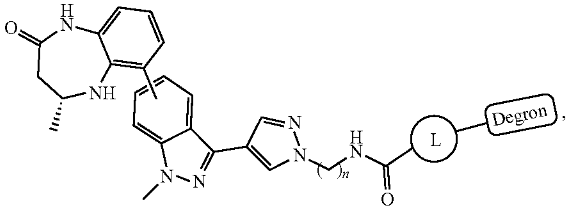

, or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker includes an alkylene chain (e.g., having 2-20 alkylene units). In other embodiments, the linker may include an alkylene chain or a bivalent alkylene chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may include a $C_1$-$C_{12}$ alkylene chain terminating in NH— group wherein the nitrogen is also bound to the degron.

In some embodiments, the linker includes an alkylene chain having 1-10 alkylene units and interrupted by or terminating in

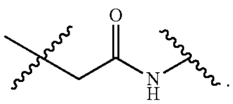 [SMILES: *CC(=O)N*]

.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of alkylene linkers that may be suitable for use in the present invention include the following:

(L1)

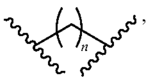

, wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

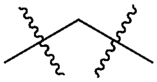

;

(L1-b)

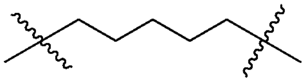

;

(L1-c)

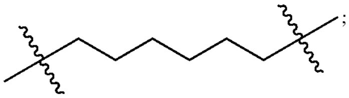

;

(L1-d)

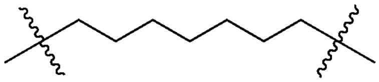

; and (L1-e)

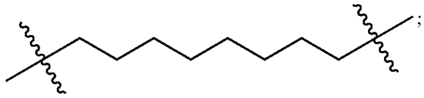

;

alkylene chains terminating in various functional groups (as described above), examples of which are as follows:

(L2-a)

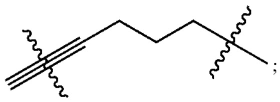

;

(L2-b)

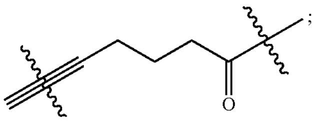

;

(L2-c)

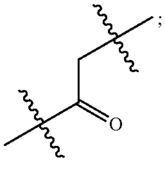

;

-continued (L2-d)

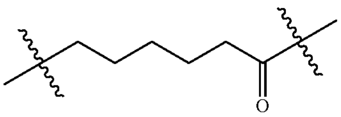

;

(L2-e)

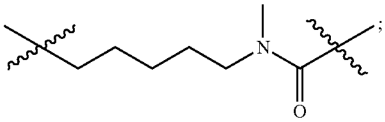

;

(L2-f)

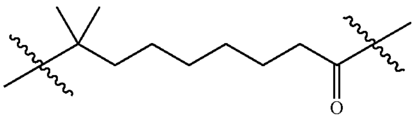

; and (L2-g)

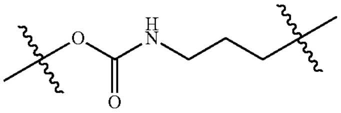

;

alkylene chains interrupted with various functional groups (as described above), examples of which are as follows:

(L3-a)

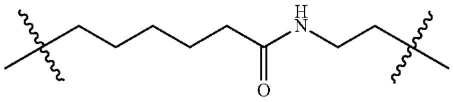

;

(L3-b)

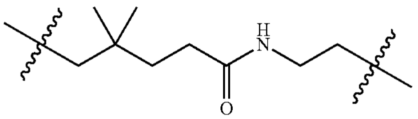

;

(L3-c)

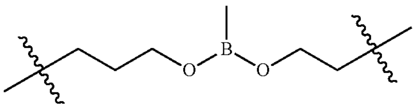

; and (L3-d)

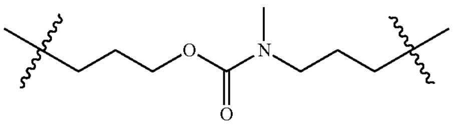

;

alkylene chains interrupted or terminating with heterocyclene groups, e.g., (L4)

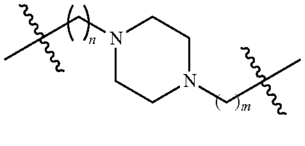

, wherein m and n are independently integers of 0-10, examples of which include:

(L4-a)

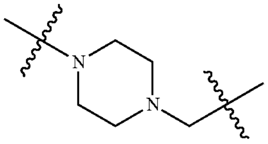

;

(L4-b)

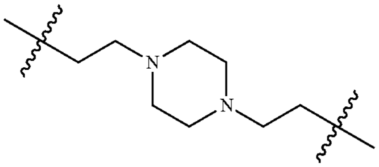

;

(L4-c)

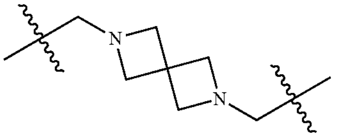

;

(L4-d)

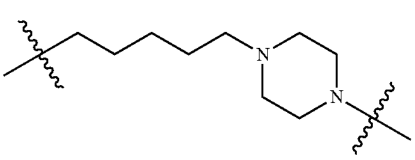

; and (L4-e)

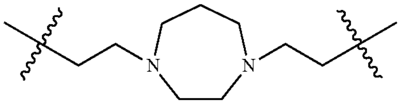

;

alkylene chains interrupted by amide, heterocyclene and/or aryl groups, examples of which include:

(L5-a)

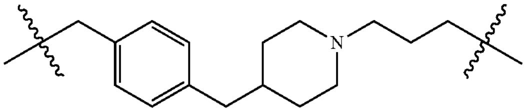

; and (L5-b)

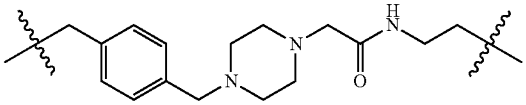

;

alkylene chains interrupted by heterocyclene and aryl groups, and a heteroatom, examples of which include:

(L6-a)

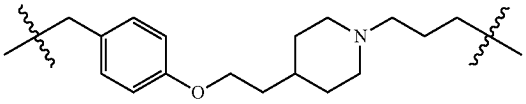

;

(L6-b)

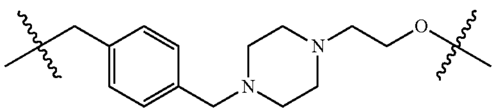

; and

-continued (L6-c)

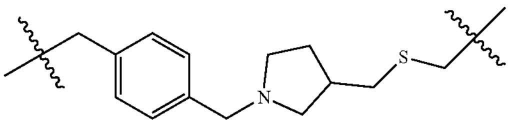

;

and alkylene chains interrupted by a heteroatom such as N, O or B, e.g., (L7)

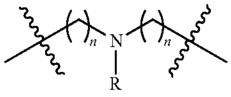

, wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

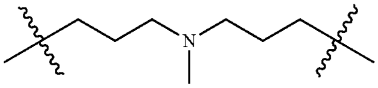

.

In some embodiments, the linker may include a polyethylene glycol chain which may terminate (at either or both termini) in at least one of —S—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 2-8 PEG units and terminating in

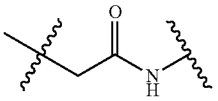

.

Examples of linkers that include a polyethylene glycol chain include:

(L8)

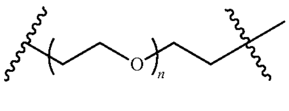

, wherein n is an integer of 2-10, examples of which include:

(L8-a)

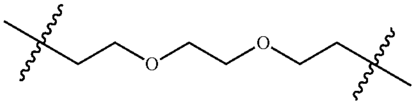

;

(L8-b)

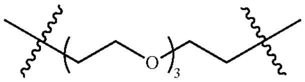

;

(L8-c)

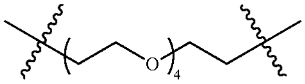

; and (L8-d)

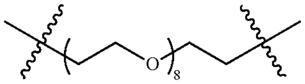

.

In some embodiments, the polyethylene glycol chain may terminate in a functional group, examples of which are as follows:

(L9-a)

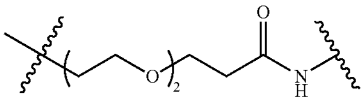

;

(L9-b)

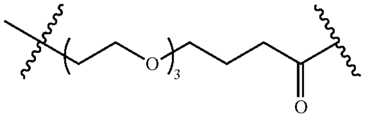

;

(L9-c)

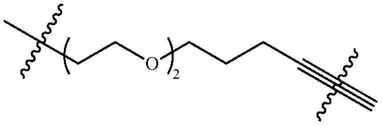

;

(L9-d)

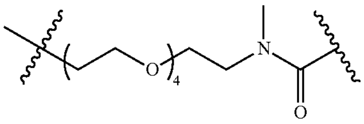

; and (L9-e)

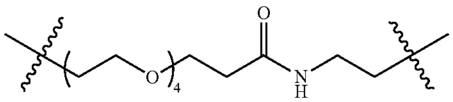

.

In some embodiments, the compounds of formula (I) include a linker that is represented by structure (L10):

(L10)

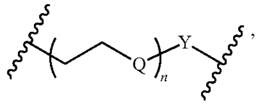

, wherein Q is $CH_2$ or O;

Y is $CH_2$, $CH_2CH_2$, or absent, provided that Y is $CH_2CH_2$ when X is O; and n is an integer between 0 and 6, inclusive.

In some embodiments, the linker is represented by any one of the following structures:

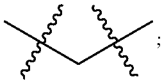;
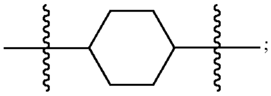;
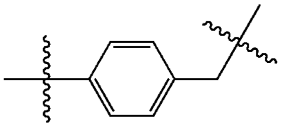;
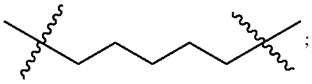;
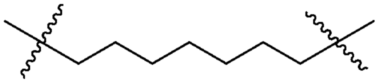;
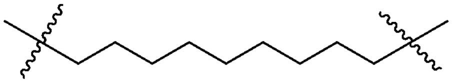;
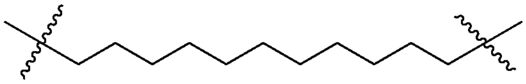;
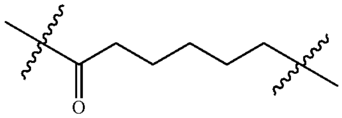;
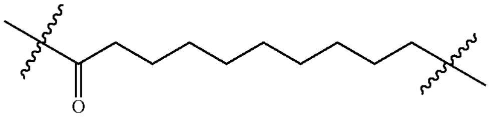;
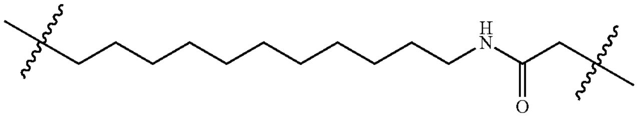;
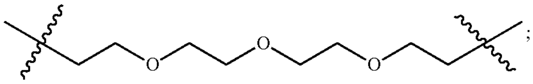;
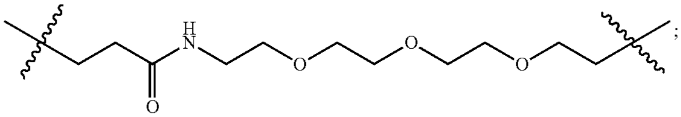;
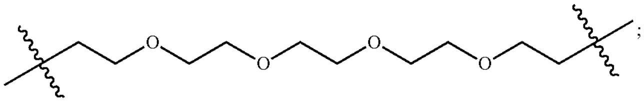;
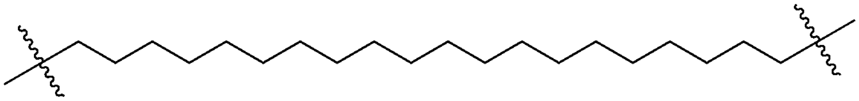;
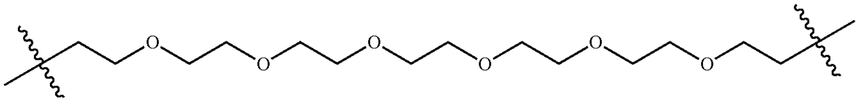;
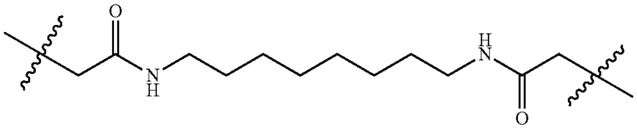;
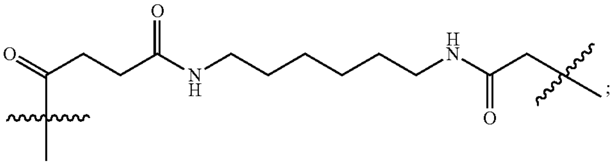; and
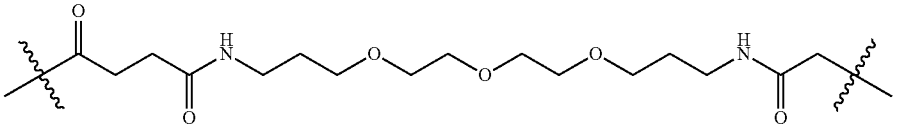.

Degrons

The degron ("D") is a functional moiety that binds an E3 ubiquitin ligase.

In some embodiments, the compound of formula (I) includes a degron that binds cereblon. Representative examples of degrons that bind cereblon and which may be suitable for use in the present invention are described in U.S. Patent Application Publication 2018/0015085 A1 (e.g., the indolinones such as isoindolinones and isoindoline-1,3-diones embraced by formulae IA ad IA' therein, and the bridged cycloalkyl compounds embraced by formulae IB and IB' therein).

In some embodiments, the degron that binds cereblon is represented by structure (D1):

(D1)

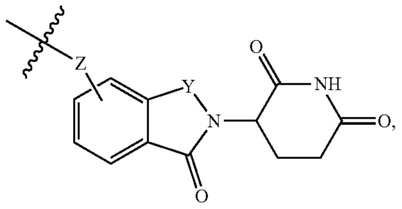

wherein Y is $CH_2$ or CO;

and Z is NH, O, or $OCH_2CO$, and the squiggle (~) represents the point of attachment for the linker and EP300/CBP targeting moiety.

In some embodiments, the degron is represented by structure (D1-a) or (D1-b):

(D1-a)

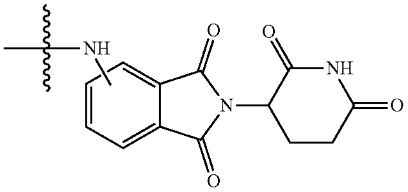

or (D1-b)

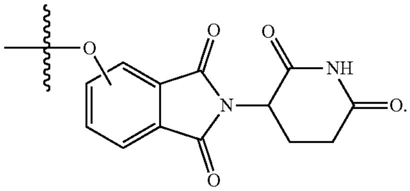

In some embodiments, the Degron binds a Von Hippel-Lindau (VHL) tumor suppressor. Representative examples of degrons that bind VHL are as follows:

(D2-a)

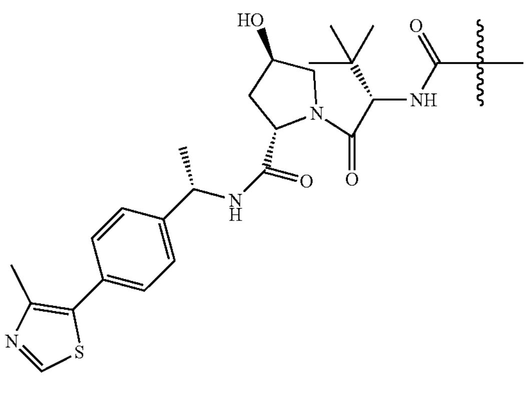

;

-continued (D2-b)

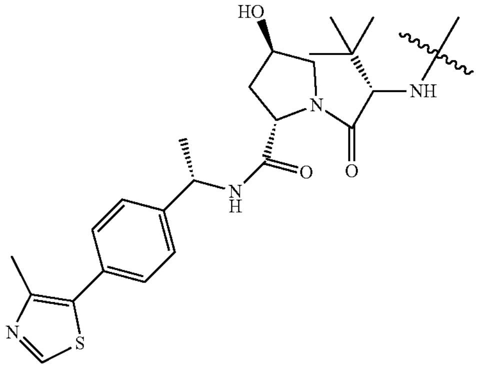

;

(D2-c)

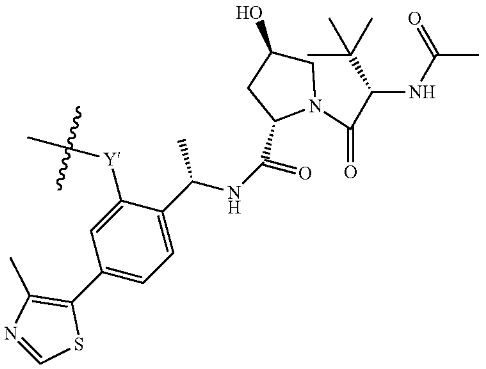

, wherein Y' is a bond, N, O or C;

(D2-d)

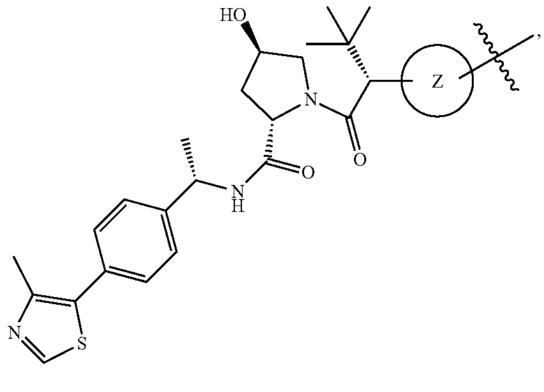

, wherein Z is a $C_5$-$C_6$ carbocyclic or $C_5$-$C_6$ heterocyclic group, and (D2-e)
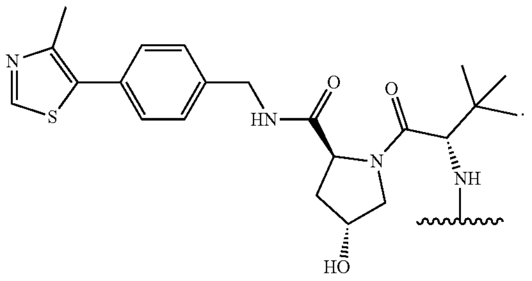
In some embodiments, Z is
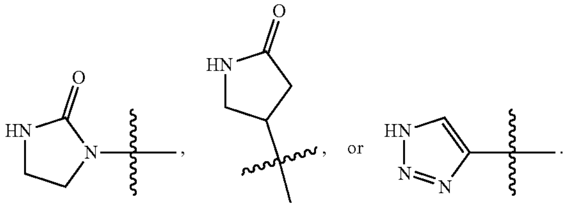 [SMILES: *N1CCNC1=O ; *C1CNC(=O)C1 ; *c1c[nH]nn1]
Yet other degrons that bind VHL and which may be suitable for use as degrons in the present invention are disclosed in U.S. Patent Application Publication 2017/0121321 A1.
In some embodiments, the bispecific compound of formula (I) or (II) is represented by any one of structures (1) to (46):
(1)
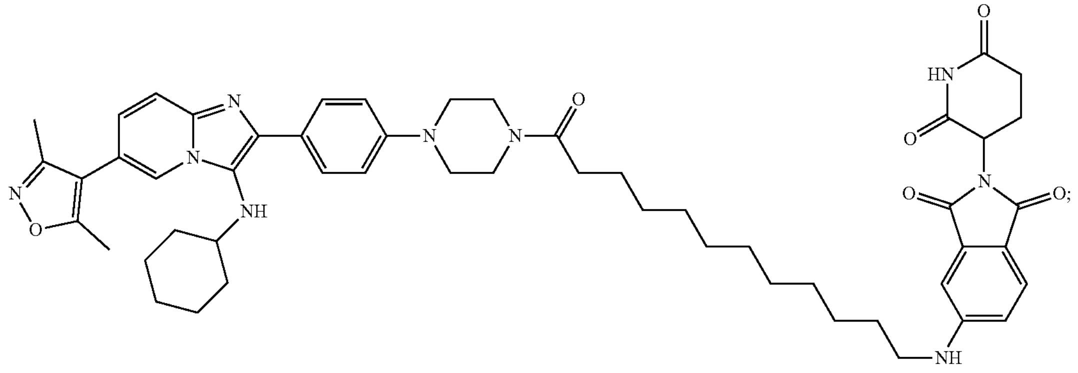
(2)
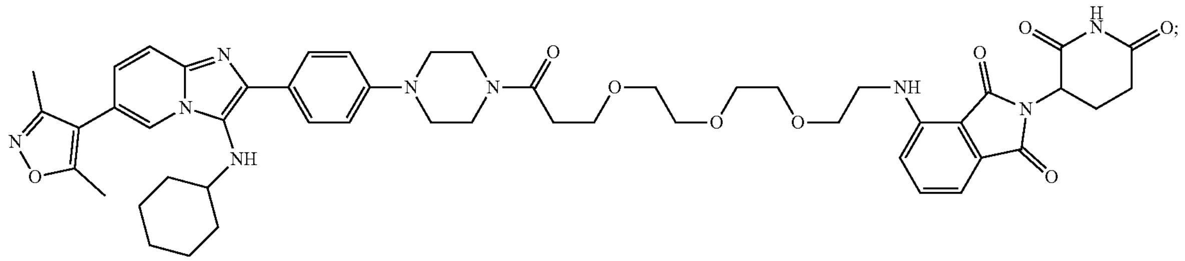
(3)
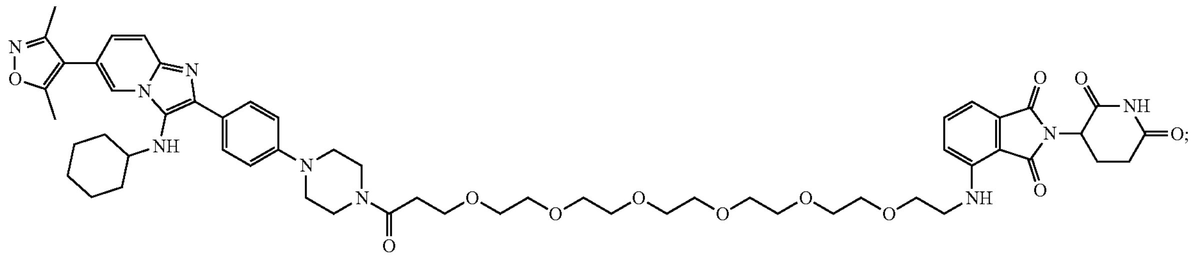

-continued
(4)
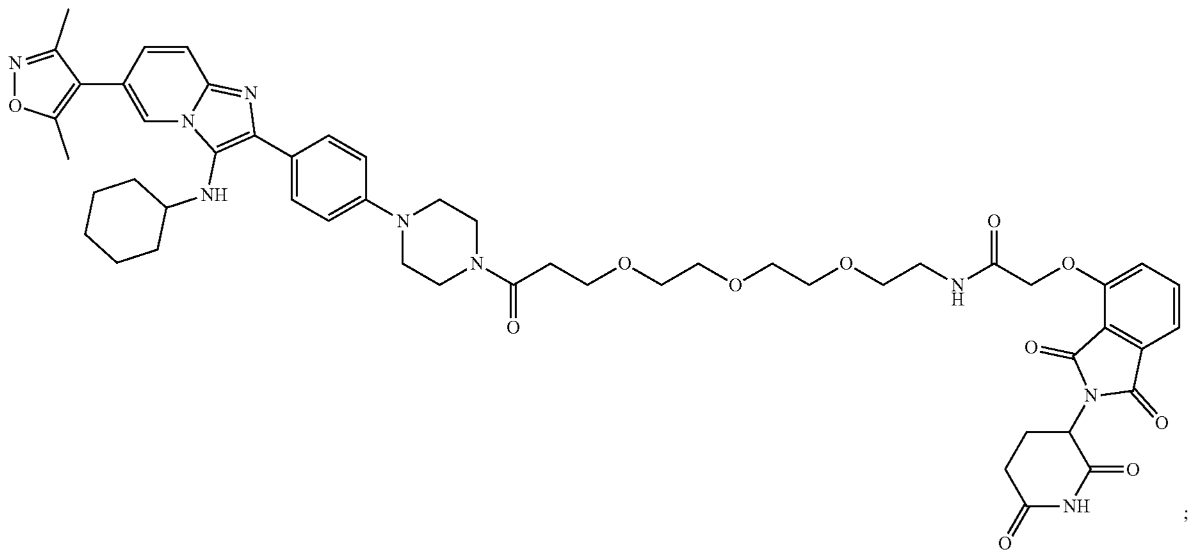
;
(5)
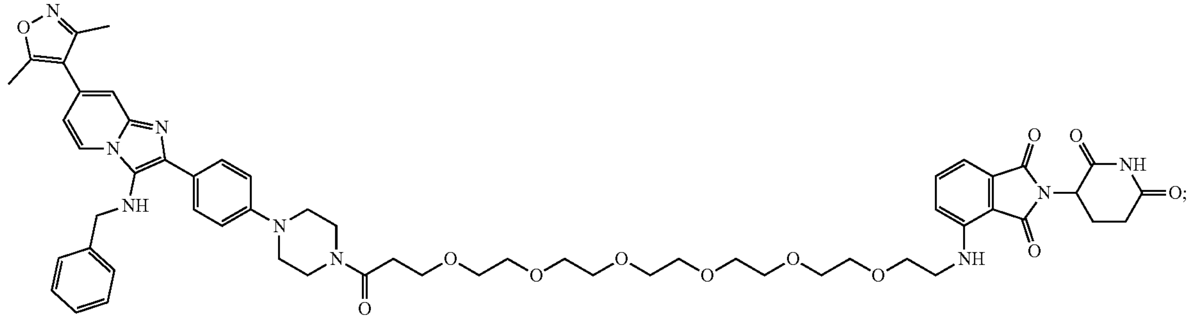
(6)
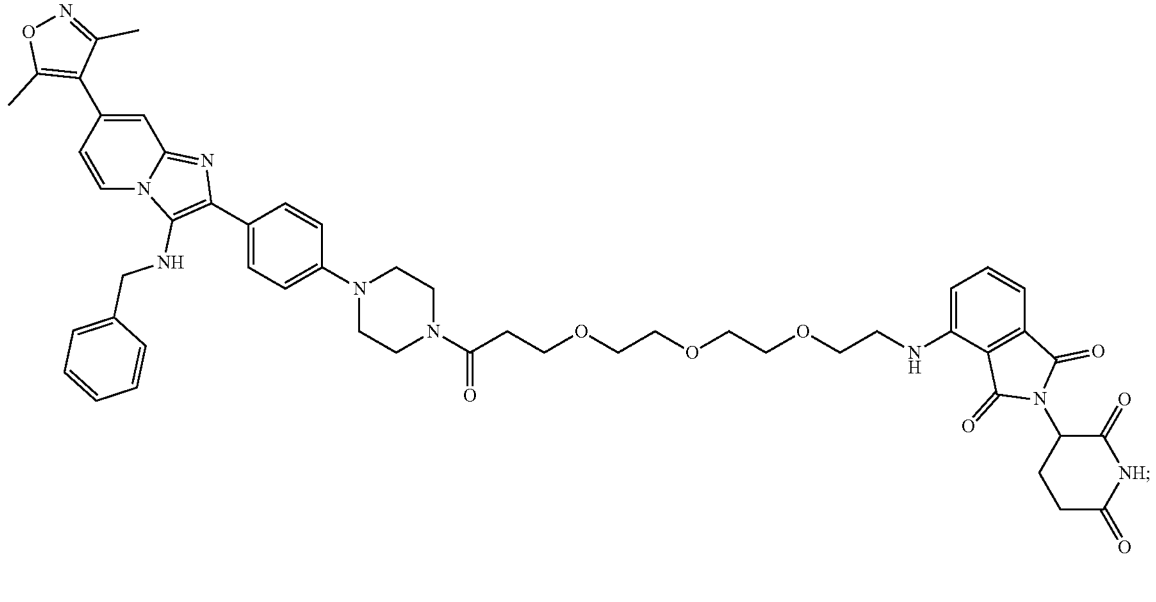

-continued
(7)
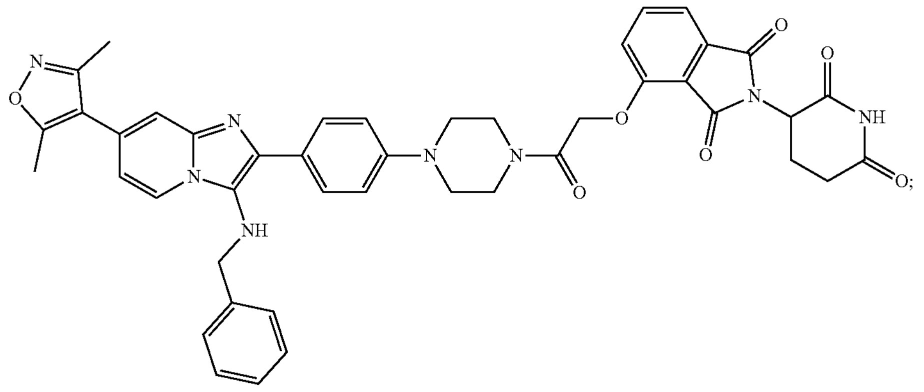
(8)
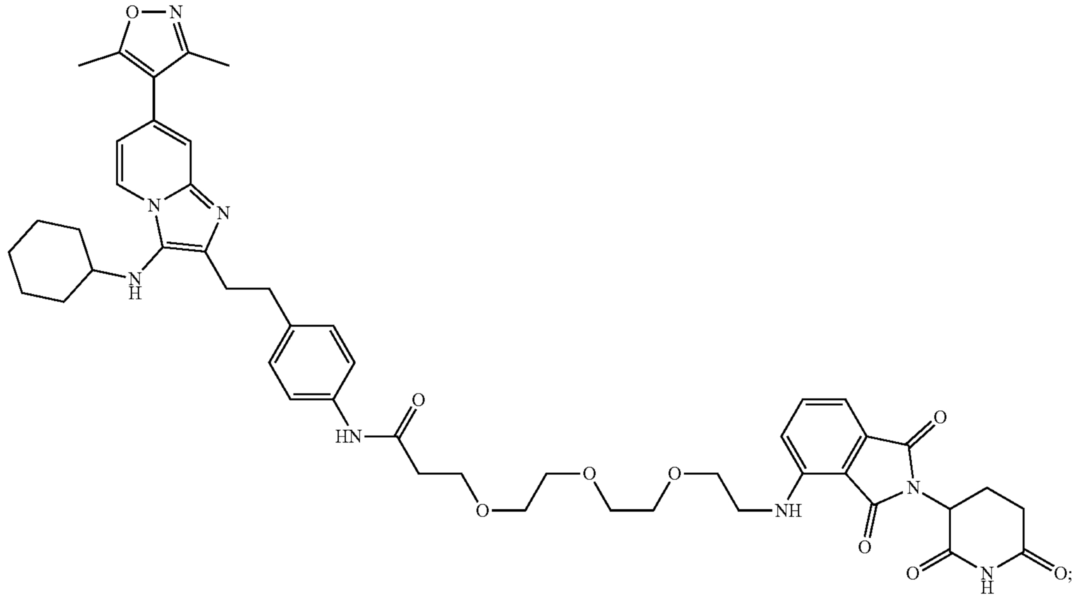
(9)
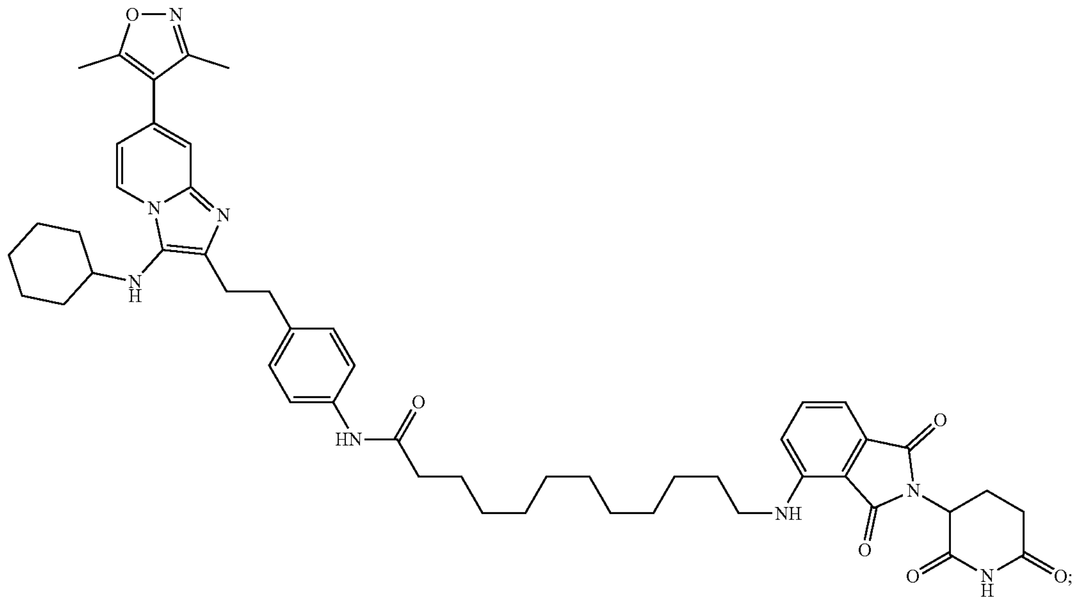

-continued
(10)
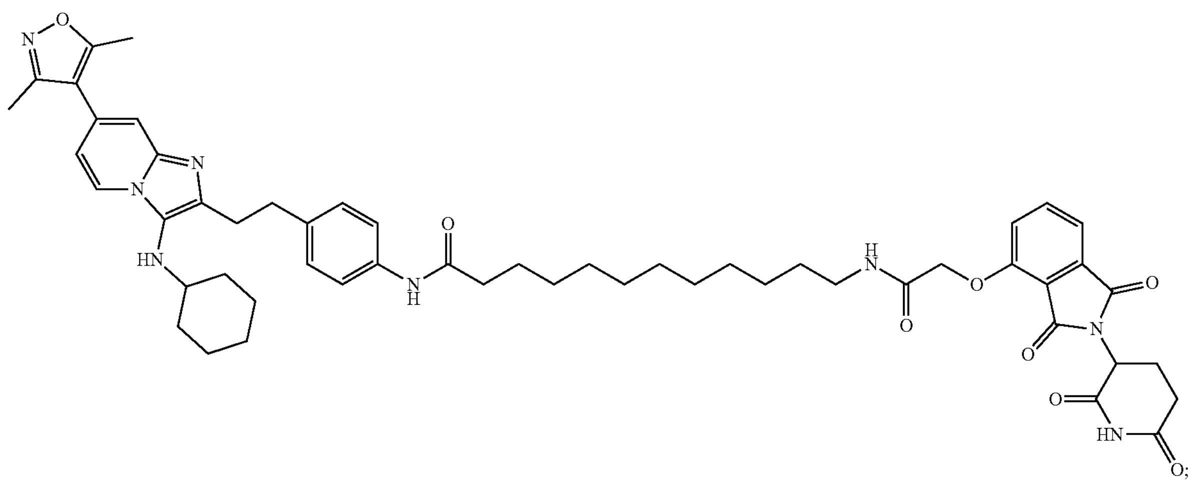
(11)
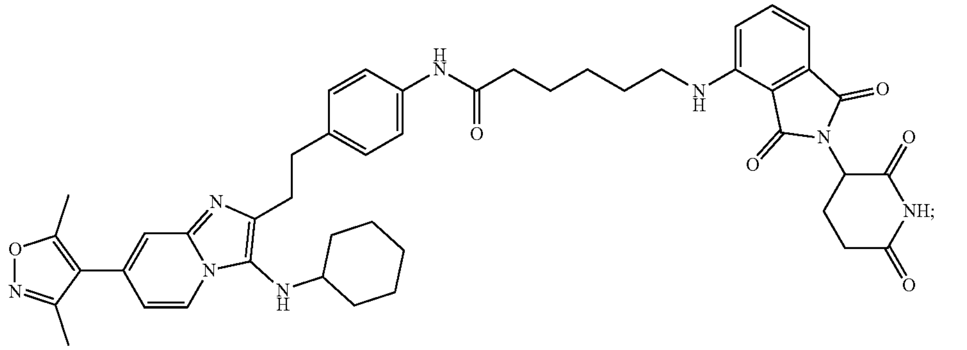
(12)
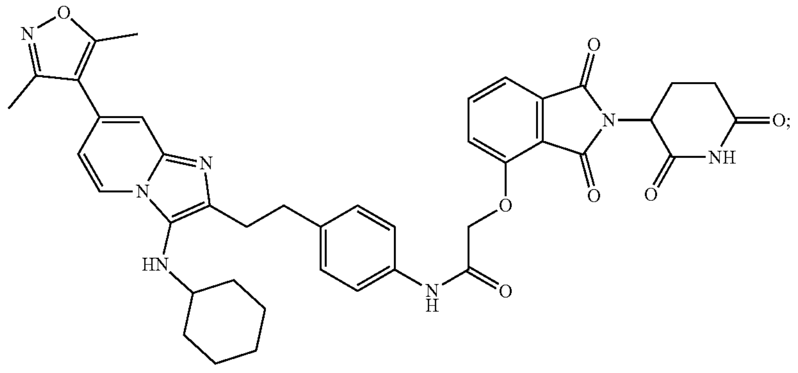
(13)
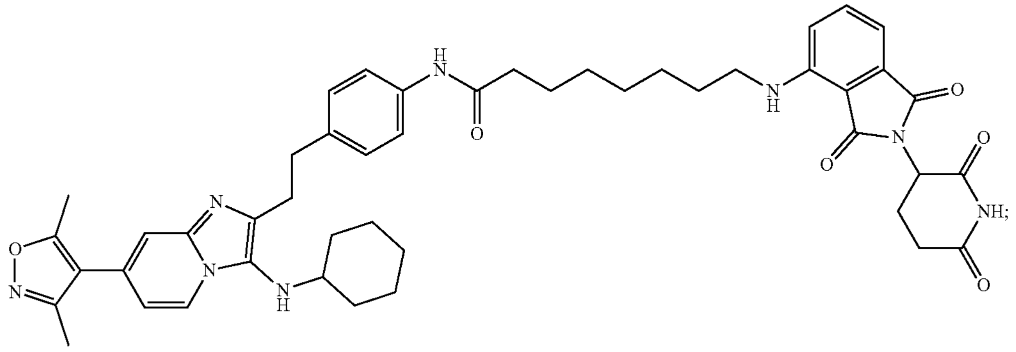

-continued
(14)
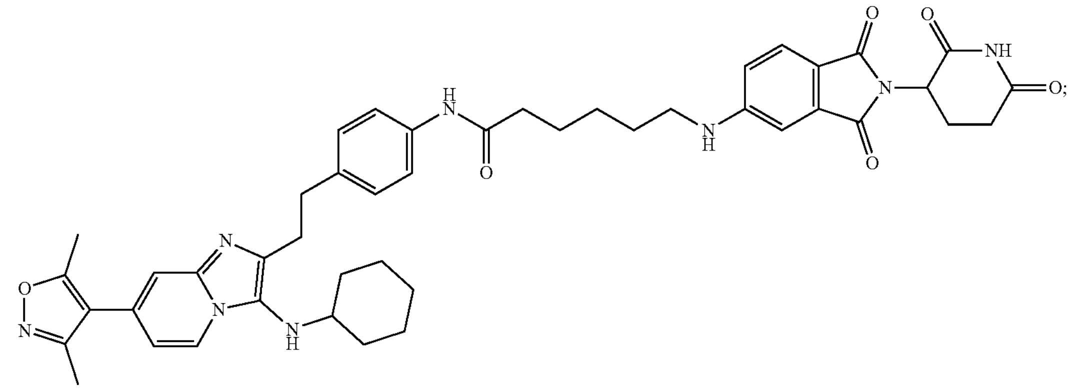
(15)
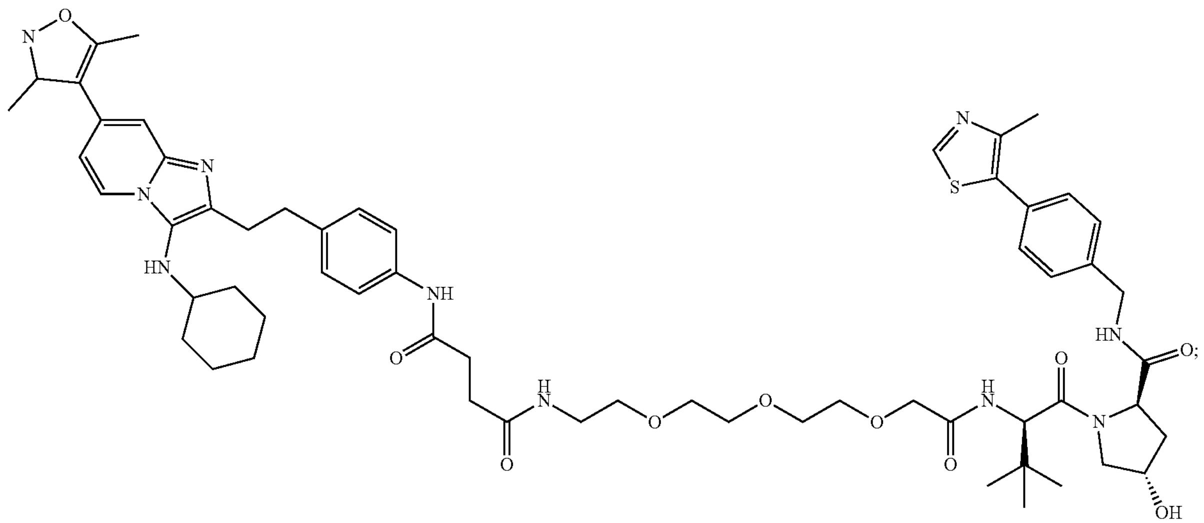
(16)
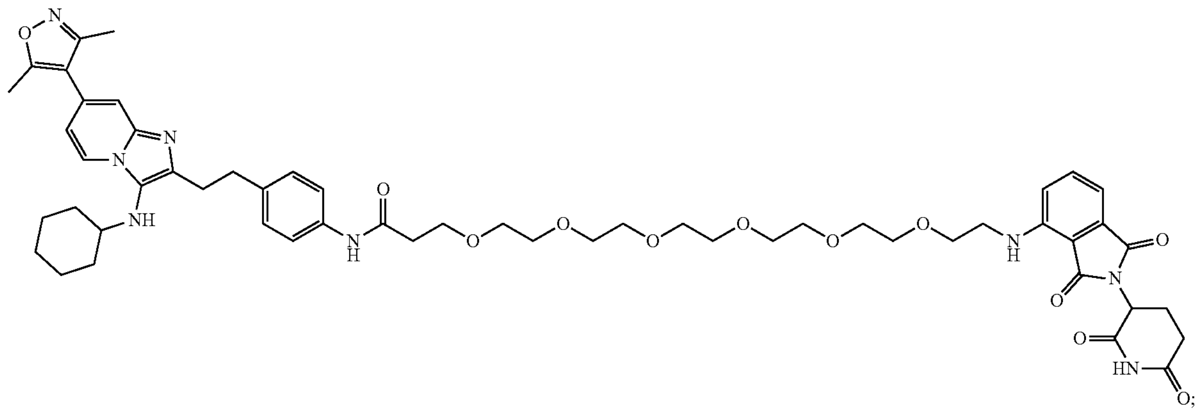

-continued
(17)
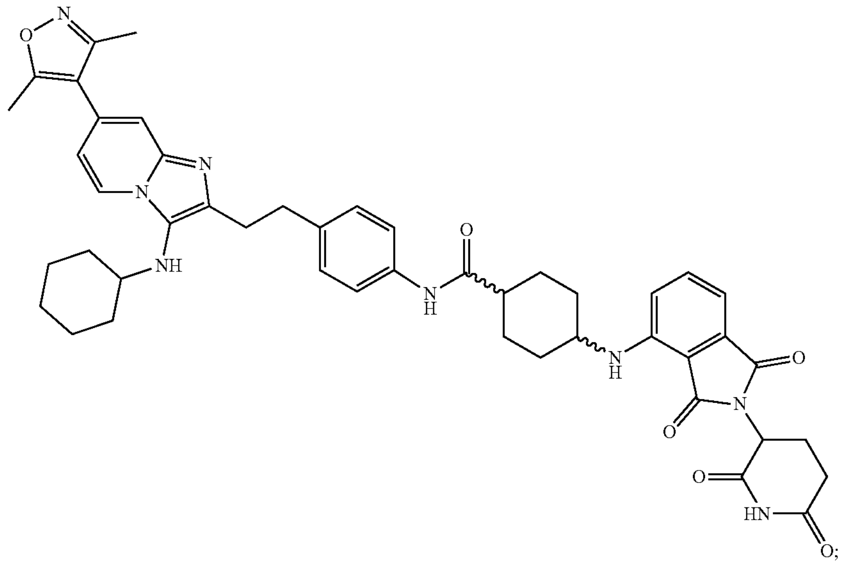
(18)
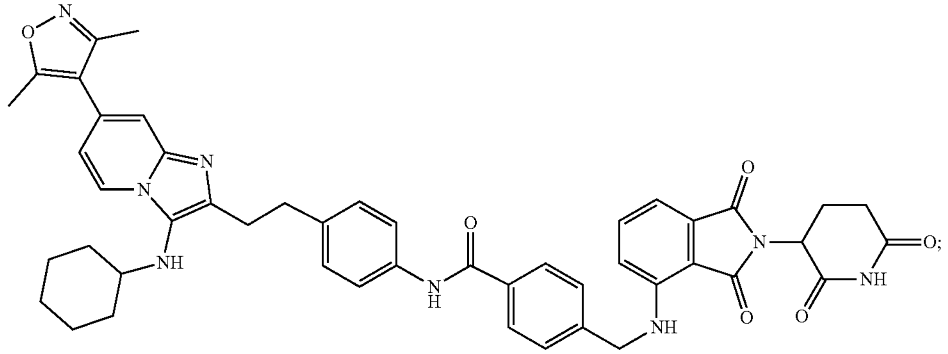
(19)
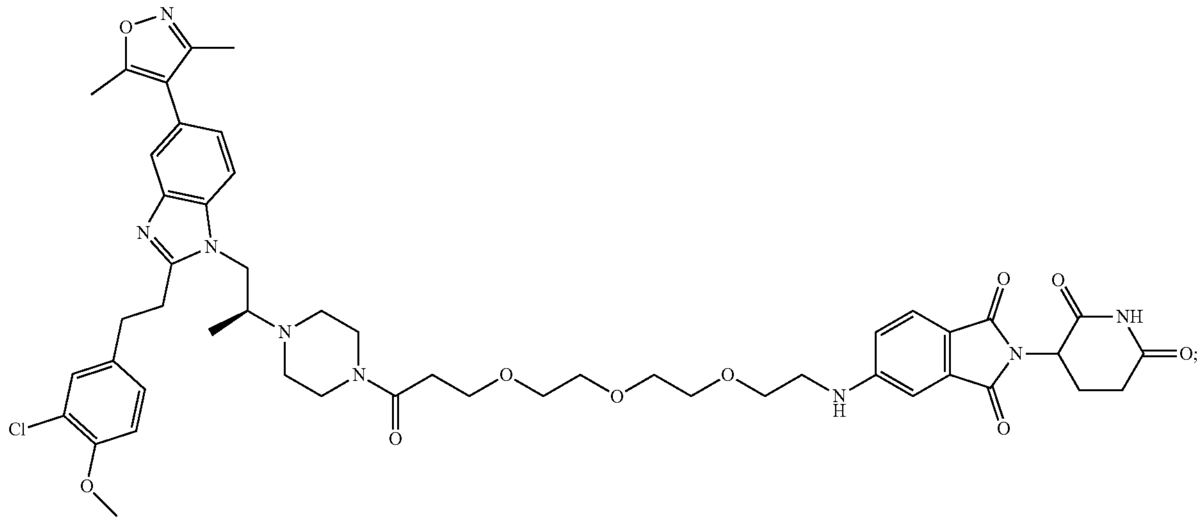

-continued
(20)
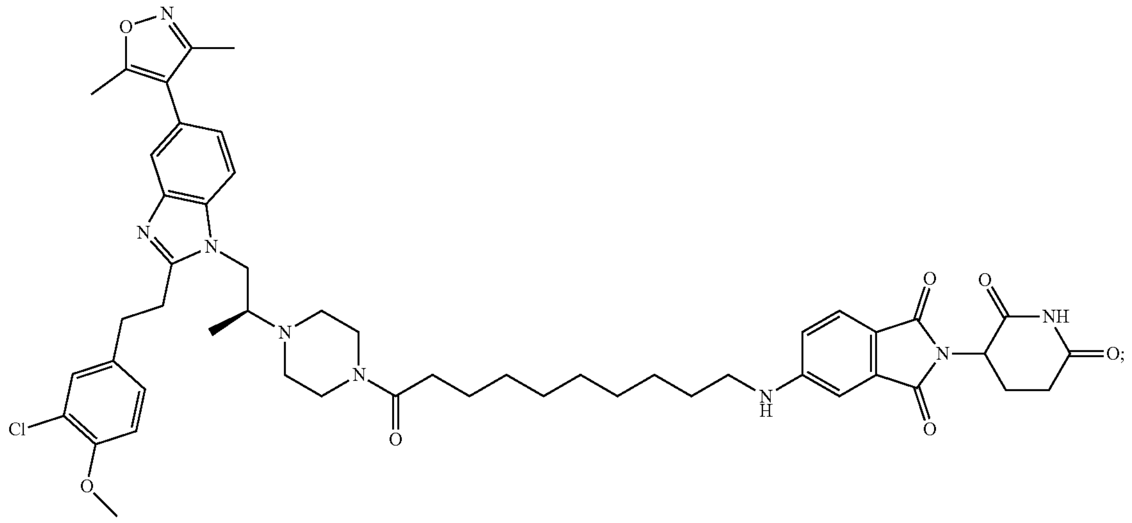
(21)
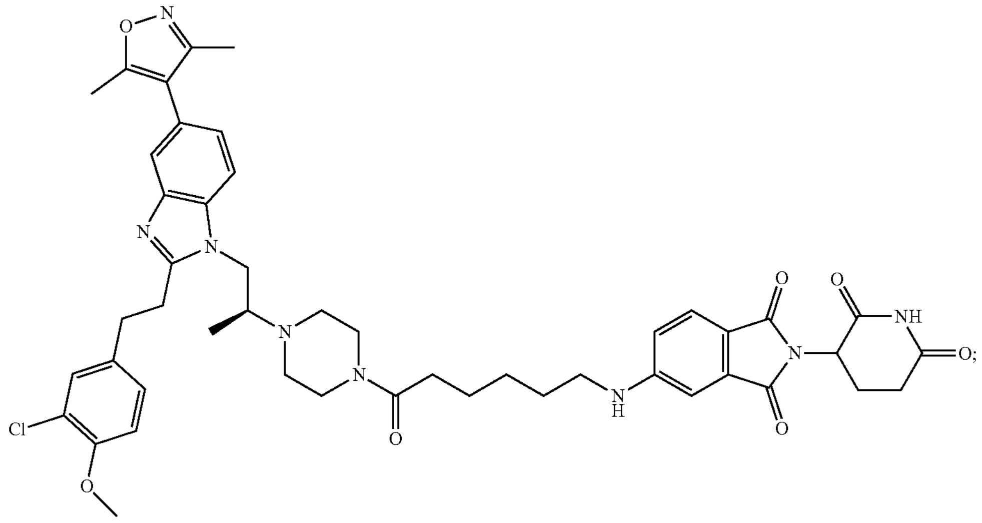
(22)
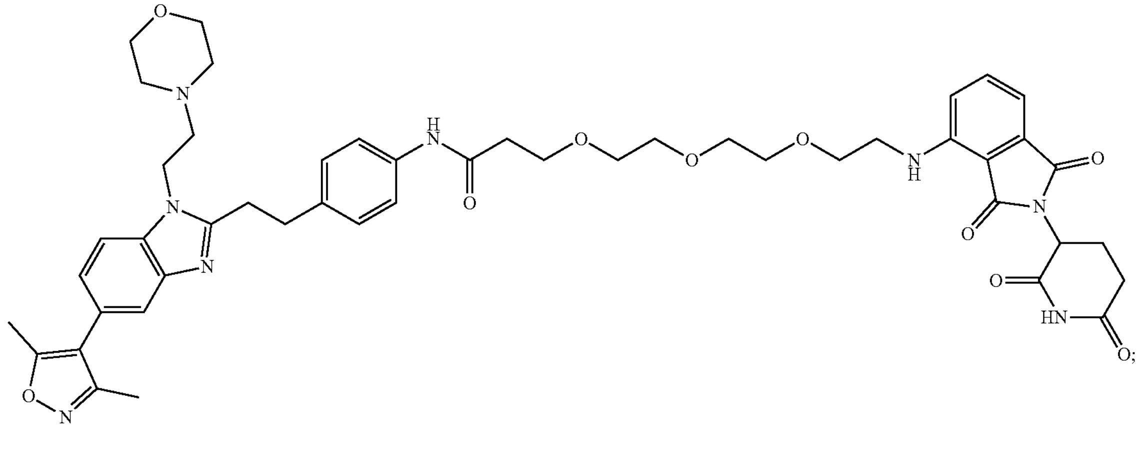

-continued
(23)
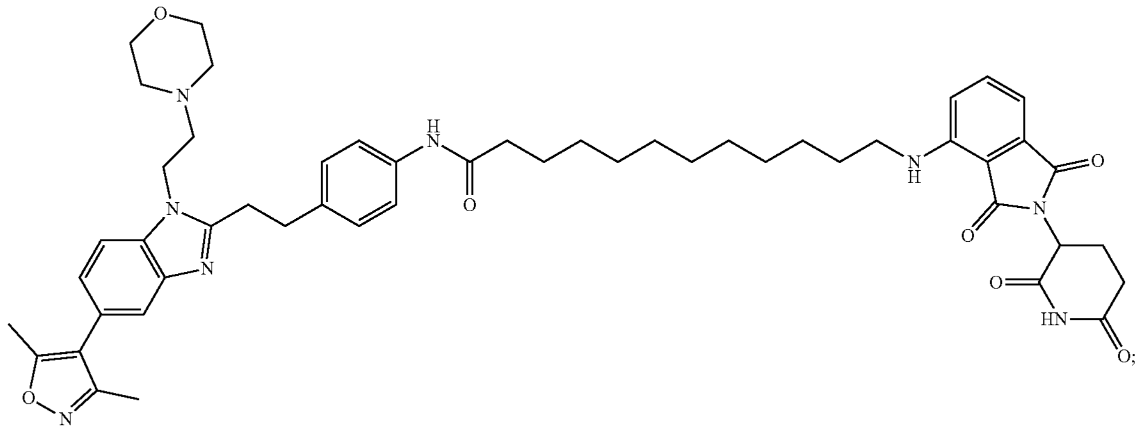
(24)
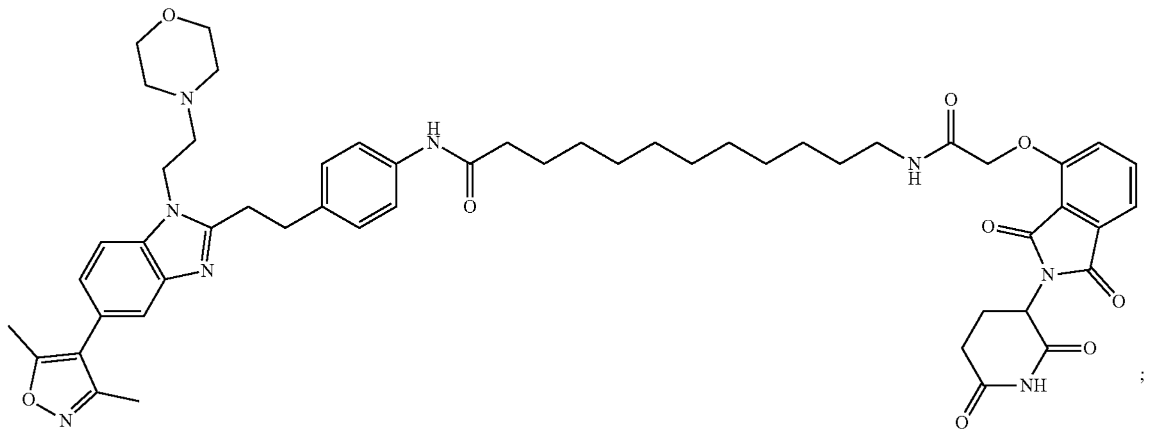
(25)
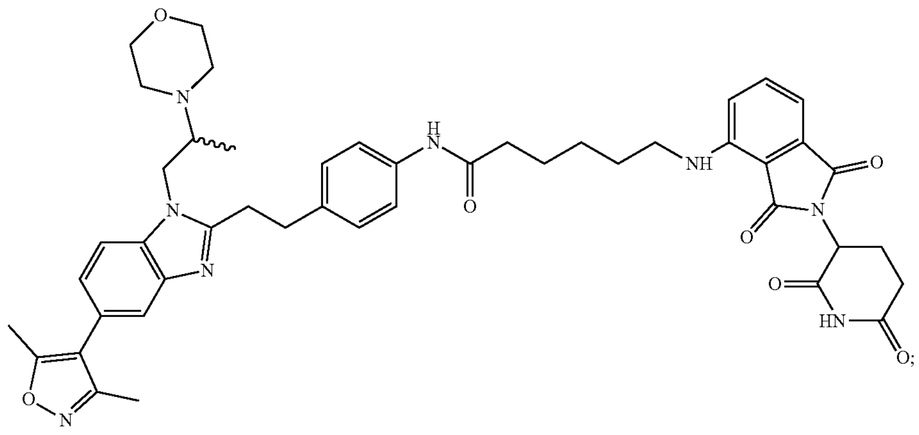

-continued
(26)
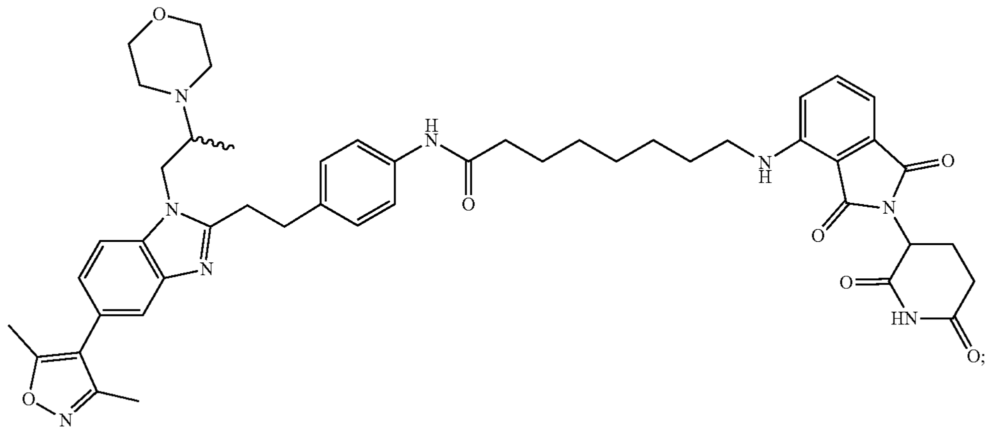
(27)
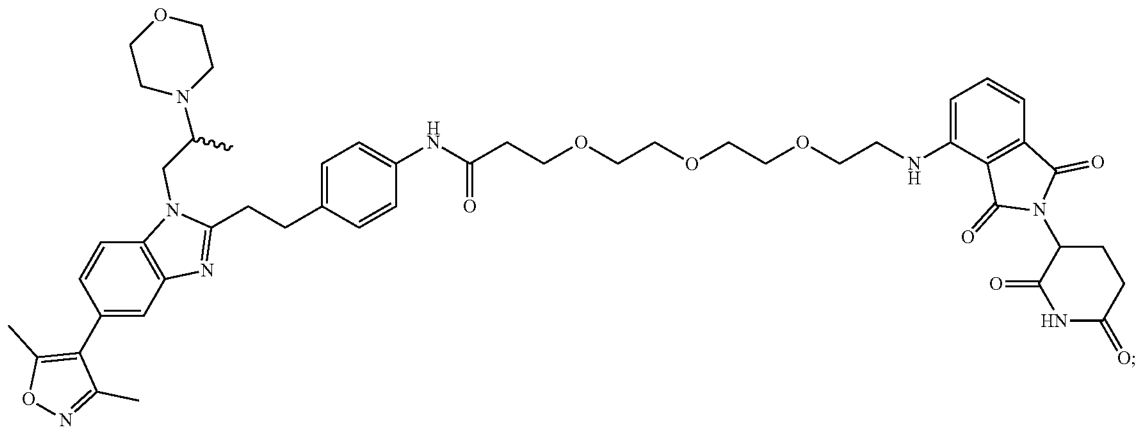
(28)
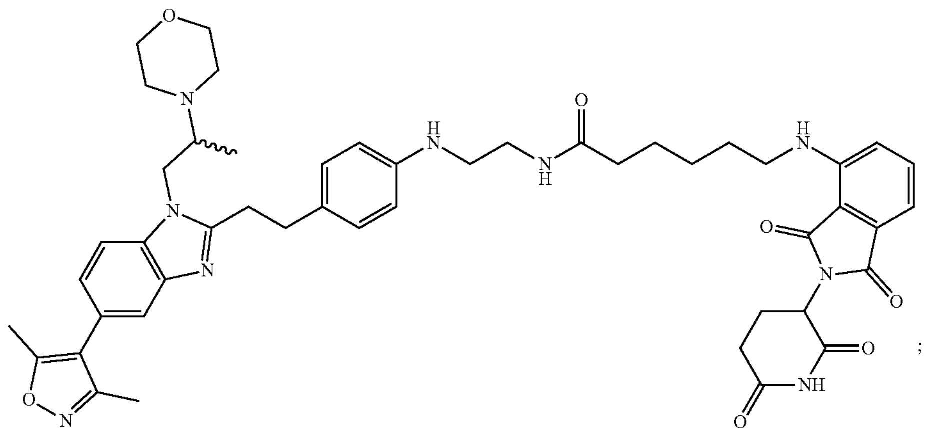

-continued
(29)
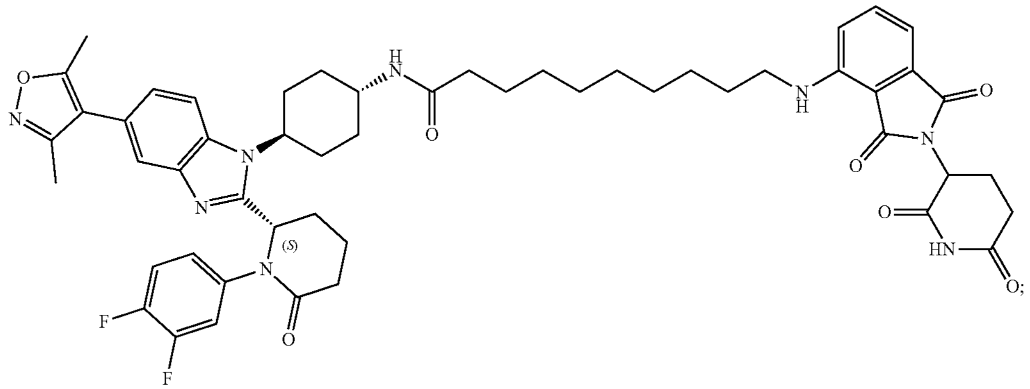
(30)
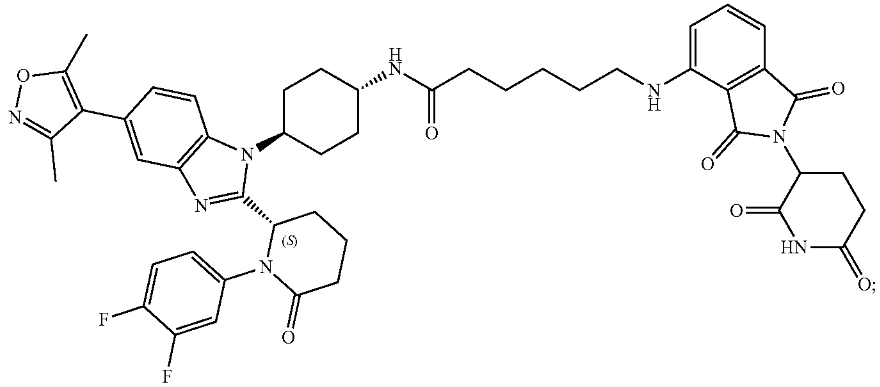
(31)
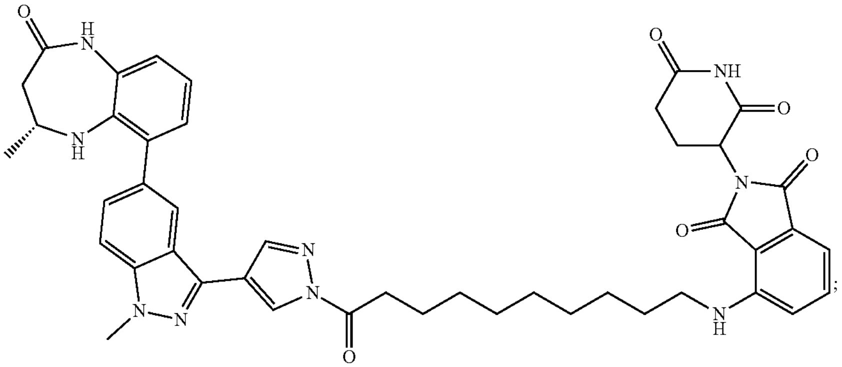
(32)
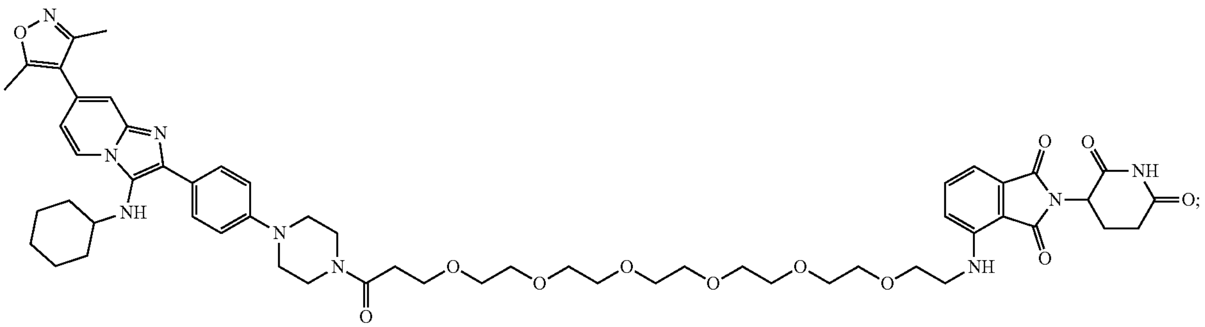

-continued
(33)
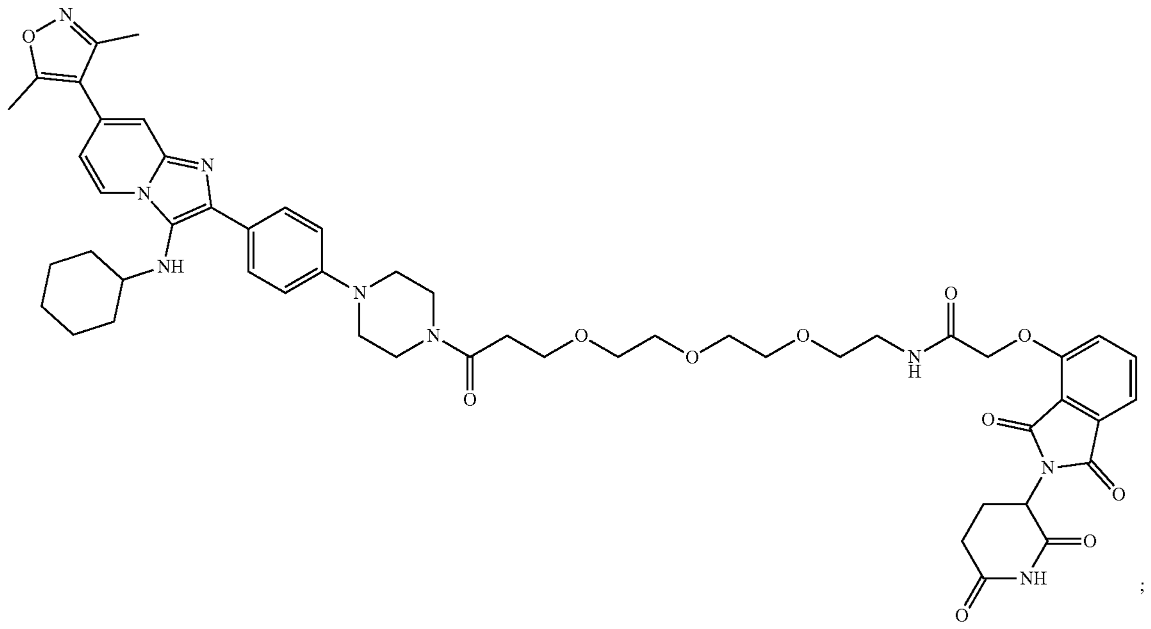
(34)
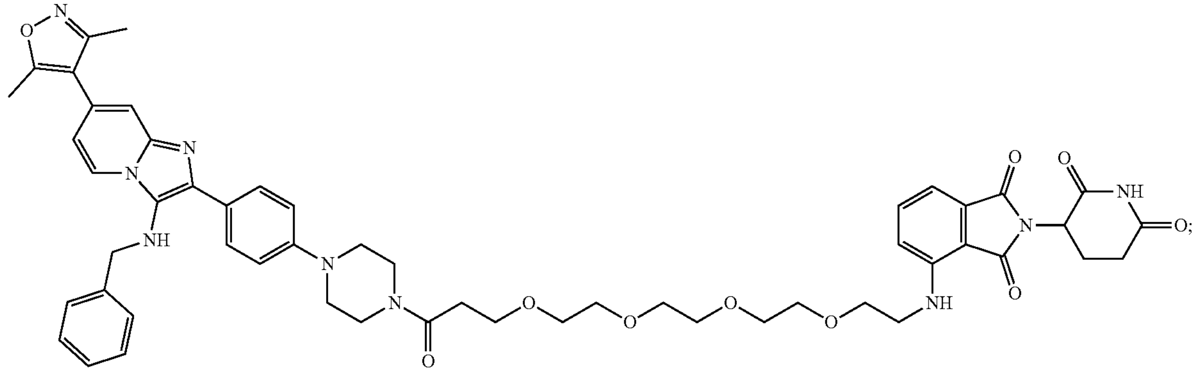
(35)
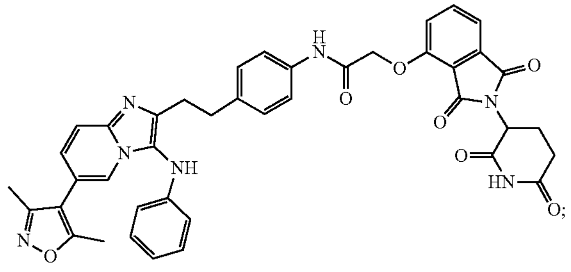
(36)
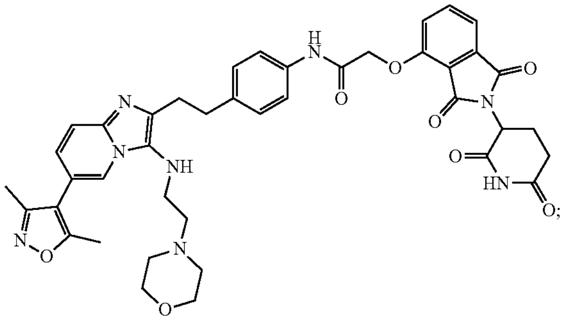

-continued
(37)
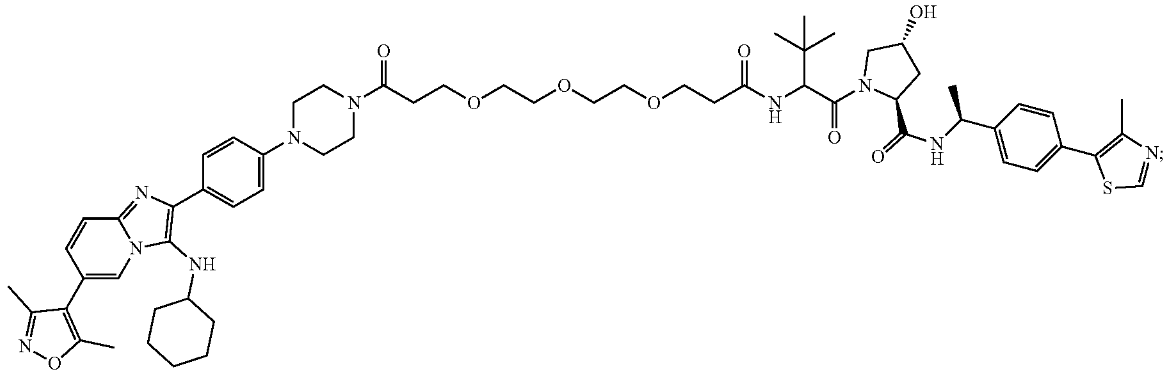
(38)
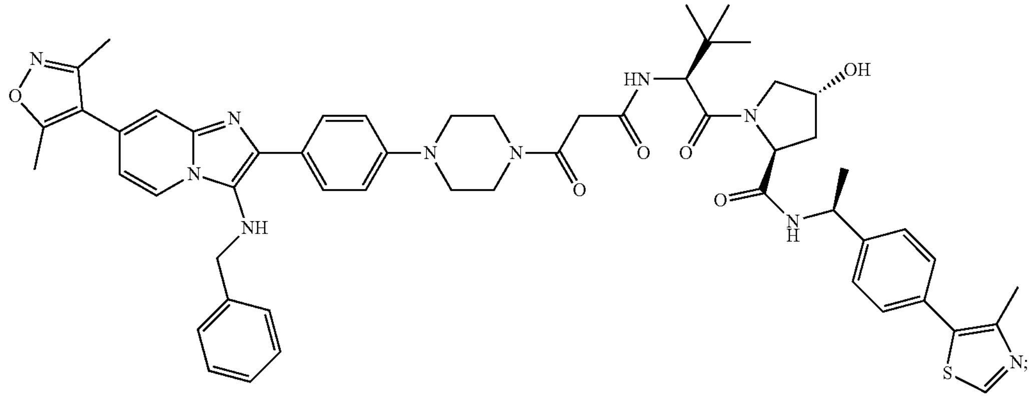
(39)
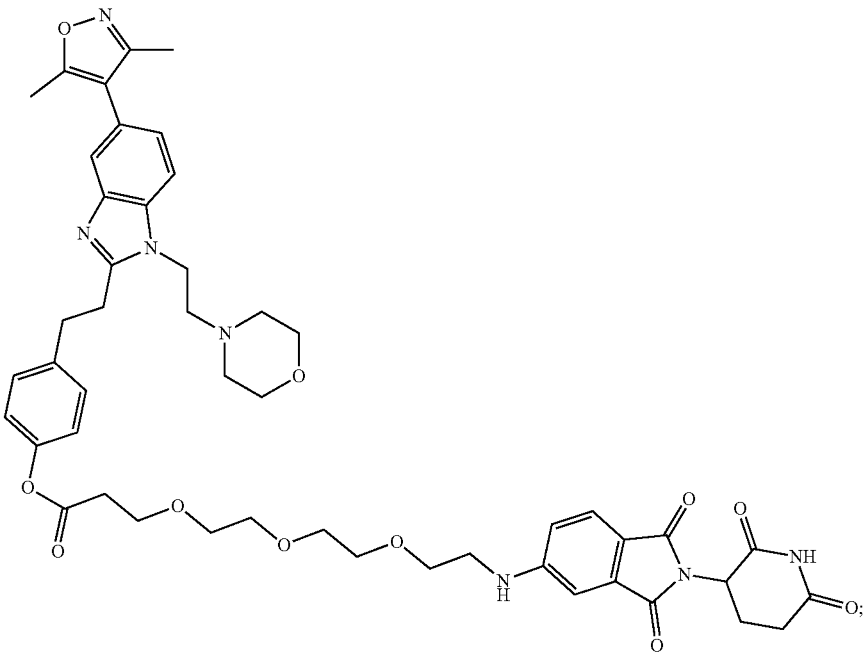

-continued
(40)
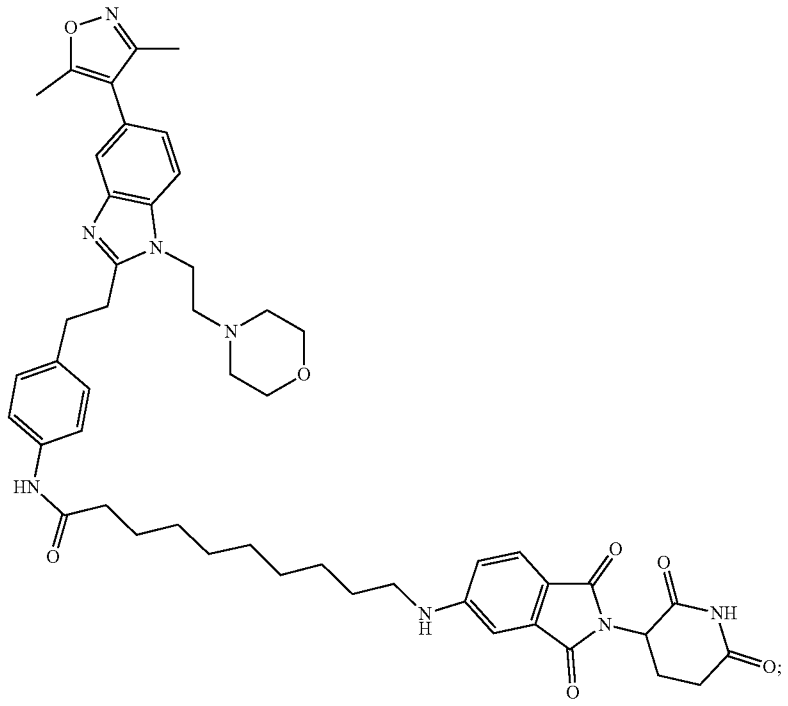
(41)
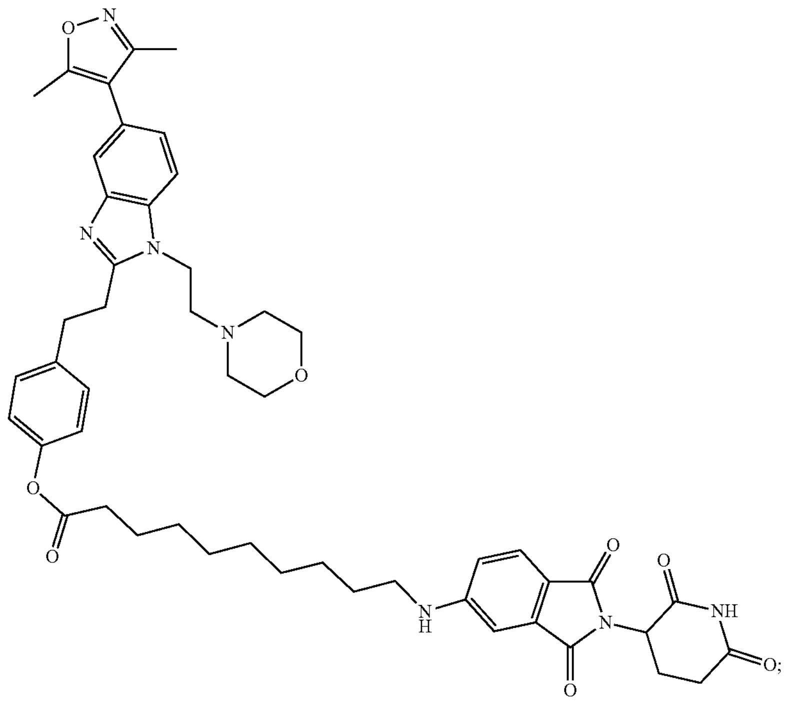

-continued
(42)
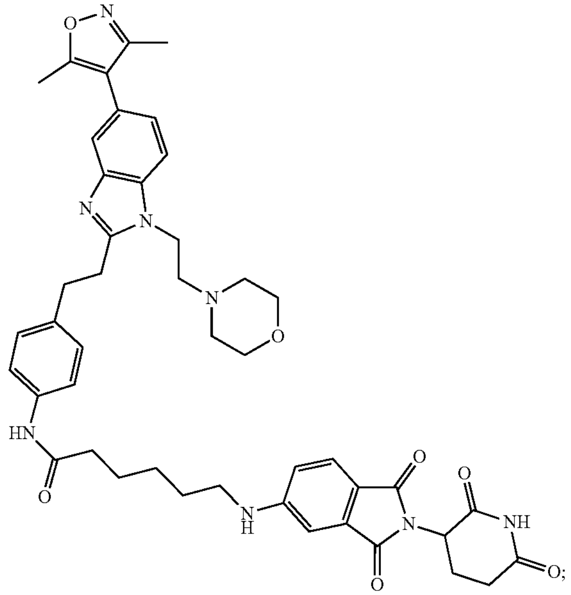
(43)
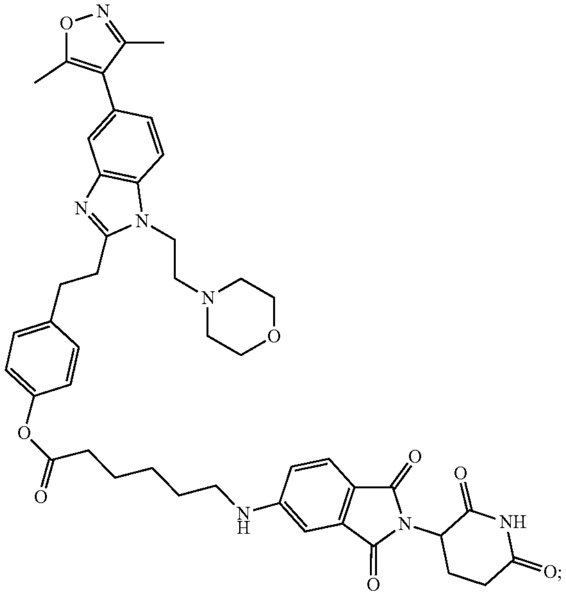
(44)
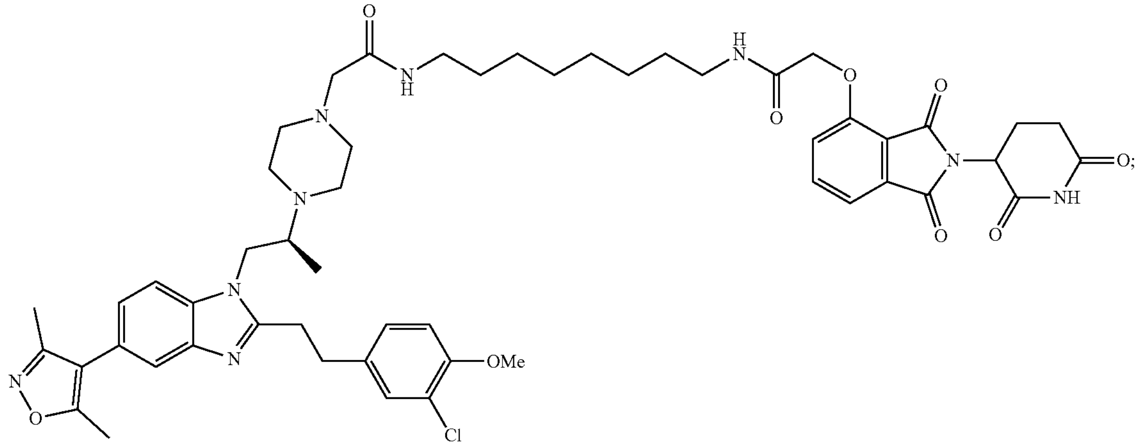
(45)
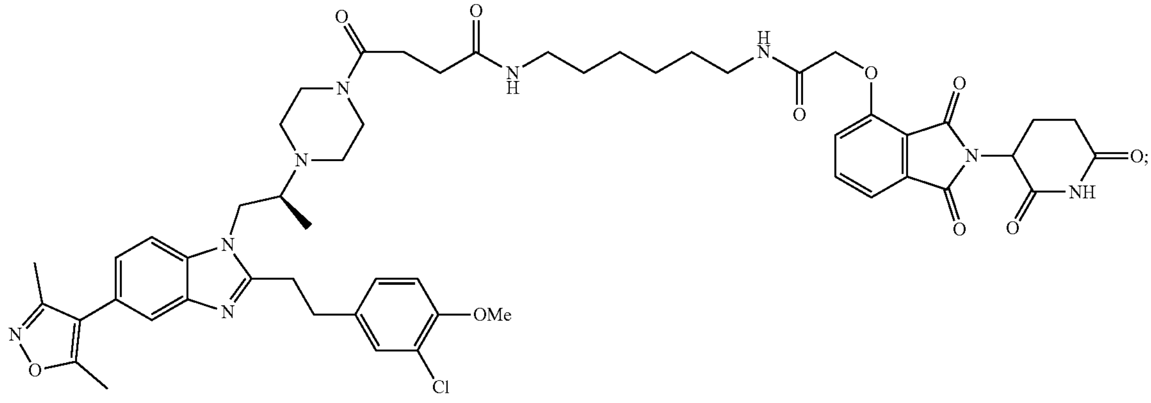
and -continued (46)

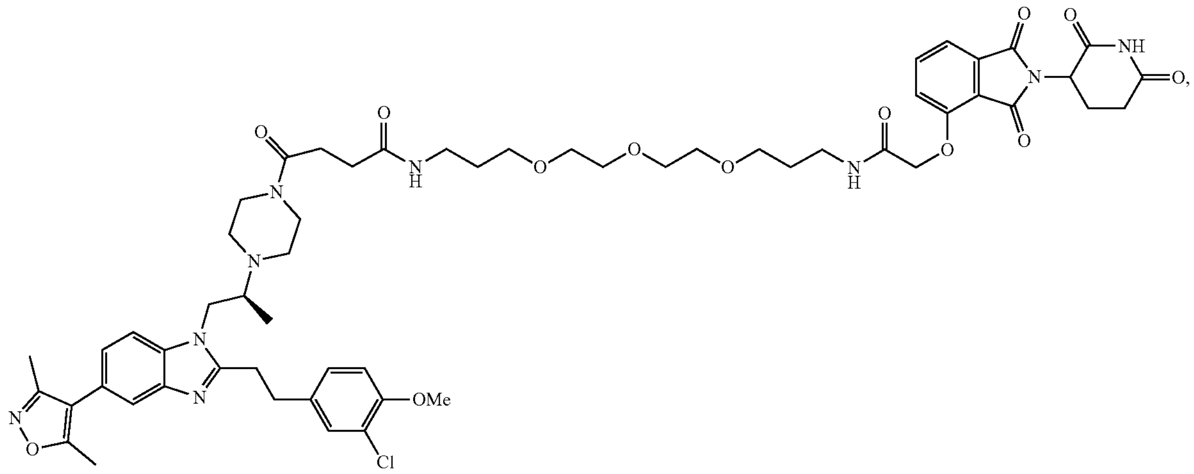

and their pharmaceutically acceptable salts and stereoisomers.

Bispecific compounds of formula (I) or (II) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bispecific compounds of formula (I) or (II) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

In some embodiments, the bispecific compound of formula (I) or (II) is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

In addition to the isotopic derivatives, the term "bispecific compounds of formula (I) or (II)" embraces N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the compounds presented herein are also considered to be disclosed herein.

Methods of Synthesis

In some embodiments, the present invention is directed to a method for making a bispecific compound of formula (I) or (II), or a pharmaceutically acceptable salt or stereoisomer thereof. Broadly, the inventive compounds or pharmaceutically-acceptable salts or stereoisomers thereof, may be prepared by any process known to be applicable to the preparation of chemically related compounds. Representative synthetic schemes are described in various working examples and illustrate non-limiting methods by which the compounds of the invention may be prepared.

Pharmaceutical Compositions

Another aspect of the present invention is directed to a pharmaceutical composition that includes a therapeutically effective amount of the bispecific compound of formula (I) or (II), or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bispecific compounds of formula (I) or (II) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, intradermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, bispecific compounds of the present invention are formulated for oral or intravenous administration (e.g., systemic intravenous injection).

Accordingly, bispecific compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bispecific compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bispecific compounds of formula (I) or (II) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bispecific compounds may be formulated for buccal or sublingual administration, examples of which include tablets, lozenges and gels.

The bispecific compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) or (II) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfate, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bispecific compound of formula (I) or (II), or a pharmaceutically acceptable salt or a stereoisomer thereof that is effective in producing the desired therapeutic response in a particular patient suffering from a disease or disorder. The term "therapeutically effective amount" thus includes the amount of the compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., neuroblastoma) cells, or reduces the amount of EP300/CBP in diseased cells.

The total daily dosage of the bispecific compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the bispecific compound; and like factors well known in the medical arts (see, for example, Goodman and Gilman's, *The Pharmacological Basis of Therapeutics,* 10th Edition, A. Gilman, J. Hardman and L. Limbird, eds., McGraw-Hill Press, 155-173, 2001).

Bispecific compounds of formula (I) or (II) may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) EP300/CBP or MYC activity, that entails administration of a therapeutically effective amount of a bispecific compound formula (I) or (II), or a pharmaceutically acceptable salt or stereoisomer thereof, to a subject in need thereof.

The diseases or disorders may be said to be characterized or mediated by aberrant (e.g., dysfunctional or dysregulated) EP300/CBP or MYC activity (e.g., elevated levels of protein or otherwise functionally abnormal relative to a non-pathological state). A "disease" ("or condition") is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, bispecific compounds of formula (I) or (II) may be useful in the treatment of cell proliferative diseases and disorders (e.g., cancer or benign neoplasms). In some embodiments bispecific compounds of formula (I) or (II) may be useful in the treatment of MYC-driven cancers (e.g., neuroblastoma). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" the treatment may be suffering from or suspected of suffering from a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from a specific disease or disorder versus subjects suspected of suffering from a specific disease or disorder are not necessarily two distinct groups.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g., hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, Lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the bispecific compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polypopsis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the disease or disorder is high-risk neuroblastoma (NB).

In some embodiments, the disease or disorder is acute myeloid leukemia (AML), multiple myeloma (MM), melanoma, rhabdomyosarcoma, or diffuse large B cell lymphoma. In other embodiments, the disease or disorder is small solid tumor. In other embodiments, the disease or disorder is colon cancer, rectum cancer, stomach cancer, breast cancer or pancreatic cancer.

The bispecific compounds of formula (I) or (II) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became unresponsive or intolerant to the particular treatment. Therapy may also be given as an adjuvant treatment, i.e., to prevent reoccurrence of cancer in patients with no currently detectable disease or after surgical removal of a tumor. Thus, in some embodiments, the compounds may be administered to a patient who has received another therapy, such as chemotherapy, radioimmunotherapy, surgical therapy, immunotherapy, radiation therapy, targeted therapy or any combination thereof.

The methods of the present invention may entail administration of bispecific compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days), followed by a 7-day "off" period. In other embodiments, the bispecific compound may be dosed twice a day (BID) over the course of two and a half days (for a total of 5 doses) or once a day (QD) over the course of two days (for a total of 2 doses). In other embodiments, the bispecific compound may be dosed once a day (QD) over the course of five days.

Combination Therapy

Bispecific compounds of formula (I) or (II) may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bispecific compound of formula (I) or (II) in combination with one or more additional therapeutics known for use in treating the disease or condition (e.g., cancer). The dosage of the additional anticancer therapeutic may be the same or even lower than known or recommended doses. See, Hardman et al., eds., Goodman & Gilman's *The Pharmacological Basis Of Basis Of Therapeutics,* 10th ed., McGraw-Hill, New York, 2001*; Physician's Desk Reference* 60th ed., 2006. For example, anti-cancer agents that may be suitable for use in combination with the inventive bispecific compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and chimeric antigen receptor T-cell (CAR-T) therapy.

In some embodiments, the bispecific compound of formula (I) or (II) and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments involving cancer treatment, the bispecific compound of formula (I) or (II) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the bispecific compound of the present invention may be used in combination other anti-NB or anti-cancer agents, examples of which include Dinutuximab (Unituxin®) (e.g., for NB), Cyclophosphamide (e.g., for NB), Busulfan plus Melphalan Hydrochloride, Carboplatin plus Etoposide Phosphate and Melphalan Hydrochloride, Doxorubicin Hydrochloride, Vincristine Sulfate, Entrectinib (e.g., for brain cancer, central nervous system (CNS) cancer), Hu3F8 plus donated natural killer cells (e.g., for persistent or recurrent NB), Hu3F8 plus granulocyte-macrophage colony-stimulating factor (GM-CSF) (e.g., for relapsed/refractory NB, Hu3F8/GM-CSF immunotherapy plus isotretinoin (e.g., for consolidation of first remission of patients with NB), Venetoclax® (e.g., for persistent or recurrent cancers, including NB, leukemia and Non-Hodgkin's lymphoma), bivalent vaccine with the immunological adjuvant OPT-821, in combination with oral ß-glucan (e.g., for NB), Trametinib (e.g., for germ cell tumors, liver cancer, kidney cancer, NB, pediatric brain tumors, osteosarcoma, Ewing sarcoma, rhabdomyosarcoma, soft tissue sarcoma, Wilms' tumor), Cobimetinib (e.g., for melanoma, pediatric brain tumors, and soft tissue sarcoma), and intrathecal radioimmunotherapy using 131I-8H9 (e.g., for primary brain tumors, brain cancer, NB, and CNS cancer).

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bispecific compound of formula (I) or (II), or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of 5-((12-(4-(4-(3-(cyclohexylamino)-6-(3,5-dimethylisoxazol-4-yl)imidazo[1,2-a]pyridin-2-yl)phenyl)piperazin-1-yl)-12-oxododecyl)amino)-2-(2,6-dioxopiperidin-3-yl)isoindoline-1,3-dione (1)

Scheme 1. Synthesis of intermeidate 1(Int-1).

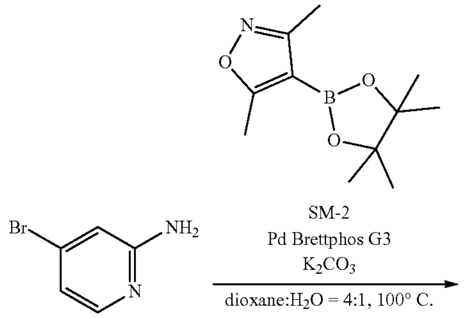

SM-2

SM-1

-continued

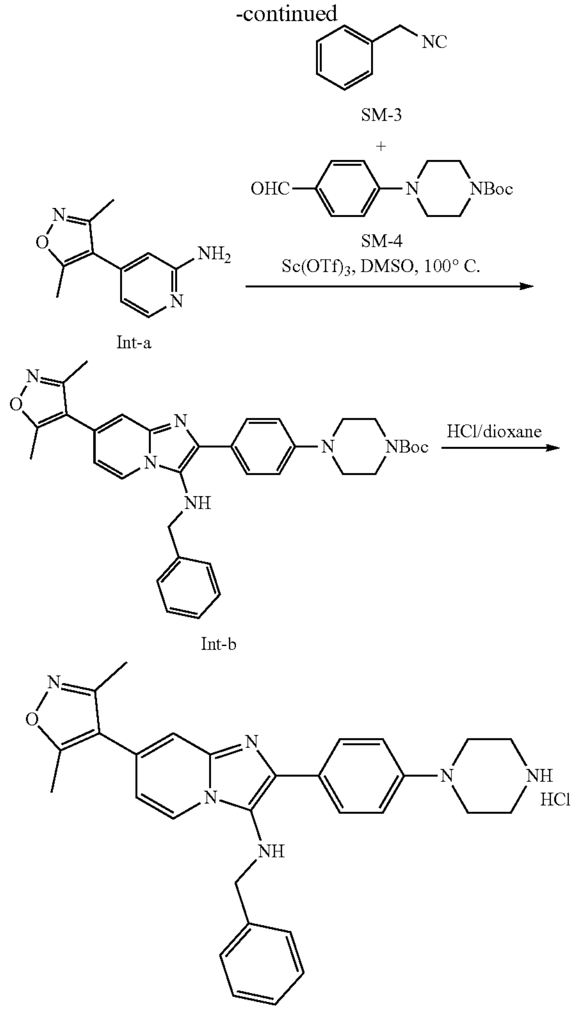

SM-3

SM-4

Int-a

Int-b

Int-1

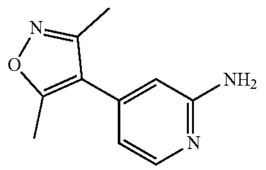

Int-a

A mixture of SM-1 (300 mg, 1.73 mmol), SM-2 (425 mg, 1.9 mmol), BrettPhos Pd G3 catalyst (78 mg, 0.086 mmol), and $K_2CO_3$ (478 mg, 3.46 mmol) in 4:1 dioxane/$H_2O$ (5 mL) was stirred in a 25-mL flask under $N_2$ atmosphere at 100° C. for 16 hours (h). After the reaction was complete, the mixture was filtered and the filtrate was concentrated under reduced pressure. The resulting residue was purified via ISCO chromatography (regular 12 g column, DCM/MeOH=20/1) to give the Int-a (130 mg, 40% yield).

MS (ESI) calcd. for $C_{10}H_{11}N_3O$: 189.09, found: 190.58, 191.19.

Int-b

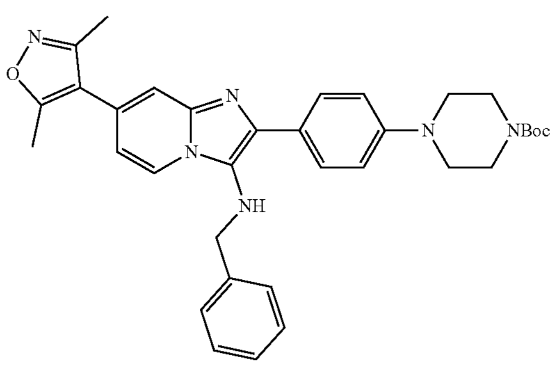

A mixture of Int-a (77 mg, 0.407 mmol), SM-3 (48 mg, 0.407 mmol), SM-4 (118 mg, 0.407 mmol), and $Sc(OTf)_3$ (20 mg, 0.0407 mmol) in DMSO (2 mL) in a 10-mL flask was stirred at 100° C. for 16 h. After the reaction was complete, the mixture was filtered and the filtrate was concentrated under reduced pressure. The resulting residue was purified via ISCO chromatography (regular 4 g column, Ethyl Acetate/Hexane=5/1) to give the Int-b (83 mg, 35% yield).

Int-1

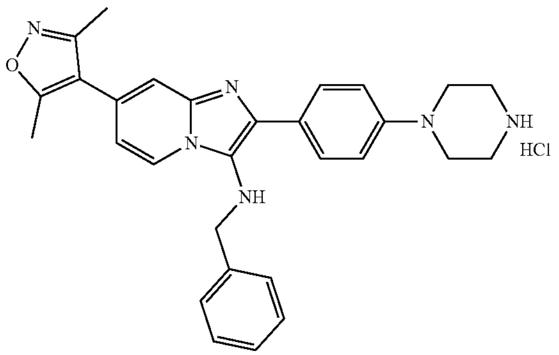

To Int-b (83 mg, 0.14 mmol) in a 10-mL flask was added HCl/Dioxane (2 mL, 4 M) at 0° C. The resulting mixture was allowed to warm to 25° C. and was stirred for 8 h. After the reaction was complete, the mixture was filtered. The resulting filter cake was washed with Ethyl Acetate (2 mL×3) and then dried under reduced pressure to give compound Int-b (70 mg, near quantitative yield).

$^1H$ NMR (500 MHz, DMSO-$d_6$) δ 9.37 (s, 2H), 8.71 (d, J=7.0 Hz, 1H), 7.96 (d, J=8.9 Hz, 2H), 7.83 (d, J=1.4 Hz, 1H), 7.51 (dd, J=7.0, 1.7 Hz, 1H), 7.33-7.23 (m, 5H), 7.21-7.16 (m, 2H), 4.17 (s, 2H), 3.56 (t, J=5.3 Hz, 4H), 3.23 (q, J=5.0 Hz, 4H), 2.54 (s, 3H), 2.34 (s, 3H).

MS (ESI) calcd. for $C_{29}H_{30}N_6O$: 478.25, found: 261.07, 479.26.

Int-2

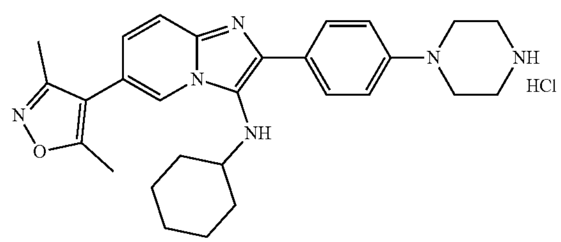

Intermediate 2 (Int-2) was prepared in an analogous manner to compound Int-1 in scheme 1 as a yellow powder (51 mg, quantitative yield).

$^1H$ NMR (500 MHz, DMSO-$d_6$) δ 9.12 (s, 2H), 8.74 (d, J=5.0 Hz, 1H), 8.04 (d, J=8.3 Hz, 2H), 7.95 (dd, J=11.3, 7.4 Hz, 2H), 7.22-7.19 (m, 2H), 5.35 (s, 1H), 3.54 (t, J=5.2 Hz, 4H), 3.25 (s, 4H), 2.89 (s, 1H), 2.50 (s, 3H), 2.31 (s, 4H), 1.80 (d, J=12.3 Hz, 2H), 1.66-1.62 (m, 2H), 1.29 (d, J=11.3 Hz, 2H), 1.10-1.07 (m, 2H).

MS (ESI) calcd. for $C_{28}H_{34}N_6O$: 470.28, found: 256.81 and 471.31.

Int-3

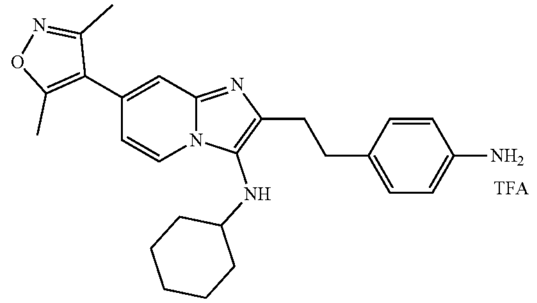

Intermediate 3 (Int-3) was prepared in an analogous manner to compound Int-1 in scheme 1 as a yellow powder (492 mg, quantitative yield).

H NMR (500 MHz, Acetone-$d_6$) δ 8.41 (d, J=7.1 Hz, 1H), 7.82 (s, 1H), 7.21 (d, J=8.2 Hz, 2H), 7.12 (d, J=7.3 Hz, 1H), 6.60 (d, J=8.3 Hz, 2H), 3.11 (q, J=3.3 Hz, 4H), 2.91 (m, 1H), 2.54 (s, 3H), 2.36 (s, 3H), 1.93-1.87 (m, 2H), 1.77-1.72 (m, 2H), 1.36-1.19 (m, 6H).

Int-4

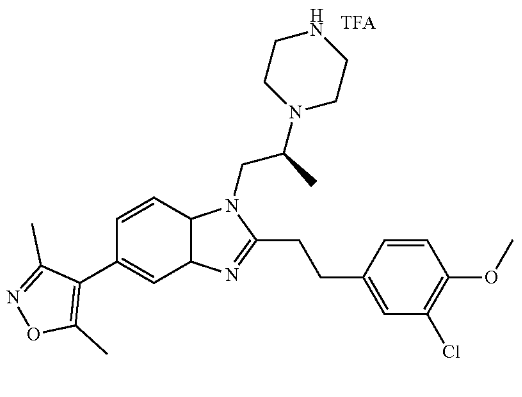

-continued
Int-5
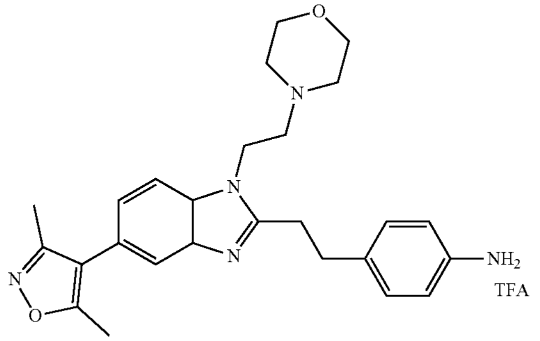
Int-6
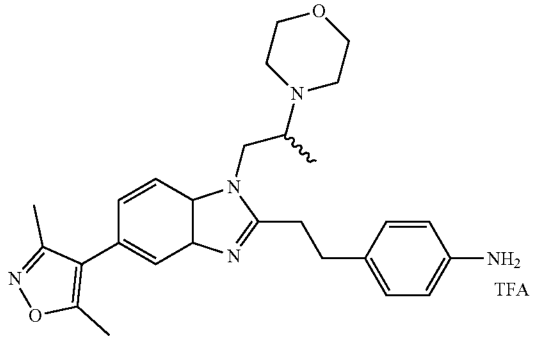
-continued
Int-7
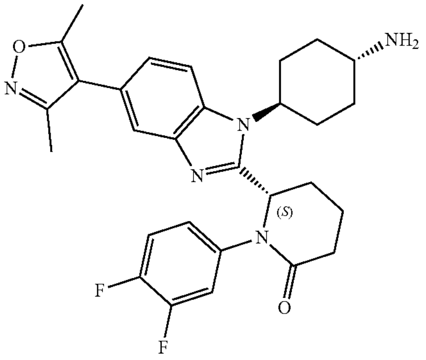
Intermediates Int-4, Int-5, Int-6, and Int-7 were prepared according to Hay et al., J. Am. Chem. Soc. 136:9308-9319 (2014) and WO2018/073586.
Int-8
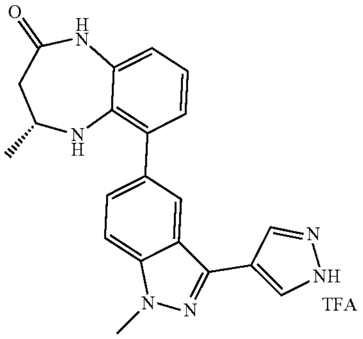
Intermediate Int-8 was prepared according to Taylor et al., ACS Med Chem Lett. 7:531-536 (2016).
Scheme 2. Synthesis of compound 1.
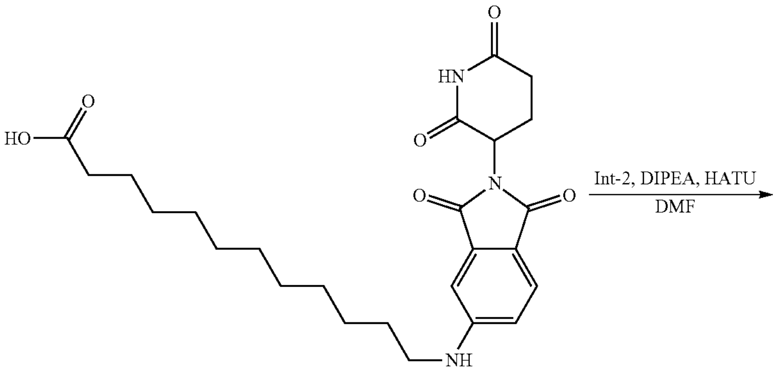
IMID acid 1

-continued

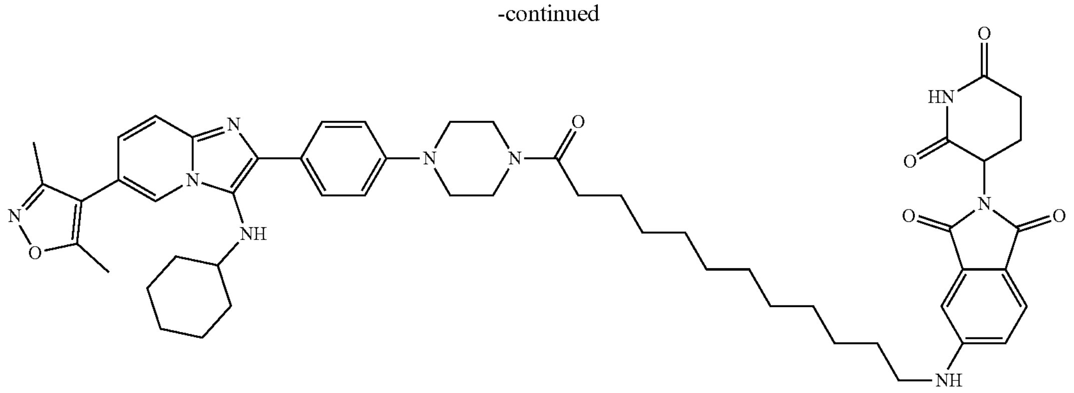

(1)

(1)

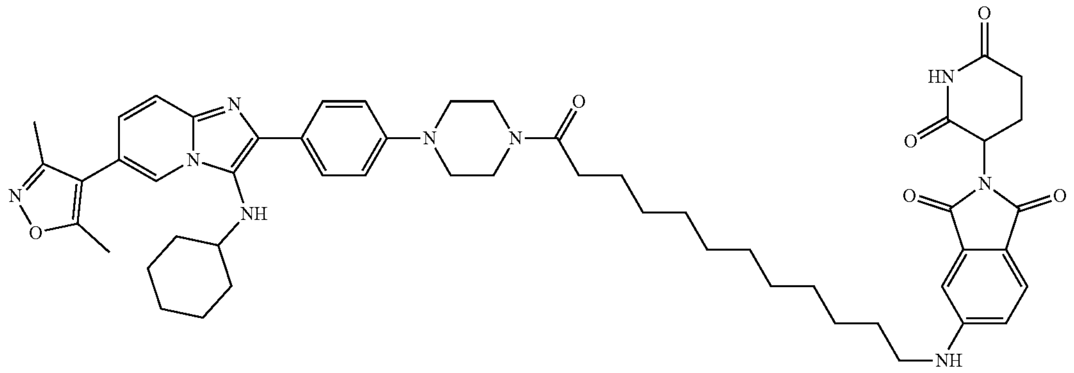

To a mixture of Int-2 (1 eq.) and immunomodulatory imide drug (IMiD) acid 1 (1 eq.) in a 10-mL flask in DMF was added N,N-diisopropylethylamine (DIPEA) (2 eq.) and 1-[bis(dimethylamino)methylene]-1H-1,2,3-triazolo[4,5-b] pyridinium 3-oxid hexafluorophosphate (HATU) (2 eq.). The reaction was stirred at 25° C. until completion (5-16 h). After the reaction was complete, the mixture was purified through Prep-HPLC to give the compound 1 as a light yellow powder (3.8 mg, 21% yield).

MS (ESI) calcd. for $C_{53}H_{65}N_9O_6$: 923.51, found: 463.18, 924.93, and 925.92.

Example 2: Synthesis of 4-((2-(2-(2-(3-(4-(4-(3-(cyclohexylamino)-6-(3,5-dimethylisoxazol-4-yl)imidazo[1,2-a]pyridin-2-yl)phenyl)piperazin-1-yl)-3-oxopropoxy)ethoxy)ethoxy)ethyl)amino)-2-(2,6-dioxopiperidin-3-yl)isoindoline-1,3-dione (2)

(2)

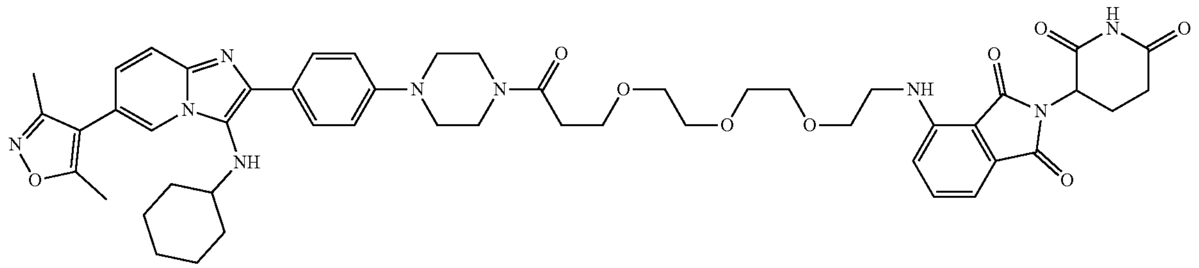

Compound 2 was prepared in an analogous manner to compound 1 in Example 1 using Int-2 and appropriate IMiD acid as a yellow powder (5.5 mg, 30% yield).

$^1$H NMR (500 MHz, DMSO-$d_6$) δ 11.10 (s, 1H), 8.69 (s, 1H), 7.98-7.88 (m, 4H), 7.61-7.53 (m, 1H), 7.14 (t, J=8.3 Hz, 3H), 7.03 (d, J=7.0 Hz, 1H), 6.59 (t, J=5.9 Hz, 1H), 5.26 (s, 1H), 5.06 (dd, J=12.7, 5.4 Hz, 1H), 3.68-3.51 (m, 24H), 2.88 (ddd, J=16.9, 13.5, 5.4 Hz, 2H), 2.64-2.53 (m, 4H), 2.50 (s, 3H), 2.31 (s, 3H), 2.06-1.99 (m, 1H), 1.79 (d, J=12.1 Hz, 2H), 1.67-1.59 (m, 2H), 1.28 (dd, J=11.8, 3.9 Hz, 2H), 1.09 (d, J=7.9 Hz, 2H).

MS (ESI) calcd. for $C_{50}H_{59}N_9O_9$: 929.44, found: 465.87, 466.52, 930.90, and 931.85.

Example 3: Synthesis of 4-((21-(4-(4-(3-(cyclohexylamino)-6-(3,5-dimethylisoxazol-4-yl)imidazo[1,2-a]pyridin-2-yl)phenyl)piperazin-1-yl)-21-oxo-3,6,9,12,15,18-hexaoxahenicosyl)amino)-2-(2,6-dioxopiperidin-3-yl)isoindoline-1,3-dione (3)

(3)

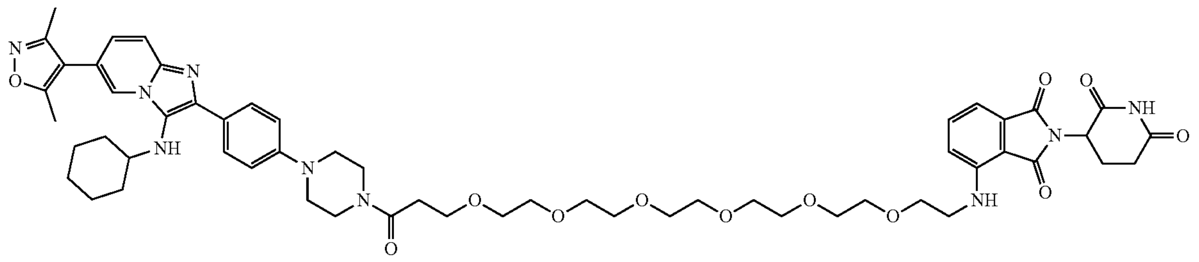

Compound 3 was prepared in an analogous manner to compound 1 in Example 1 using Int-2 and appropriate IMiD acid as a yellow powder (4.7 mg, 45% yield).

MS (ESI) calcd. for $C_{56}H_{71}N_9O_{12}$: 1061.52, found: 531.77, 532.80, 1063.00, and 1063.95.

Example 4: Synthesis of N-(2-(2-(2-(3-(4-(4-(3-(cyclohexylamino)-6-(3,5-dimethylisoxazol-4-yl)imidazo[1,2-a]pyridin-2-yl)phenyl)piperazin-1-yl)-3-oxopropoxy)ethoxy)ethoxy)ethyl)-2-((2-(2,6-dioxopiperidin-3-yl)-1,3-dioxoisoindolin-4-yl)oxy)acetamide (4)

(4)

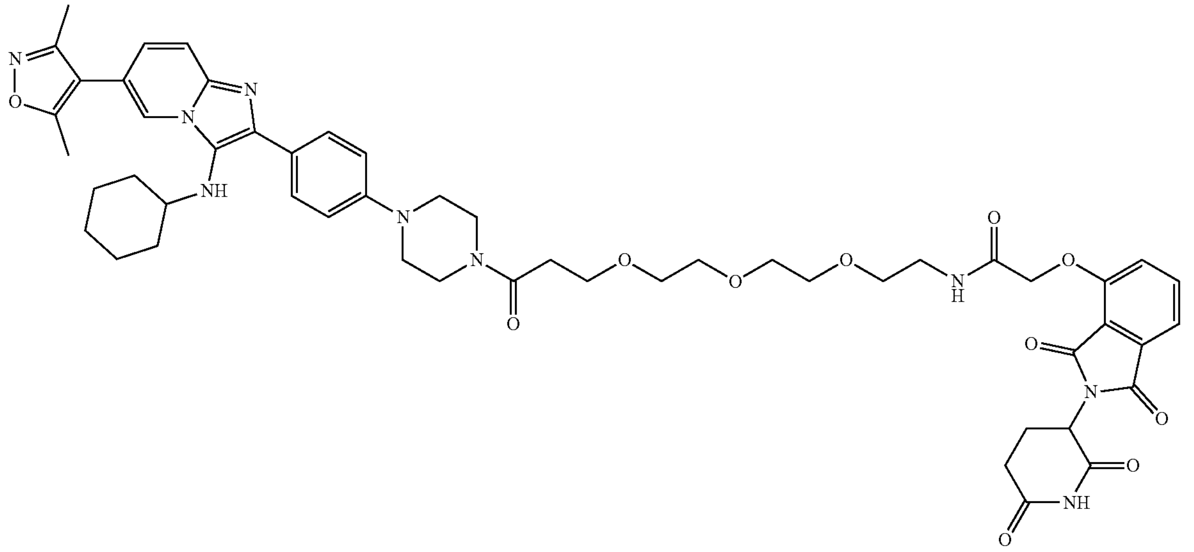

Compound 4 was prepared in an analogous manner to compound 1 in Example 1 using Int-2 and appropriate IMiD acid as a yellow powder (3.7 mg, 38% yield).

MS (ESI) calcd. for $C_{52}H_{61}N_9O_{11}$: 987.45, found: 495.18, 988.85, and 989.80.

Example 5: Synthesis of 4-((21-(4-(4-(3-(benzylamino)-7-(3,5-dimethylisoxazol-4-yl)imidazo[1,2-a]pyridin-2-yl)phenyl)piperazin-1-yl)-21-oxo-3,6,9,12,15,18-hexaoxahenicosyl)amino)-2-(2,6-dioxopiperidin-3-yl)isoindoline-1,3-dione (5)

(5)

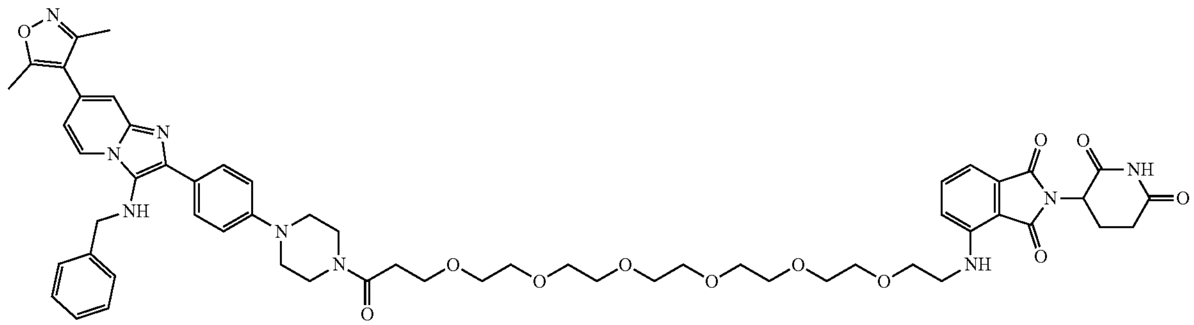

Compound 5 was prepared in an analogous manner to compound 1 in Example 1 using Int-1 and appropriate IMiD acid as a yellow powder (3.9 mg, 37% yield).

$^1$H NMR (500 MHz, DMSO-$d_6$) δ 11.09 (s, 1H), 8.65 (d, J=7.1 Hz, 1H), 7.86 (d, J=8.7 Hz, 2H), 7.76 (s, 1H), 7.60-7.56 (m, 1H), 7.50 (d, J=7.0 Hz, 1H), 7.35-7.22 (m, 5H), 7.14 (dd, J=8.8, 3.2 Hz, 3H), 7.04 (d, J=7.0 Hz, 1H), 6.60 (s, 1H), 5.91 (s, 1H), 5.05 (dd, J=12.8, 5.4 Hz, 1H), 4.16 (d, J=3.2 Hz, 2H), 3.68-3.59 (m, 10H), 3.57-3.49 (m, 21H), 3.35-3.26 (m, 6H), 2.88 (ddd, J=16.9, 13.8, 5.4 Hz, 1H), 2.65 (d, J=6.5 Hz, 4H), 2.54 (s, 3H), 2.34 (s, 3H), 2.05-1.99 (m, 1H).

MS (ESI) calcd. for $C_{57}H_{67}N_9O_{12}$: 1069.49, found: 536.10, 1070.94, and 1071.89.

Example 6: Synthesis of 4-((2-(2-(2-(3-(4-(4-(3-(benzylamino)-7-(3,5-dimethylisoxazol-4-yl)imidazo pyridin-2-yl)phenyl)piperazin-1-yl)-3-oxopropoxy) ethoxy)ethoxy)ethyl)amino)-2-(2,6-dioxopiperidin-3-yl)isoindoline-1,3-dione (6)

(6)

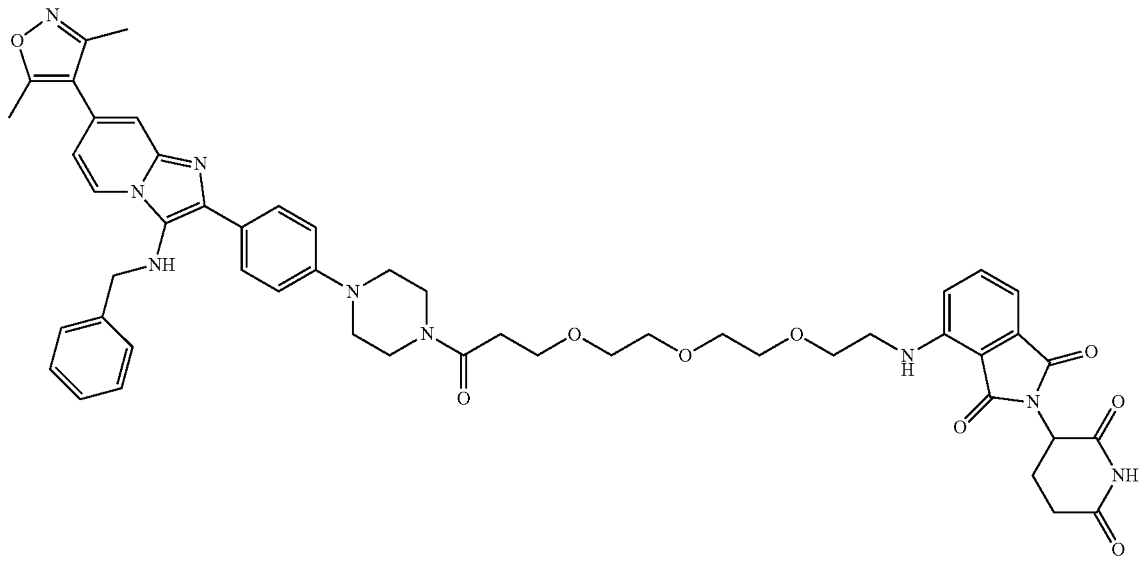

Compound 6 was prepared in an analogous manner to compound 1 in Example 1 using Int-1 and appropriate IMiD acid as a yellow powder (6.9 mg, 72% yield).

$^1$H NMR (500 MHz, DMSO-$d_6$) δ 11.10 (s, 1H), 8.65 (d, J=7.1 Hz, 1H), 7.86 (d, J=8.7 Hz, 2H), 7.78 (s, 1H), 7.60-7.54 (m, 1H), 7.51 (d, J=6.9 Hz, 1H), 7.35-7.23 (m, 5H), 7.13 (dd, J=8.7, 5.4 Hz, 3H), 7.03 (d, J=7.1 Hz, 1H), 6.59 (s, 1H), 5.92 (s, 1H), 5.05 (dd, J=12.7, 5.5 Hz, 1H), 4.16 (s, 2H), 3.48-3.25 (m, 22H), 2.88 (ddd, J=16.9, 13.8, 5.4 Hz, 1H), 2.66-2.55 (m, 4H), 2.54 (s, 3H), 2.35 (s, 3H), 2.02 (ddd, J=12.8, 5.8, 3.0 Hz, 1H).

MS (ESI) calcd. for $C_{53}H_{59}N_9O_{10}$: 937.41, found: 469.79, 470.51, 938.80, and 939.75.

Example 7: Synthesis of 4-(2-(4-(4-(3-(benzylamino)-7-(3,5-dimethylisoxazol-4-yl)imidazo[1,2-a]pyridin-2-yl)phenyl)piperazin-1-yl)-2-oxoethoxy)-2-(2,6-dioxopiperidin-3-yl)isoindoline-1,3-dione (7)

(7)

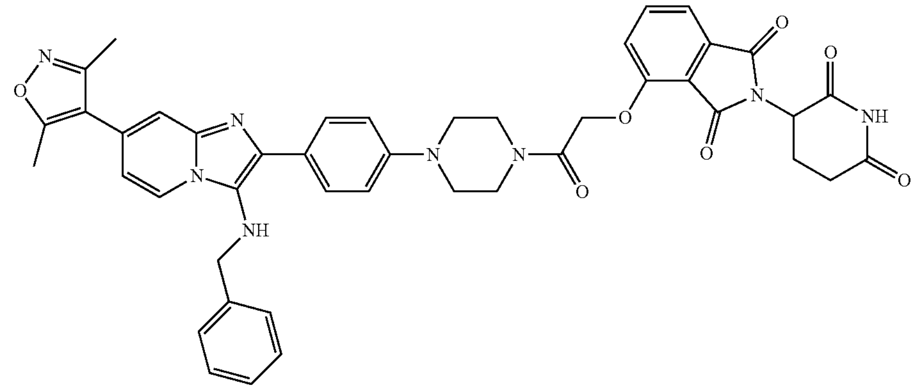

Compound 7 was prepared in an analogous manner to compound 1 in Example 1 using Int-1 and appropriate IMiD acid as a yellow powder (4.9 mg, 63% yield).

MS (ESI) calcd. for $C_{44}H_{40}N_8O_7$: 792.30, found: 793.64, 794.59.

Example 8: Synthesis of N-(4-(2-(3-(cyclohexylamino)-7-(3,5-dimethylisoxazol-4-yl)imidazo[1,2-a]pyridin-2-yl)ethyl)phenyl)-3-(2-(2-(2-((2-(2,6-dioxopiperidin-3-yl)-1,3-dioxoisoindolin-4-yl)amino)ethoxy)ethoxy)ethoxy)propanamide (8)

(8)

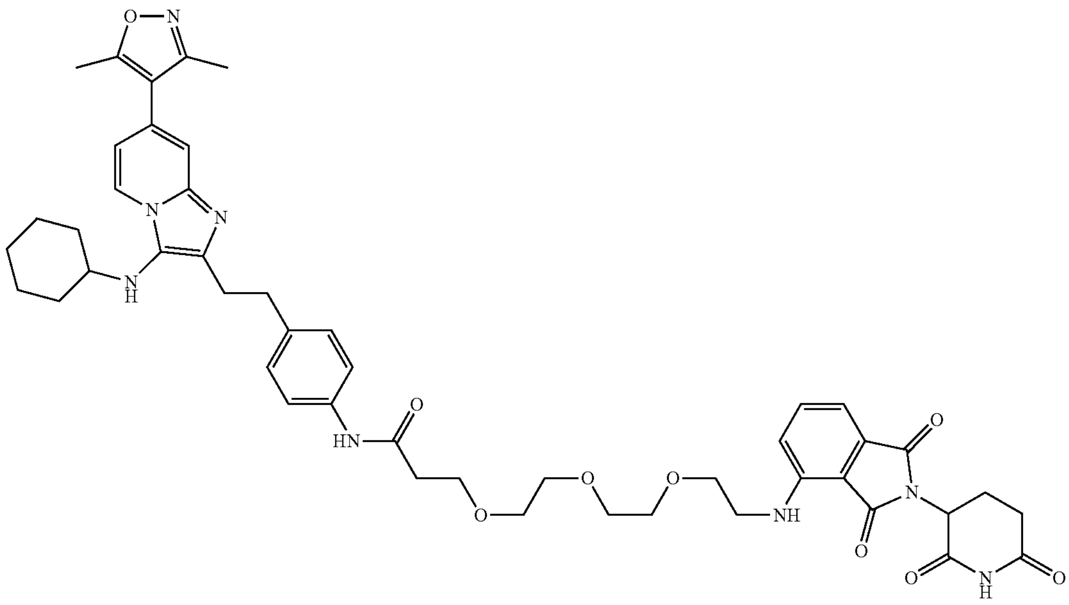

Compound 8 was prepared in an analogous manner to compound 1 in Example 1 using Int-3 and appropriate IMiD acid as a yellow powder (12 mg, 73% yield).

$^1$H NMR (500 MHz, Acetone-$d_6$) δ 10.16 (s, 1H), 9.11 (s, 1H), 8.50 (d, J=7.0 Hz, 1H), 7.67 (s, 1H), 7.61-7.50 (m, 4H), 7.24-7.19 (m, 1H), 7.16 (d, J=8.1 Hz, 2H), 7.11 (d, J=8.5 Hz, 1H), 7.04 (d, J=7.0 Hz, 1H), 6.60 (t, J=5.7 Hz, 1H), 5.09 (dd, J=12.6, 5.4 Hz, 1H), 3.79 (t, J=6.0 Hz, 2H), 3.72 (t, J=5.4 Hz, 3H), 3.63 (d, J=4.2 Hz, 8H), 3.52-3.49 (m, 2H), 3.15 (dd, J=8.7, 6.3 Hz, 2H), 3.07 (t, J=7.6 Hz, 2H), 2.99-2.93 (m, 1H), 2.87 (q, J=4.7, 4.1 Hz, 1H), 2.80-2.75 (m, 2H), 2.57 (t, J=6.0 Hz, 2H), 2.52 (s, 3H), 2.33 (s, 3H), 2.22 (dddd, J=10.2, 7.5, 5.4, 2.5 Hz, 1H), 1.87 (d, J=11.8 Hz, 2H), 1.74-1.69 (m, 2H), 1.35-1.21 (m, 6H).

Example 9: Synthesis of N-(4-(2-(3-(cyclohexylamino)-7-(3,5-dimethylisoxazol-4-yl)imidazo[1,2-a]pyridin-2-yl)ethyl)phenyl)-12-((2-(2,6-dioxopiperidin-3-yl)-1,3-dioxoisoindolin-4-yl)amino)dodecanamide (9)

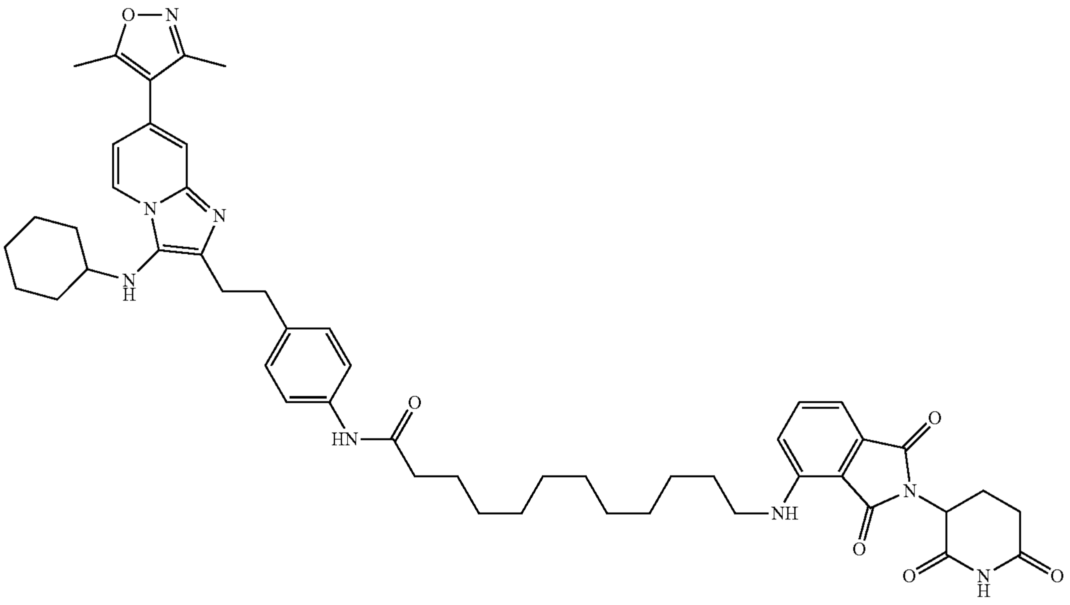

(9)

Compound 9 was prepared in an analogous manner to compound 1 in Example 1 using Int-3 and appropriate IMiD acid as a yellow powder (15 mg, 92% yield).

$^1$H NMR (500 MHz, Acetone-$d_6$) δ 10.15 (s, 1H), 9.05 (s, 1H), 8.22 (dd, J=7.0, 1.0 Hz, 1H), 7.62-7.56 (m, 3H), 7.40 (t, J=1.3 Hz, 1H), 7.15 (d, J=8.5 Hz, 2H), 7.09 (d, J=8.5 Hz, 1H), 7.04 (d, J=7.0 Hz, 1H), 6.85 (dd, J=7.0, 1.8 Hz, 1H), 6.42 (t, J=5.8 Hz, 1H), 5.08 (dd, J=12.6, 5.4 Hz, 1H), 3.38 (ddd, J=7.0, 3.0, 1.3 Hz, 2H), 3.08-3.00 (m, 4H), 2.99-2.93 (m, 2H), 2.89 (s, 3H), 2.83-2.74 (m, 4H), 2.49 (s, 3H), 2.32 (s, 3H), 2.22 (dddd, J=10.3, 5.3, 3.2, 1.5 Hz, 1H), 2.16 (t, J=7.5 Hz, 1H), 1.86-1.78 (m, 2H), 1.70 (td, J=10.5, 8.7, 5.6 Hz, 6H), 1.62-1.54 (m, 2H), 1.46-1.43 (m, 2H), 1.33 (s, 12H).

MS (ESI) calcd. for $C_{51}H_{62}N_8O_6$: 882.48, found: 883.39 [M+1], 884.37, 884.94.

Example 10: Synthesis of N-(4-(2-(3-(cyclohexylamino)-7-(3,5-dimethylisoxazol-4-yl)imidazo[1,2-a]pyridin-2-yl)ethyl)phenyl)-12-(2-((2-(2,6-dioxopiperidin-3-yl)-1,3-dioxoisoindolin-4-yl)oxy)acetamido)dodecanamide (10)

(10)

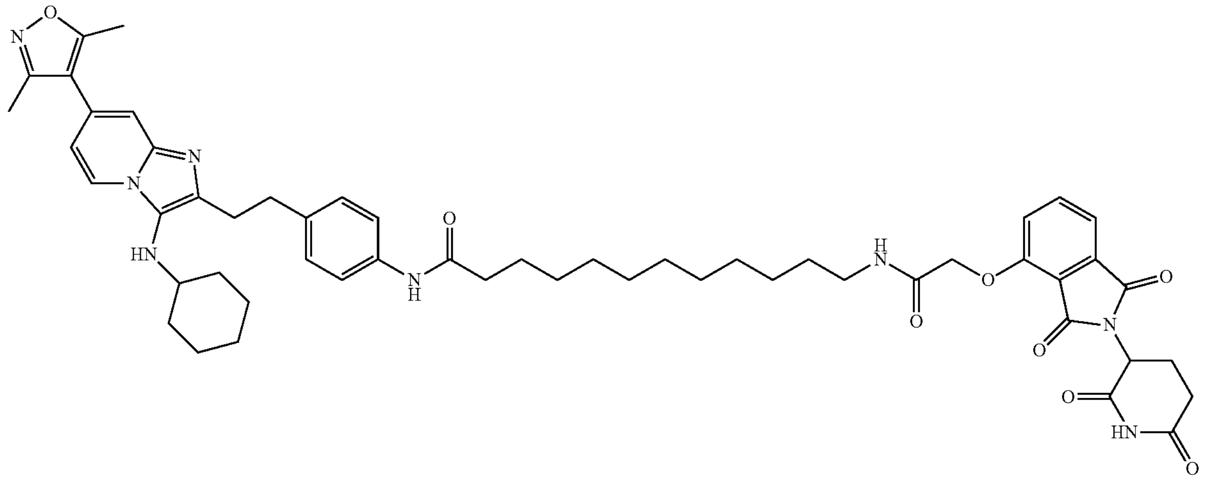

Compound 10 was prepared in an analogous manner to compound 1 in Example 1 using Int-3 and appropriate IMiD acid as a white powder (16 mg, 81% yield).

MS (ESI) calcd. for $C_{53}H_{64}N_8O_8$: 940.48, found: 941.75 [M+1], 942.70.

Example 11: Synthesis of N-(4-(2-(3-(cyclohexylamino)-7-(3,5-dimethylisoxazol-4-yl)imidazo[1,2-a]pyridin-2-yl)ethyl)phenyl)-6-((2-(2,6-dioxopiperidin-3-yl)-1,3-dioxoisoindolin-4-yl)amino)hexanamide (11)

(11)

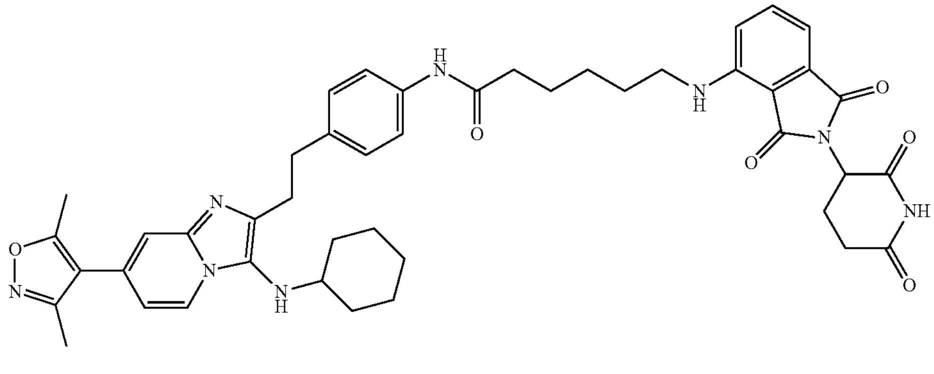

Compound 11 was prepared in an analogous manner to compound 1 in Example 1 using Int-3 and appropriate IMiD acid as a yellow powder (14 mg, 94% yield).

$^1$H NMR (500 MHz, Acetone-$d_6$) δ 9.92 (s, 1H), 9.09 (s, 1H), 8.72 (dd, J=7.2, 1.0 Hz, 1H), 7.91 (dd, J=1.7, 0.9 Hz, 1H), 7.58 (ddd, J=8.6, 4.5, 2.8 Hz, 3H), 7.52 (dd, J=7.1, 1.7 Hz, 1H), 7.22-7.15 (m, 2H), 7.10 (d, J=8.5 Hz, 1H), 7.03 (d, J=7.0 Hz, 1H), 6.43 (t, J=5.9 Hz, 1H), 5.08 (dd, J=12.6, 5.4 Hz, 1H), 3.43-3.38 (m, 2H), 3.27 (dd, J=8.3, 7.0 Hz, 2H), 3.13 (dd, J=8.5, 6.8 Hz, 2H), 3.02-2.93 (m, 1H), 2.92-2.85 (m, 1H), 2.83-2.73 (m, 2H), 2.55 (s, 3H), 2.40 (t, J=7.4 Hz, 2H), 2.35 (s, 3H), 2.25-2.17 (m, 1H), 1.93-1.86 (m, 2H), 1.74 (ddd, J=20.5, 11.6, 6.7 Hz, 6H), 1.51 (q, J=6.7 Hz, 4H), 1.31 (dd, J=10.8, 3.1 Hz, 2H), 1.23-1.17 (m, 2H).

MS (ESI) calcd. for $C_{45}H_{50}N_8O_6$: 798.39, found: 799.29 [M+1], 800.28, 800.85.

Example 12: Synthesis of N-(4-(2-(3-(cyclohexylamino)-7-(3,5-dimethylisoxazol-4-yl)imidazo[1,2-a]pyridin-2-yl)ethyl)phenyl)-2-((2-(2,6-dioxopiperidin-3-yl)-1,3-dioxoisoindolin-4-yl)oxy)acetamide (12)

(12)

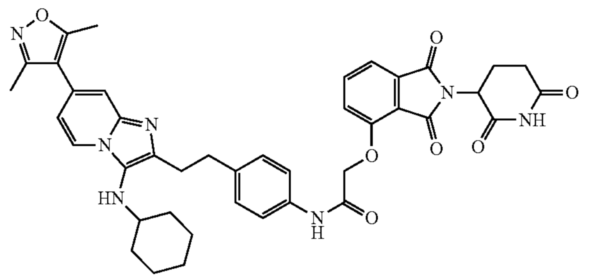

Compound 12 was prepared in an analogous manner to compound 1 in Example 1 using Int-3 and appropriate IMiD acid as a light yellow powder (16 mg, 9 9% yield).

$^1$H NMR (500 MHz, Acetone-$d_6$) δ 9.99 (s, 1H), 9.53 (s, 1H), 8.75-8.72 (m, 1H), 8.42 (dd, J=8.4, 1.4 Hz, 1H), 7.97-7.89 (m, 2H), 7.74-7.67 (m, 2H), 7.60 (dd, J=16.7, 7.9 Hz, 2H), 7.56-7.45 (m, 2H), 7.27 (d, J=8.2 Hz, 2H), 5.21 (dd, J=12.5, 5.4 Hz, 1H), 4.95 (s, 2H), 3.30 (t, J=7.6 Hz, 2H), 3.17 (t, J=7.6 Hz, 2H), 3.02 (dd, J=5.3, 3.3 Hz, 1H), 2.87-2.77 (m, 2H), 2.56 (s, 3H), 2.36 (s, 3H), 2.30 (ddd, J=10.4, 6.8, 4.3 Hz, 1H), 1.91 (dd, J=12.8, 3.8 Hz, 2H), 1.72 (dt, J=13.4, 3.2 Hz, 2H), 1.50 (t, J=6.3 Hz, 3H), 1.36-1.29 (m, 2H), 1.22 (ddd, J=12.0, 8.9, 2.6 Hz, 2H).

MS (ESI) calcd. for $C_{41}H_{41}N_7O_7$: 743.31, found: 744.27 [M+1], 744.80, 745.52.

Example 13: Synthesis of N-(4-(2-(3-(cyclohexylamino)-7-(3,5-dimethylisoxazol-4-yl)imidazo[1,2-a]pyridin-2-yl)ethyl)phenyl)-8-((2-(2,6-dioxopiperidin-3-yl)-1,3-dioxoisoindolin-4-yl)amino)octanamide (13)

(13)

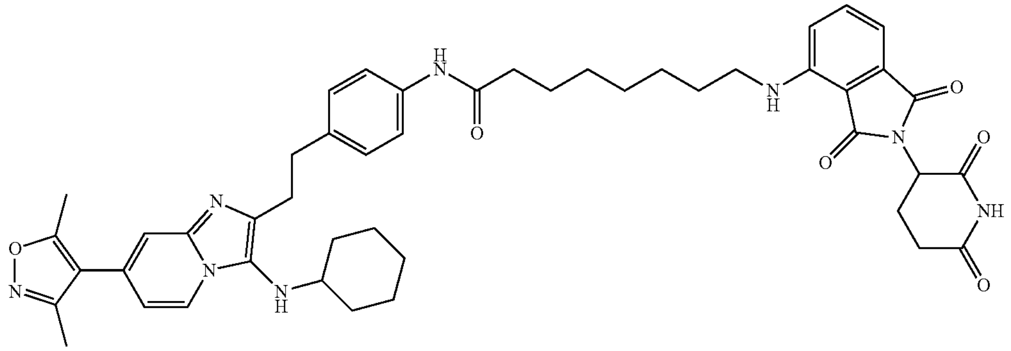

Compound 13 was prepared in an analogous manner to compound 1 in Example 1 using Int-3 and appropriate IMiD acid as a yellow powder (20 mg, 99% yield).

MS (ESI) calcd. for $C_{47}H_{54}N_8O_6$: 826.42, found: 827.68 [M+1], 828.63.

Example 14: Synthesis of N-(4-(2-(3-(cyclohexylamino)-7-(3,5-dimethylisoxazol-4-yl)imidazo[1,2-a]pyridin-2-yl)ethyl)phenyl)-6-((2-(2,6-dioxopiperidin-3-yl)-1,3-dioxoisoindolin-5-yl)amino)hexanamide (14)

(14)

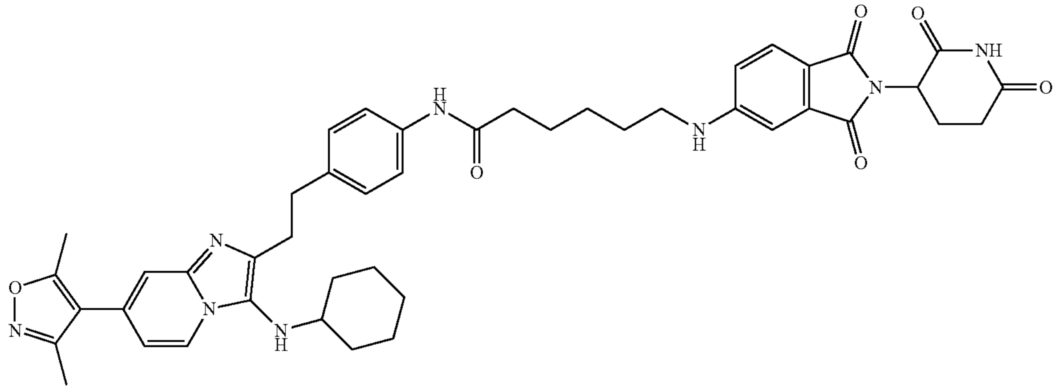

Compound 14 was prepared in an analogous manner to compound 1 in Example 1 using Int-3 and appropriate IMiD acid as a yellow powder (20 mg, 99% yield).

$^1$H NMR (500 MHz, Acetone-$d_6$) δ 9.97 (s, 1H), 9.09 (s, 1H), 8.64 (dd, J=7.1, 0.9 Hz, 1H), 7.83 (t, J=1.3 Hz, 1H), 7.56 (dd, J=8.4, 5.9 Hz, 3H), 7.42-7.39 (m, 1H), 7.20-7.15 (m, 2H), 7.01 (d, J=2.2 Hz, 1H), 6.92 (dd, J=8.4, 2.2 Hz, 1H), 6.34 (t, J=5.5 Hz, 1H), 5.06 (dd, J=12.6, 5.4 Hz, 1H), 3.34-3.28 (m, 2H), 3.23 (dd, J=8.3, 6.5 Hz, 2H), 3.11 (dd, J=8.6, 6.7 Hz, 2H), 3.02-2.92 (m, 1H), 2.83-2.74 (m, 2H), 2.54 (s, 3H), 2.39 (t, J=7.3 Hz, 2H), 2.34 (s, 3H), 2.18 (dddd, J=12.7, 7.6, 5.5, 2.5 Hz, 1H), 1.91-1.84 (m, 2H), 1.73 (dq, J=10.4, 6.9, 6.4 Hz, 6H), 1.55-1.49 (m, 2H), 1.32-1.26 (m, 5H), 1.21-1.15 (m, 2H).

MS (ESI) calcd. for $C_{45}H_{50}N_8O_6$: 798.39, found: 799.63 [M+1], 800.62.

Example 15: Synthesis of N1-(4-(2-(3-(cyclohexylamino)-7-(3,5-dimethylisoxazol-4-yl)imidazo[1,2-a]pyridin-2-yl)ethyl)phenyl)-N4-((R)-13-((2R,4S)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecyl)succinamide (15)

(15)

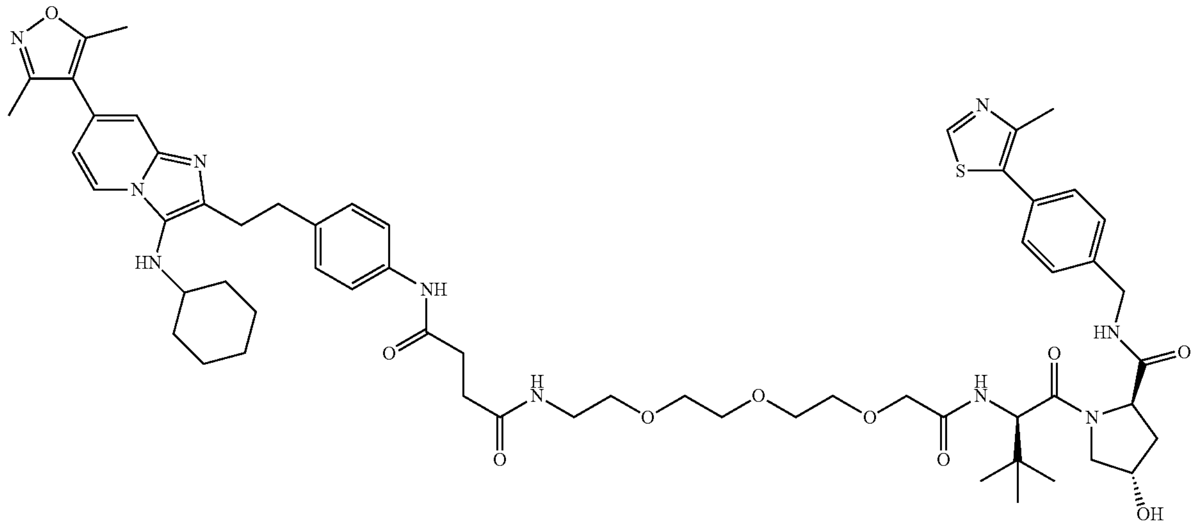

Compound 15 was prepared in an analogous manner to compound 1 in Example 1 using Int-3 and appropriate IMiD acid as a yellow powder (2.64 mg, 18% yield).

$^1$H NMR (500 MHz, Acetone-$d_6$) δ 9.49 (s, 1H), 8.85 (s, 1H), 8.55 (dd, J=4.4, 1.4 Hz, 1H), 8.32-8.26 (m, 2H), 7.69 (d, J=8.3 Hz, 2H), 7.57 (dd, J=12.1, 3.7 Hz, 2H), 7.49 (d, J=8.2 Hz, 2H), 7.43-7.41 (m, 2H), 7.36 (dd, J=8.4, 4.4 Hz, 2H), 6.94-6.87 (m, 1H), 4.75-4.68 (m, 2H), 4.61-4.55 (m, 2H), 4.38 (dd, J=15.4, 5.1 Hz, 1H), 4.03 (d, J=3.8 Hz, 2H), 3.88 (d, J=10.7 Hz, 1H), 3.81 (dd, J=10.8, 4.1 Hz, 1H), 3.73-3.67 (m, 4H), 3.65-3.60 (m, 4H), 3.54-3.50 (m, 2H), 3.35 (t, J=5.0 Hz, 2H), 3.16 (q, J=7.3 Hz, 2H), 2.68-2.65 (m, 2H), 2.58 (dd, J=6.5, 2.1 Hz, 2H), 2.53 (s, 3H), 2.48 (s, 3H), 2.35 (s, 3H), 1.78 (d, J=10.3 Hz, 2H), 1.62 (d, J=11.3 Hz, 2H), 1.35-1.28 (m, 10H), 1.04 (s, 9H).

MS (ESI) calcd. for $C_{60}H_{78}N_{10}O_{10}S$: 1130.56, found: 1129.82, 1130.81[M+1].

Example 16: Synthesis of N-(4-(2-(3-(cyclohexylamino)-7-(3,5-dimethylisoxazol-4-yl)imidazo[1,2-a]pyridin-2-yl)ethyl)phenyl)-1-((2-(2,6-dioxopiperidin-3-yl)-1,3-dioxoisoindolin-4-yl)amino)-3,6,9,12,15,18-hexaoxahenicosan-21-amide (16)

(16)

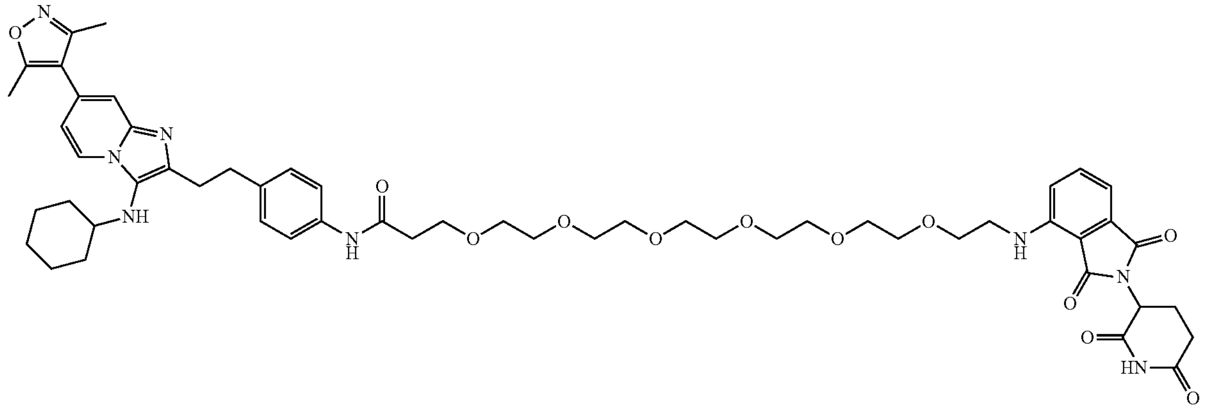

Compound 16 was prepared in an analogous manner to compound 1 in Example 1 using Int-3 and appropriate IMiD acid as a yellow powder (10 mg, 85% yield).

$^1$H NMR (500 MHz, Acetone-$d_6$) δ 9.15 (s, 1H), 8.35 (dd, J=7.0, 0.9 Hz, 1H), 7.61-7.56 (m, 3H), 7.54-7.51 (m, 1H), 7.21-7.17 (m, 2H), 7.13 (d, J=8.5 Hz, 1H), 7.07 (dd, J=12.4, 7.8 Hz, 2H), 7.02 (dd, J=7.0, 1.8 Hz, 1H), 6.62 (t, J=5.7 Hz, 1H), 5.09 (dd, J=12.7, 5.5 Hz, 1H), 3.80 (t, J=5.9 Hz, 2H), 3.76 (t, J=5.3 Hz, 2H), 3.67-3.55 (m, 28H), 2.99-2.93 (m, 2H), 2.80 (d, J=4.4 Hz, 2H), 2.61 (t, J=5.9 Hz, 2H), 2.51 (s, 3H), 2.33 (s, 3H), 2.25-2.20 (m, 1H), 1.87-1.83 (m, 2H), 1.74-1.70 (m, 2H), 1.51 (d, J=6.6 Hz, 4H).

MS (ESI) calcd. for $C_{54}H_{68}N_8O_{12}$: 1020.50, found: 1021.90[M+1], 1022.85.

Example 17: Synthesis of N-(4-(2-(3-(cyclohexylamino)-7-(3,5-dimethylisoxazol-4-yl)imidazo[1,2-a]pyridin-2-yl)ethyl)phenyl)-4-((2-(2,6-dioxopiperidin-3-yl)-1,3-dioxoisoindolin-4-yl)amino)cyclohexane-1-carboxamide (17)

(17)

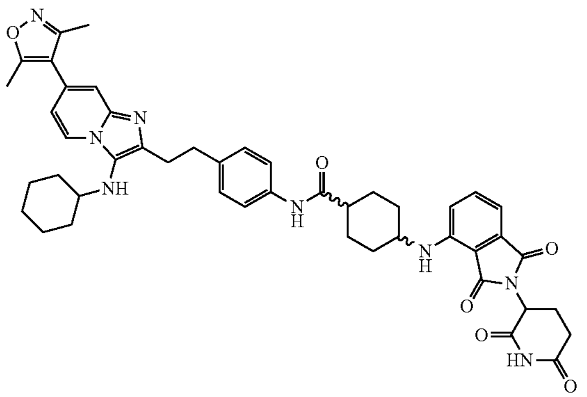

Compound 17 was prepared in an analogous manner to compound 1 in Example 1 using Int-3 and appropriate IMiD acid as a yellow powder (7.2 mg, 64% yield).

Example 18: Synthesis of N-(4-(2-(3-(cyclohexylamino)-7-(3,5-dimethylisoxazol-4-yl)imidazo[1,2-a]pyridin-2-yl)ethyl)phenyl)-4-(((2-(2,6-dioxopiperidin-3-yl)-1,3-dioxoisoindolin-4-yl)amino)methyl)benzamide (18)

(18)

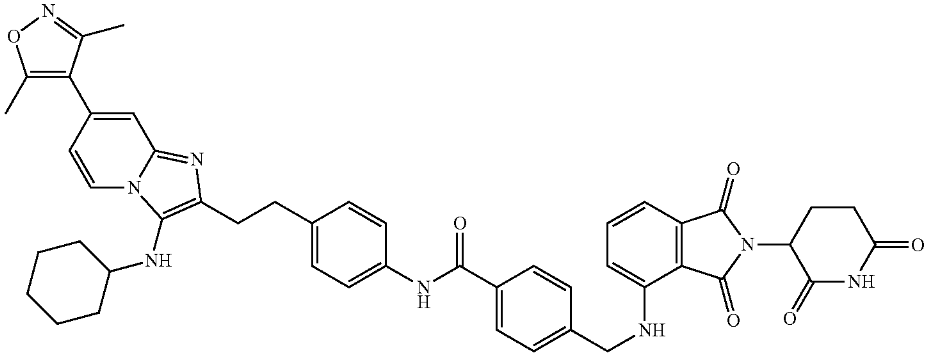

Compound 18 was prepared in an analogous manner to compound 1 in Example 1 using Int-3 and appropriate IMiD acid as a yellow powder (4.2 mg, 32% yield).

$^1$H NMR (500 MHz, Acetone-$d_6$) δ 9.99 (s, 1H), 9.46 (s, 1H), 8.25 (dd, J=7.0, 1.0 Hz, 1H), 7.99-7.94 (m, 2H), 7.77-7.72 (m, 2H), 7.60-7.51 (m, 3H), 7.41 (dd, J=1.7, 1.0 Hz, 1H), 7.25-7.21 (m, 2H), 7.10 (dd, J=14.2, 6.7 Hz, 2H), 7.02 (d, J=8.5 Hz, 1H), 6.88 (dd, J=7.0, 1.7 Hz, 1H), 5.11 (dd, J=12.6, 5.4 Hz, 1H), 4.77 (d, J=5.8 Hz, 2H), 3.08 (ddd, J=15.1, 6.3, 2.4 Hz, 4H), 2.85-2.76 (m, 4H), 2.50 (s, 3H), 2.33 (s, 3H), 2.28-2.20 (m, 1H), 1.87-1.83 (m, 2H), 1.75-1.67 (m, 2H), 1.33-1.21 (m, 6H).

MS (ESI) calcd. for $C_{47}H_{46}N_8O_6$: 818.35, found: 819.66 [M+1], 820.61.

Example 19: Synthesis of 5-((2-(2-(2-(3-(4-((S)-1-(2-(3-chloro-4-methoxyphenethyl)-5-(3,5-dimethylisoxazol-4-yl)-1H-benzo[d]imidazol-1-yl)propan-2-yl)piperazin-1-yl)-3-oxopropoxy)ethoxy)ethoxy)ethyl)amino)-2-(2,6-dioxopiperidin-3-yl)isoindoline-1,3-dione (19)

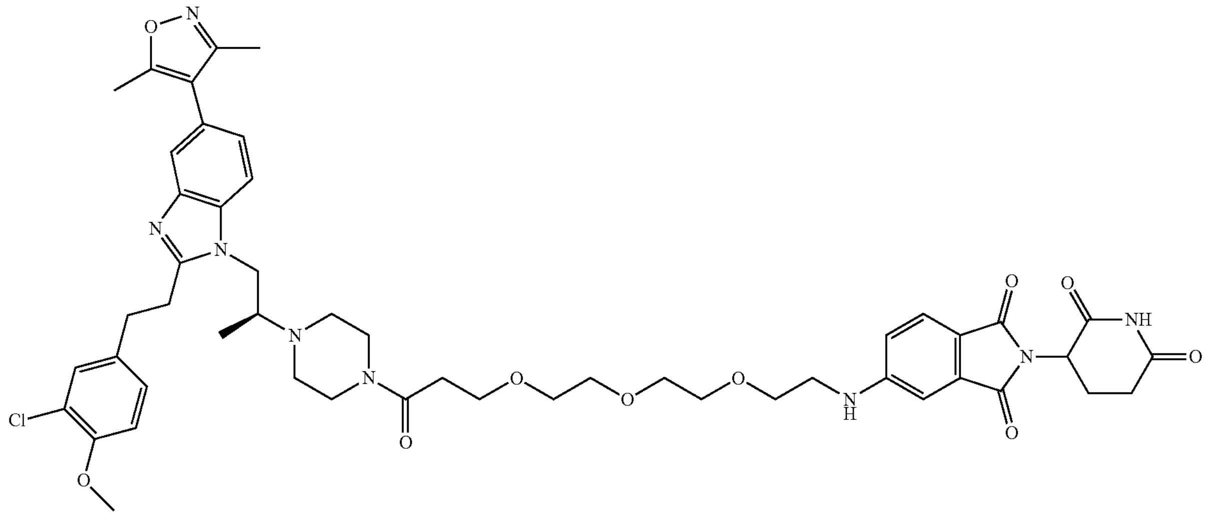

(19)

Compound 19 was prepared in an analogous manner to compound 1 in Example 1 using Int-4 and appropriate IMiD acid as a yellow powder (5 mg, 33% yield).

$^1$H NMR (500 MHz, Acetone-$d_6$) δ 10.03 (s, 1H), 7.61-7.54 (m, 3H), 7.41 (d, J=2.2 Hz, 1H), 7.27 (dd, J=8.4, 2.2 Hz, 1H), 7.19 (dd, J=8.3, 1.7 Hz, 1H), 7.13 (d, J=8.6 Hz, 1H), 7.04 (t, J=7.5 Hz, 2H), 6.63 (t, J=5.6 Hz, 1H), 5.08 (dd, J=12.7, 5.4 Hz, 1H), 4.36 (dd, J=14.9, 7.6 Hz, 1H), 4.10 (dd, J=14.9, 6.2 Hz, 1H), 3.87 (s, 3H), 3.74 (d, J=5.3 Hz, 2H), 3.69 (t, J=6.7 Hz, 2H), 3.66-3.60 (m, 4H), 3.57-3.52 (m, 4H), 3.41 (s, 4H), 3.27 (t, J=3.5 Hz, 4H), 3.14 (q, J=6.9 Hz, 1H), 3.01-2.94 (m, 2H), 2.80 (dd, J=4.3, 1.7 Hz, 2H), 2.77-2.75 (m, 2H), 2.54 (t, J=6.7 Hz, 2H), 2.43 (s, 3H), 2.39 (d, J=5.7 Hz, 1H), 2.27 (s, 3H), 2.21 (ddd, J=9.4, 4.7, 2.6 Hz, 1H), 1.30 (d, J=1.8 Hz, 2H), 1.04 (d, J=6.8 Hz, 3H).

MS (ESI) calcd. for $C_{50}H_{59}ClN_8O_{10}$: 966.40, found: 967.33[M+1], 969.61, 970.41.

Example 20: Synthesis of 5-((10-(4-((S)-1-(2-(3-chloro-4-methoxyphenethyl)-5-(3,5-dimethylisoxazol-4-yl)-1H-benzo[d]imidazol-1-yl)propan-2-yl)piperazin-1-yl)-10-oxodecyl)amino)-2-(2,6-dioxopiperidin-3-yl)isoindoline-1,3-dione (20)

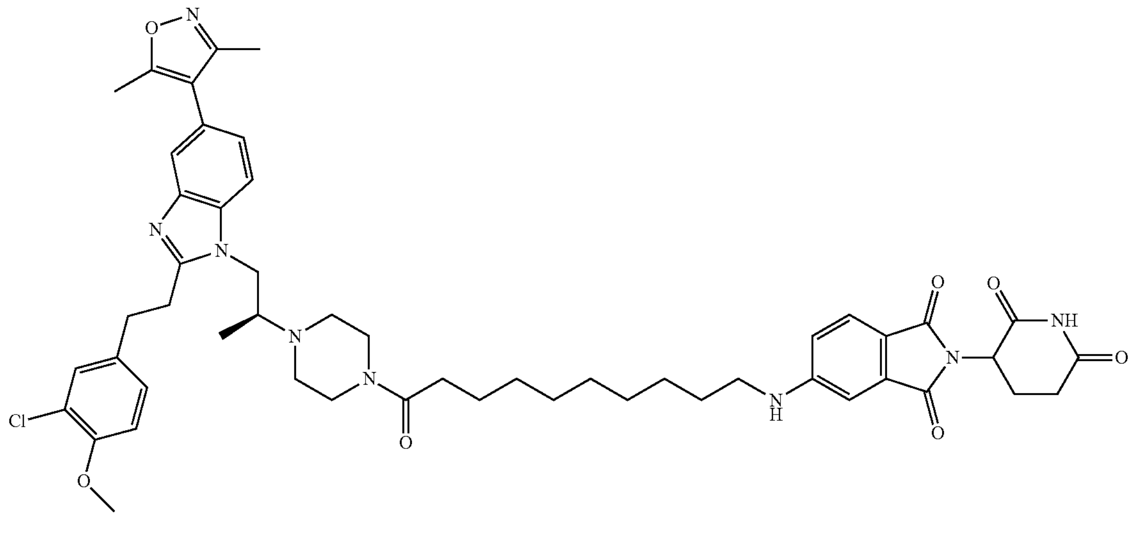

(20)

Compound 20 was prepared in an analogous manner to compound 1 in Example 1 using Int-4 and appropriate IMiD acid as a yellow powder (14 mg, 96% yield).

MS (ESI) calcd. for $C_{51}H_{61}ClN_8O_7$: 932.44, found: 933.55[M+1], 935.52.

Example 21: Synthesis of 5-((6-(4-((S)-1-(2-(3-chloro-4-methoxyphenethyl)-5-(3,5-dimethylisoxazol-4-yl)-1H-benzo[d]imidazol-1-yl)propan-2-yl)piperazin-1-yl)-6-oxohexyl)amino)-2-(2,6-dioxopiperidin-3-yl)isoindoline-1,3-dione (21)

(21)

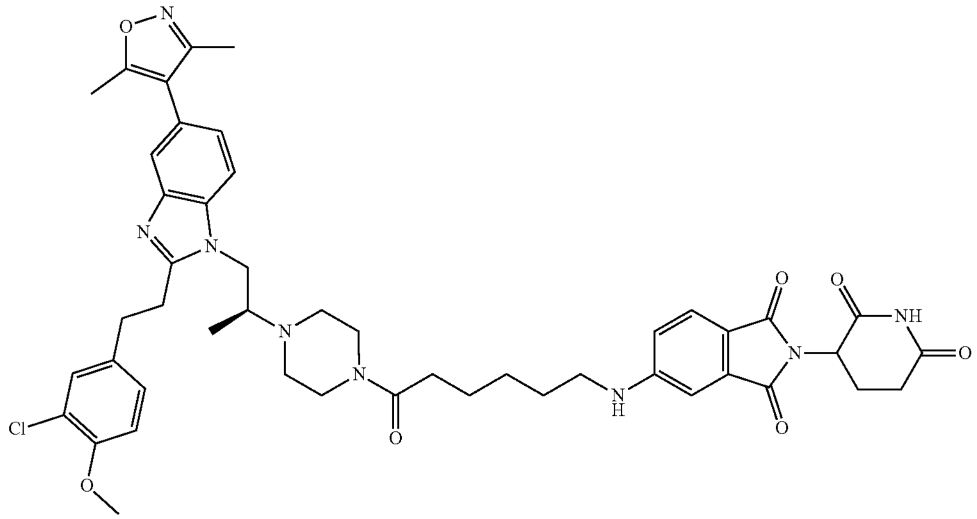

Compound 21 was prepared in an analogous manner to compound 1 in Example 1 using Int-4 and appropriate IMiD acid as a yellow powder (11 mg, 80% yield).

$^1$H NMR (500 MHz, Acetone-$d_6$) δ 10.01 (s, 1H), 7.59 (ddd, J=4.3, 2.1, 1.2 Hz, 2H), 7.57-7.54 (m, 1H), 7.41 (d, J=2.1 Hz, 1H), 7.27 (dd, J=8.4, 2.3 Hz, 1H), 7.19 (dd, J=8.3, 1.7 Hz, 1H), 7.10 (d, J=8.5 Hz, 1H), 7.05-7.01 (m, 2H), 6.42 (t, J=5.9 Hz, 1H), 5.08 (dd, J=12.6, 5.4 Hz, 1H), 4.36 (dd, J=14.9, 7.6 Hz, 1H), 4.11 (dd, J=14.9, 6.1 Hz, 1H), 3.87 (s, 3H), 3.45 (d, J=6.3 Hz, 1H), 3.40-3.37 (m, 4H), 3.29-3.24 (m, 4H), 3.15-3.12 (m, 1H), 3.01-2.92 (m, 2H), 2.83-2.78 (m, 2H), 2.77-2.67 (m, 4H), 2.43 (s, 3H), 2.34 (t, J=7.4 Hz, 2H), 2.26 (s, 3H), 2.24-2.19 (m, 1H), 1.75-1.69 (m, 2H), 1.66-1.61 (m, 2H), 1.48 (td, J=8.4, 4.2 Hz, 2H), 1.04 (d, J=6.8 Hz, 3H).

MS (ESI) calcd. for $C_{47}H_{53}ClN_8O_7$: 876.37, found: 877.46[M+1], 878.37, 879.43.

Example 22: Synthesis of N-(4-(2-(5-(3,5-dimethylisoxazol-4-yl)-1-(2-morpholinoethyl)-1H-benzo[d]imidazol-2-yl)ethyl)phenyl)-3-(2-(2-(2-((2-(2,6-dioxopiperidin-3-yl)-1,3-dioxoisoindolin-4-yl)amino)ethoxy)ethoxy)ethoxy)propanamide (22)

(22)

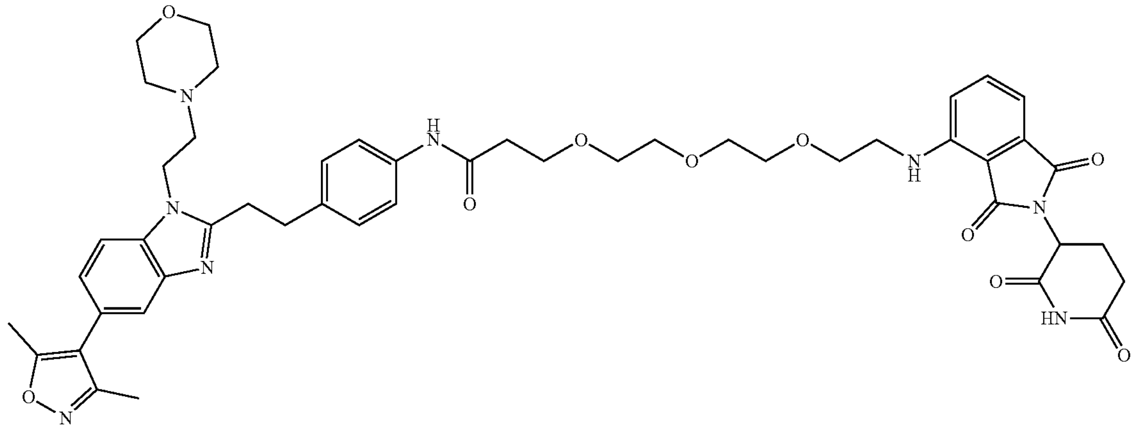

Compound 22 was prepared in an analogous manner to compound 1 in Example 1 using Int-5 and appropriate IMiD acid as a yellow powder (3.7 mg, 23% yield).

$^1$H NMR (500 MHz, Acetone-$d_6$) δ 10.09 (s, 1H), 9.08 (s, 1H), 7.62-7.57 (m, 5H), 7.26 (d, J=8.5 Hz, 2H), 7.20 (dd, J=8.2, 1.6 Hz, 1H), 7.11 (d, J=8.5 Hz, 1H), 7.04 (d, J=7.0 Hz, 1H), 6.61 (t, J=5.5 Hz, 1H), 5.08 (dd, J=12.6, 5.5 Hz, 1H), 4.34 (t, J=6.5 Hz, 2H), 3.79 (t, J=6.0 Hz, 2H), 3.72 (t, J=5.2 Hz, 2H), 3.63 (h, J=2.1 Hz, 8H), 3.57 (t, J=4.6 Hz, 4H), 3.52-3.49 (m, 2H), 3.30-3.23 (m, 4H), 2.97-2.94 (m, 2H), 2.80-2.77 (m, 2H), 2.68 (t, J=6.5 Hz, 2H), 2.57 (t, J=6.0 Hz, 2H), 2.48 (s, 2H), 2.43 (s, 3H), 2.26 (s, 3H), 2.24-2.20 (m, 1H).

MS (ESI) calcd. for $C_{48}H_{56}N_8O_{10}$: 904.41, found: 905.65 [M+1], 906.60.

Example 23: Synthesis of N-(4-(2-(5-(3,5-dimethylisoxazol-4-yl)-1-(2-morpholinoethyl)-1H-benzo[d]imidazol-2-yl)ethyl)phenyl)-12-((2-(2,6-dioxopiperidin-3-yl)-1,3-dioxoisoindolin-4-yl)amino)dodecanamide (23)

(23)

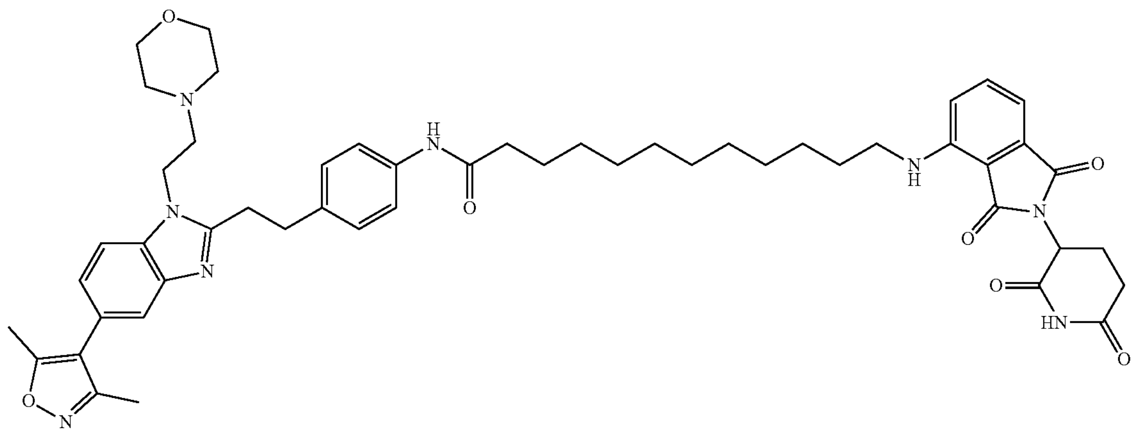

Compound 23 was prepared in an analogous manner to compound 1 in Example 1 using Int-5 and appropriate IMiD acid as a yellow powder (3.2 mg, 34% yield).

$^1$H NMR (500 MHz, Acetone-$d_6$) δ 9.96 (s, 1H), 9.03 (s, 1H), 7.62-7.57 (m, 5H), 7.28-7.24 (m, 2H), 7.21 (dd, J=8.2, 1.6 Hz, 1H), 7.10 (d, J=8.5 Hz, 1H), 7.04 (d, J=7.1 Hz, 1H), 6.43 (t, J=5.7 Hz, 1H), 5.08 (dd, J=12.6, 5.4 Hz, 1H), 4.37 (t, J=6.4 Hz, 2H), 4.03 (p, J=6.6 Hz, 2H), 3.58 (t, J=4.6 Hz, 4H), 3.51 (q, J=7.3 Hz, 2H), 3.41-3.37 (m, 2H), 3.33-3.28 (m, 2H), 3.27-3.23 (m, 2H), 2.99-2.95 (m, 2H), 2.80-2.76 (m, 2H), 2.70 (t, J=6.4 Hz, 2H), 2.43 (s, 3H), 2.35 (t, J=7.4 Hz, 2H), 2.26 (s, 3H), 2.22 (ddt, J=13.0, 5.6, 2.8 Hz, 1H), 1.70 (dt, J=3.9, 7.0 Hz, 4H), 1.51 (t, J=6.5 Hz, 11H), 1.48-1.42 (m, 3H).

MS (ESI) calcd. for $C_{51}H_{62}N_8O_7$: 898.47, found: 899.73 [M+1], 900.64.

Example 24: Synthesis of N-(4-(2-(5-(3,5-dimethylisoxazol-4-yl)-1-(2-morpholinoethyl)-1H-benzo[d]imidazol-2-yl)ethyl)phenyl)-12-(2-((2-(2,6-dioxopiperidin-3-yl)-1,3-dioxoisoindolin-4-yl)oxy)acetamido)dodecanamide (24)

(24)

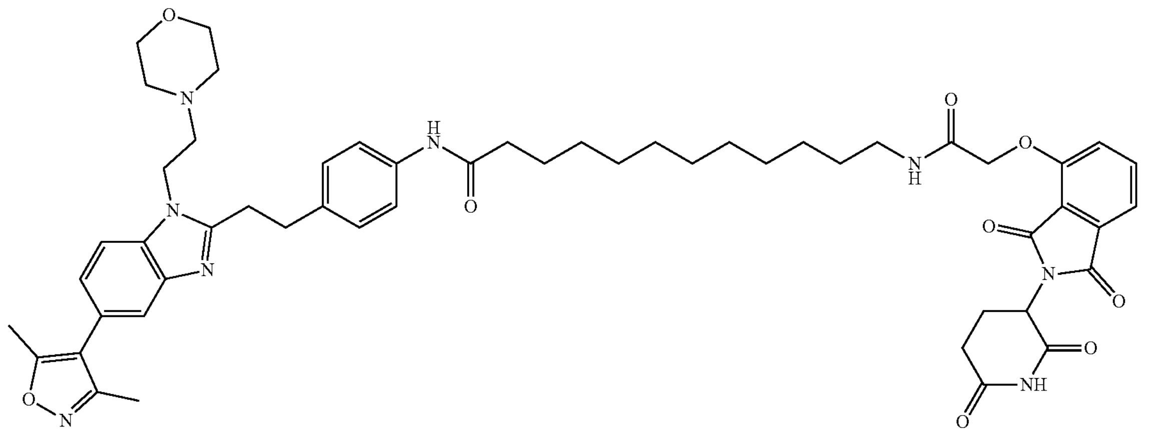

Compound 24 was prepared in an analogous manner to compound 1 in Example 1 using Int-5 and appropriate IMiD acid as a yellow powder (4.1 mg, 24% yield).

MS (ESI) calcd. for $C_{53}H_{64}N_8O_9$: 956.48, found: 957.71 [M+1], 958.66.

Example 25: Synthesis of N-(4-(2-(5-(3,5-dimethylisoxazol-4-yl)-1-(2-morpholinopropyl)-1H-benzo[d]imidazol-2-yl)ethyl)phenyl)-6-((2-(2,6-dioxopiperidin-3-yl)-1,3-dioxoisoindolin-4-yl)amino)hexanamide (25)

(25)

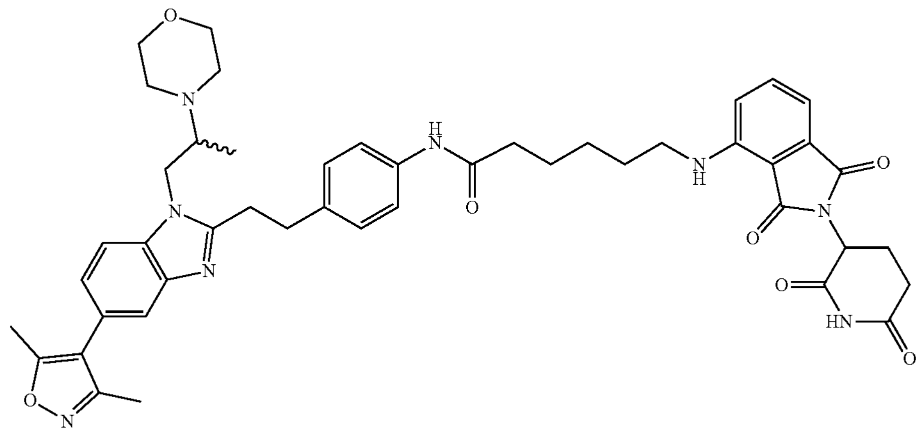

Compound 25 was prepared in an analogous manner to compound 1 in Example 1 using Int-6 and appropriate IMiD acid as a yellow powder (10.7 mg, 59% yield).

$^1$H NMR (500 MHz, Acetone-$d_6$) δ 10.01 (s, 1H), 9.09 (s, 1H), 7.63-7.56 (m, 5H), 7.29-7.24 (m, 2H), 7.23 (dd, J=8.3, 1.6 Hz, 1H), 7.10 (d, J=8.5 Hz, 1H), 7.03 (d, J=7.0 Hz, 1H), 6.44 (t, J=5.9 Hz, 1H), 5.08 (dd, J=12.6, 5.4 Hz, 1H), 4.39 (dd, J=14.9, 7.5 Hz, 1H), 4.12 (dd, J=14.9, 6.3 Hz, 1H), 3.53 (t, J=4.6 Hz, 4H), 3.43-3.38 (m, 2H), 3.36-3.30 (m, 2H), 3.30-3.25 (m, 2H), 3.06 (q, J=6.8 Hz, 1H), 3.01-2.92 (m, 1H), 2.81-2.78 (m, 1H), 2.78-2.71 (m, 3H), 2.46 (t, J=5.3 Hz, 1H), 2.42 (s, 3H), 2.40 (t, J=7.3 Hz, 2H), 2.26 (s, 3H), 2.24-2.18 (m, 1H), 1.75 (ddd, J=14.6, 11.6, 7.3 Hz, 4H), 1.56-1.48 (m, 3H), 1.07 (d, J=6.8 Hz, 3H).

MS (ESI) calcd. for $C_{46}H_{52}N_8O_7$: 828.40, found: 829.62 [M+1], 830.53.

Example 26: Synthesis of N-(4-(2-(5-(3,5-dimethylisoxazol-4-yl)-1-(2-morpholinopropyl)-1H-benzo[d]imidazol-2-yl)ethyl)phenyl)-8-((2-(2,6-dioxopiperidin-3-yl)-1,3-dioxoisoindolin-4-yl)amino)octanamide (26)

(26)

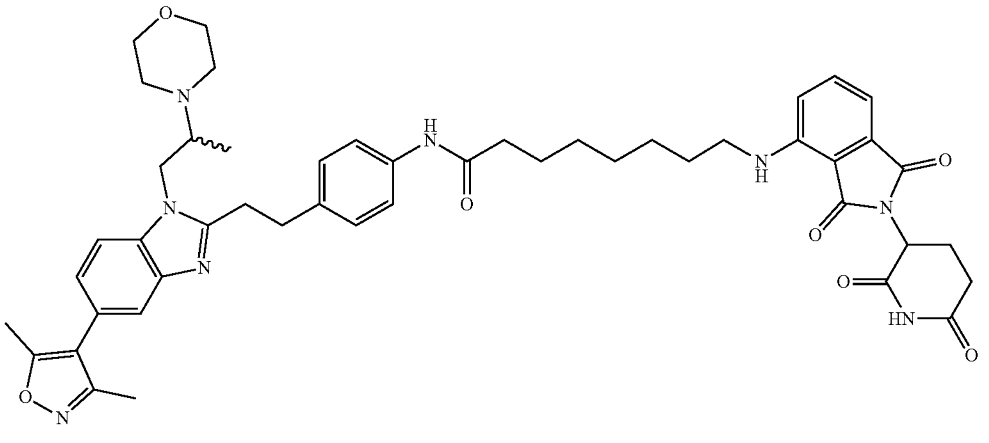

Compound 26 was prepared in an analogous manner to compound 1 in Example 1 using Int-6 and appropriate IMiD acid as a yellow powder (13.4 mg, 72% yield).

MS (ESI) calcd. for $C_{48}H_{56}N_8O_7$: 856.43, found: 857.66 [M+1], 858.65.

Example 27: Synthesis of N-(4-(2-(5-(3,5-dimethylisoxazol-4-yl)-1-(2-morpholinopropyl)-1H-benzo[d]imidazol-2-yl)ethyl)phenyl)-3-(2-(2-(2-((2-(2,6-dioxopiperidin-3-yl)-1,3-dioxoisoindolin-4-yl)amino)ethoxy)ethoxy)ethoxy)propanamide (27)

(27)

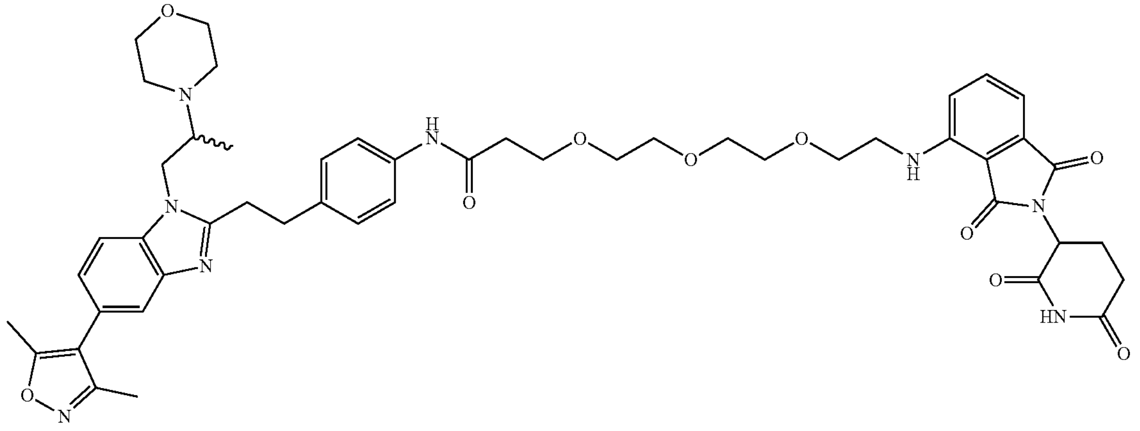

Compound 27 was prepared in an analogous manner to compound 1 in Example 1 using Int-6 and appropriate IMiD acid as a yellow powder (14 mg, 70% yield).

$^1$H NMR (500 MHz, Acetone-$d_6$) δ 10.05 (s, 1H), 9.14 (s, 1H), 7.74-7.67 (m, 2H), 7.57 (td, J=7.2, 3.6 Hz, 3H), 7.31 (dd, J=8.4, 1.5 Hz, 1H), 7.25 (d, J=8.1 Hz, 2H), 7.10 (d, J=8.6 Hz, 1H), 7.03 (d, J=7.1 Hz, 1H), 6.60 (s, 1H), 5.08 (dd, J=12.7, 5.4 Hz, 1H), 4.50 (dd, J=14.8, 7.5 Hz, 1H), 4.25 (dd, J=14.8, 6.5 Hz, 1H), 3.80 (t, J=6.0 Hz, 2H), 3.72 (t, J=5.3 Hz, 2H), 3.63 (s, 8H), 3.58 (s, 4H), 3.50 (q, J=5.4 Hz, 2H), 3.44-3.39 (m, 2H), 3.28 (t, J=7.7 Hz, 2H), 3.17 (q, J=6.8 Hz, 1H), 3.00-2.91 (m, 1H), 2.88-2.81 (m, 2H), 2.80-2.73 (m, 2H), 2.58 (t, J=5.9 Hz, 4H), 2.43 (s, 3H), 2.26 (s, 3H), 2.23-2.19 (m, 1H), 1.12 (d, J=6.8 Hz, 3H).

MS (ESI) calcd. for $C_{49}H_{58}N_8O_{10}$: 918.43, found: 919.68 [M+1], 920.85.

Example 28: Synthesis of N-(2-((4-(2-(5-(3,5-dimethylisoxazol-4-yl)-1-(2-morpholinopropyl)-1H-benzo[d]imidazol-2-yl)ethyl)phenyl)amino)ethyl)-6-((2-(2,6-dioxopiperidin-3-yl)-1,3-dioxoisoindolin-4-yl)amino)hexanamide (28)

(28)

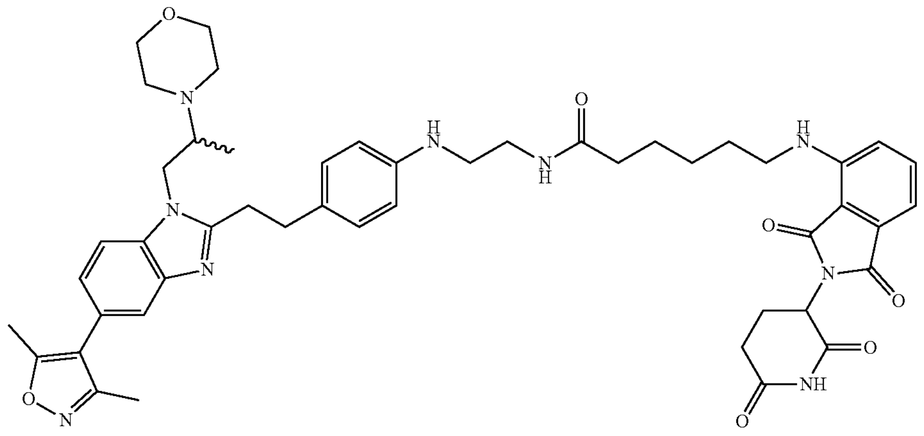

Compound 28 was prepared in an analogous manner to compound 1 in Example 1 using Int-6 and appropriate IMiD acid as a yellow powder (5.9 mg, 34% yield).

$^1$H NMR (500 MHz, Acetone-$d_6$) δ 10.06 (s, 1H), 7.61-7.56 (m, 2H), 7.54 (d, J=8.2 Hz, 1H), 7.27-7.21 (m, 1H), 7.17 (dd, J=8.2, 1.6 Hz, 1H), 7.09-7.02 (m, 4H), 6.57 (d, J=8.4 Hz, 2H), 6.41 (t, J=5.8 Hz, 1H), 5.07 (dd, J=12.6, 5.5 Hz, 1H), 4.29 (dd, J=14.9, 7.2 Hz, 1H), 4.03 (dd, J=14.9, 6.4 Hz, 1H), 3.54 (t, J=4.6 Hz, 4H), 3.42 (q, J=6.3 Hz, 2H), 3.37-3.33 (m, 2H), 3.24-3.15 (m, 4H), 3.14-3.10 (m, 2H), 3.02 (q, J=6.8 Hz, 1H), 2.97-2.92 (m, 1H), 2.80-2.75 (m, 2H), 2.70 (dt, J=11.2, 4.6 Hz, 2H), 2.46 (d, J=4.6 Hz, 1H), 2.43 (s, 3H), 2.27 (s, 3H), 2.24-2.16 (m, 4H), 1.69 (dt, J=9.1, 7.3 Hz, 4H), 1.46 (tt, J=7.0, 1.9 Hz, 2H), 1.03 (d, J=6.8 Hz, 3H).

MS (ESI) calcd. for $C_{48}H_{57}N_9O_7$: 871.44, found: 872.63 [M+1], 873.58.

Example 29: Synthesis of N-((1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexyl)-10-((2-(2,6-dioxopiperidin-3-yl)-1,3-dioxoisoindolin-4-yl)amino)decanamide (29)

(29)

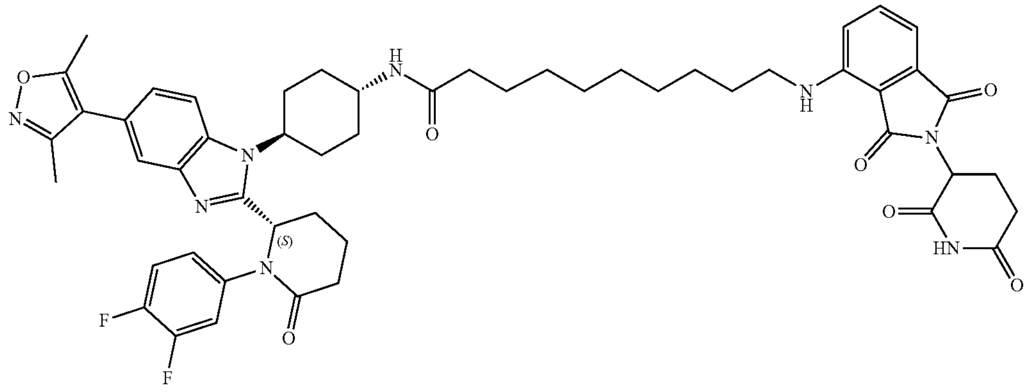

Compound 29 was prepared in an analogous manner to compound 1 in Example 1 using Int-7 and appropriate IMiD acid as a yellow powder (12 mg, 44% yield).

MS (ESI) calcd. for $C_{52}H_{58}F_2N_8O_7$: 944.44, found: 945.55[M+1], 946.54.

Example 30: Synthesis of N-((1S,4r)-4-(2-((S)-1-(3,4-difluorophenyl)-6-oxopiperidin-2-yl)-5-(3,5-dimethylisoxazol-4-yl)-1H-benzo[d]imidazol-1-yl)cyclohexyl)-6-((2-(2,6-dioxopiperidin-3-yl)-1,3-dioxoisoindolin-4-yl)amino)hexanamide (30)

(30)

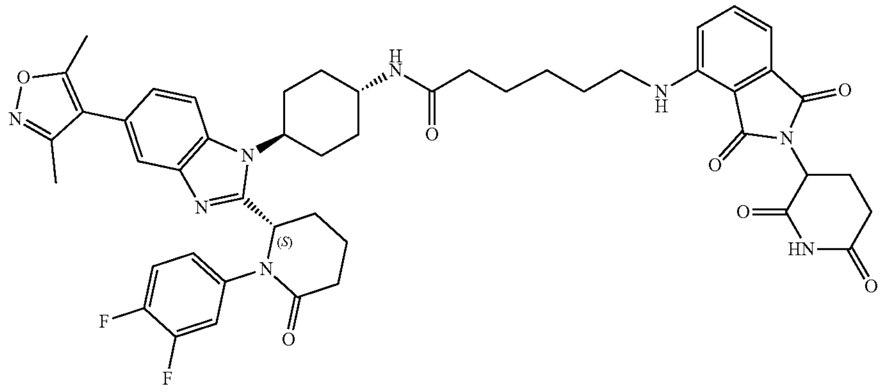

Compound 30 was prepared in an analogous manner to compound 1 in Example 1 using Int-7 and appropriate IMiD acid as a yellow powder (15 mg, 59% yield).

MS (ESI) calcd. for: $C_{48}H_{50}F_2N_8O_7$: 888.38, found: 889.50[M+1], 890.38.

Example 31: Synthesis of 2-(2,6-dioxopiperidin-3-yl)-4-((10-(4-(1-methyl-5-((R)-4-methyl-2-oxo-2,3,4,5-tetrahydro-1H-benzo[b][1,4]diazepin-6-yl)-1H-indazol-3-yl)-1H-pyrazol-1-yl)-10-oxodecyl)amino)isoindoline-1,3-dione (31)

(31)

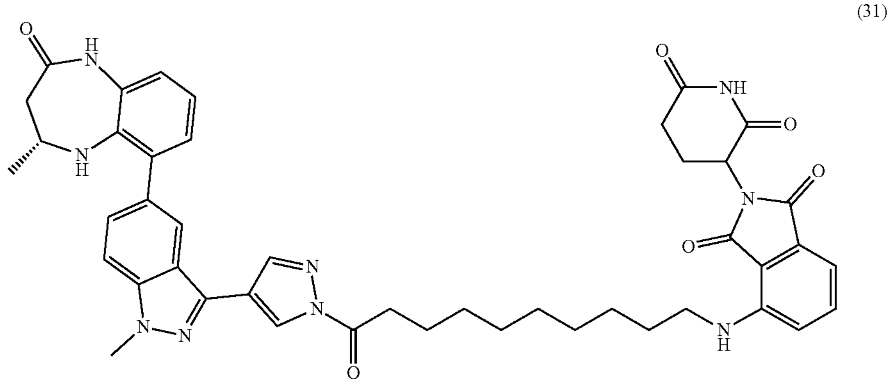 [SMILES: C[C@@H]1CC(=O)Nc2cccc(-c3ccc4c(c3)c(-c3cnn(C(=O)CCCCCCCCCNc5cccc6c5C(=O)N(C5CCC(=O)NC5=O)C6=O)c3)nn4C)c2N1]

Compound 31 was prepared in an analogous manner to compound 1 in Example 1 using Int-8 and appropriate IMiD acid as a yellow powder (5.32 mg, 17% yield). MS (ESI) calcd. for $C_{44}H_{47}N_9O_6$: 797.36, found: 798.46[M+1], 799.37.

Example 32: Cellular Degradation Assay with Inventive Compounds (ATPlite™)

Kelly Neuroblastoma cells were seeded at 1,000 cells per well in 384 well, white plates and were treated in a dose-dependent manner for 72 h. Using ATPlite™ Luminescence Assay System (Perkin Elmer, catalog no. 6016943), cells were assessed for viability as a measure of their luminescence and normalized to DMSO treated control cells.

The results illustrated in FIG. 2 show that relative to histone acetyltransferase (HAT) p300 inhibitor, A485, and the cereblon binders, Lenalidomide, Thalidomide, and Pomalidomide, bispecific compound 2 killed Kelly Neuroblastoma cells in a dose-dependent and more potent manner at 72 h. The $IC_{50}$ of bispecific compound 2 was about 10-fold more potent than A485 (Table 1).

TABLE 1

| Compound | $IC_{50}$ |
|---|---|
| (2) | 91.83 ± 6.584 nM |

Figure 4:
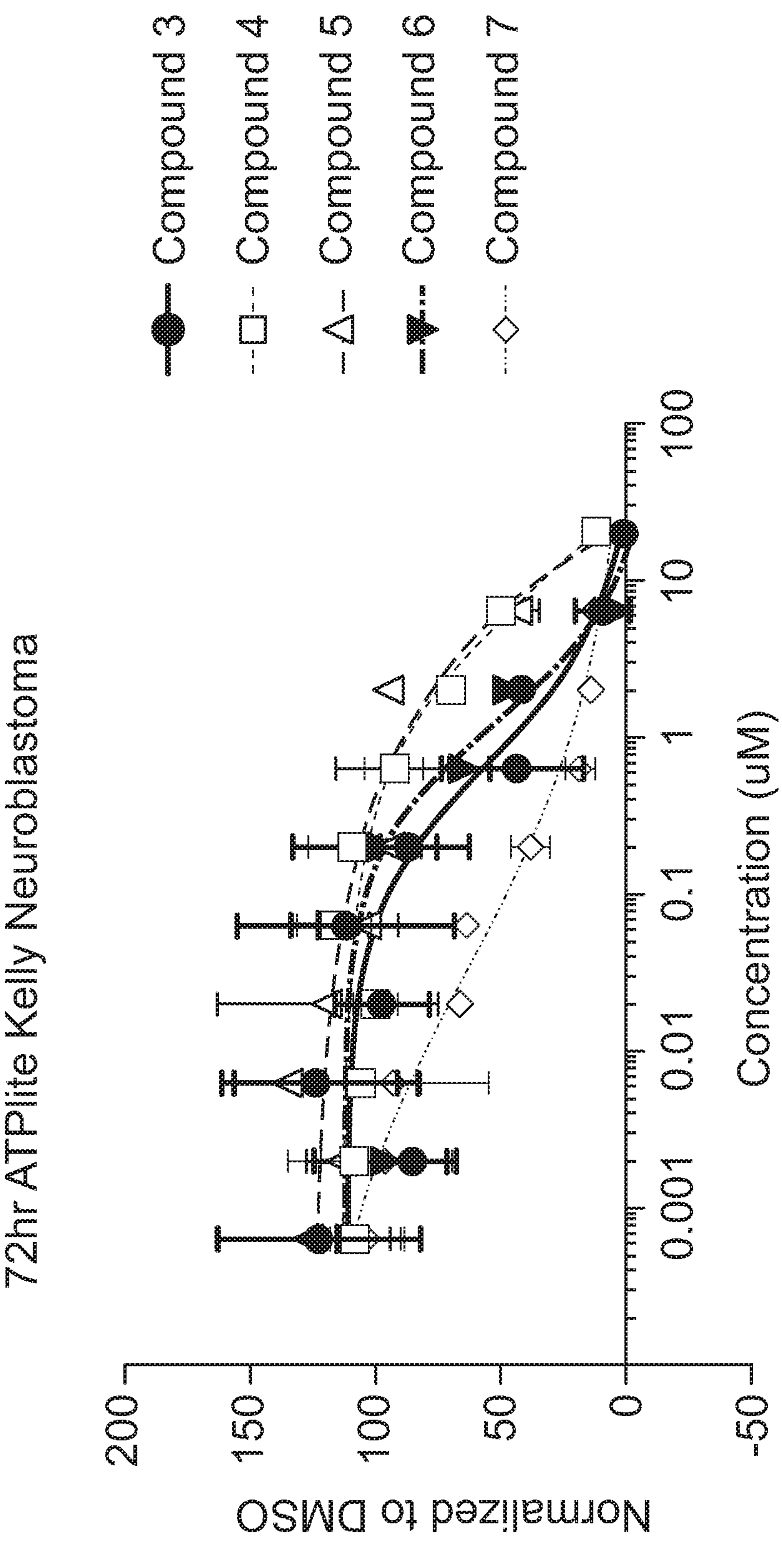
FIG. 4 is a graph that shows relative cell growth after a 72-hour treatment of Kelly neuroblastoma cell lines with bispecific compounds 3, 4, 5, 6, and 7 by ATPlite™ Luminescence Assay.

The results illustrated in FIG. 4 show that bispecific compounds 3, 6 and 7 were potent inhibitors of Kelly Neuroblastoma cell proliferation at 72 h. $IC_{50}$ values of bispecific compounds 3, 6 and 7 were in the micromolar and sub-micromolar range (Table 2).

TABLE 2

| | Compound 3 | Compound 6 | Compound 7 |
|---|---|---|---|
| $IC_{50}$ (μM) | 0.7055 | 1.268 | 0.03308 |
| Std. Error (μM) | 0.5048 | 0.71 | 0.02438 |

A summary of $IC_{50}$ of bispecific compounds 1-31 is set forth below in table 3.

TABLE 3

$IC_{50}$ of inventive bispecific compounds.

| Compound | $IC_{50}$ |
|---|---|
| 1 | ++ |
| 2 | +++ |
| 3 | ++ |
| 4 | – |
| 5 | – |
| 6 | + |
| 7 | +++ |
| 8 | ++ |
| 9 | – |
| 10 | – |
| 11 | ++ |
| 12 | + |
| 13 | – |
| 14 | + |
| 15 | – |
| 16 | + |
| 17 | + |
| 18 | – |
| 19 | – |
| 20 | – |
| 21 | – |
| 22 | – |
| 23 | – |
| 24 | – |
| 25 | – |
| 26 | – |
| 27 | – |
| 28 | – |
| 29 | +++ |
| 30 | ++ |
| 31 | N.D. |

"+++", $IC_{50}$ <0.1 μM
"++", 0.1 μM < $IC_{50}$ < 1 μM
"+", 1 μM < $IC_{50}$ < 10 μM
"–" $Ic_{50}$ >10 μM
N.D., not detected.

Example 33: CBP (Bromodomain) AlphaScreen® Assay

Assays were performed with minimal modifications from the manufacturer's protocol (PerkinElmer®, USA). All reagents were diluted in 50 mM 4-(2-hydroxyethyl)-1-piperazineethanesulfonic acid (HEPES), 150 mM NaCl, 0.1% w/v bovine serum albumin (BSA), 0.01% w/v Tween® 20, pH 7.5 and allowed to equilibrate to room temperature prior to addition to plates. After addition of AlphaScreen® acceptor beads to master solutions, all subsequent steps were performed under low light conditions. A 2× solution of components with final concentrations of CBP bromodomain at 40 nM, Ni-coated Acceptor Bead at 10 μg/ml, and 7.2 nM biotinylated-Int-2 was added in 10 μL to 384-well plates (AlphaPlate-384, PerkinElmer®, USA). Plates were spun down at 150×g, 100 nL of compound in dimethyl sulfoxide (DMSO) from stock plates were added by pin transfer using a Janus® Workstation (PerkinElmer®, USA). The streptavidin-coated donor beads (10 ng/ml final) were added as with previous the solution in a 2×10 μL volume. Following this addition, plates were sealed with foil to prevent light exposure and evaporation. The plates were spun down again at 150×g. Plates were incubated at room temperature for 1 hour and then read on a 2104 EnVision® Multilabel Plate Reader (PerkinElmer®, USA) using the manufacturer's protocol.

Figure 6:
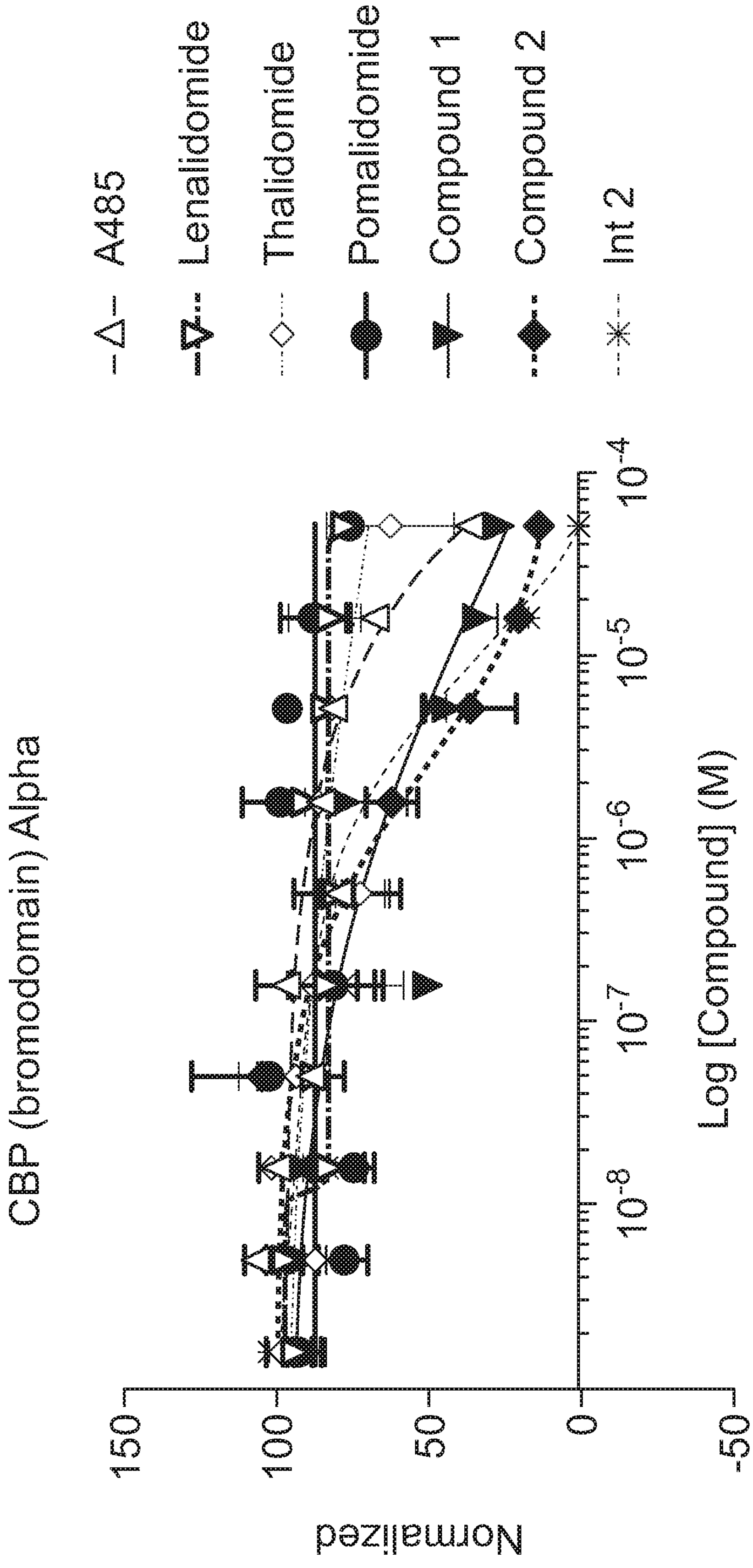
FIG. 6 is a graph that shows relative binding of bispecific compounds 1, 2, and Int-2 to the CBP bromodomain by AlphaScreen® Assay.

The results illustrated in FIG. 6 show that bispecific compounds 1, 2 and int-2 bound to CBP (bromodomain) in the 10-μM range. $IC_{50}$ values of bispecific compounds 1 and 2 are shown in Table 4.

TABLE 4

| Compound | $IC_{50}$ (μM) |
|---|---|
| 1 | 18.86 |
| 3 | 2.34 |

Example 34: Western Blot for E300/CBP Degradation with Inventive Compounds

Kelly Neuroblastoma cells were seeded at 1,000,000 cells per well in 6 well plates and were treated in a dose-dependent manner for 24 hours. Whole cell lysates were collected using ice cold lysis buffer [300 mM NaCl, 50 mM Tris-HCl, pH 7.5, 0.5% Triton X-100, 1% sodium dodecyl sulfate (SDS), 1 mM dithiothreitol (DTT) (Invitrogen™), Roche®'s cOmplete™ protease inhibitor cocktail (1:000), 25 units/mL Benzonase®] and blotted at a protein concentration of 30 μg for EP300 and CBP and 10 μg for histone H3 and H3K27ac. Lysates were also blotted for bromodomain-containing protein 4 (BRD4). Lysates were resolved in NuPAGE™ 3-8% Tris-Acetate polyacrylamide gels (EA03785BOX, Invitrogen™) for EP300 and CBP and Bolt 4-12% Bis-Tris polyacrylamide gels (NW04125BOX, Invitrogen™) for H3 and H3K27ac. Afterwards, gels were transferred to nitrocellulose membranes (LC2001, Invitrogen™). Primary and secondary antibodies used included anti-p300 at 1:500 dilution (ab10485, Abcam®), anti-CBP at 1:500 dilution (D6C5, Cell Signaling Technology®), anti-Actin at 1:5000 dilution (3700S, Cell Signaling Technology®), anti-H3 at 1:1000 dilution (4499S, Cell Signaling Technology®), anti-H3K27ac at 1:1000 dilution (ab4729, Abcam®), IRDye®800 goat anti-rabbit at 1:5000 dilution (926-32211, LiCor® Biosciences) and IRDye®680 goat anti-mouse at 1:5000 dilution (926-68070, LiCor®). Visualization was performed on an Odyssey infrared imaging system (LiCor® Biosciences).

Figure 3A:
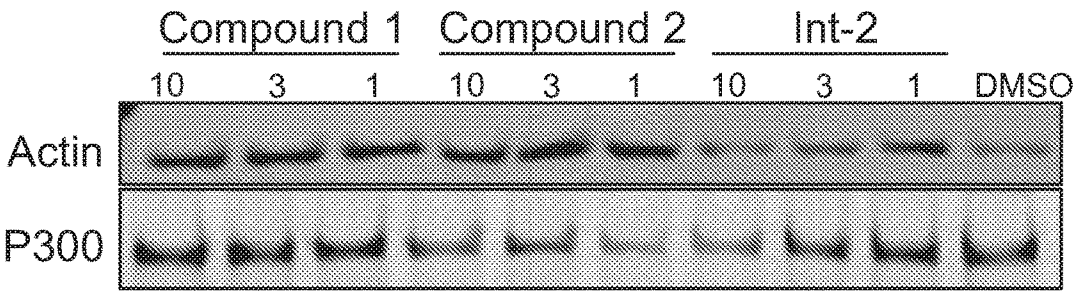
FIG. 3A is an immunoblot that shows EP300 degradation after treating Kelly NB cells with bispecific compounds 1, 2, and Int-2 at 24 hours.
Figure 3B:
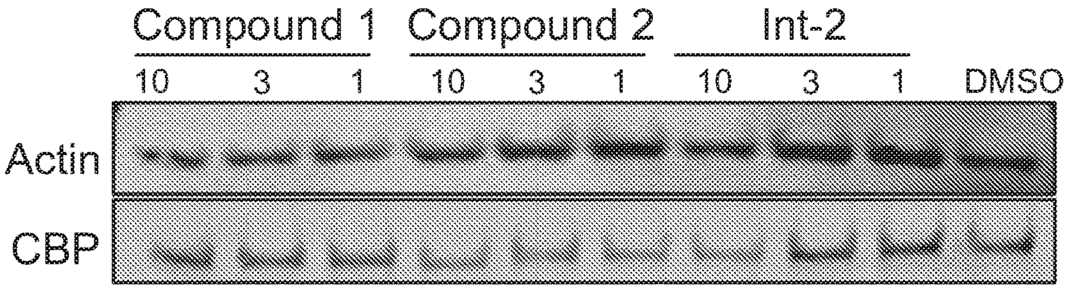
FIG. 3B is an immunoblot that shows CBP degradation after treating Kelly NB cells with bispecific compounds 1, 2, and Int-2 at 24 hours.
Figure 3C:
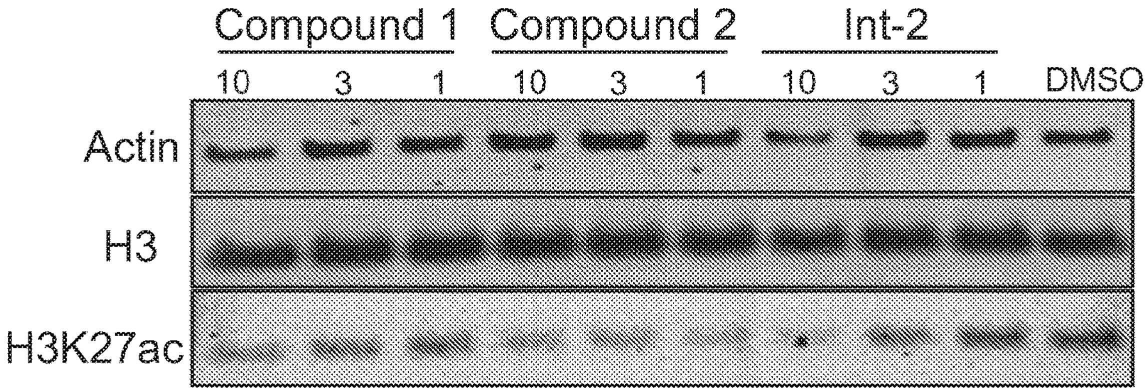
FIG. 3C is an immunoblot that shows levels of histone H3 and H3K27ac after treating Kelly NB cells with bispecific compounds 1, 2, and Int-2 at 24 hours.

The results illustrated in FIG. 3A-FIG. 3C show that bispecific compound 2 was a potent degrader of both EP300 and CBP with evident reduction in H2K27ac. However, Int 2, which is the targeting ligand in bispecific compound 2, seemed to have general cytotoxicity. Although bispecific compound 1 did not display detectable degradation of EP300 and CBP, there was a reduction in H3K27ac, indicating that bispecific compound 1 likely acted as an inhibitor rather than a degrader.

Figure 5A:
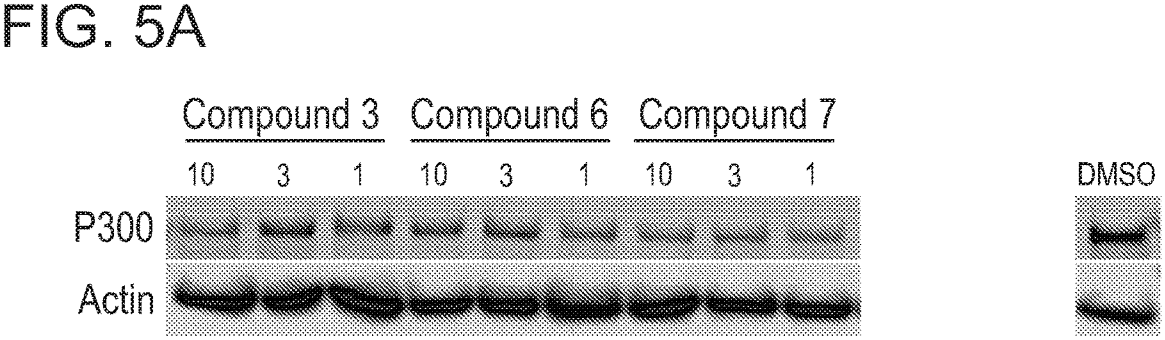
FIG. 5A is an immunoblot that shows EP300 degradation after treating Kelly NB cells with bispecific compounds 3, 6, and 7 at 24 hours.
Figure 5B:
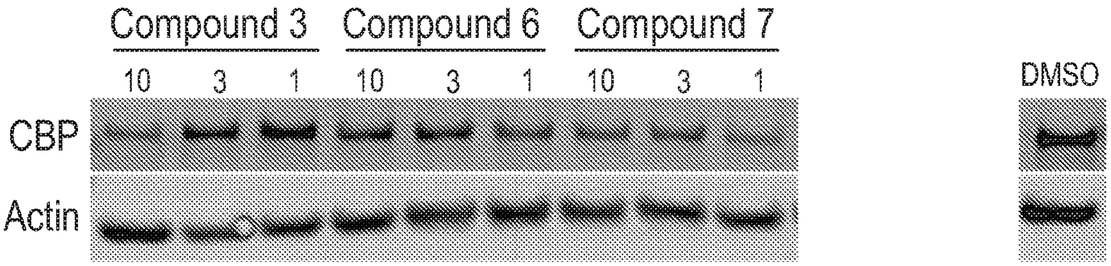
FIG. 5B is an immunoblot that shows CBP degradation after treating Kelly NB cells with bispecific compounds 3, 6, and 7 at 24 hours.
Figure 5C:
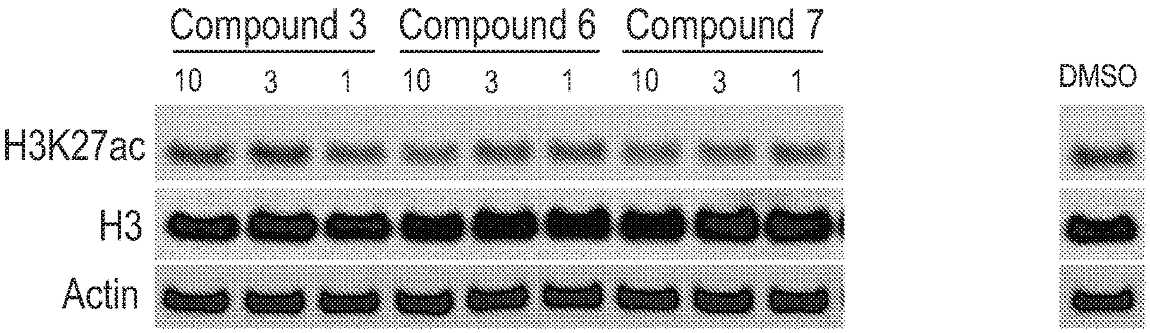
FIG. 5C is an immunoblot that shows levels of histone H3 and H3K27ac after treating Kelly NB cells with bispecific compounds 3, 6, and 7 at 24 hours.

The results illustrated in FIG. 5A-FIG. 5C show that bispecific compound 7 was a potent degrader of both P300 and CBP with noticeable degradation at 1 μM and a slight reduction in acetylation levels. Bispecific compound 3 showed some degradation at 10 μM, whereas bispecific compound 6 showed little to no degradation.

Figure 7A:
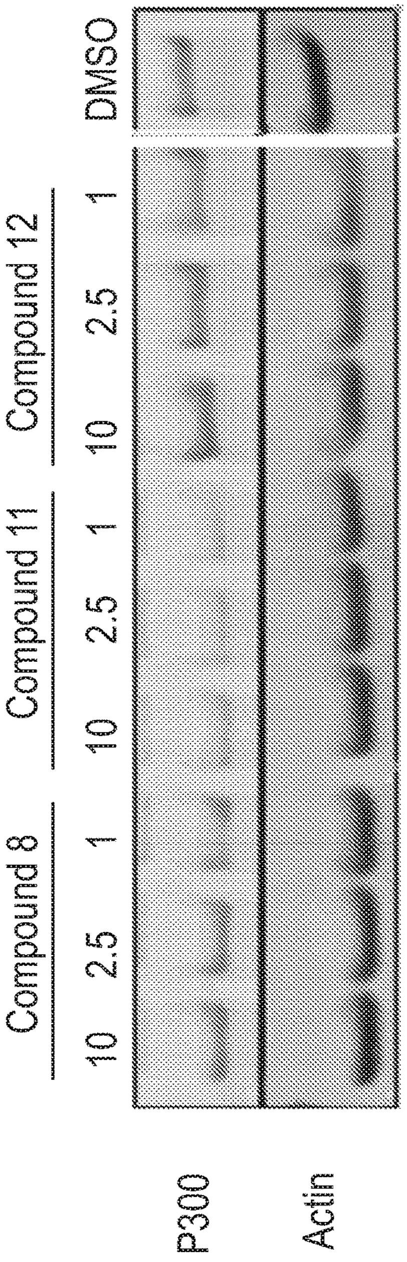
FIG. 7A is an immunoblot that shows EP300 degradation after treating Kelly NB cells with bispecific compounds 8, 11, and 12 at 24 hours.
Figure 7B:
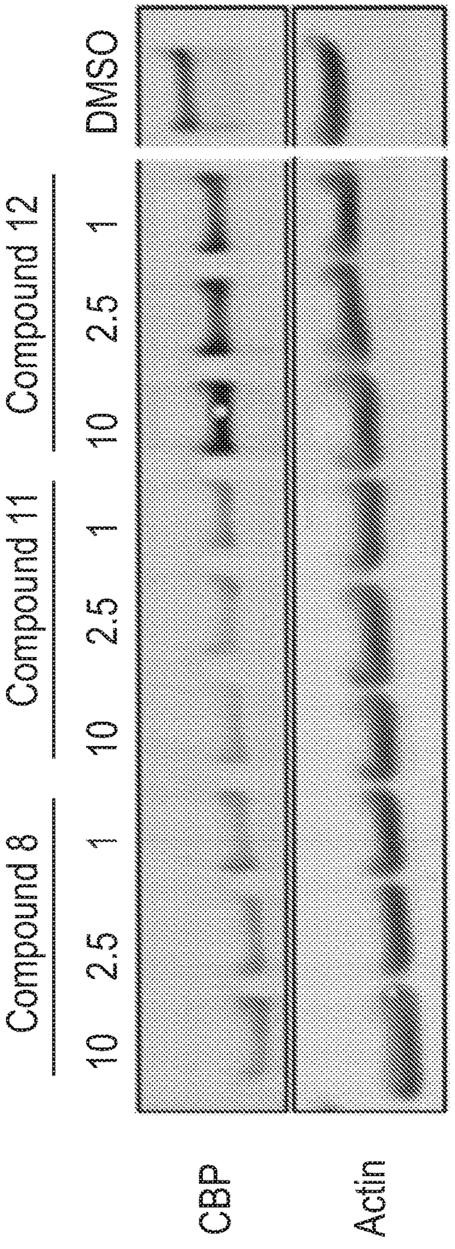
FIG. 7B is an immunoblot that shows CBP degradation after treating Kelly NB cells with bispecific compounds 8, 11, and 12 at 24 hours.
Figure 7C:
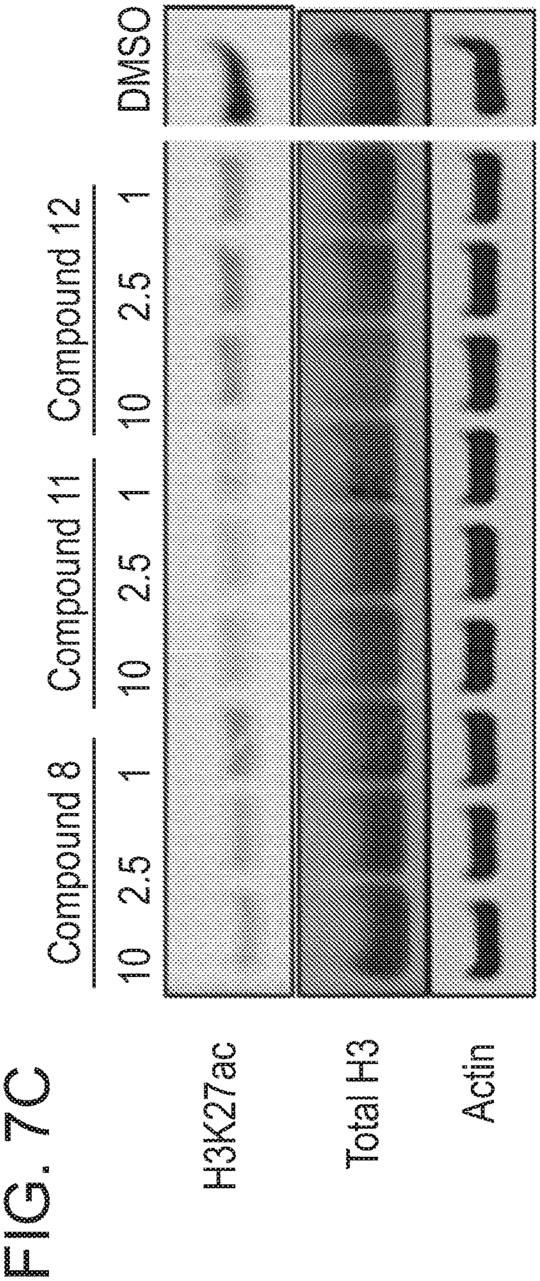
FIG. 7C is an immunoblot that shows levels of histone H3 and H3K27ac after treating Kelly NB cells with bispecific compounds 8, 11, and 12 at 24 hours.
Figure 7D:
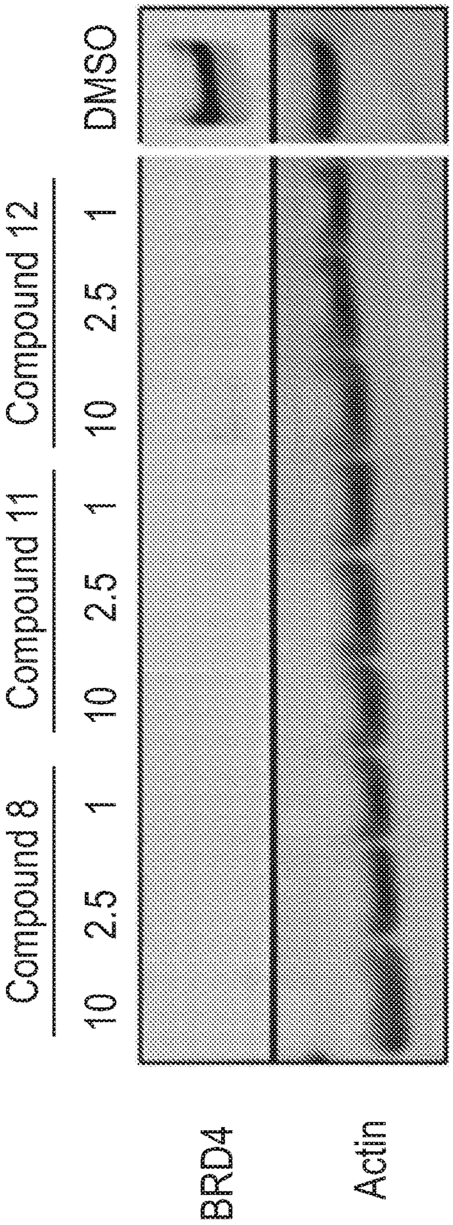
FIG. 7D is an immunoblot that shows levels of bromodomain-containing protein 4 (BRD4) after treating Kelly NB cells with bispecific compounds 8, 11, and 12 at 24 hours.
Figure 7E:
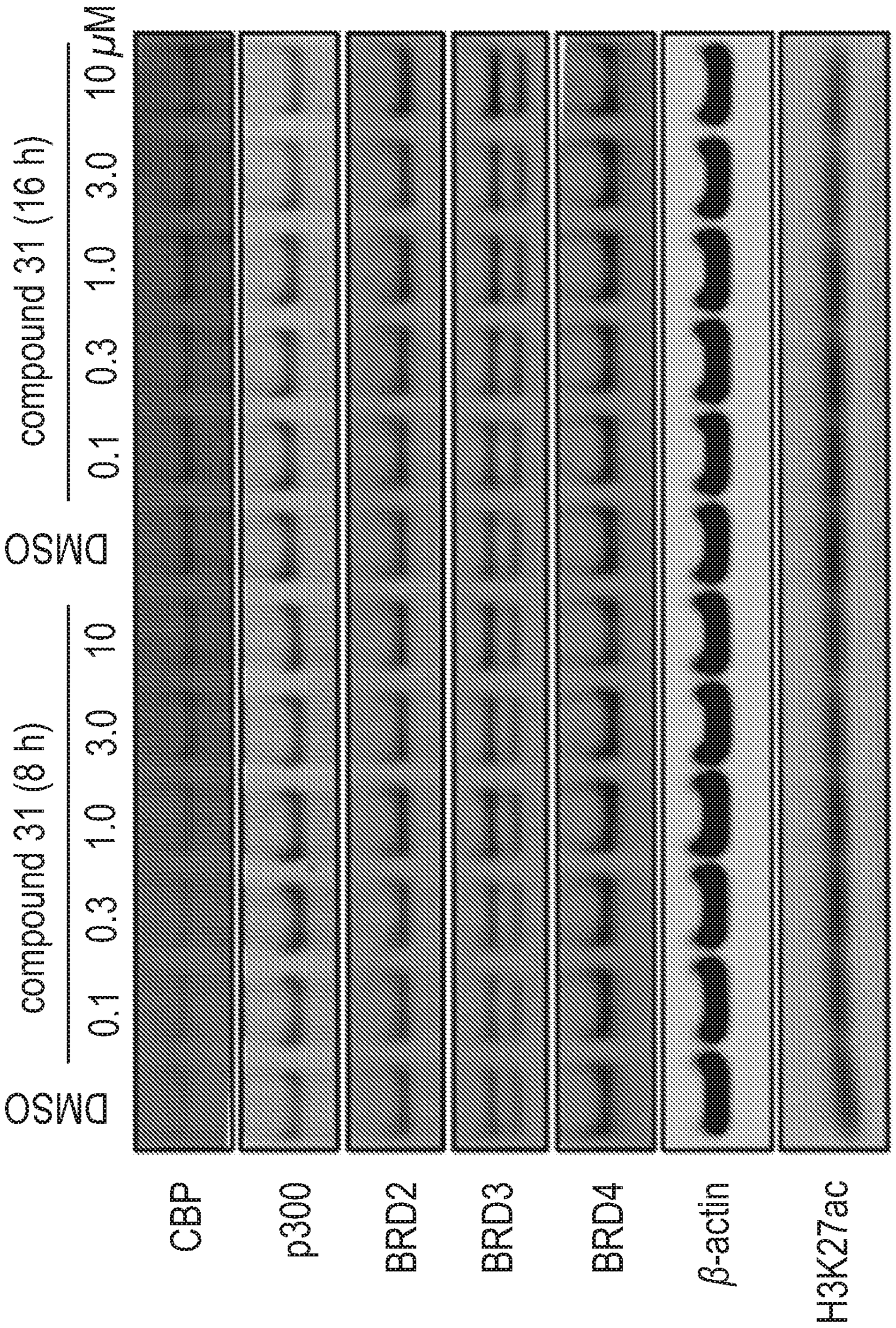
FIG. 7E is an immunoblot that shows levels of CBP, EP300 (p300), bromodomain-containing protein 2 (BRD2), BRD3, BRD4, (3-actin and H3K27ac after treating Kelly NB cells with bispecific compound 31 at 8 and 16 hours.

The results illustrated in FIG. 7A-FIG. 7D show that bispecific compounds 8 and 11 were potent degraders of both P300 and CBP with noticeable degradation and reduction in acetylation levels at 1 μM. Bispecific compound 12 showed noticeable degradation of P300 and reduction in acetylation levels at 1 μM. BRD4 degradation was observed at 1 μM of bispecific compounds 8, 11, and 12 at 24 h. The results in FIG. 7E show that bispecific compound 31 was a potent and selective degrader of P300 and CBP against BRD2/3/4 with noticeable degradation at 3 μM.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A bispecific compound comprising a targeting ligand that binds histone acetyltransferases p300 (EP300) and cAMP-responsive element-binding protein-binding protein (CBP), a degron (D) that binds an E3 ubiquitin ligase, and a linker (L) that covalently attaches the targeting ligand and the degron, wherein the compound has a structure represented by formula (I):

(I)

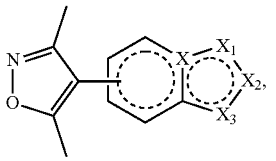

wherein X represents C or N, $X_1$ is $CR_1$ or $NR_3$, $X_2$ is $CR_2$ or $CR_4$, $X_3$ is N, provided that when X is N, $X_1$ is $CR_1$, $X_2$ is $CR_2$, and $X_3$ is N,

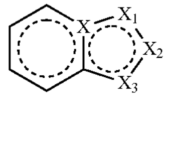

represents

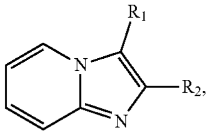

and when X is C, $X_1$ is $NR_3$, $X_2$ is $CR_4$, and $X_3$ is N,

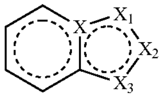

represents

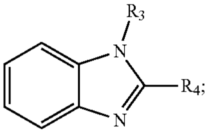

$R_1$ represents $NHR^1$, wherein $R^1$ is an optionally substituted C1-C3 alkyl or an optionally substituted C5-C6 carbocyclic;

$R_2$ represents

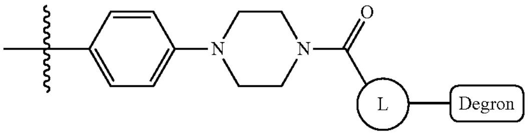

or

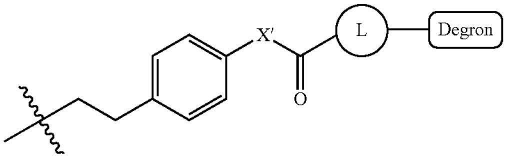

, wherein X' is O, $HNC_2H_4NH$, or NH;

$R_3$ represents an optionally substituted C1-C3 alkyl,

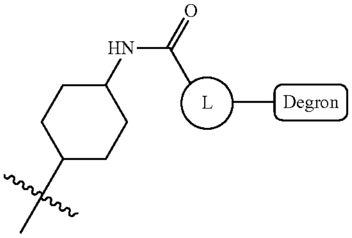

,

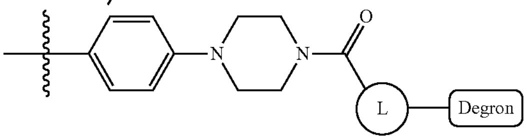

,

-continued

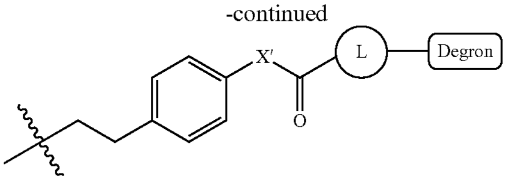

or

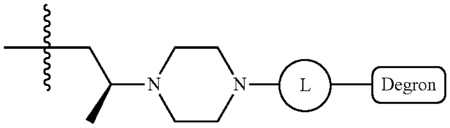

, $R_4$ represents an optionally substituted C5-C6 carbocyclic or an optionally substituted C5-C6 heterocyclic,

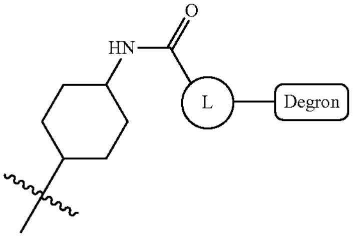

,

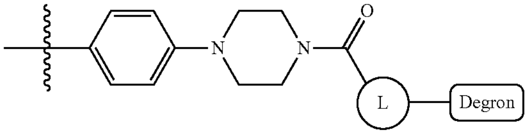

,

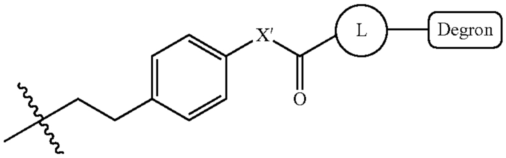

or

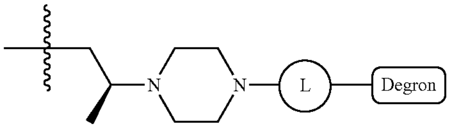

, provided that one of $R_3$ and $R_4$ is

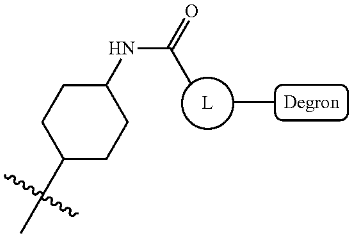

,

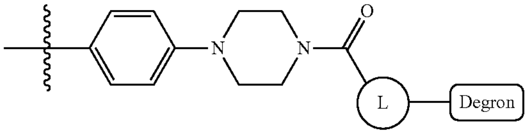

,

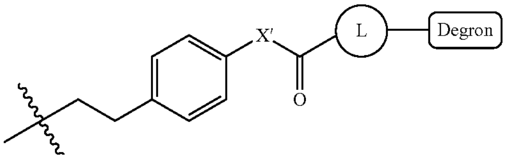

, or

-continued

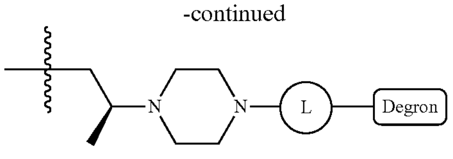, or a pharmaceutically acceptable salt or stereoisomer thereof.

2. The bispecific compound of claim 1, wherein when X is N, $X_1$ is $CR_1$, $X_2$ is $CR_2$, and $X_3$ is N,

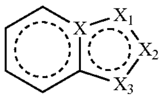

represents

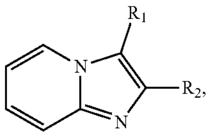

$R_1$ represents $NHR^1$, $R^1$ is an optionally substituted C1-C3 alkyl or an optionally substituted C5-C6 carbocyclic, $R_2$ represents

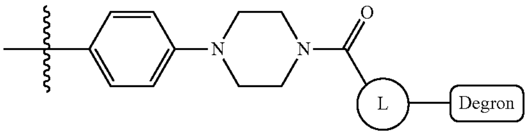 or

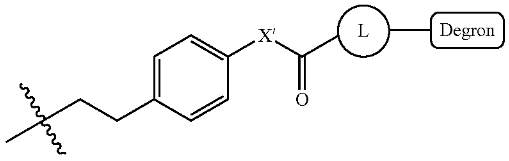, wherein X' is O or NH, or a pharmaceutically acceptable salt or stereoisomer thereof.

3. The bispecific compound of claim 1, wherein when X is C, $X_1$ is $NR_3$, $X_2$ is $CR_4$, $X_3$ is N,

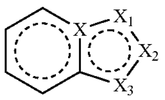

represents

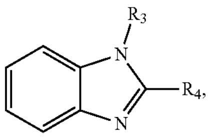

$R_3$ represents an optionally substituted C1-C3 alkyl,

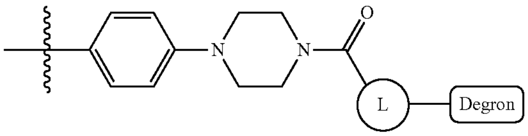,

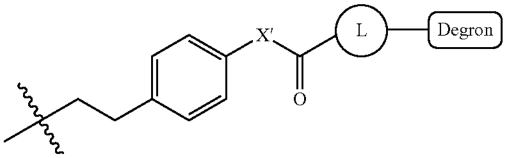 or

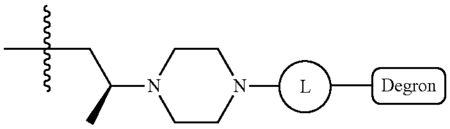, and $R_4$ represents an optionally substituted C5-C6 carbocyclic,

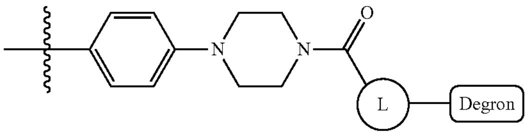,

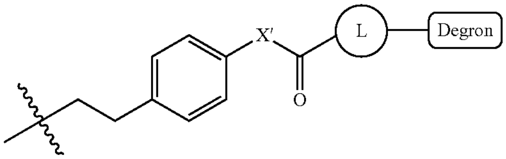 or

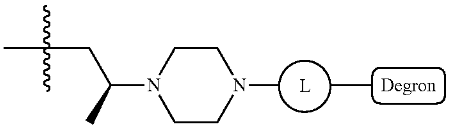, provided that one of $R_3$ and $R_4$ is

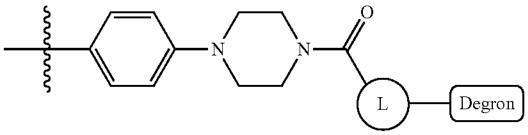,

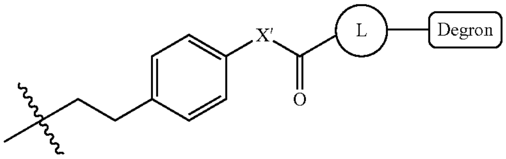, or

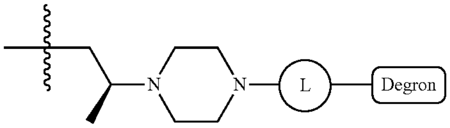, or a pharmaceutically acceptable salt or stereoisomer thereof.

4. The bispecific compound of claim 1, wherein when X is N, $X_1$ is $CR_1$, $X_2$ is $CR_2$, and $X_3$ is N,

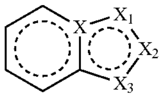

represents

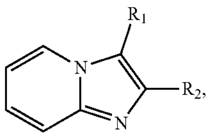

$R_1$ represents $NHR^1$, $R^1$ is an optionally substituted C1-C3 alkyl or an optionally substituted C5-C6 carbocyclic, $R_2$ represents

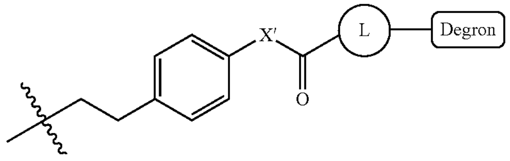

and X' is $NHC_2H_4NH$, or a pharmaceutically acceptable salt or stereoisomer thereof.

5. The bispecific compound of claim 1, wherein when X is C, $X_1$ is $NR_3$, $X_2$ is $CR_4$, and $X_3$ is N,

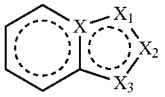

represents

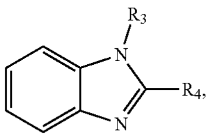

$R_3$ represents an optionally substituted C1-C3 alkyl or

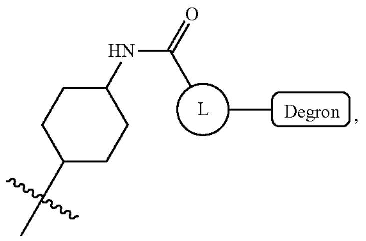

and $R_4$ represents an optionally substituted C5-C6 carbocyclic group or an optionally substituted C5-C6 heterocyclic group, or

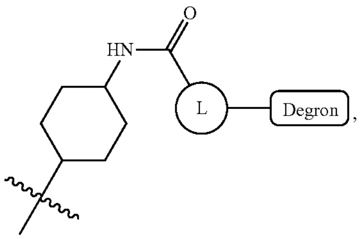

provided that one of $R_3$ and $R_4$ is

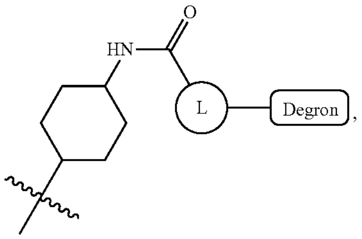

or a pharmaceutically acceptable salt or stereoisomer thereof.

6. The bispecific compound of claim 1, wherein $R^1$ is an optionally substituted C1-C3 alkyl, methoxy, or an optionally substituted C5-C6 carbocyclic.

7. The bispecific compound of claim 6, wherein the optionally substituted C5-C6 carbocyclic is an optionally substituted aralkyl, or wherein an optionally substituted C1-C3 alkyl is methyl.

8. The bispecific compound of claim 1, wherein $R_3$ is an optionally substituted C1-C3 alkyl or C1-C3 alkyl substituted with dimethylaminyl, morpholinyl, or piperazinyl, and $R_4$ is

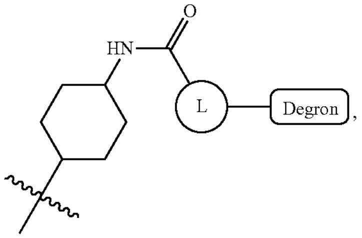

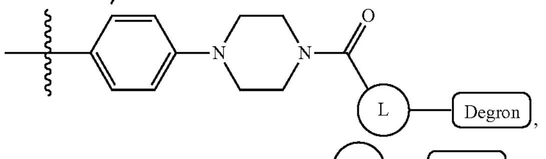

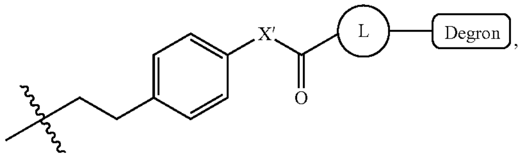

or

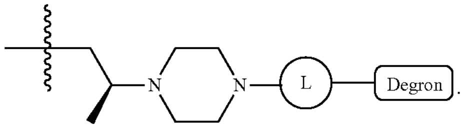

9. The bispecific compound of claim 1, wherein $R_4$ is an optionally substituted C5-C6 carbocyclic or an optionally substituted C5-C6 heterocyclic, and $R_3$ is

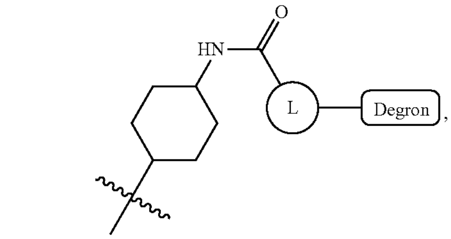

,

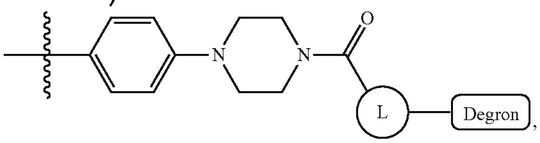

,

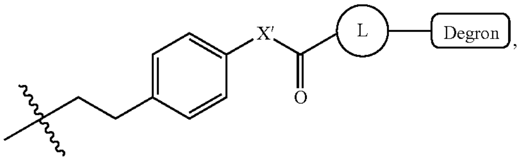

, or

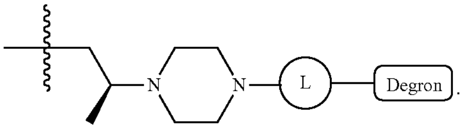

.

10. The bispecific compound of claim 9, wherein the optionally substituted C5-C6 carbocyclic group is an optionally substituted aralkyl; or wherein the optionally substituted C5-C6 heterocyclic group is

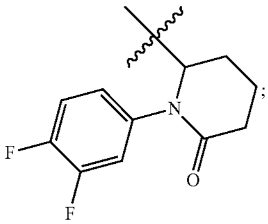 [SMILES: *C1CCCC(=O)N1c1ccc(F)c(F)c1]

;

or wherein the optionally substituted C5-C6 carbocyclic group is an aralkyl substituted with halogen, $NH_2$, OH, or methoxy.

11. The bispecific compound of claim 1, wherein when X is N, $X_1$ is $CR_1$, $X_2$ is $CR_2$, and $X_3$ is N, which has a structure represented by formula (I-1):

(I-1)

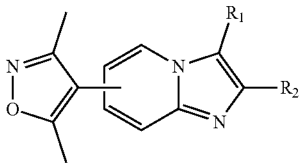

or a pharmaceutically acceptable salt or stereoisomer thereof.

12. The bispecific compound of claim 11, wherein $R^1$ is optionally substituted C1-C3 alkyl and $R_2$ is

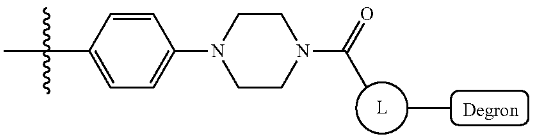

or

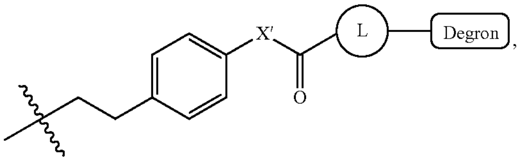

, which has a structure represented by any one of formulas (I-1a) to (I-1d):

(I-1a)

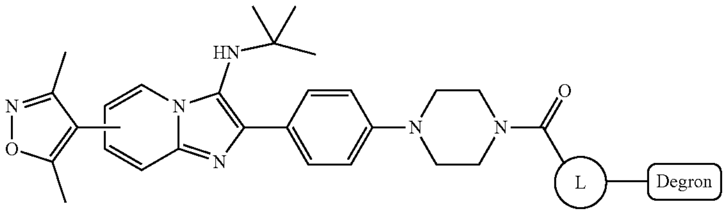

;

-continued
(I-1b)
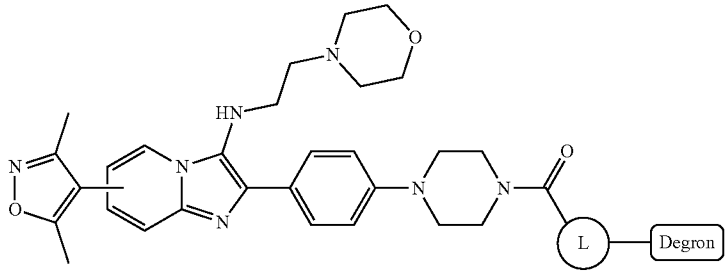
;
(I-1c)
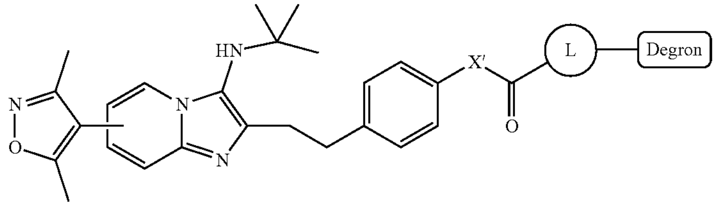
; and
(I-1d)
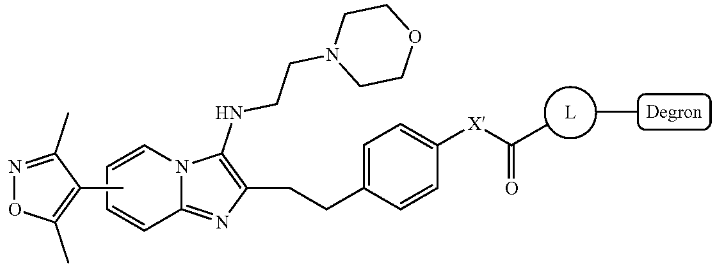
,
or a pharmaceutically acceptable salt or stereoisomer thereof; or wherein $R^1$ is an optionally substituted C5-C6 carbocyclic and $R_2$ is
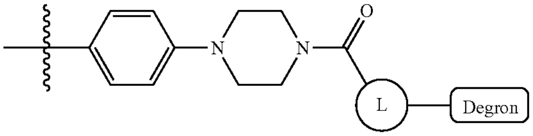
or
-continued
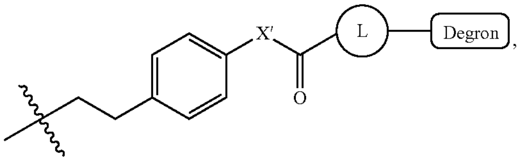
,
and the bispecific compound has a structure represented by formula (I-1e) or (I-1f):
(I-1e)
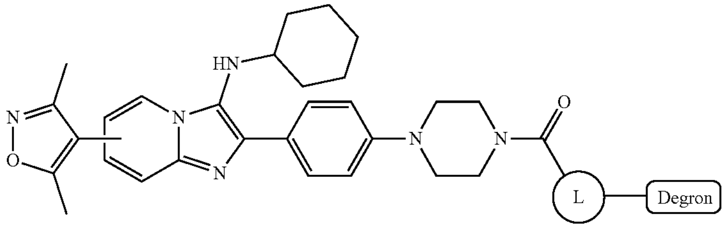
or
(I-1f)
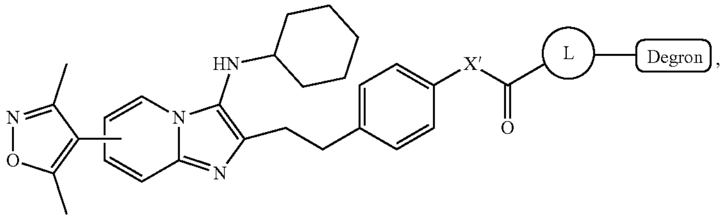
, or a pharmaceutically acceptable salt or stereoisomer thereof; or wherein $R^1$ is an optionally substituted C5-C6 aralkyl and $R_2$ is
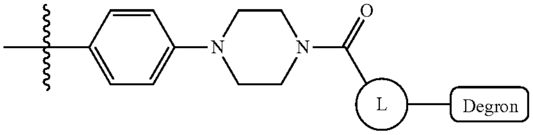
or
-continued
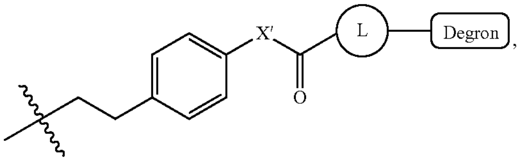
,
and the bispecific compound has a structure represented by any one of formulas (I-1g) to (I-1j);
(I-1g)
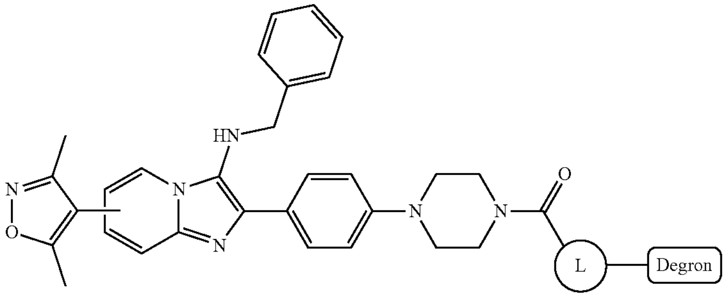
;
(I-1h)
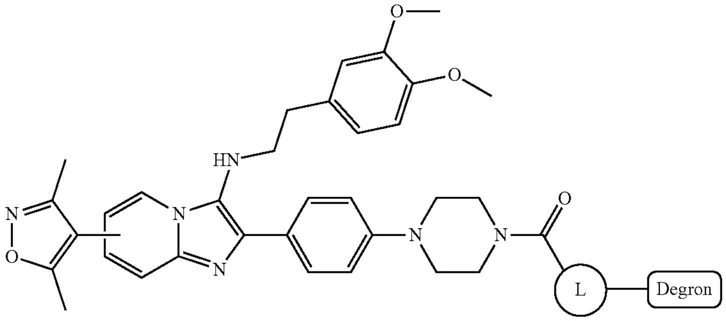
;
(I-1i)
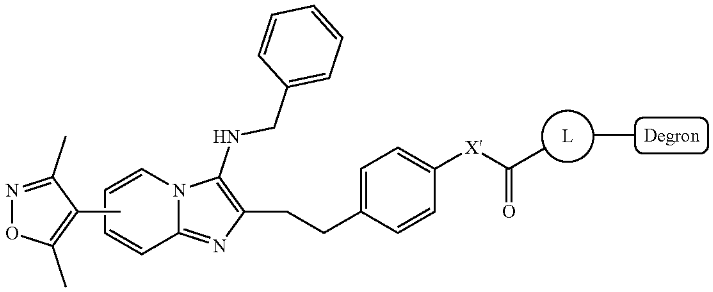
; and
(I-1j)
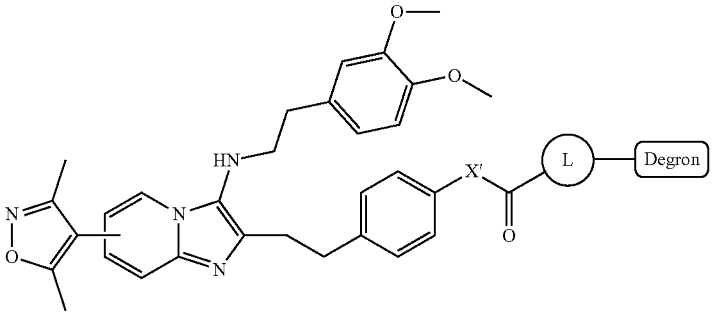
, or a pharmaceutically acceptable salt or stereoisomer thereof.

13. The bispecific compound of claim 1, wherein X is C, $X_1$ is $NR_3$, $X_2$ is $CR_4$, and $X_3$ is N, and which has a structure represented by formula (I-2):

(I-2)

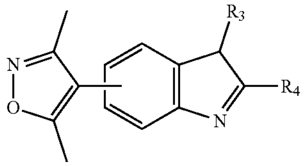

or a pharmaceutically acceptable salt or stereoisomer thereof.

14. The bispecific compound of claim 13, wherein $R_3$ is an optionally substituted C1-C3 alkyl, and $R_4$ is

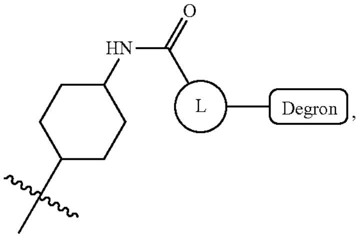

,

-continued

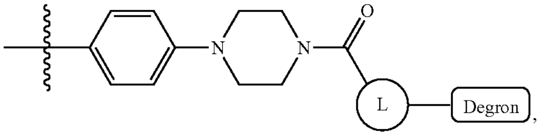

,

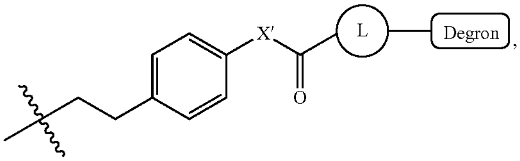

, or

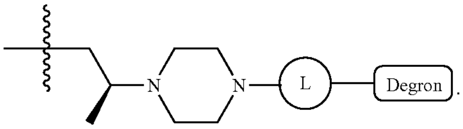

.

which has a structure represented by any one of formulas (I-2a) to (I-2p):

(I-2a)

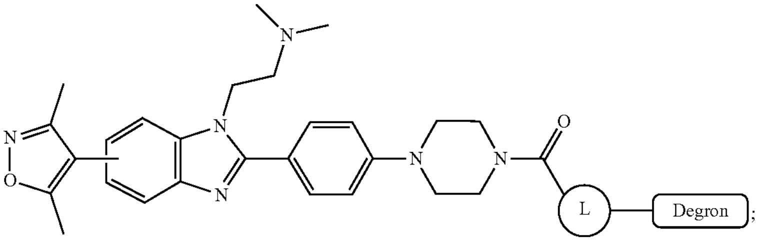

;

(I-2b)

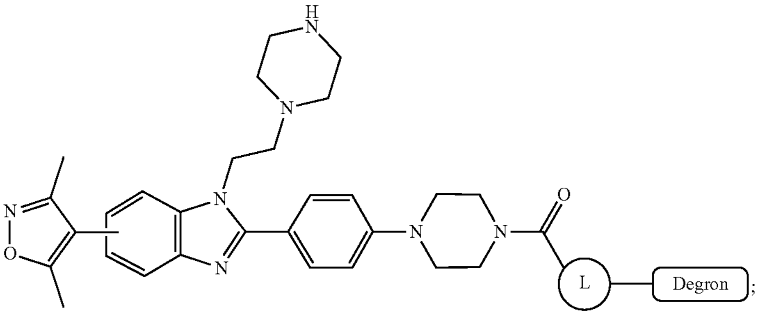

;

-continued
(I-2c)
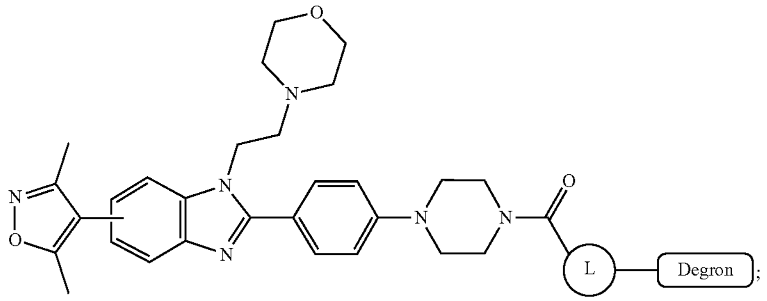
(I-2d)
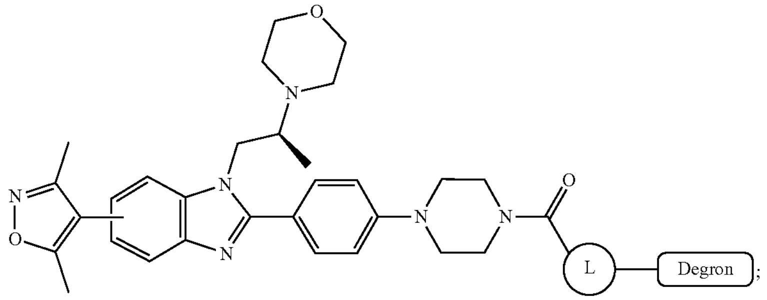
(I-2e)
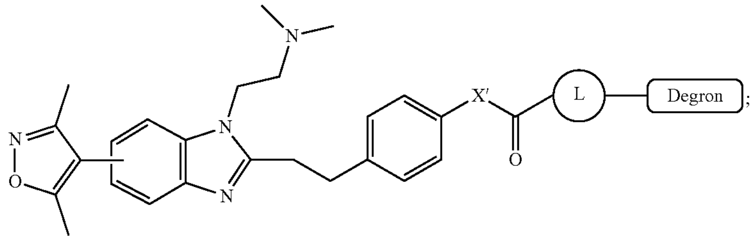
(I-2f)
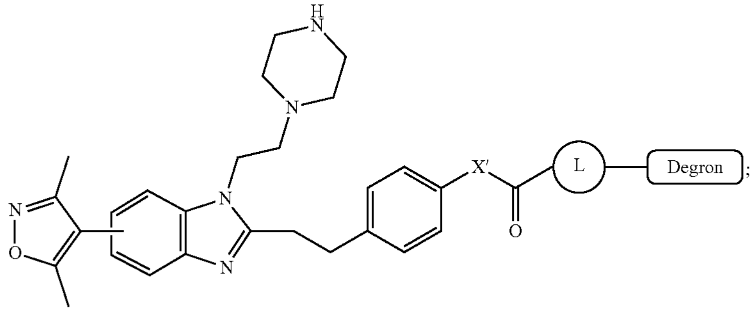
(I-2g)
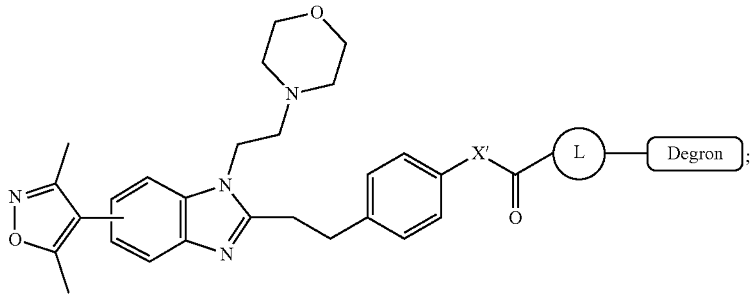

-continued
(I-2h)
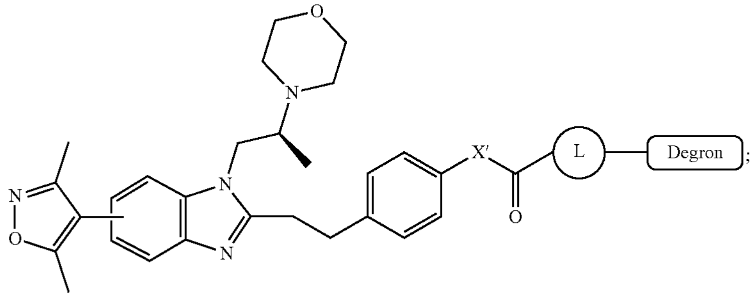
(I-2i)
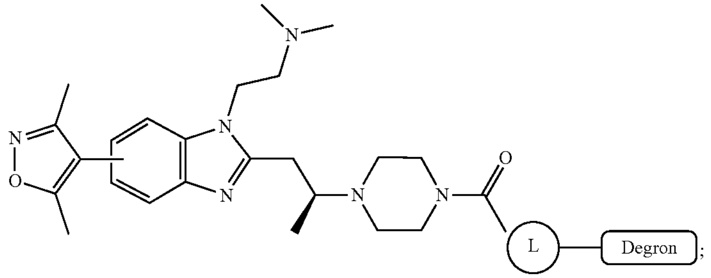
(I-2j)
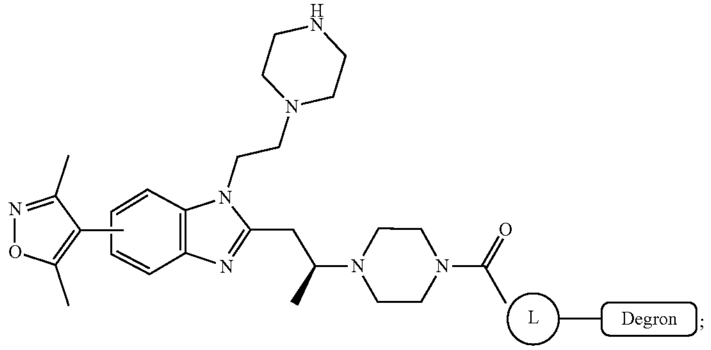
(I-2k)
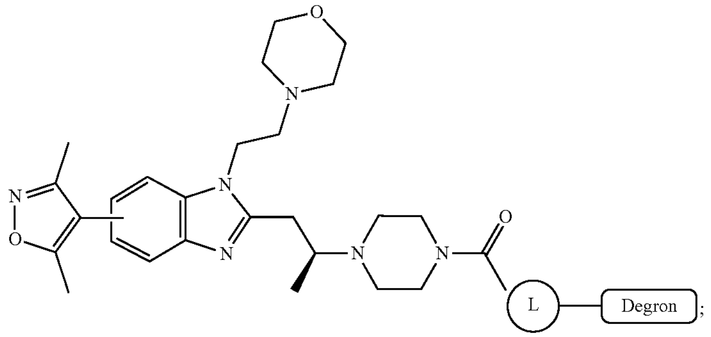
(I-2l)
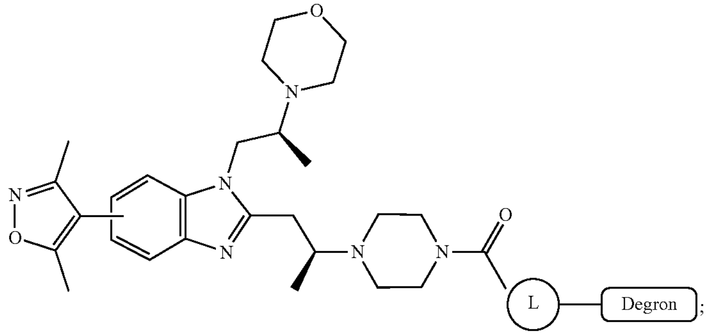

-continued
(I-2m)
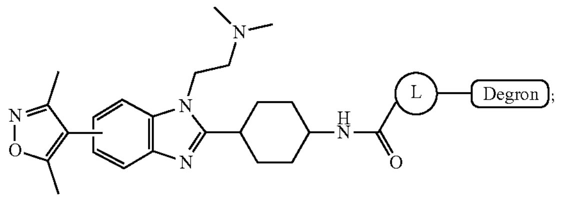
(I-2n)
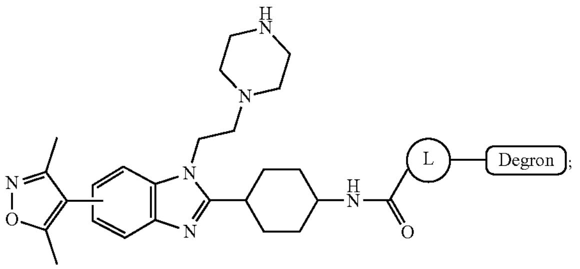
(I-2o)
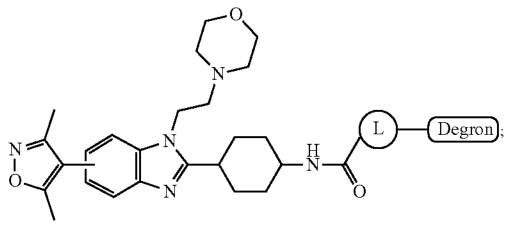
and
(I-2p)
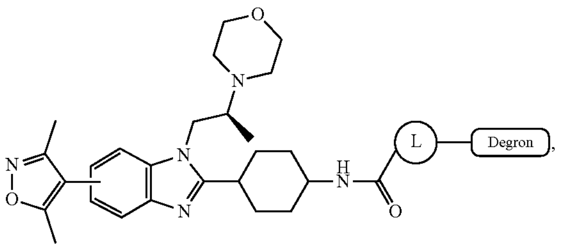
or a pharmaceutically acceptable salt or stereoisomer thereof; or wherein $R_3$ is optionally substituted C5-C6 aralkyl or
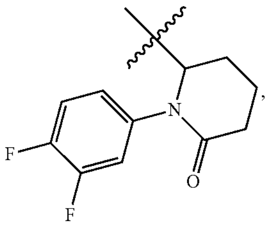 [SMILES: *C1CCCC(=O)N1c1ccc(F)c(F)c1]
and $R_4$ is
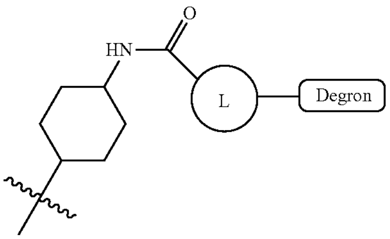
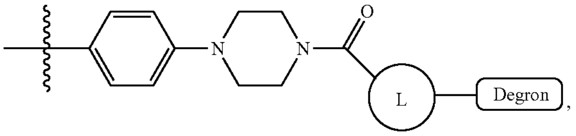
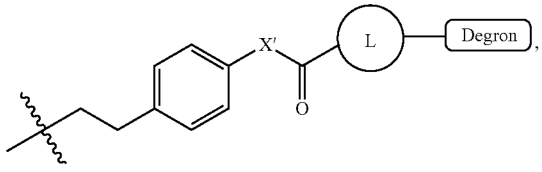
or
-continued
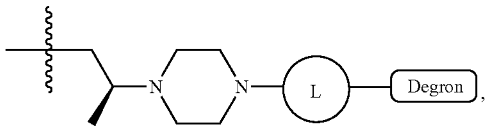
and the bispecific compound has a structure represented by any one of formulas (I-2q) to (I-2z and from (I-2a') to (I-2k'):
(I-2q)
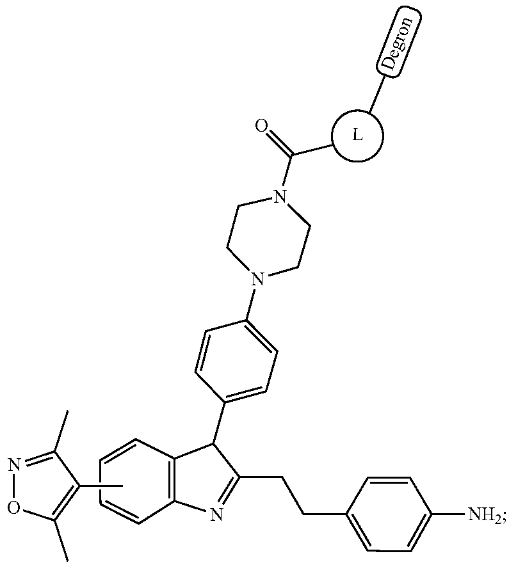

-continued
(I-2r)
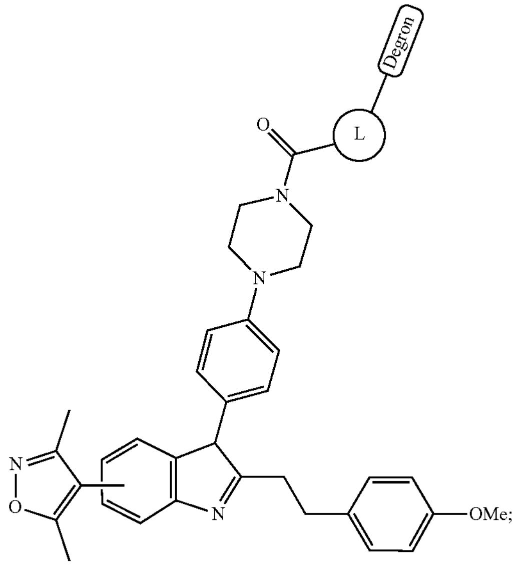
(I-2s)
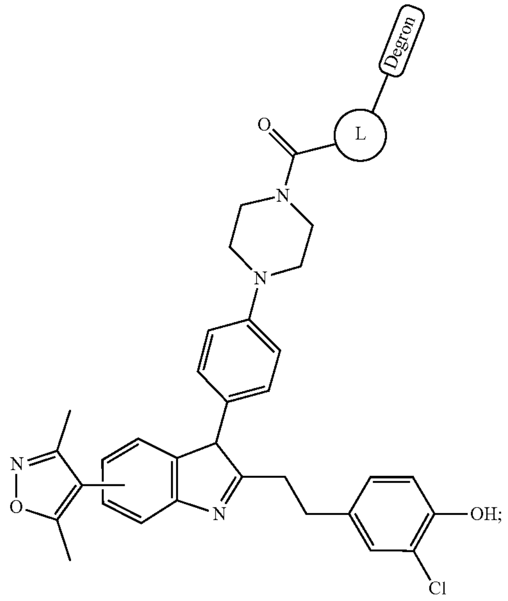
-continued
(I-2t)
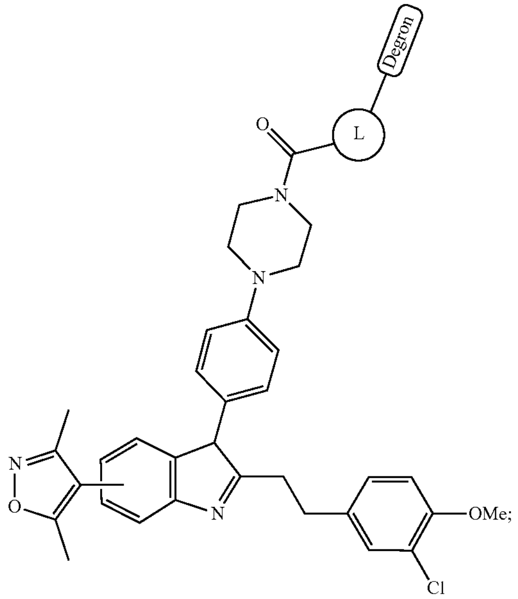
(I-2u)
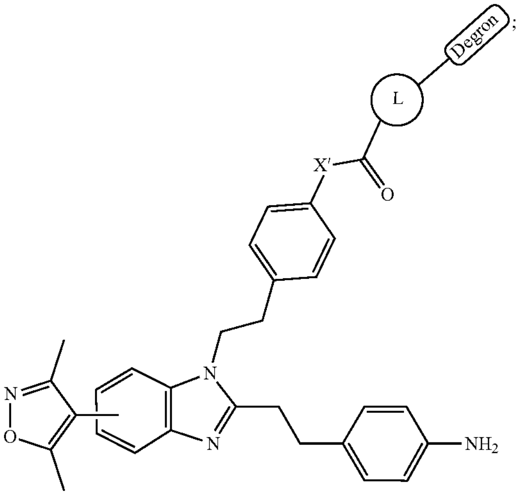
(I-2v)
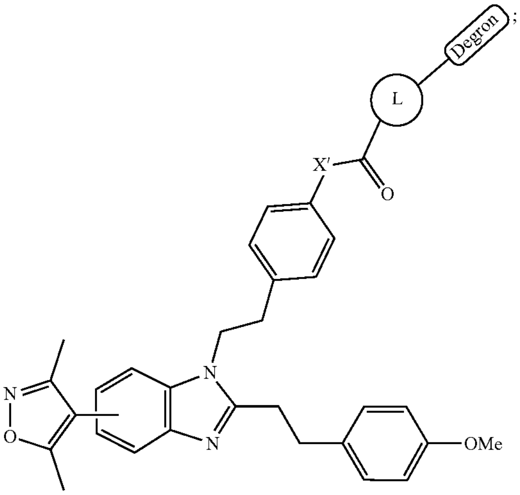

-continued
(I-2w)
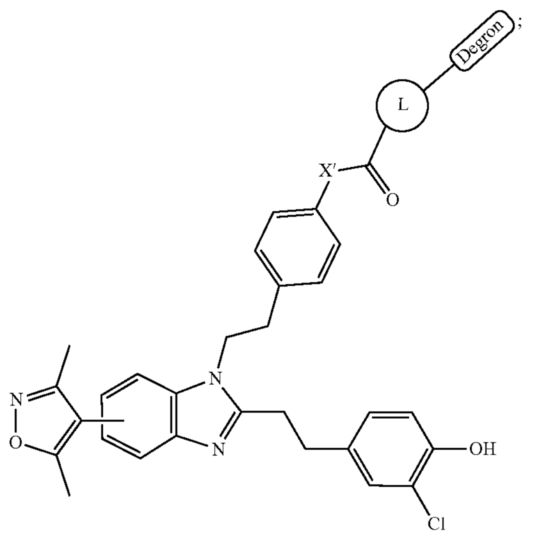
(I-2x)
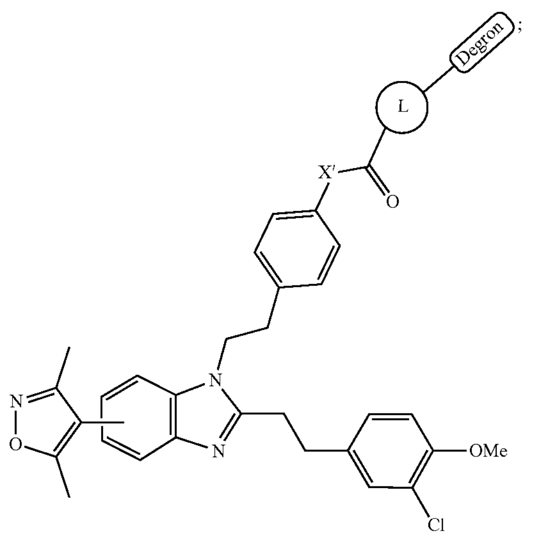
(I-2y)
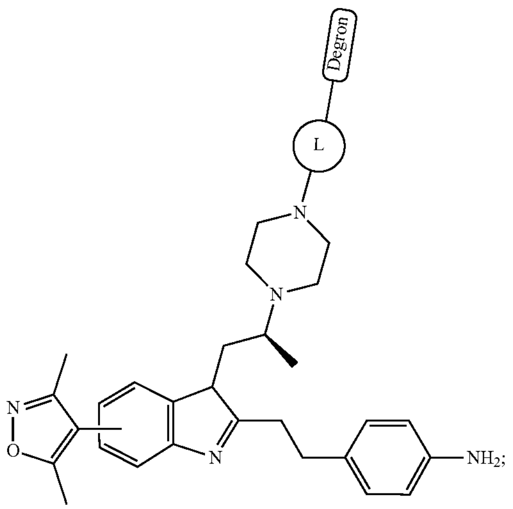
-continued
(I-2z)
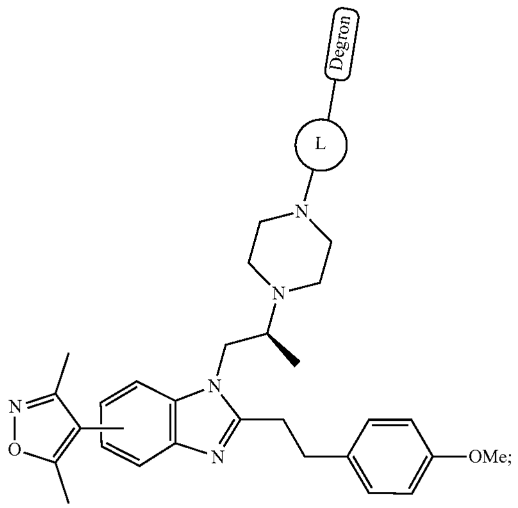
(I-2a')
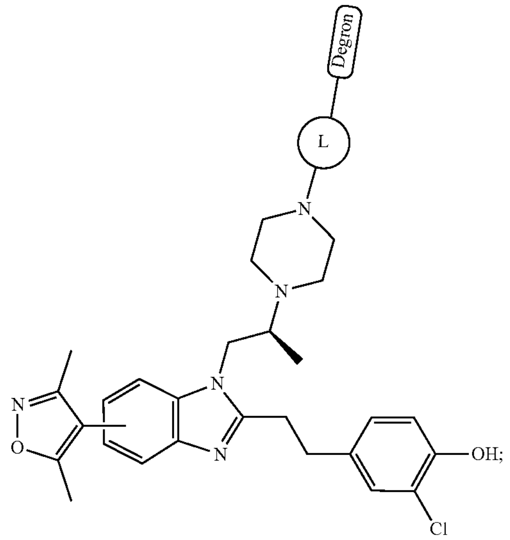
(I-2b')
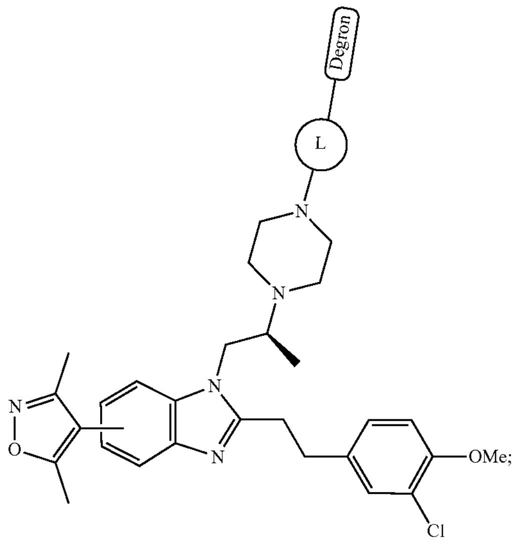

-continued
(I-2c′)
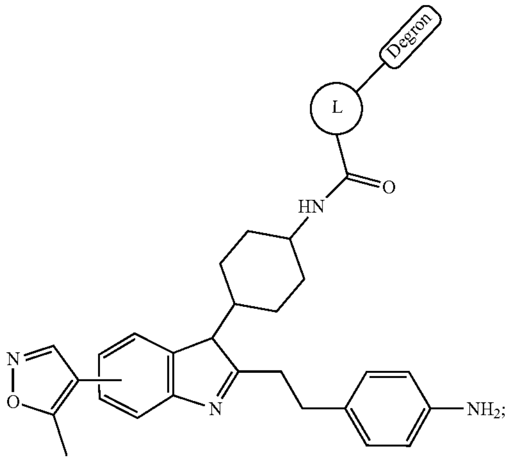
(I-2d′)
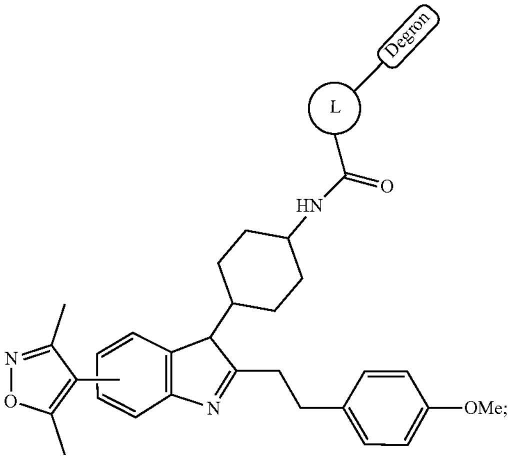
(I-2e′)
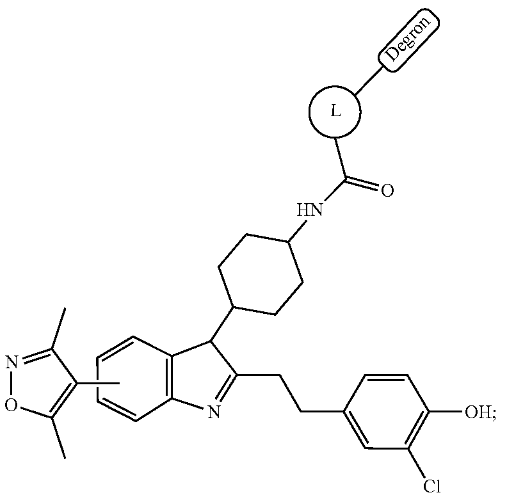
-continued
(I-2f′)
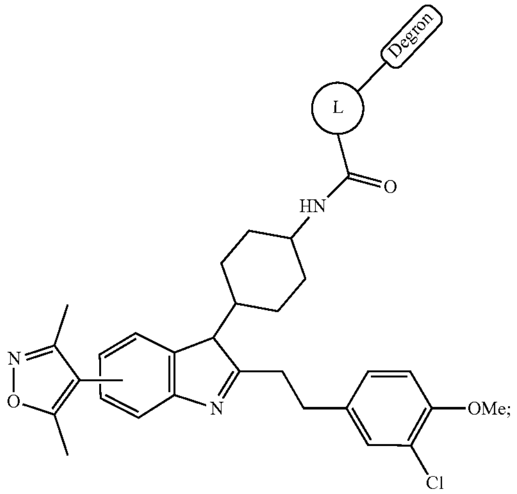
(I-2g′)
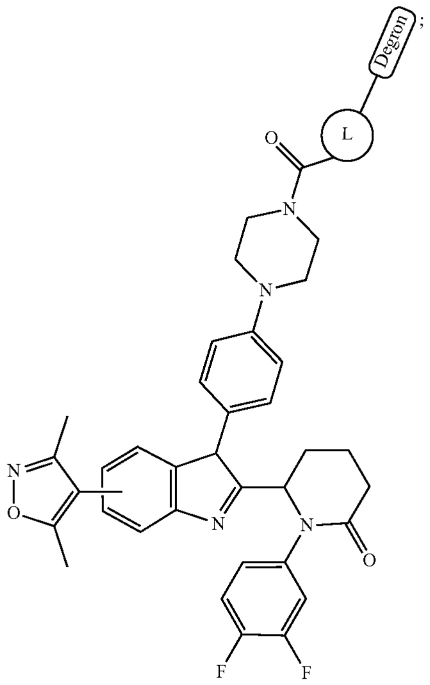

-continued
(I-2i')
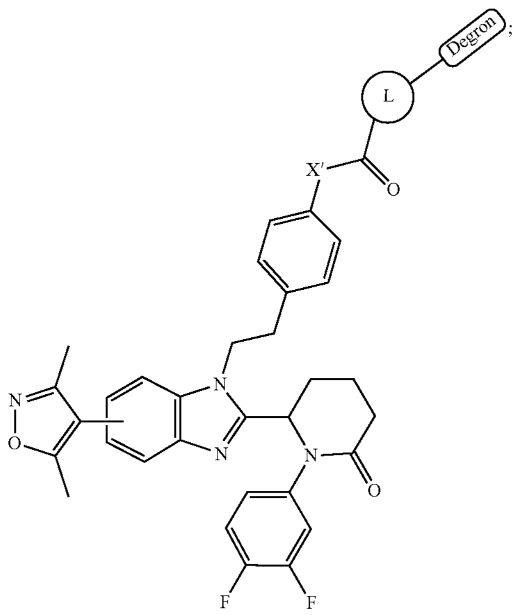
(I-2j')
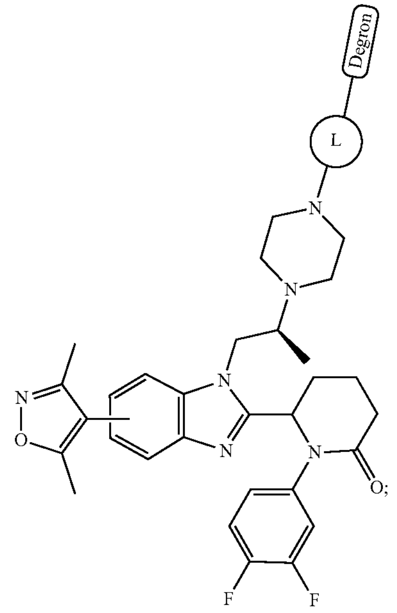
and
-continued
(I-2k')
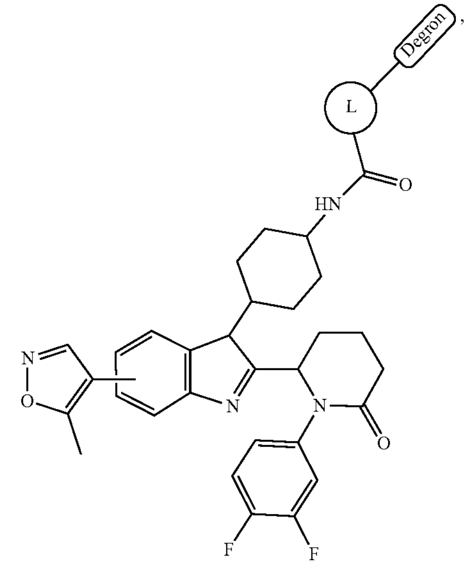
or a pharmaceutically acceptable salt or stereoisomer thereof.
15. The bispecific compound of claim 1, wherein the linker is represented by any one of structures:
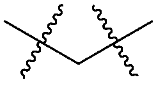
;
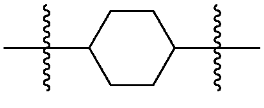
;
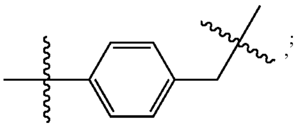
;
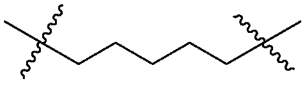
;
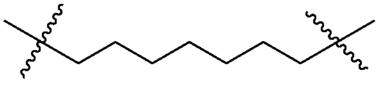
;
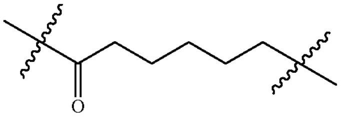
;
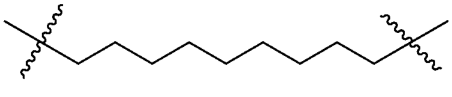
;
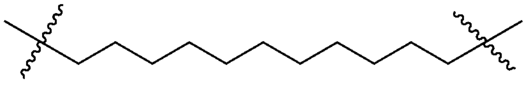
;

-continued

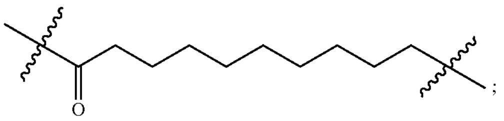

;

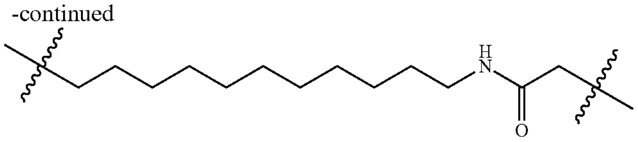

;

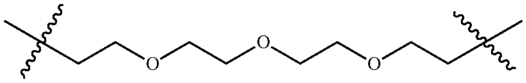

;

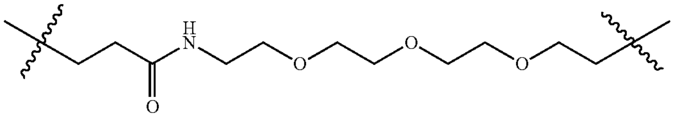

;

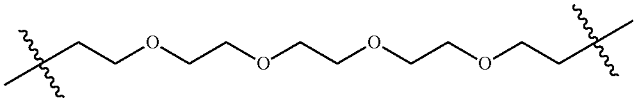

;

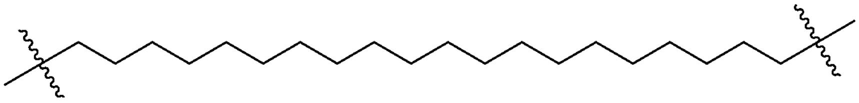

;

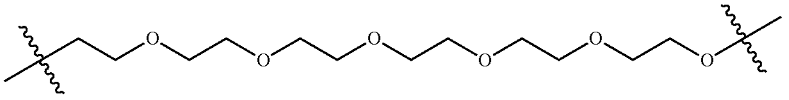

;

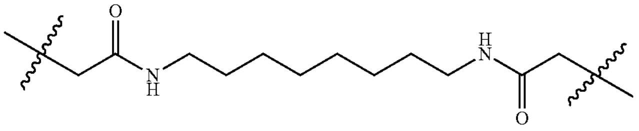

;

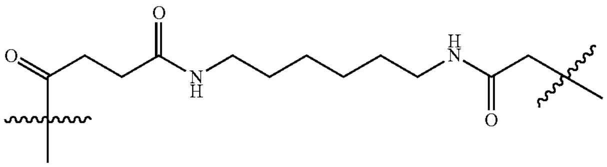

; and

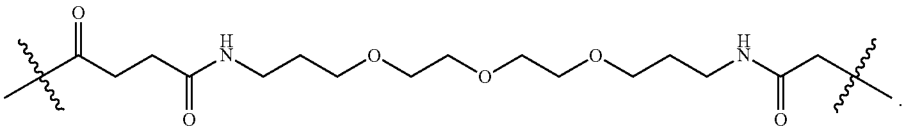

.

16. The bispecific compound of claim 1, wherein the degron binds cereblon (CRBRN) and is represented by structure (D1):

(D1)

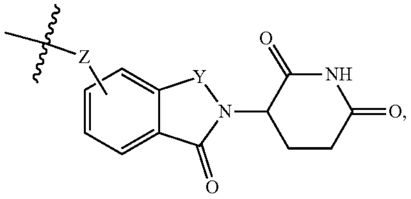

wherein Y is $CH_2$ or CO; and Z is NH, O, or $OCH_2CO$.

17. The bispecific compound of claim 16, wherein the degron is represented by structure (D1-a) or (D1-b):

(D1-a)

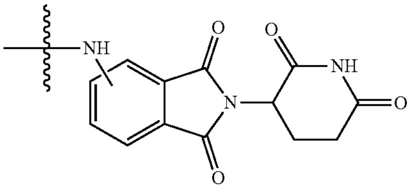

or (D1-b)

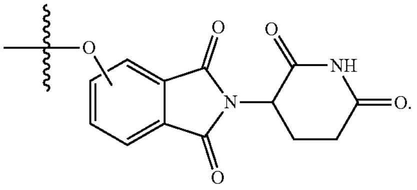

18. The bispecific compound of claim 1, wherein the degron binds VHL and has a structure represented by any one of formulas (D2-a) to (D2-e):

(D2-a)
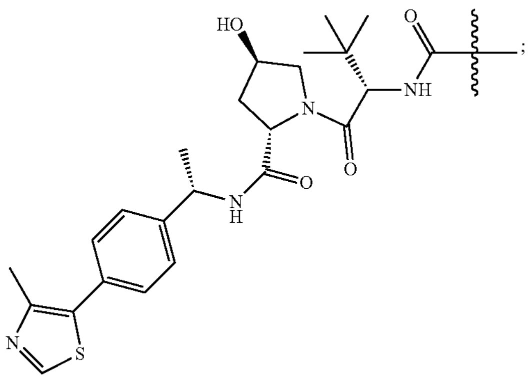
;
(D2-b)
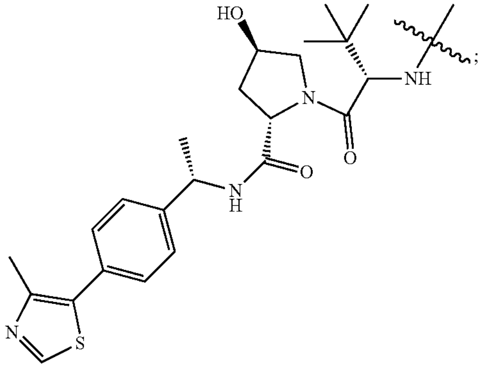
;
(D2-c)
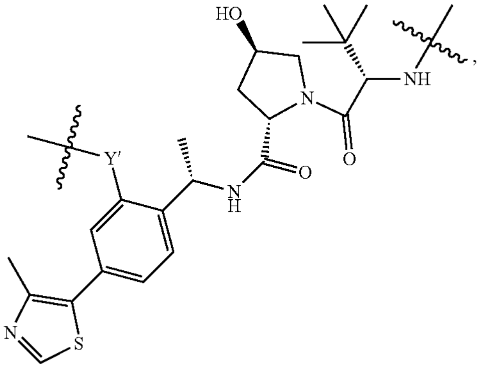
,
wherein Y' is a bond, N, O or C;
(D2-d)
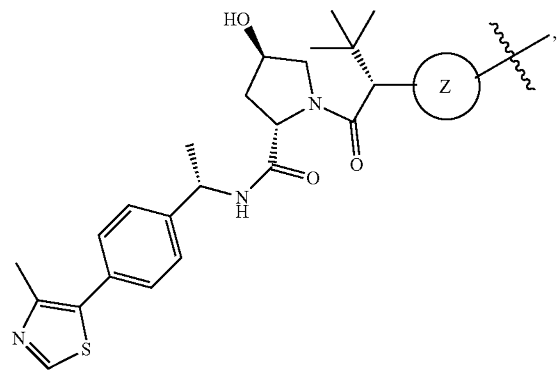
,
wherein Z is a C5-C6 carbocyclic or C5-C6 heterocyclic group, and
(D2-e)
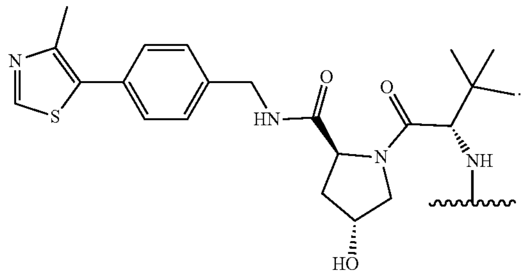
.
19. The bispecific compound of claim 18, wherein Z is
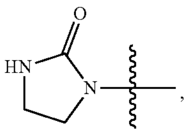
,
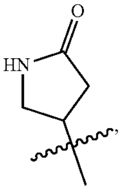
, or
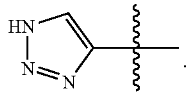
.
20. A bispecific compound, which is represented by any one of structures (1) to (46):
(1)
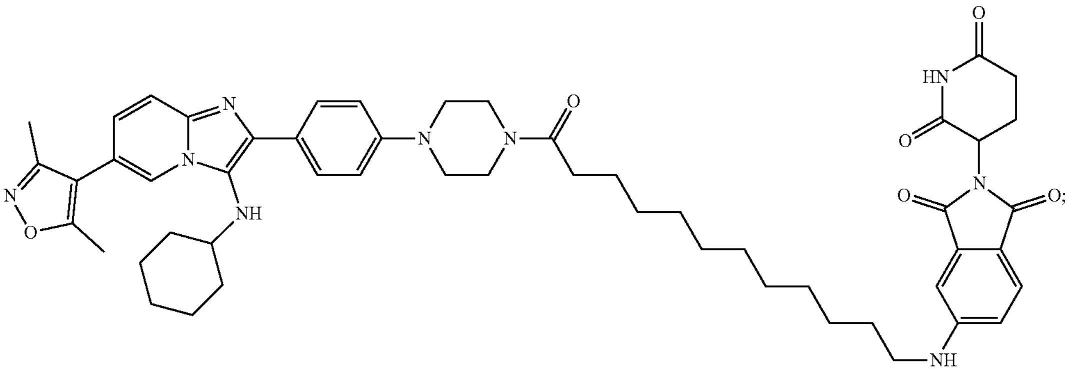
;

-continued
(2)
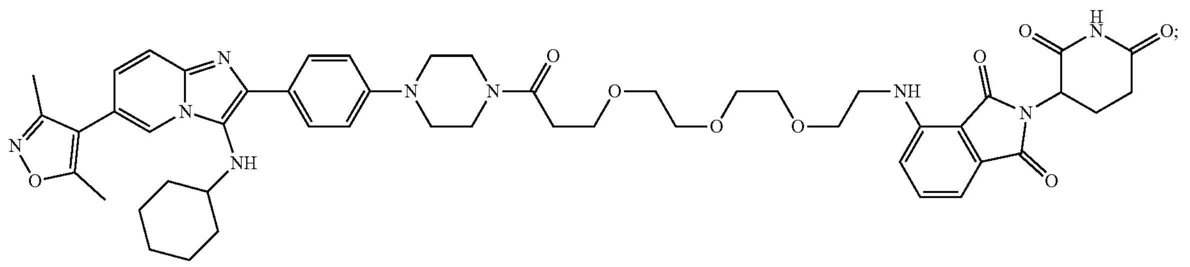
(3)
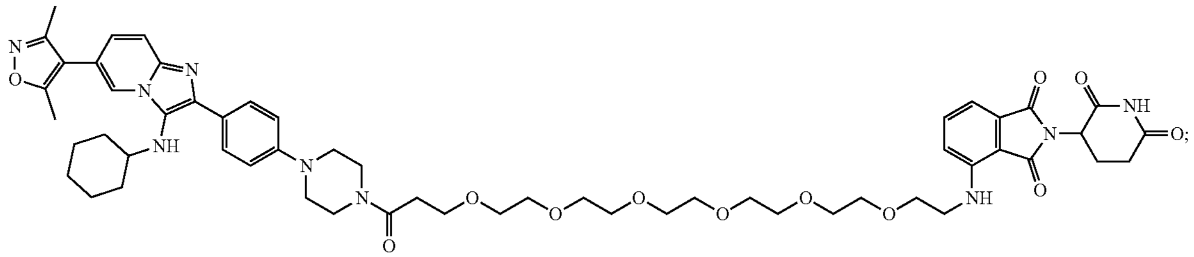
(4)
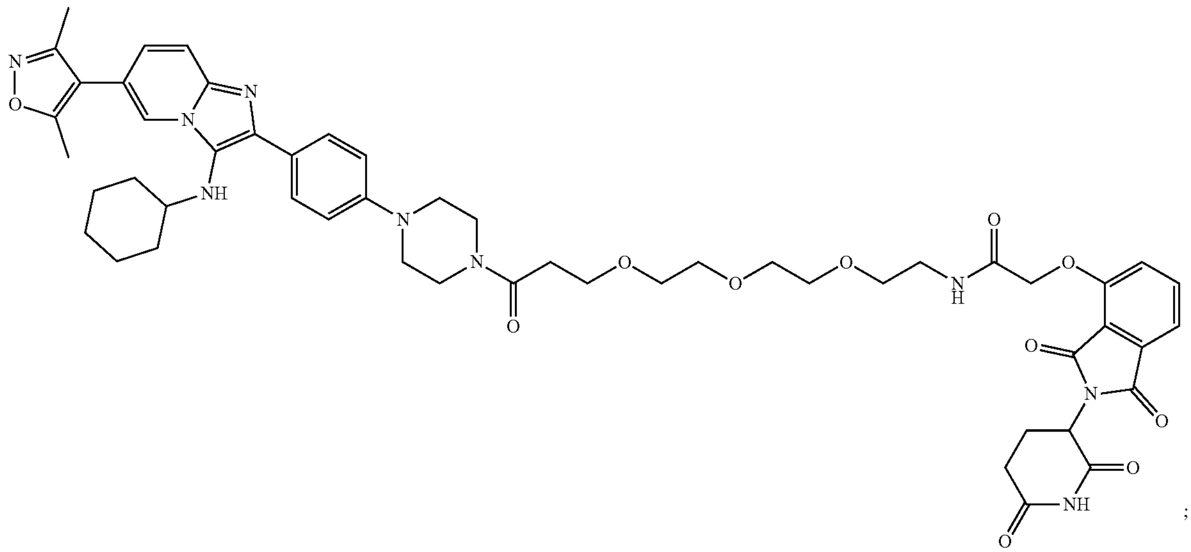
;
(5)
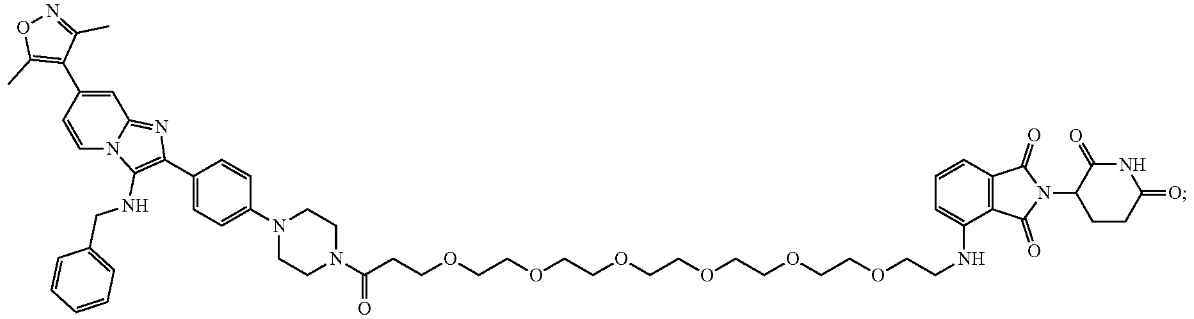

-continued
(6)
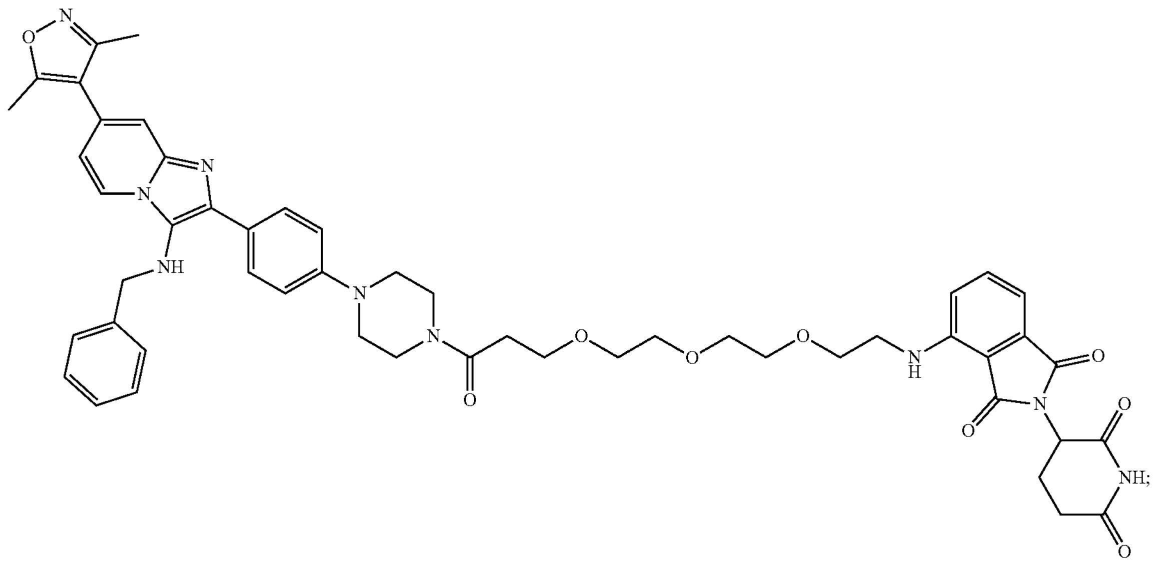
(7)
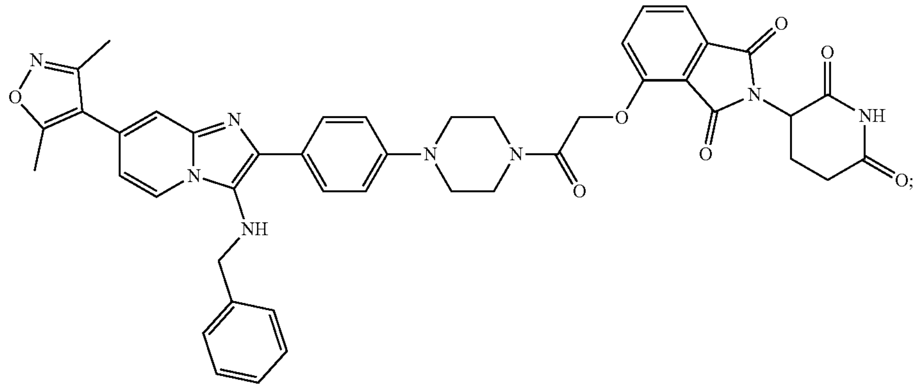
(8)
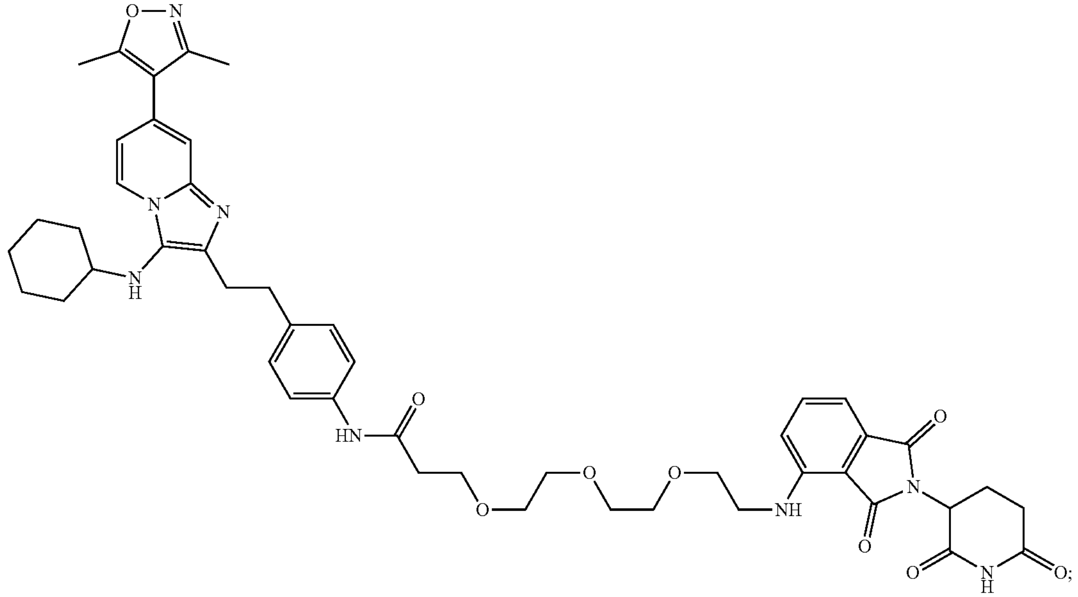

-continued
(9)
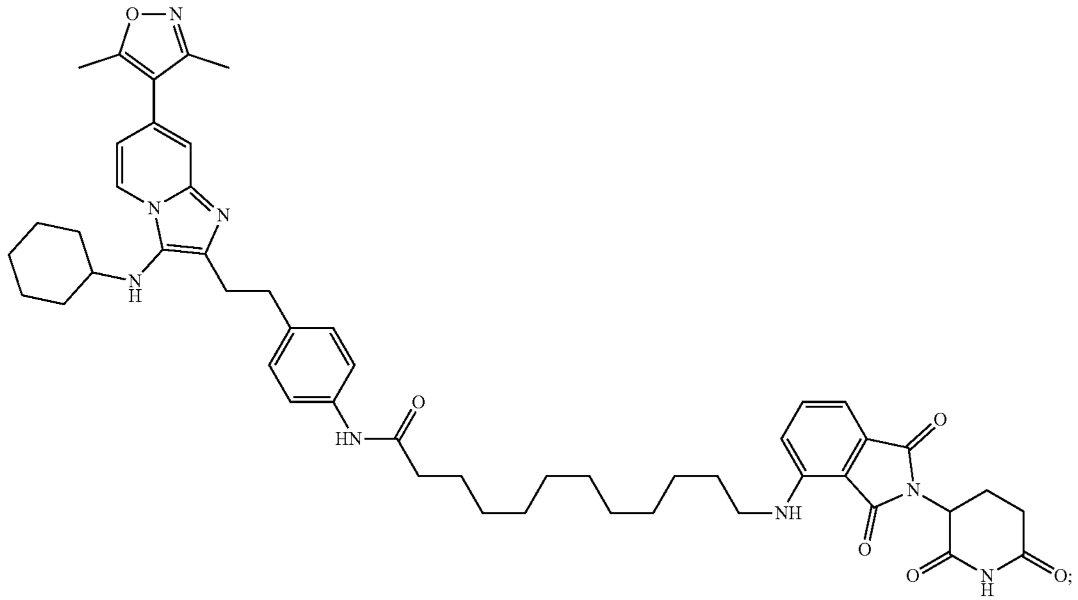
(10)
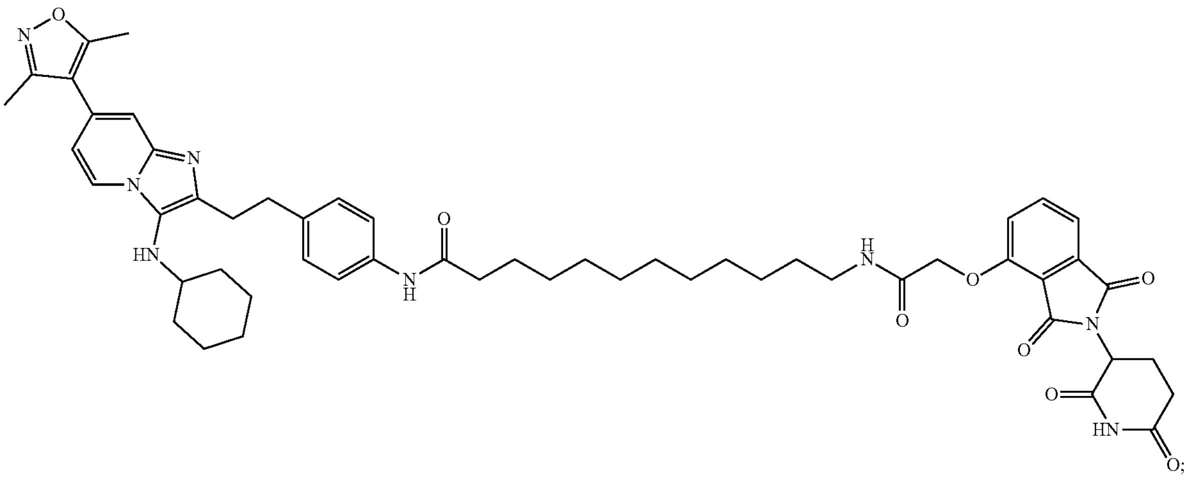
(11)
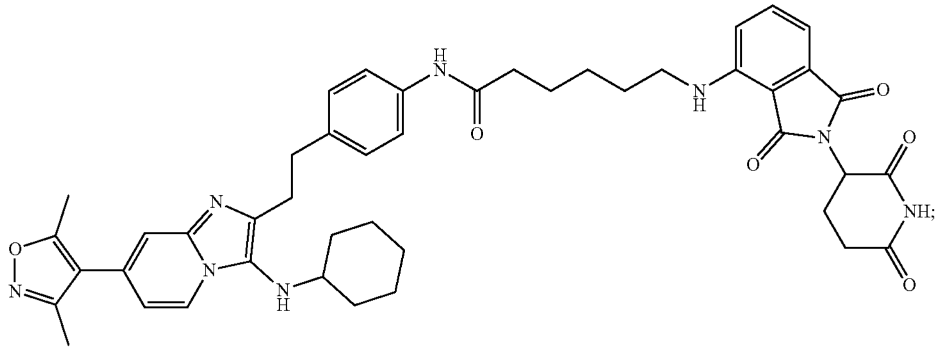

-continued
(12)
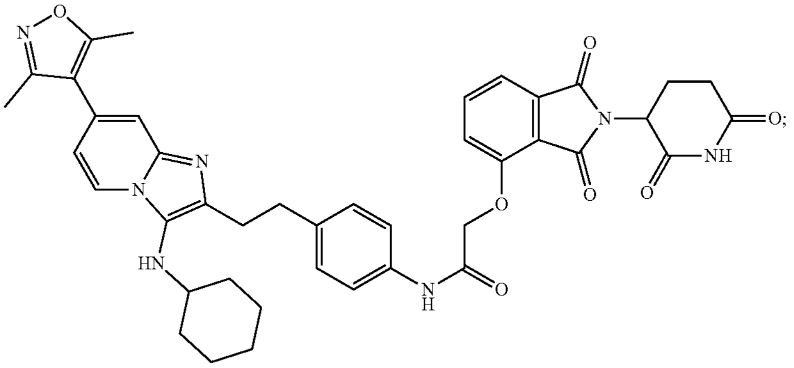
(13)
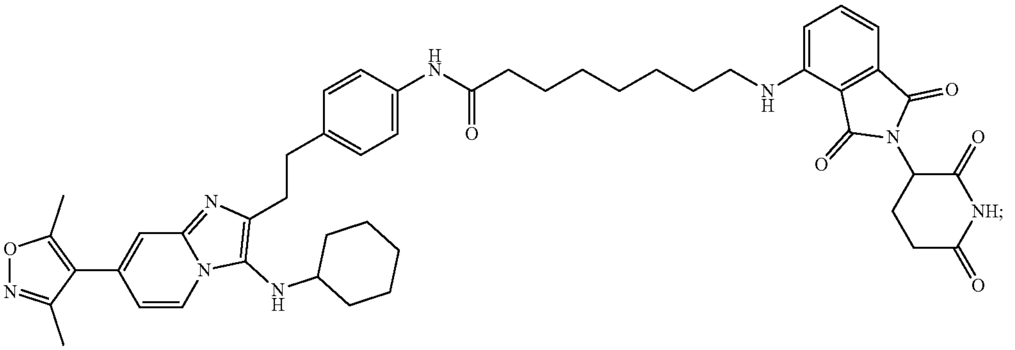
(14)
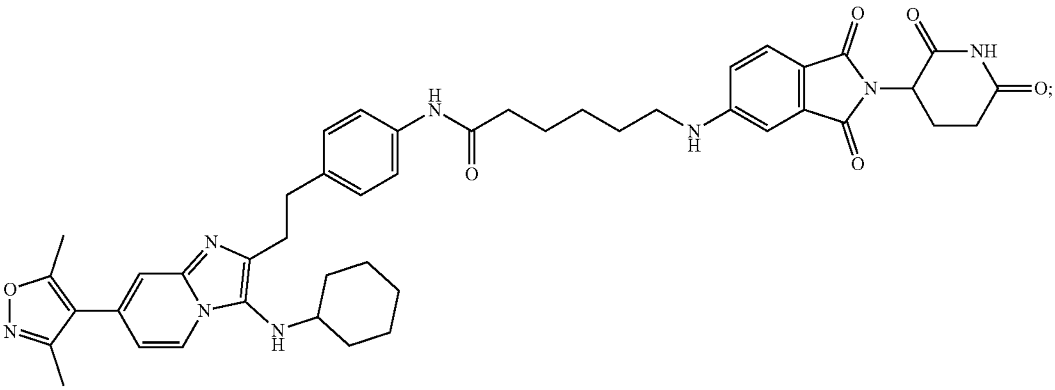
(15)
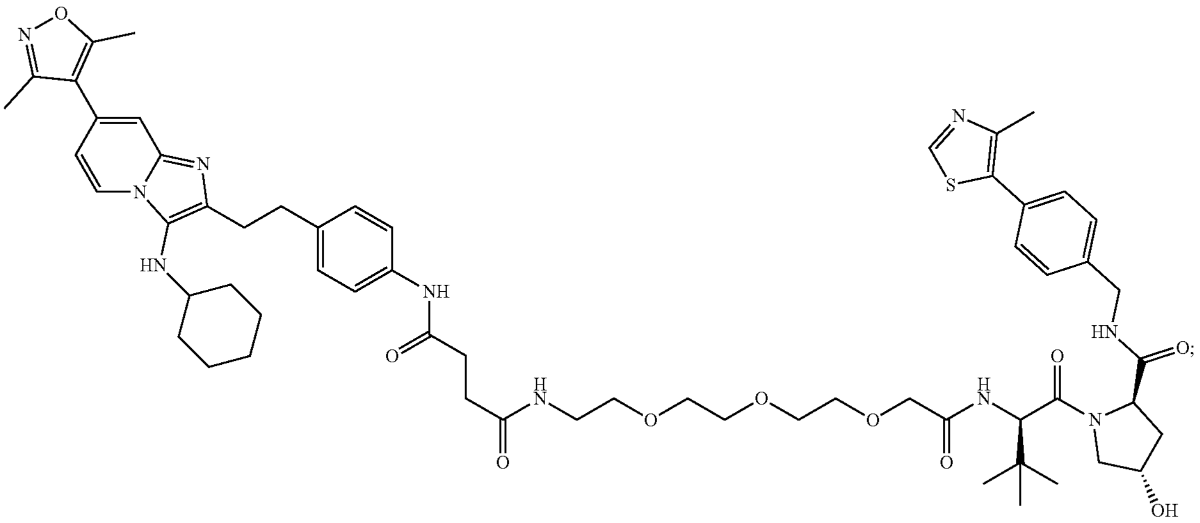

-continued
(16)
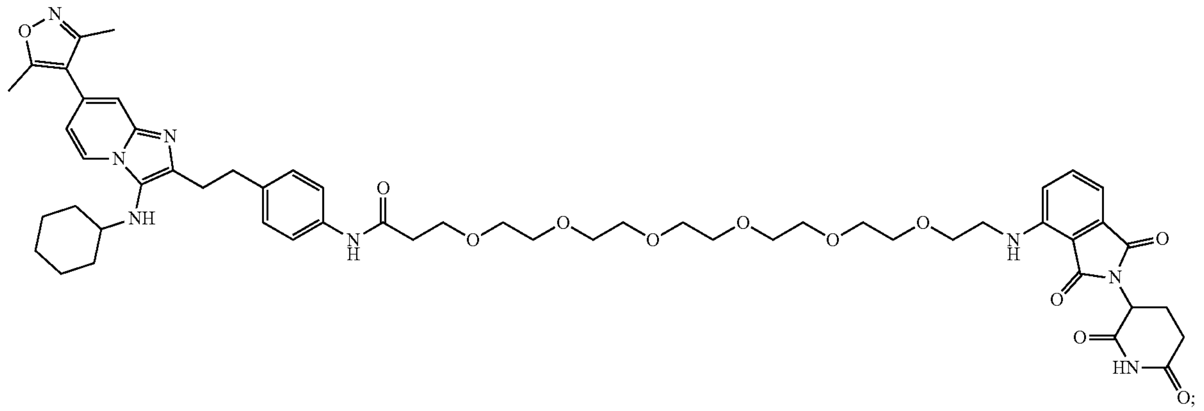
(17)
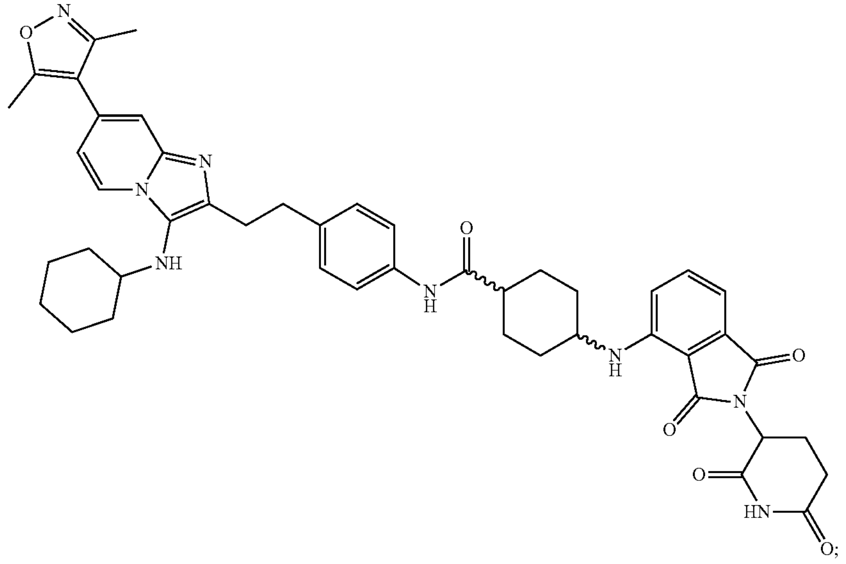
(18)
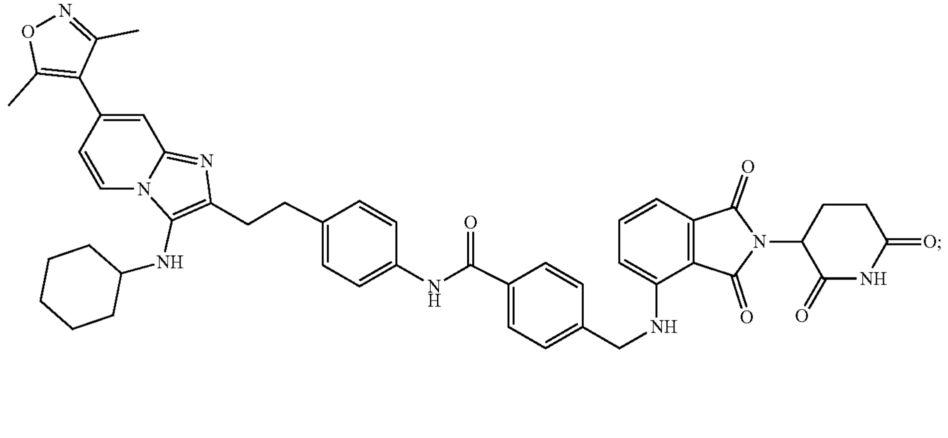

-continued
(19)
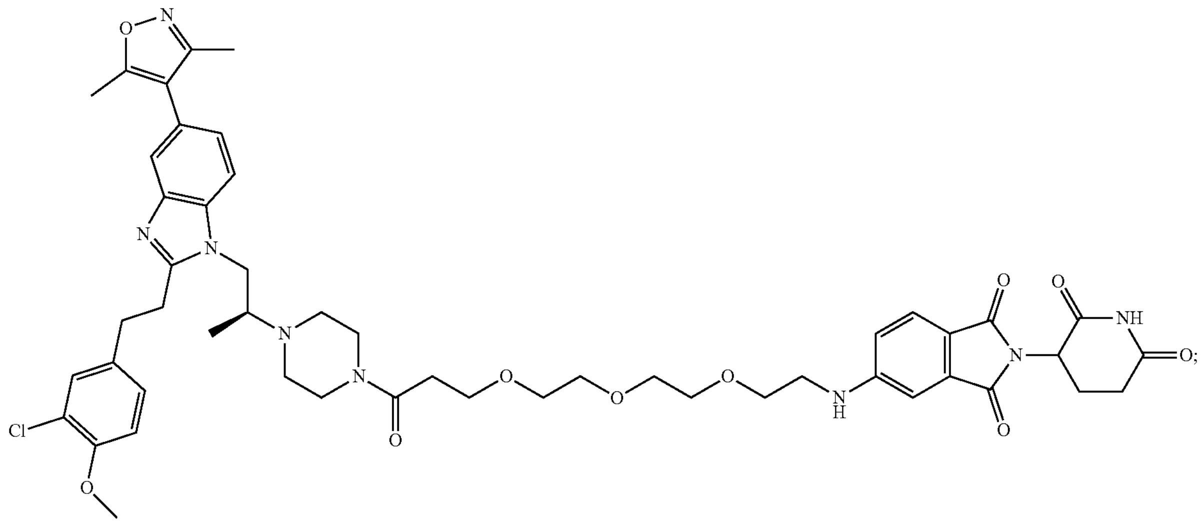
(20)
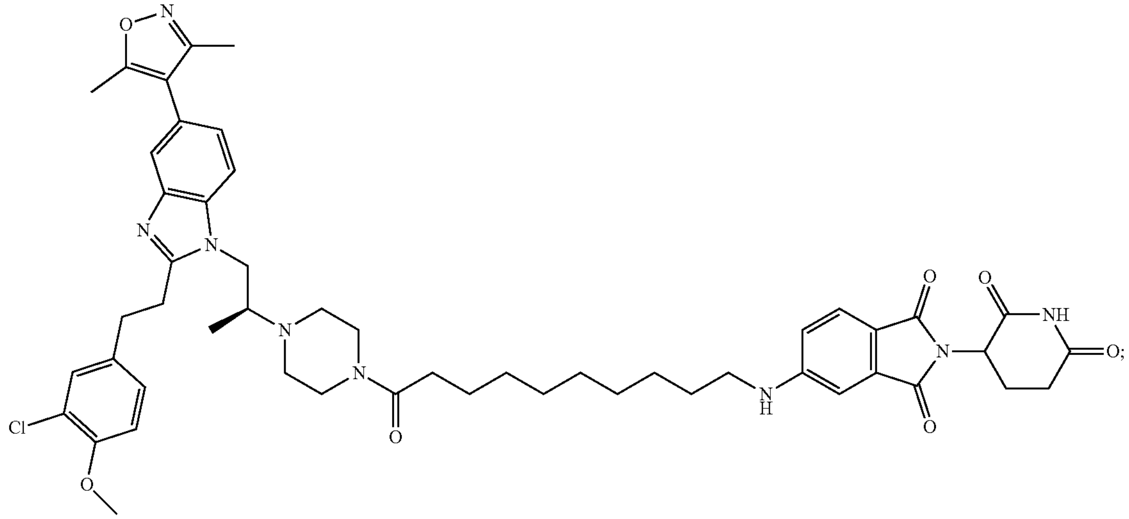
(21)
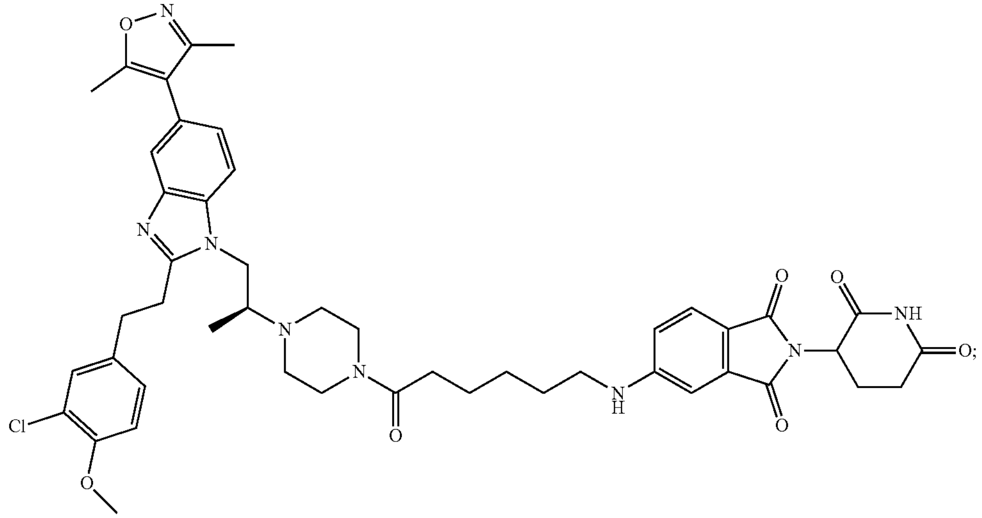

-continued
(22)
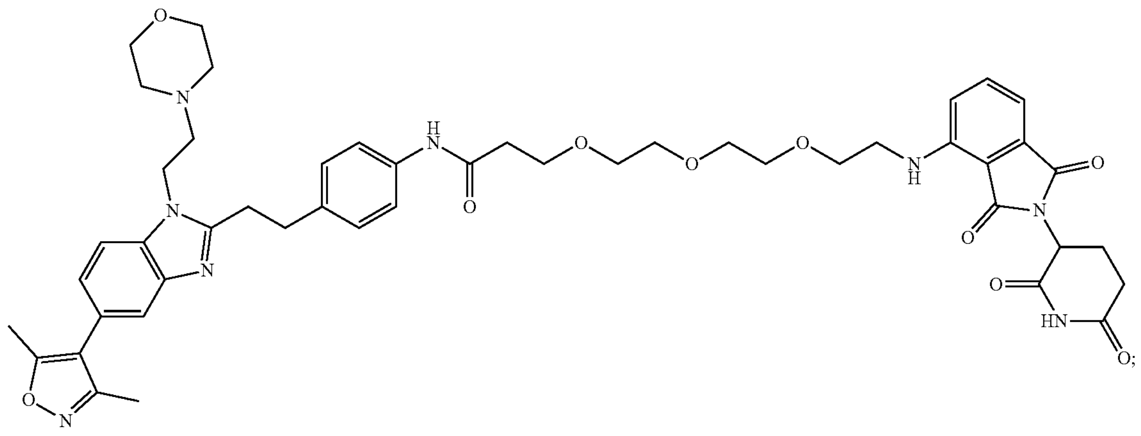
(23)
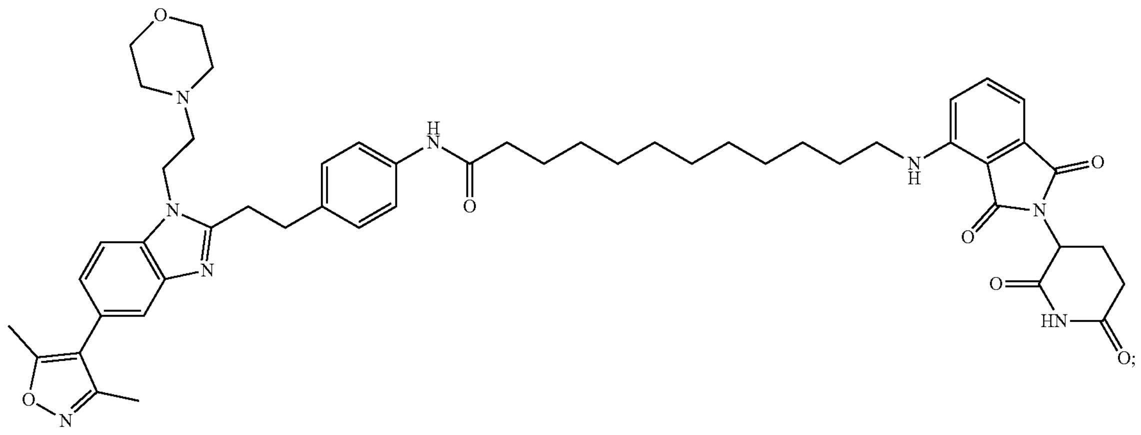
(24)
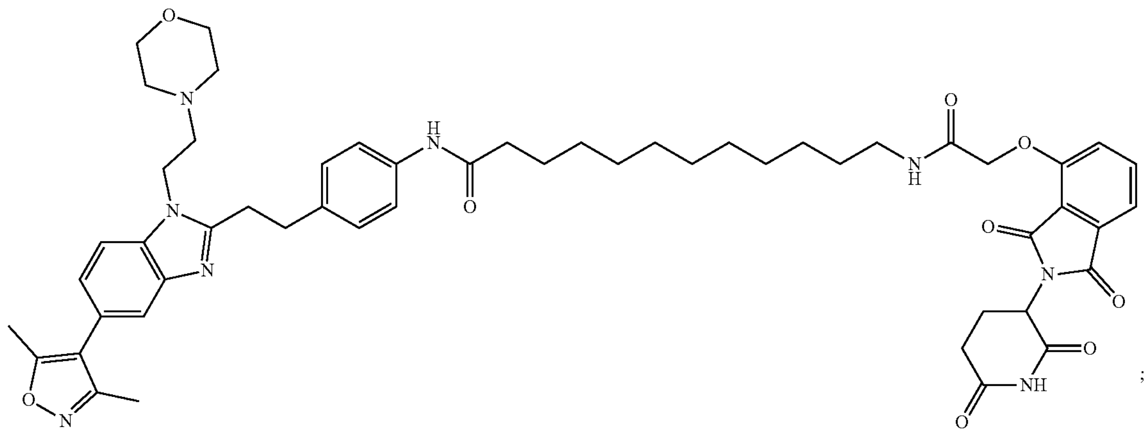
;

-continued
(25)
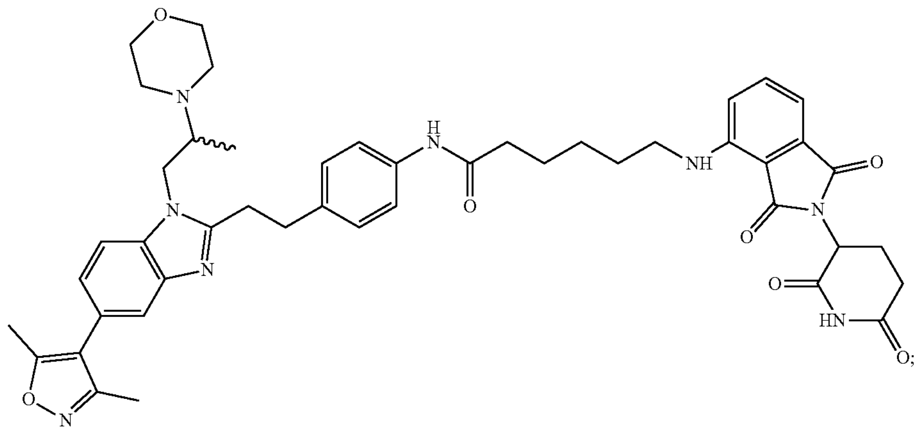
(26)
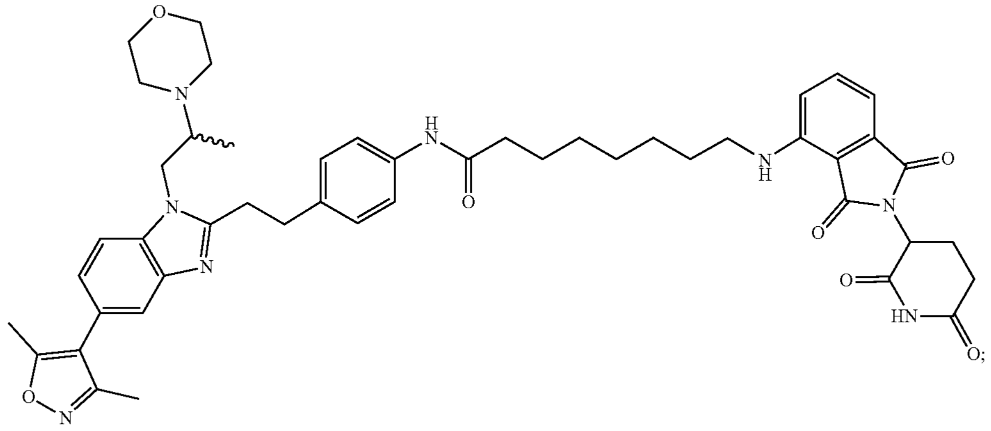
(27)
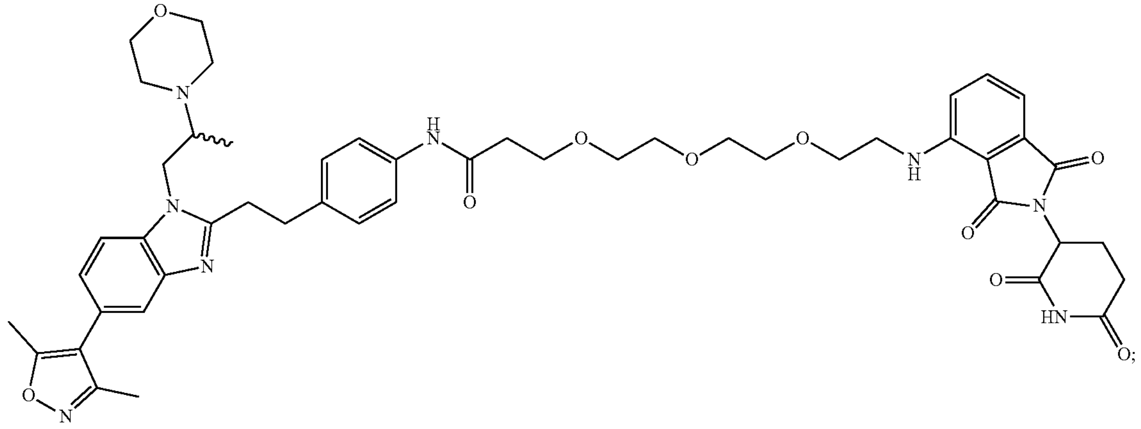

-continued
(28)
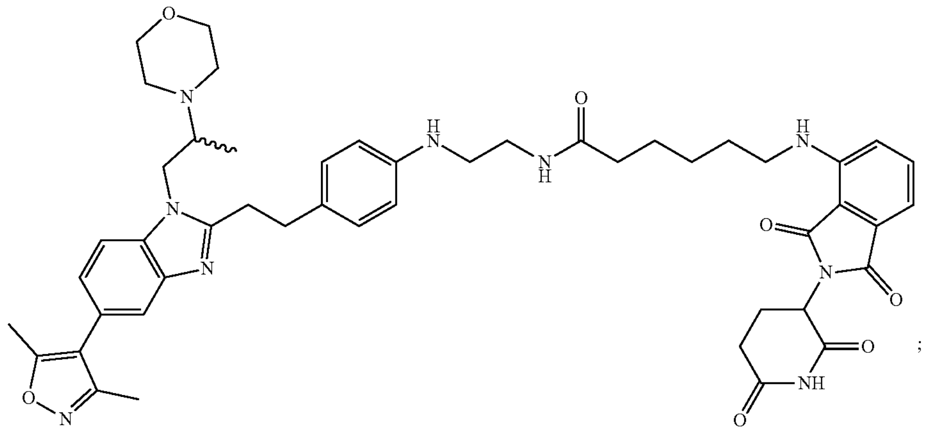
(29)
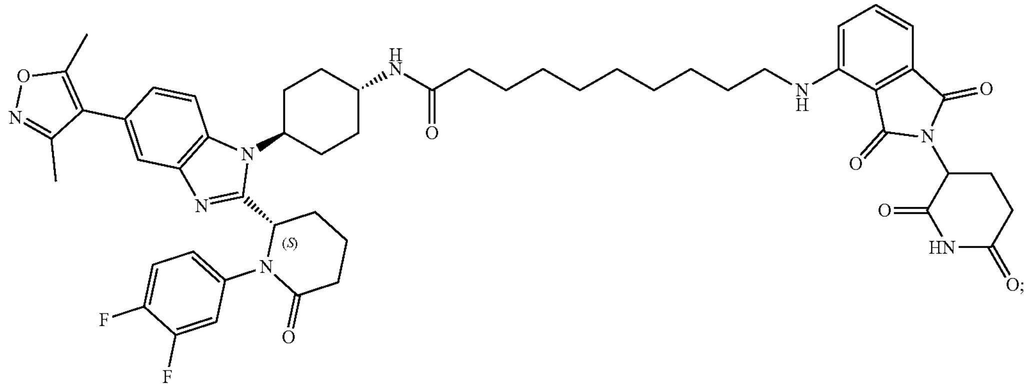
(30)
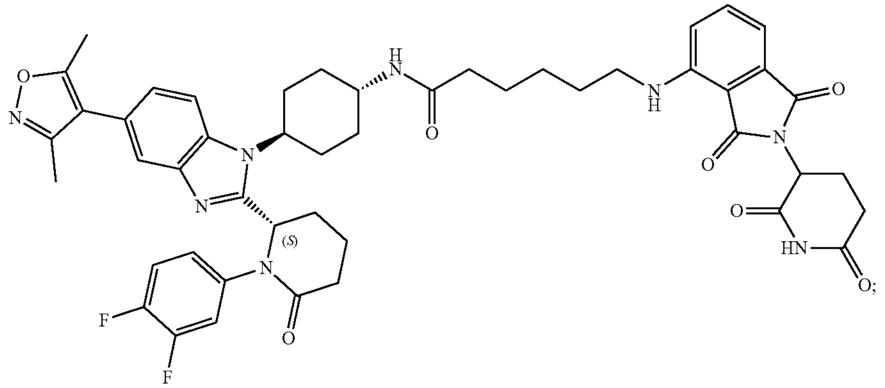
(31)
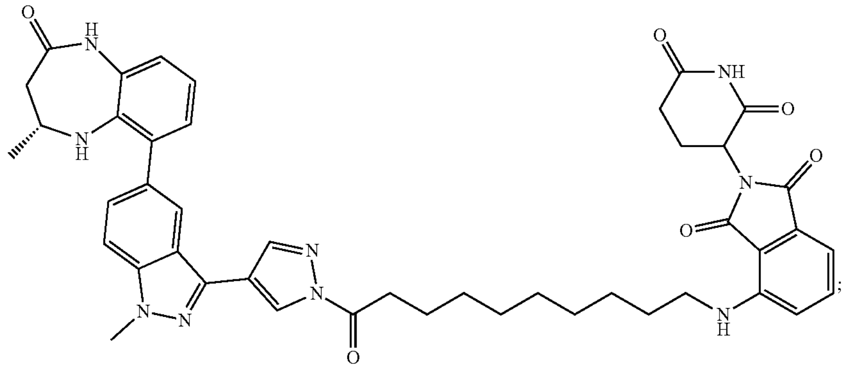

-continued
(32)
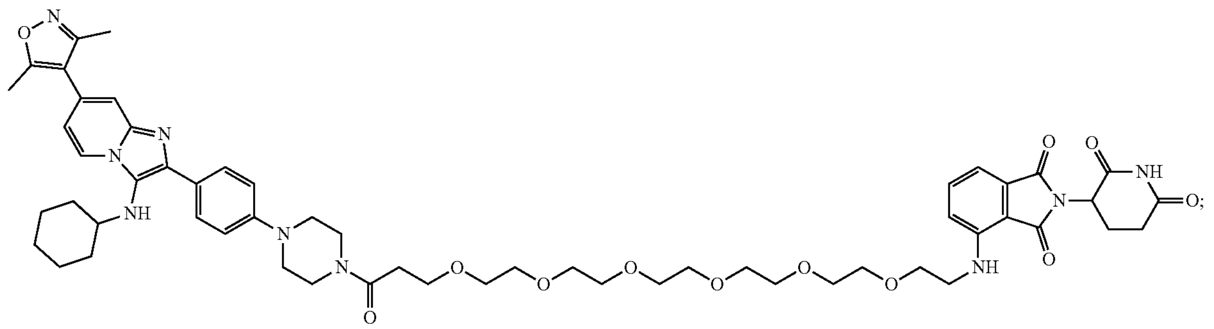
(33)
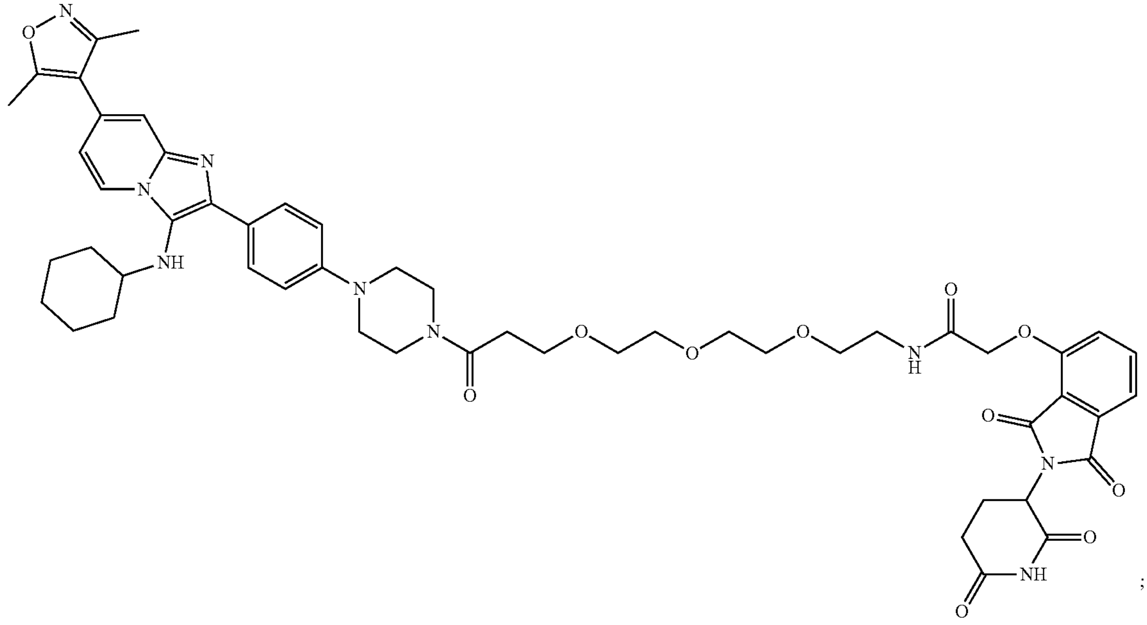
;
(34)
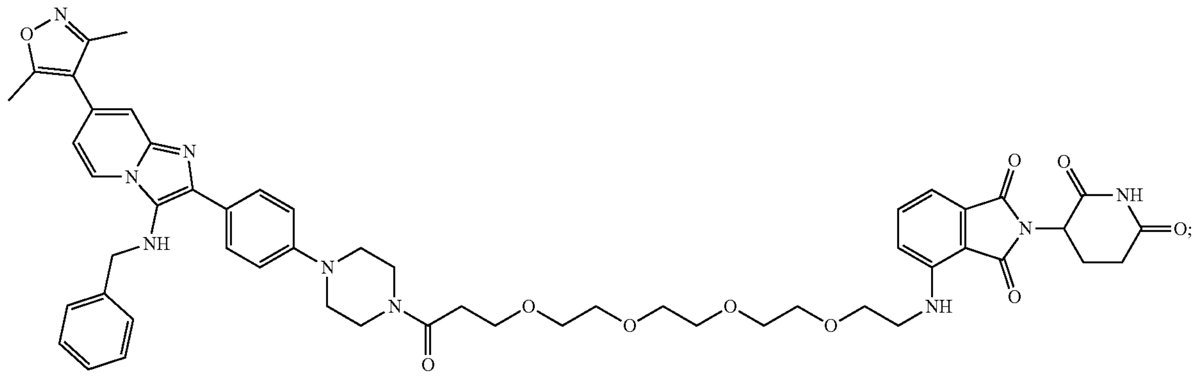

-continued
(35)
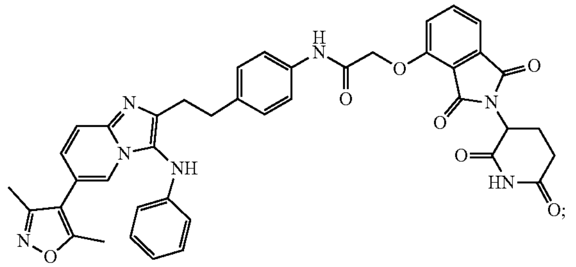
(36)
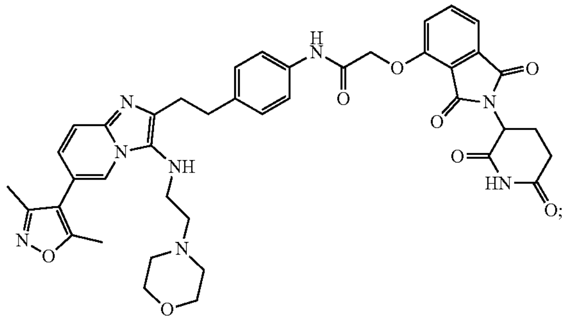
(37)
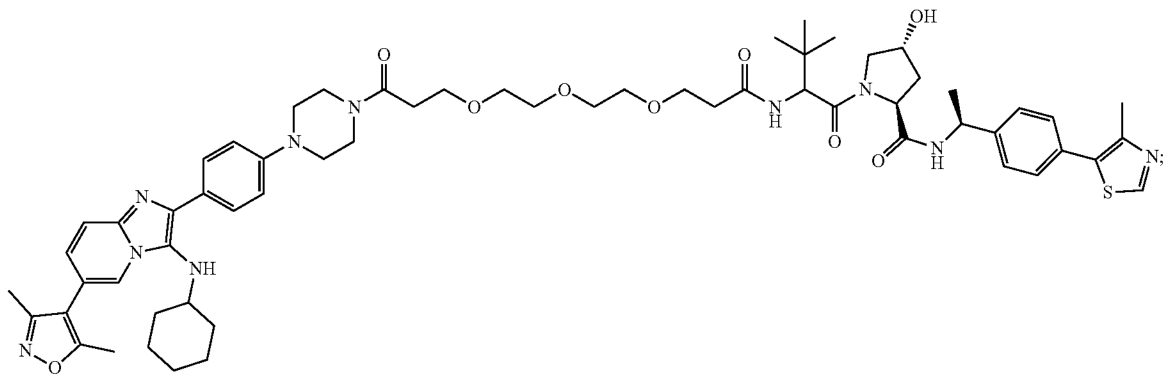
(38)
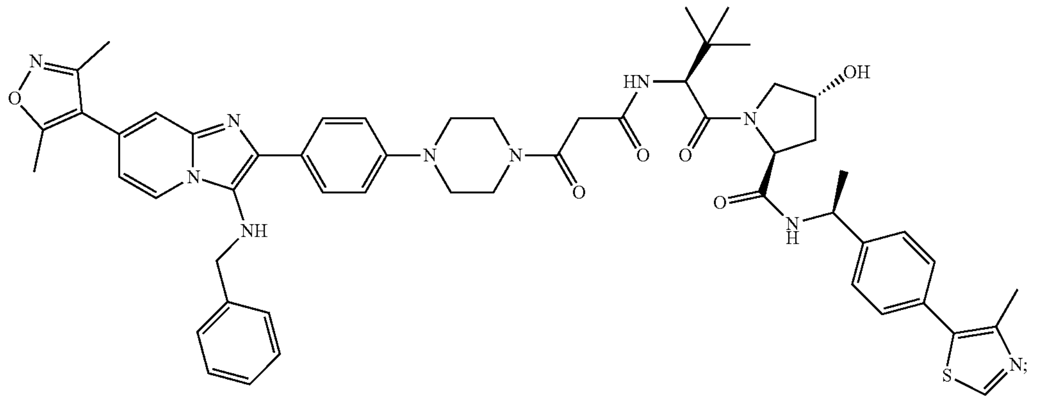

-continued
(39)
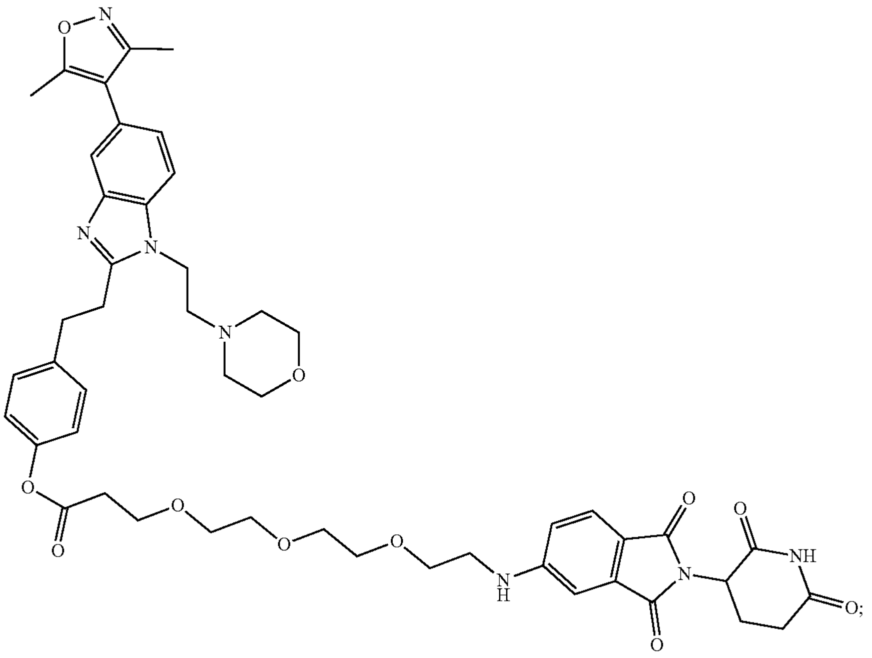
(40)
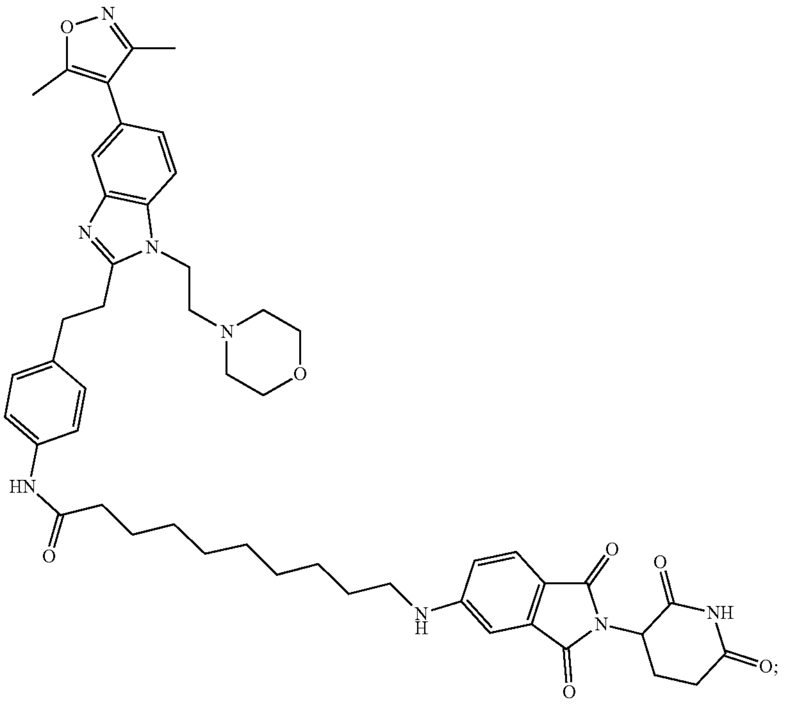

-continued
(41)
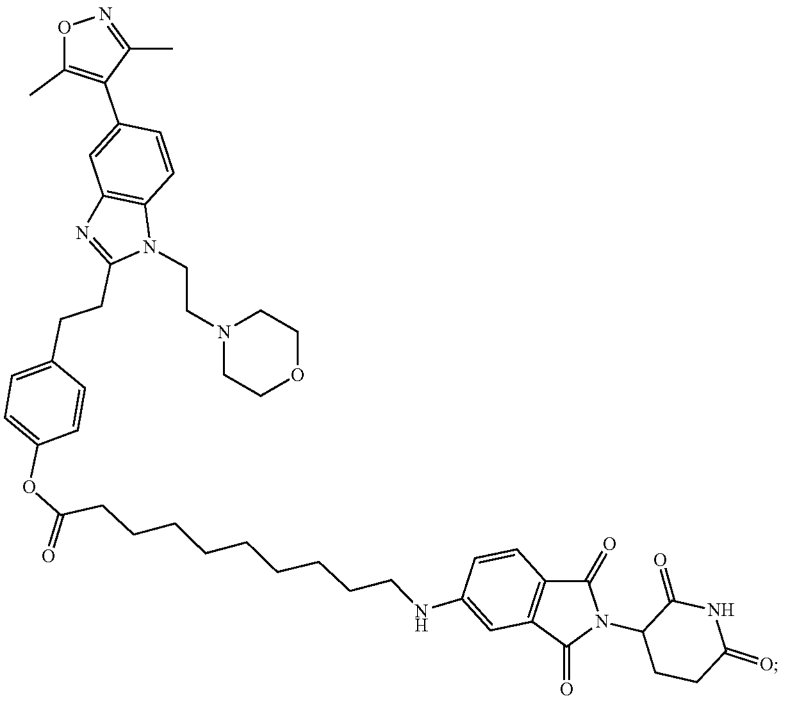
(42)
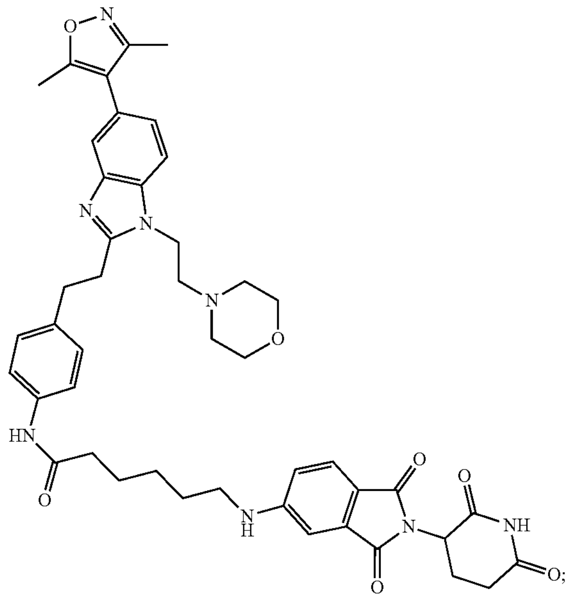
(43)
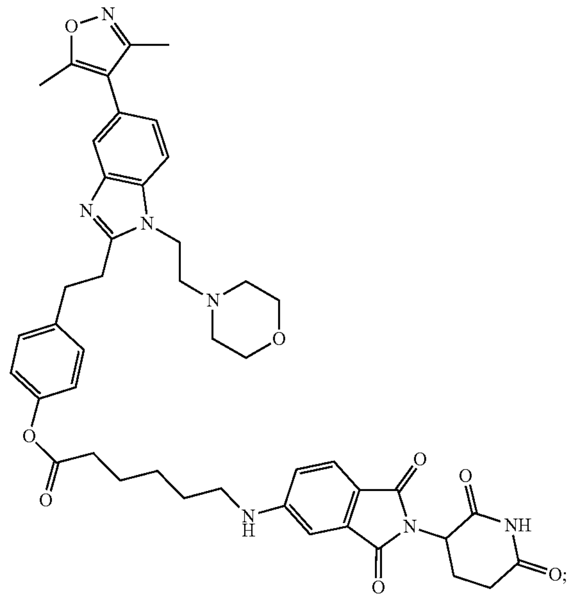

-continued (44)

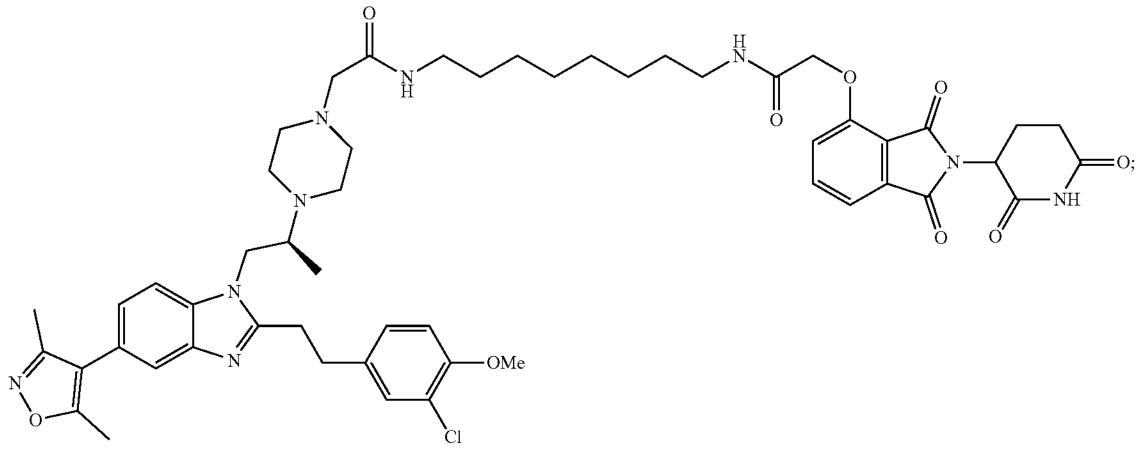

(45)

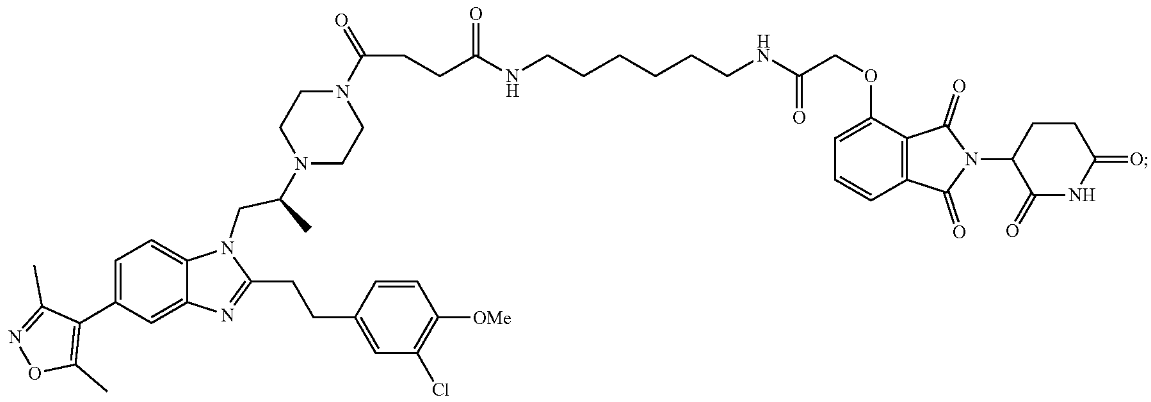

and (46)

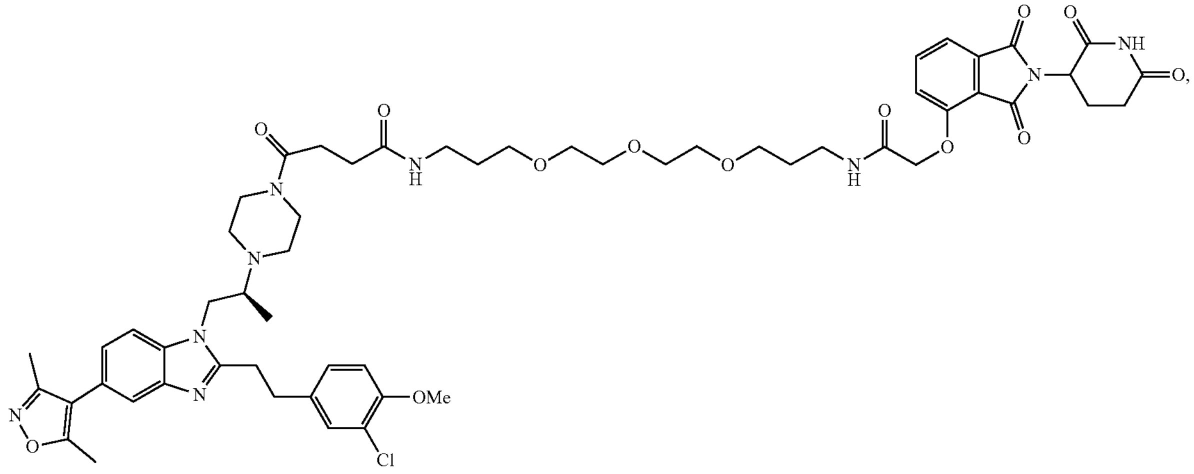

or a pharmaceutically acceptable salt or stereoisomer thereof.

21. A pharmaceutical composition comprising a therapeutically effective amount of the bispecific compound or a pharmaceutically acceptable salt or stereoisomer thereof of claim 1, and a pharmaceutically acceptable carrier.

22. The pharmaceutical composition of claim 21, which is in the form of a tablet or a capsule.

23. A method of treating a disease or disorder involving aberrant EP-300/CBP activity, comprising administering a therapeutically effective amount of the bispecific compound or a pharmaceutically acceptable salt or stereoisomer thereof of claim 1, to a subject in need thereof, wherein the disease or disorder is an EP300/CPB-dependent and MYC-driven cancer.

24. The method of claim 23, wherein the cancer is a hematological cancer or a solid tumor.

25. The method of claim 24, wherein the hematological cancer is acute myeloid leukemia (AML), multiple myeloma (MM), or diffuse large B cell lymphoma, or wherein the solid tumor is neuroblastoma (NB), melanoma, rhabdomyosarcoma, colon cancer, rectum cancer, stomach cancer, breast cancer or pancreatic cancer.

* * * * *